(12) United States Patent
Leese et al.

(10) Patent No.: US 7,893,284 B2
(45) Date of Patent: Feb. 22, 2011

(54) OESTROGEN DERIVATIVES AS INHIBITORS OF STEROID SULPHATASE

(75) Inventors: Matthew Leese, Slough (GB); Atul Purohit, Slough (GB); Michael John Reed, Slough (GB); Simon Paul Newman, Slough (GB); Surinder Kuman Chander, Slough (GB); Fabrice Jourdan, Slough (GB); Barry Victor Lloyd Potter, Slough (GB)

(73) Assignee: Sterix Limited, Slough, Berkshire (GB)

( * ) Notice: Subject to any disclaimer, the term of this patent is extended or adjusted under 35 U.S.C. 154(b) by 1420 days.

(21) Appl. No.: 11/233,945

(22) Filed: Sep. 23, 2005

(65) Prior Publication Data

US 2006/0094696 A1    May 4, 2006

Related U.S. Application Data

(63) Continuation-in-part of application No. PCT/GB2004/000705, filed on Feb. 20, 2004.

(51) Int. Cl.
*C07J 3/00* (2006.01)
*C07J 1/00* (2006.01)

(52) U.S. Cl. ............... 552/610; 552/626; 552/631

(58) Field of Classification Search ............ 552/610, 552/626, 631
See application file for complete search history.

(56) References Cited

U.S. PATENT DOCUMENTS

| | | | |
|---|---|---|---|
| 4,994,439 A * | 2/1991 | Longenecker et al. | 514/3 |
| 6,046,186 A | 4/2000 | Tanabe et al. | |
| 6,436,917 B1 | 8/2002 | Droescher et al. | |
| 2007/0225256 A1 * | 9/2007 | Leese et al. | 514/79 |

FOREIGN PATENT DOCUMENTS

| | | |
|---|---|---|
| EP | 1284272 | 2/2003 |
| JP | 2002-510295 | 4/2002 |
| WO | 99/27936 | 7/1999 |
| WO | 99/33858 | 7/1999 |
| WO | 99/64013 | 12/1999 |
| WO | 00/43408 | 7/2000 |
| WO | 00/66095 | 11/2000 |
| WO | WO 01/85755 | 11/2001 |
| WO | 02/16392 | 2/2002 |
| WO | WO 02/16395 | 2/2002 |
| WO | WO 02/062347 A1 | 8/2002 |

OTHER PUBLICATIONS

J.R. Bull and AJ. Hodgkinson, Steroidal Analogues of Unnatural Configuration—VIII, 29 Tetrahedron 1109 (1973).*
G. Hobe, et al, Species Differences in Biotransformation of 17a-cyanomethylestradiol 3-methyl ether, 36 Steroids 131 (1980).*
Roch P. Boivin, et al "Structure-Activity Relationships of 17 α-Derivatives of Estradiol as Inhibitors of Steriod Sulfatase" 43 J. Med Chem (2000): 4465-4478.
Lucy MacCarthy-Morrogh, et al "Differential Effects of Estrone and Estrone-3-*O*-Sulfamate Derivatives on Mitotic Arrest, Apoptosis, and Microtubule Assembly in Human Breast Cancer Cells" 60 Cancer Research (2000): 5441-5450.
G. Hobe, et al "Species Differences in Biotranformation of 17 α-Cyanomethylestradiol 3-Methyl Ester" 36 Steroids (1980): 131-147.
Y. Hirmai, et al "Synthesis and Antimicrobial Activities of Some Steroidal Amines" 39 Agr. Biol. Chem. (1975): 843-850.

* cited by examiner

*Primary Examiner*—Jeffrey S Lundgren
*Assistant Examiner*—Sean Basquill
(74) *Attorney, Agent, or Firm*—Frommer Lawrence & Haug LLP; Sandra Kuzmich; Russell A. Garman

(57) ABSTRACT

The present invention provides a compound comprising a steroidal ring system and an optional group $R^1$ selected from any one of —OH, a sulphamate group, a phosphonate group, a thiophosphonate group, a sulphonate group or a sulphonamide group; wherein the D ring of the steroidal ring system is substituted by a group $R^2$ of the formula -L-$R^3$, wherein L is an optional linker group and $R^3$ is selected from groups which are or which comprise one of a nitrite group, an alcohol, an ester, an ether, an amine and an alkene, provided that when $R^3$ is or comprises an alcohol, L is present; and wherein the A ring of the steroidal ring system is substituted at position 2 or 4 with a group $R^4$, wherein $R^4$ is a hydrocarbyl group.

21 Claims, 17 Drawing Sheets

OESTROGEN DERIVATIVES AS INHIBITORS OF STEROID SULPHATASE

This application is a continuation-in-part of the International Patent Application PCT/GB2004/000705 filed Feb. 20, 2004 and published as WO 2004/085459 on Oct. 7, 2004 which claims priority to Great Britain Application Numbers 0306717.0 filed Mar. 24, 2003 and 0315885.4 filed Jul. 7, 2003. Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention

FIELD OF INVENTION

The present invention relates to a compound.

In particular the present invention relates to a compound and to a pharmaceutical composition comprising the compound. The present invention also relates to the use of the compound or composition in therapy applications.

BACKGROUND TO THE INVENTION

Evidence suggests that oestrogens are the major mitogens involved in promoting the growth of tumours in endocrine-dependent tissues, such as the breast and endometrium. Although plasma oestrogen concentrations are similar in women with or without breast cancer, breast tumour oestrone and oestradiol levels are significantly higher than in normal breast tissue or blood. In situ synthesis of oestrogen is thought to make an important contribution to the high levels of oestrogens in tumours and therefore inhibitors, in particular specific inhibitors, of oestrogen biosynthesis are of potential value for the treatment of endocrine-dependent tumours.

Over the past two decades, there has been considerable interest in the development of inhibitors of the aromatase pathway—which converts the androgen precursor androstenedione to oestrone. However, there is now evidence that the oestrone sulphatase (E1-STS) pathway, i.e. the hydrolysis of oestrone sulphate to oestrone (E1S to E1), and aromatase (i.e. conversion of androstenedione to oestrone) account for the production of oestrogens in breast tumours.

FIGS. 1 and 2 are schematic diagrams showing some of the enzymes involved in the in situ synthesis of oestrone from oestrone sulphate, oestradiol and androstenedione.

In FIG. 2, which schematically shows the origin of oestrogenic steroids in postmenopausal women, "ER" denotes Oestrogen Receptor, "DHA-S" denotes Dehydroepiandrosterone-Sulphate, "Adiol" denotes Androstenediol, "E1-STS" denotes Oestrone Sulphatase, "DHA-STS" denotes DHA-sulphatase, "Adiol-STS" denotes Adiol Sulphatase, and "17B-HSD" denotes Oestradiol 17B-hydroxysteroid dehydrogenase.

As can be seen, the main two enzymes that are involved in the peripheral synthesis of oestrogens are the aromatase enzyme and the enzyme oestrone sulphatase.

In short, the aromatase enzyme converts androstenedione, which is secreted in large amounts by the adrenal cortex, to oestrone. Recent reports have suggested that some flavones could inhibit aromatase activity.

Much of the oestrone so formed, however, is converted to oestrone sulphate (E1S) and there is now a considerable body of evidence showing that E1S in plasma and tissue acts as a reservoir for the formation of oestrone by the action of oestrone sulphatase.

In this regard, it is now believed that the oestrone sulphatase (E1-STS) pathway—i.e. the hydrolysis of oestrone sulphate to oestrone (E1S to E1) is a major source of oestrogen in breast tumours. This theory is supported by a modest reduction of plasma oestrogen concentration in postmenopausal women with breast cancer treated by aromatase inhibitors, such as aminoglutethimide and 4-hydroxyandrostenedione and also by the fact that plasma E1S concentration in these aromatase inhibitor-treated patients remains relatively high. The long half-life of E1S in blood (10-12 h) compared with the unconjugated oestrogens (20 min) and high levels of steroid sulphatase activity in liver and, normal and malignant breast tissues, also lend support to this theory.

Thus, oestrogen formation in malignant breast and endometrial tissues via the sulphatase pathway makes a major contribution to the high concentration of oestrogens which are present in these tumours.

PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters, such as N,N-dimethyl oestrone-3-sulphamate and, preferably, oestrone-3-sulphamate (otherwise known as "EMATE"). EMATE has the following structure:

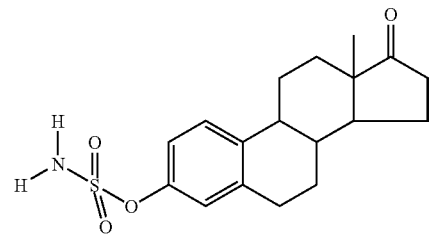

It is known that EMATE is a potent E1-STS inhibitor as it displays more than 99% inhibition of E1-STS activity in intact MCF-7 cells at 0.1 nM. EMATE also inhibits the E1-STS enzyme in a time- and concentration-dependent manner, indicating that it acts as an active site-directed inactivator. Although EMATE was originally designed for the inhibition of E1-STS, it also inhibits dehydroepiandrosterone sulphatase (DHA-STS), which is an enzyme that is believed to have a pivotal role in regulating the biosynthesis of the oestrogenic steroid androstenediol. Also, there is now evidence to suggest that androstenediol may be of even greater importance as a promoter of breast tumour growth. EMATE is also active in vivo as almost complete inhibition of rat liver E1-STS (99%) and DHA-STS (99%) activities resulted when it is administered either orally or subcutaneously. In addition, EMATE has been shown to have a memory enhancing effect in rats. Studies in mice have suggested an association between DHA-STS activity and the regulation of part of the immune response. It is thought that this may also occur in humans. The bridging O-atom of the sulphamate moiety in EMATE is important for inhibitory activity. Thus, when the 3-O-atom is replaced by other heteroatoms as in oestrone-3-N-sulphamate and oestrone-3-S-sulphamate, these analogues are weaker non-time-dependent inactivators.

In addition to oestrone, the other major steroid with oestrogenic properties which is produced by postmenopausal women is androstenediol (see FIG. 2).

Androstenediol, although an androgen, can bind to the oestrogen receptor (ER) and can stimulate the growth of ER positive breast cancer cells and the growth of carcinogen-induced mammary tumours in the rat. Importantly, in postmenopausal women 90% of the androstenediol produced originates from the androgen dehydroepiandrosterone sulphate (DHA-S) which is secreted in large amounts by the adrenal cortex. DHA-S is converted to DHA by DHA sulphatase, which may be the same as, or different from, the enzyme, oestrone sulphatase, which is responsible for the hydrolysis of E1S.

During the last 10-15 years considerable research has also been carried out to develop potent aromatase inhibitors, some of which are now marketed. However, in three recent reports of postmenopausal women with breast cancer who received aromatase inhibitor therapy, plasma E1S concentrations remained between 400-1000 pg/ml.

In summation therefore in situ synthesis of oestrogen is thought to make an important contribution to the high levels of oestrogens in tumours and therefore specific inhibitors of oestrogen biosynthesis are of potential value for the treatment of endocrine-dependent tumours.

Moreover, even though oestrogen formation in malignant breast and endometrial tissues via the sulphatase pathway makes a major contribution to the high concentration of oestrogens, there are still other enzymatic pathways that contribute to in vivo synthesis of oestrogen.

SUMMARY ASPECTS OF THE PRESENT INVENTION

The present invention is based on the surprising finding that steroidal compounds carrying a group on the D ring which is selected from groups which are or which comprise one of a nitrile group, an alcohol, an ester, an ether, an amine and an alkene could be used as effective steroid sulphatase (STS) inhibitors; cell cycling modulators, apoptosis modulators; cell growth modulators; glucose uptake prevention and/or suppression agents; tumour angiogenesis prevention agents or inhibitors; microtubules disruptors; and/or apoptosis inducers.

The compounds of the present invention may comprise other substituents. These other substituents may, for example, further increase the activity of the compounds of the present invention and/or increase stability (ex vivo and/or in vivo).

DETAILED ASPECTS OF THE PRESENT INVENTION

According to one aspect of the present invention, there is provided a compound comprising a steroidal ring system and an optional group $R^1$ selected from any one of —OH, a sulphamate group, a phosphonate group, a thiophosphonate group, a sulphonate group or a sulphonamide group; wherein the D ring of the steroidal ring system is substituted by a group $R^2$ of the formula -L-$R^3$, wherein L is an optional linker group and $R^3$ is selected from groups which are or which comprise one of a nitrile group, an alcohol, an ester, an ether, an amine and an alkene, provided that when $R^3$ is or comprises an alcohol, L is present; and wherein the A ring of the steroidal ring system is substituted at position 2 or 4 with a group $R^4$, wherein $R^4$ is a hydrocarbyl group.

According to one aspect of the present invention, there is provided a composition comprising i) a compound as defined herein; and ii) a biological response modifier.

According to one aspect of the present invention, there is provided a pharmaceutical composition comprising (a) (i) a compound as defined herein, or (ii) a composition as defined herein, and (b) a pharmaceutically acceptable carrier, diluent, excipient or adjuvant.

According to one aspect of the present invention, there is provided a (i) compound as defined herein, or (ii) composition as defined herein, for use in medicine.

According to one aspect of the present invention, there is provided use of (i) a compound as defined herein, or (ii) a composition as defined herein, in the manufacture of a medicament to prevent and/or inhibit tumour growth.

According to one aspect of the present invention, there is provided use of (i) a compound as defined herein, or (ii) a composition as defined herein, in the manufacture of a medicament for use in the therapy of a condition or disease associated with one or more of steroid sulphatase (STS) activity; cell cycling; apoptosis; cell growth; glucose uptake by a tumour; tumour angiogenesis; microtubules formation; and apoptosis.

According to one aspect of the present invention, there is provided use of (i) a compound as defined herein, or (ii) a composition as defined herein, in the manufacture of a medicament for use in the therapy of a condition or disease associated with one or more of adverse steroid sulphatase (STS) activity; cell cycling; apoptosis; cell growth; glucose uptake by a tumour; tumour angiogenesis; microtubules formation; and apoptosis.

According to one aspect of the present invention, there is provided use of (i) a compound as defined herein, or (ii) a composition as defined herein, in the manufacture of a medicament for one or more of inhibiting steroid sulphatase (STS) activity; modulating cell cycling; modulating apoptosis; modulating cell growth; preventing and/or suppressing glucose uptake by a tumour; preventing and/or inhibiting tumour angiogenesis; disrupting microtubules; and inducing apoptosis.

According to one aspect of the present invention, there is provided use of (i) a compound as defined herein, or (ii) a composition as defined herein, in the manufacture of a medicament for inhibiting steroid sulphatase (STS) activity.

According to one aspect of the present invention, there is provided use of (i) a compound as defined herein, or (ii) a composition as defined herein, in the manufacture of a medicament for modulating cell growth.

According to one aspect of the present invention, there is provided a method of treatment comprising administering to a subject in need of treatment (i) a compound as defined herein, or (ii) a composition as defined herein.

According to one aspect of the present invention, there is provided a method of treatment comprising administering to a subject in need of treatment (i) a compound as defined herein, or (ii) a composition as defined herein, in order to inhibit steroid sulphatase (STS) activity; modulate cell cycling; modulate apoptosis; modulate cell growth; prevent and/or suppress glucose uptake by a tumour; prevent and/or inhibit tumour angiogenesis; disrupt microtubules; and/or induce apoptosis.

According to one aspect of the present invention, there is provided a method comprising (a) performing an assay for one or more of steroid sulphatase (STS) inhibition; cell cycling modulation; apoptosis modulation; cell growth modulation; prevention and/or suppression of glucose uptake by a tumour; tumour angiogenesis prevention and/or inhibition; microtubules disruption; and apoptosis induction, with one or more candidate compounds defined herein; (b) determining whether one or more of said candidate compounds is/are capable of one or more of steroid sulphatase (STS) inhibition; cell cycling modulation; apoptosis modulation;

cell growth modulation; prevention and/or suppression of glucose uptake by a tumour; tumour angiogenesis prevention and/or inhibition; microtubules disruption; and apoptosis induction; and (c) selecting one or more of said candidate compounds that is/are capable of one or more of steroid sulphatase (STS) inhibition; cell cycling modulation; apoptosis modulation; cell growth modulation; prevention and/or suppression of glucose uptake by a tumour; tumour angiogenesis prevention and/or inhibition; microtubules disruption; and apoptosis induction.

In any one of the methods of the present invention, one or more additional steps may be present. For example, the method may also include the step of modifying the identified candidate compound (such as by chemical and/or enzymatic techniques) and the optional additional step of testing that modified compound for one or more of steroid sulphatase (STS) inhibition; cell cycling modulation; apoptosis modulation; cell growth modulation; prevention and/or suppression of glucose uptake by a tumour; tumour angiogenesis prevention and/or inhibition; microtubules disruption; and apoptosis induction. By way of further example, the method may also include the step of determining the structure (such as by use of crystallographic techniques) of the identified candidate compound and then performing computer modelling studies—such as to further increase its action. Thus, the present invention also encompasses a computer having a dataset (such as the crystallographic co-ordinates) for said identified candidate compound. The present invention also encompasses that identified candidate compound when presented on a computer screen for the analysis thereof—such as enzyme and/or protein binding studies.

According to one aspect of the present invention, there is provided a compound identified by the method of the present invention.

The present invention also encompasses the novel compounds of the present invention (such as those presented herein), as well as processes for making same (such as the processes presented herein) as well as novel intermediates (such as those presented herein) for use in those processes.

BROAD ASPECTS

According to one broad aspect of the present invention, there is provided use of a compound in the manufacture of a medicament for use in the therapy of a condition or disease associated with one or more of cell cycling; apoptosis; cell growth; glucose uptake by a tumour; tumour angiogenesis; microtubules formation; and apoptosis; wherein the compound comprises a steroidal ring system and an optional group $R^1$ selected from any one of —OH, a sulphamate group, a phosphonate group, a thiophosphonate group, a sulphonate group or a sulphonamide group; and wherein the D ring of the steroidal ring system is substituted by a group $R^2$ of the formula -L-$R^3$, wherein L is an optional linker group and $R^3$ is selected from groups which are or which comprise one of a nitrile group, an alcohol, an ester, an ether, an amine and an alkene, provided that when $R^3$ is or comprises an alcohol, L is present.

According to one broad aspect of the present invention, there is provided use of a composition in the manufacture of a medicament for use in the therapy of a condition or disease associated with one or more of cell cycling; apoptosis; cell growth; glucose uptake by a tumour; tumour angiogenesis; microtubules formation; and apoptosis; wherein the composition comprises i) a compound comprising a steroidal ring system and an optional group $R^1$ selected from any one of —OH, a sulphamate group, a phosphonate group, a thiophosphonate group, a sulphonate group or a sulphonamide group; and wherein the D ring of the steroidal ring system is substituted by a group $R^2$ of the formula -L-$R^3$, wherein L is an optional linker group and $R^3$ is selected from groups which are or which comprise one of a nitrile group, an alcohol, an ester, an ether, an amine and an alkene, provided that when. $R^3$ is or comprises an alcohol, L is present; and ii) a biological response modifier.

According to another broad aspect of the present invention, there is provided use of a compound in the manufacture of a medicament for use in the therapy of a condition or disease associated with one or more of adverse cell cycling; apoptosis; cell growth; glucose uptake by a tumour; tumour angiogenesis; microtubules formation; and apoptosis; wherein the compound comprises a steroidal ring system and an optional group $R^1$ selected from any one of —OH, a sulphamate group, a phosphonate group, a thiophosphonate group, a sulphonate group or a sulphonamide group; and wherein the D ring of the steroidal ring system is substituted by a group $R^2$ of the formula -L-$R^3$, wherein L is an optional linker group and $R^3$ is selected from groups which are or which comprise one of a nitrile group, an alcohol, an ester, an ether, an amine and an alkene, provided that when $R^3$ is or comprises an alcohol, L is present.

According to another broad aspect of the present invention, there is provided use of a composition in the manufacture of a medicament for use in the therapy of a condition or disease associated with one or more of adverse cell cycling; apoptosis; cell growth; glucose uptake by a tumour; tumour angiogenesis; microtubules formation; and apoptosis; wherein the composition comprises i) a compound comprising a steroidal ring system and an optional group $R^1$ selected from any one of —OH, a sulphamate group, a phosphonate group, a thiophosphonate group, a sulphonate group or a sulphonamide group; and wherein the D ring of the steroidal ring system is substituted by a group $R^2$ of the formula -L-$R^3$, wherein L is an optional linker group and $R^3$ is selected from groups which are or which comprise one of a nitrile group, an alcohol, an ester, an ether, an amine and an alkene, provided that when $R^3$ is or comprises an alcohol, L is present; and ii) a biological response modifier.

According to a further broad aspect of the present invention, there is provided use of a compound in the manufacture of a medicament for one or more of modulating cell cycling; modulating apoptosis; modulating cell growth; preventing and/or suppressing glucose uptake by a tumour; preventing and/or inhibiting tumour angiogenesis; disrupting microtubules; and inducing apoptosis; wherein the compound comprises a steroidal ring system and an optional group $R^1$ selected from any one of —OH, a sulphamate group, a phosphonate group, a thiophosphonate group, a sulphonate group or a sulphonamide group; and wherein the D ring of the steroidal ring system is substituted by a group $R^2$ of the formula -L-$R^3$, wherein L is an optional linker group and $R^3$ is selected from groups which are or which comprise one of a nitrile group, an alcohol, an ester, an ether, an amine and an alkene, provided that when $R^3$ is or comprises an alcohol, L is present.

According to a further broad aspect of the present invention, there is provided use of a composition in the manufacture of a medicament for one or more of modulating cell cycling; modulating apoptosis; modulating cell growth; preventing and/or suppressing glucose uptake by a tumour; preventing and/or inhibiting tumour angiogenesis; disrupting microtubules; and inducing apoptosis wherein the composition comprises i) a compound comprising a steroidal ring system and an optional group $R^1$ selected from any one of —OH, a sulphamate group, a phosphonate group, a thiophosphonate group, a sulphonate group or a sulphonamide group; and wherein the D ring of the steroidal ring system is substituted by a group $R^2$ of the formula -L-$R^3$, wherein L is an optional linker group and $R^3$ is selected from groups which are or which comprise one of a nitrile group, an alcohol, an ester, an ether, an amine and an alkene, provided that when $R^3$ is or comprises an alcohol, L is present; and ii) a biological response modifier.

According to a broad aspect of the present invention, there is provided use of a compound in the manufacture of a medicament for modulating cell growth; wherein the compound comprises a steroidal ring system and an optional group $R^1$ selected from any one of —OH, a sulphamate group, a phosphonate group, a thiophosphonate group, a sulphonate group or a sulphonamide group; and wherein the D ring of the steroidal ring system is substituted by a group $R^2$ of the formula -L-$R^3$, wherein L is an optional linker group and $R^3$ is selected from groups which are or which comprise one of a nitrile group, an alcohol, an ester, an ether, an amine and an alkene, provided that when $R^3$ is or comprises an alcohol, L is present.

According to a broad aspect of the present invention, there is provided use of a composition in the manufacture of a medicament for modulating cell growth wherein the composition comprises i) a compound comprising a steroidal ring system and an optional group $R^1$ selected from any one of —OH, a sulphamate group, a phosphonate group, a thiophosphonate group, a sulphonate group or a sulphonamide group; and wherein the D ring of the steroidal ring system is substituted by a group $R^2$ of the formula -L-$R^3$, wherein L is an optional linker group and $R^3$ is selected from groups which are or which comprise one of a nitrile group, an alcohol, an ester, an ether, an amine and an alkene, provided that when $R^3$ is or comprises an alcohol, L is present; and ii) a biological response modifier.

According to a broad aspect of the present invention, there is provided a method of treatment comprising administering to a subject in need of treatment a compound in order to modulate cell cycling; modulate apoptosis; modulate cell growth; prevent and/or suppress glucose uptake by a tumour; prevent and/or inhibit tumour angiogenesis; disrupt microtubules; and/or induce apoptosis wherein the compound comprises a steroidal ring system and an optional group $R^1$ selected from any one of —OH, a sulphamate group, a phosphonate group, a thiophosphonate group, a sulphonate group or a sulphonamide group; and wherein the D ring of the steroidal ring system is substituted by a group $R^2$ of the formula -L-$R^3$, wherein L is an optional linker group and $R^3$ is selected from groups which are or which comprise one of a nitrile group, an alcohol, an ester, an ether, an amine and an alkene, provided that when $R^3$ is or comprises an alcohol, L is present.

According to a broad aspect of the present invention, there is provided a method of treatment comprising administering to a subject in need of treatment a composition in order to modulate cell cycling; modulate apoptosis; modulate cell growth; prevent and/or suppress glucose uptake by a tumour; prevent and/or inhibit tumour angiogenesis; disrupt microtubules; and/or induce apoptosis wherein the composition comprises i) a compound comprising a steroidal ring system and an optional group $R^1$ selected from any one of —OH, a sulphamate group, a phosphonate group, a thiophosphonate group, a sulphonate group or a sulphonamide group; and wherein the D ring of the steroidal ring system is substituted by a group $R^2$ of the formula -L-$R^3$, wherein L is an optional linker group and $R^3$ is selected from groups which are or which comprise one of a nitrile group, an alcohol, an ester, an ether, an amine and an alkene, provided that when $R^3$ is or comprises an alcohol, L is present; and ii) a biological response modifier.

According to one broad aspect of the present invention, there is provided use of a compound in the manufacture of a medicament for use in the therapy of a condition or disease associated with carbonic anhydrase; wherein the compound comprises a steroidal ring system and an optional group $R^1$ selected from any one of —OH, a sulphamate group, a phosphonate group, a thiophosphonate group, a sulphonate group or a sulphonamide group; and wherein the D ring of the steroidal ring system is substituted by a group $R^2$ of the formula -L-$R^3$, wherein L is an optional linker group and $R^3$ is selected from groups which are or which comprise one of a nitrile group, an alcohol, an ester, an ether, an amine and an alkene, provided that when $R^3$ is or comprises an alcohol, L is present.

According to one broad aspect of the present invention, there is provided use of a composition in the manufacture of a medicament for use in the therapy of a condition or disease associated with carbonic anhydrase; wherein the composition comprises i) a compound comprising a steroidal ring system and an optional group $R^1$ selected from any one of —OH, a sulphamate group, a phosphonate group, a thiophosphonate group, a sulphonate group or a sulphonamide group; and wherein the D ring of the steroidal ring system is substituted by a group $R^2$ of the formula -L-$R^3$, wherein L is an optional linker group and $R^3$ is selected from groups which are or which comprise one of a nitrile group, an alcohol, an ester, an ether, an amine and an alkene, provided that when $R^3$ is or comprises an alcohol, L is present; and ii) a biological response modifier.

According to another broad aspect of the present invention, there is provided use of a compound in the manufacture of a medicament for use in the therapy of a condition or disease associated with adverse carbonic anhydrase activity; wherein the compound comprises a steroidal ring system and an optional group $R^1$ selected from any one of —OH, a sulphamate group, a phosphonate group, a thiophosphonate group, a sulphonate group or a sulphonamide group; and wherein the D ring of the steroidal ring system is substituted by a group $R^2$ of the formula -L-$R^3$, wherein L is an optional linker group and $R^3$ is selected from groups which are or which comprise one of a nitrile group, an alcohol, an ester, an ether, an amine and an alkene, provided that when $R^3$ is or comprises an alcohol, L is present.

According to another broad aspect of the present invention, there is provided use of a composition in the manufacture of a medicament for use in the therapy of a condition or disease associated with adverse carbonic anhydrase activity; wherein the composition comprises i) a compound comprising a steroidal ring system and an optional group $R^1$ selected from any one of —OH, a sulphamate group, a phosphonate group, a thiophosphonate group, a sulphonate group or a sulphonamide group; and wherein the D ring of the steroidal ring system is substituted by a group $R^2$ of the formula -L-$R^3$, wherein L is an optional linker group and $R^3$ is selected from groups which are or which comprise one of a nitrile group; an alcohol, an ester, an ether, an amine and an alkene, provided that when $R^3$ is or comprises an alcohol, L is present; and ii) a biological response modifier.

According to a further broad aspect of the present invention, there is provided use of a compound in the manufacture of a medicament for modulating carbonic anhydrase activity; wherein the compound comprises a steroidal ring system and an optional group $R^1$ selected from any one of —OH, a sulphamate group, a phosphonate group, a thiophosphonate group, a sulphonate group or a sulphonamide group; and wherein the D ring of the steroidal ring system is substituted by a group $R^2$ of the formula -L-$R^3$, wherein L is an optional linker group and $R^3$ is selected from groups which are or which comprise one of a nitrile group, an alcohol, an ester, an ether, an amine and an alkene, provided that when $R^3$ is or comprises an alcohol, L is present.

According to a further broad aspect of the present invention, there is provided use of a composition in the manufacture of a medicament for modulating carbonic anhydrase activity wherein the composition comprises i) a compound comprising a steroidal ring system and an optional group $R^1$ selected from any one of —OH, a sulphamate group, a phosphonate group, a thiophosphonate group, a sulphonate group or a sulphonamide group; and wherein the D ring of the steroidal ring system is substituted by a group $R^2$ of the formula -L-$R^3$, wherein L is an optional linker group and $R^3$ is selected from groups which are or which comprise one of a nitrile group, an alcohol, an ester, an ether, an amine and an alkene, provided that when $R^3$ is or comprises an alcohol, L is present; and ii) a biological response modifier.

According to a broad aspect of the present invention, there is provided a method of treatment comprising administering to a subject in need of treatment a compound in order to modulate carbonic anhydrase activity; wherein the compound comprises a steroidal ring system and an optional group $R^1$ selected from any one of —OH, a sulphamate group, a phosphonate group, a thiophosphonate group, a sulphonate group or a sulphonamide group; and wherein the D ring of the steroidal ring system is substituted by a group $R^2$ of the formula -L-$R^3$, wherein L is an optional linker group and $R^3$ is selected from groups which are or which comprise one of a nitrile group, an alcohol, an ester, an ether, an amine and an alkene, provided that when $R^3$ is or comprises an alcohol, L is present.

According to a broad aspect of the present invention, there is provided a method of treatment comprising administering to a subject in need of treatment a composition in order to modulate carbonic anhydrase activity; wherein the composition comprises i) a compound comprising a steroidal ring system and an optional group $R^1$ selected from any one of —OH, a sulphamate group, a phosphonate group, a thiophosphonate group, a sulphonate group or a sulphonamide group; and wherein the D ring of the steroidal ring system is substituted by a group $R^2$ of the formula -L-$R^3$, wherein L is an optional linker group and $R^3$ is selected from groups which are or which comprise one of a nitrile group, an alcohol, an ester, an ether, an amine and an alkene, provided that when $R^3$ is or comprises an alcohol, L is present; and ii) a biological response modifier.

In these broad aspects, preferably $R^1$, $R^2$, $R^3$ and L are as herein defined.

For ease of reference, these and further aspects of the present invention are now discussed under appropriate section headings. However, the teachings under each section are not necessarily limited to each particular section.

SOME ADVANTAGES

One key advantage of the present invention is that the compounds of the present invention can inhibit steroid sulphatase (STS) activity.

One key advantage of the present invention is that the compounds of the present invention can modulate cell cycling.

One key advantage of the present invention is that the compounds of the present invention can modulate apoptosis.

One key advantage of the present invention is that the compounds of the present invention can modulate cell growth.

One key advantage of the present invention is that the compounds of the present invention can prevent and/or suppress glucose uptake by a tumour.

One key advantage of the present invention is that the compounds of the present invention can prevent and/or inhibit tumour angiogenesis.

One key advantage of the present invention is that the compounds of the present invention can disrupt microtubules.

In this respect, microtubules, together with microfilaments and intermediate filaments form part of the cytoskeletal system of a cell. Microtubules are responsible for many of cell movements-examples include the beating of cilia and flagella and the transport of membrane vesicles in the cytoplasm. All these movements result from the polymerisation and depolymerisation of microtubules or the actions of the microtubule motor proteins dynein and kinesins. Some other cell movements, such as the alignment and separation of chromosomes during meiosis and mitosis result from both mechanisms. Microtubules also direct cell movement but in some cases, microtubules serve purely structural functions.

A microtubule is composed of subunits that are heterodimers of α-tubulin and β-tubulin monomers. There are two populations of microtubules: stable, long-lived microtubules and dynamic, short lived microtubules. Dynamic microtubules are found when the microtubule structures need to assemble and dissemble quickly. For example, during mitosis, the cytosolic microtubule network characteristic of interphase cells disappears and the tubulin from it is used to form the spindle apparatus which partitions chromosomes equally to the daughter cells. When mitosis is complete, the spindle disassembles and the interphase microtubule network reforms.

Drugs that inhibit mitosis provide a useful means to manipulate the microtubules in a cell. Three drugs: colchicine, vinblastine and taxol—all purified from plants—have proved to be very powerful probes of microtubule function partly because they bind only to tubulin or microtubules and not to other proteins and also because their concentrations in cells can be easily controlled.

Because of their effects on mitosis, microtubule inhibitors have been widely used to treat illness and more recently as anticancer agents, since blockage of spindle formation will preferentially inhibit rapidly dividing cells like cancer cells.

A highly effective anti-ovarian cancer agent is taxol. In ovarian cancer cells, which undergo rapid cell divisions, mitosis is blocked by taxol treatment while other functions carried out by intact microtubules are not affected. A comprehensive review of microtubules can be found in "Molecular Cell Biology" (Ed: Lodish et al 1995 WH Freeman and Co. New York pp 1051-1122).

One key advantage of the present invention is that the compounds of the present invention can induce apoptosis.

Apoptosis is induced by MT-targeting drugs, a process which may involve the phosphorylation (and inactivation) of the apoptosis regulator, the bcl-2 protein (Halder, Cancer Res. 57:229, 1997).

The present invention is based on the surprising finding that the compound provides an effective treatment of cancer.

Another advantage of the compounds of the present invention is that they may be potent in vivo.

Some of the compounds of the present invention may be non-oestrogenic compounds. Here, the term "non-oestrogenic" means exhibiting no or substantially no oestrogenic activity. Here, by the term "non-oestrogenic" means exhibiting no or substantially no systemic oestrogenic activity, such as that determined by Protocol 4.

For some applications, the compounds have an oestrogenic effect.

Another advantage is that some of the compounds may not be capable of being metabolised to compounds which display or induce hormonal activity.

For some applications, preferably the compounds have a reversible action.

For some applications, preferably the compounds have an irreversible action.

Some of the compounds of the present invention are also advantageous in that they may be orally active.

Some of the compounds of the present invention may useful for the prevention and/or treatment of cancer, such as breast cancer, as well as (or in the alternative) non-malignant conditions, such as the prevention and/or treatment of inflammatory conditions—such as conditions associated with any one or more of: autoimmunity, including for example, rheumatoid arthritis, type I and II diabetes, systemic lupus erythematosus, multiple sclerosis, myasthenia gravis, thyroiditis, vasculitis, ulcerative colitis and Crohn's disease, skin disorders e.g. acne, psoriasis and contact dermatitis; graft versus host disease; eczema; asthma and organ rejection following transplantation. The compounds of the present invention are useful particularly when pharmaceuticals may need to be administered from an early age.

In one embodiment, the compounds of the present invention are useful for the treatment of breast cancer.

Thus, some of the compounds of the present invention are also believed to have therapeutic uses other than for the treatment of endocrine-dependent cancers, such as the treatment of autoimmune diseases.

For ease of reference, these and further aspects of the present invention are now discussed under appropriate section headings. However, the teachings under each section are not necessarily limited to each particular section.

PREFERABLE ASPECTS

Compound

As described above the present invention provides a compound comprising a steroidal ring system and an optional group $R^1$ selected from any one of —OH, a sulphamate group, a phosphonate group, a thiophosphonate group, a sulphonate group or a sulphonamide group; wherein the D ring of the steroidal ring system is substituted by a group $R^2$ of the formula -L-$R^3$, wherein L is an optional linker group and $R^3$ is selected from groups which are or which comprise one of a nitrile group, an alcohol, an ester, an ether, an amine and an alkene, provided that when $R^3$ is or comprises an alcohol, L is present; and wherein the A ring of the steroidal ring system is substituted at position 2 or 4 with a group $R^4$, wherein $R^4$ is a hydrocarbyl group.

In one preferred aspect the compound is capable of one or more of inhibiting steroid sulphatase (STS) activity; modulating cell cycling; modulating apoptosis; modulating cell growth; preventing and/or suppressing glucose uptake by a tumour; preventing and/or inhibiting tumour angiogenesis; disrupting microtubules; and inducing apoptosis.

Steroidal Ring System

The compound of the present invention has a steroidal ring component—that is to say a cyclopentanophenanthrene skeleton, or bio-isosteres thereof.

As is well known in the art, a classical steroidal ring structure has the generic formula of:

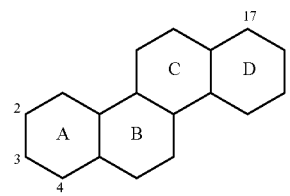

In the above formula, the rings have been labelled and numbered in the conventional manner.

In one aspect, the steroidal ring structure may contain any one or more of C, H, O, N, P, halogen (including Cl, Br and I), S and P.

At least one of the cyclic groups of the steroidal ring structure may be a heterocyclic group (a heterocycle) or a non-heterocyclic group.

At least one of the cyclic groups of the steroidal ring structure may be a saturated ring structure or an unsaturated ring structure (such as an aryl group).

Preferably, at least one of the cyclic groups of the steroidal ring structure is an aryl ring.

An example of a bio-isostere is when any one or more of rings A, B, C and D is a heterocyclic ring and/or when any one or more of rings A, B, C and D has been substituted and/or when any one or more of rings A, B, C and D has been modified; but wherein the bio-isostere has steroidal properties.

In this regard, the structure of a preferred steroidal ring structure can be presented as:

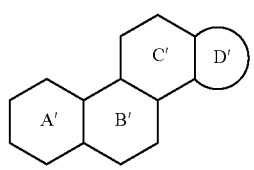

wherein each ring A', B', C' and D' independently represents a heterocyclic ring or a non-heterocyclic ring, which rings may be independently substituted or unsubstituted, saturated or unsaturated.

By way of example, any one or more of rings A', B', C' and D' may be independently substituted with suitable groups—such as an alkyl group, an allyl group, an hydroxy group, a halo group, a hydrocarbyl group, an oxyhydrocarbyl group etc.

The term "hydrocarbyl group" as used herein means a group comprising at least C and H and may optionally comprise one or more other suitable substituents. Examples of such substituents may include halo-, alkoxy-, nitro-, a hydrocarbon group, an N-acyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen.

In one preferred embodiment of the present invention, the hydrocarbyl group is a hydrocarbon group.

Here the term "hydrocarbon" means any one of an alkyl group, an alkenyl group, an alkynyl group, an acyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

In one preferred embodiment of the present invention, the hydrocarbyl group is an oxyhydrocarbyl group.

The term "oxyhydrocarbyl group" as used herein means a group comprising at least C, H and O and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the oxyhydrocarbyl group comprises more than one C then those carbons need not necessarily be linked to each other. For example, at least two of the carbons may be linked via a suitable element or group. Thus, the oxyhydrocarbyl group may contain hetero atoms. Suitable hetero atoms will be apparent to those skilled in the art and include, for instance, sulphur and nitrogen.

In one preferred embodiment of the present invention, the oxyhydrocarbyl group is a oxyhydrocarbon group.

Here the term "oxyhydrocarbon" means any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch.

Preferably the oxyhydrocarbyl group is an alkoxy group. Preferably the oxyhydrocarbyl group is of the formula $C_{1-6}O$ (such as a $C_{1-3}O$).

An example of D' is a five or six membered non-heterocyclic ring having at least one substituent.

In one preferred embodiment, the ring D' is substituted with a ethinyl group.

If any one of rings A', B', C' and D' is a heterocyclic ring, then preferably that heterocyclic ring comprises a combination of C atoms and at least one N atom and/or at least one O atom. Other heterocyclic atoms may be present in the ring.

Examples of suitable, preferred steroidal nuclei rings A'-D' of the compounds of the present invention include rings A-D of oestrone and dehydroepiandrosterone.

Preferred steroidal nuclei rings A'-D' of the compounds of the present invention include rings A-D of:

Oestrones and Substituted Oestrones, Viz:

oestrone

2-OH-oestrone 2-alkoxy-oestrone (such as $C_{1-6}$ alkoxy-oestrone, such as 2-methoxy-oestrone)

4-OH-oestrone

6α-OH-oestrone

7α-OH-oestrone

16α-OH-oestrone

16β-OH-oestrone

Oestradiols and Substituted Oestradiols, Viz:

2-OH-17β-oestradiol 2-alkoxy-17β-oestradiol (such as $C_{1-6}$ alkoxy-17β-oestradiol, such as 2-methoxy-17β-oestradiol)

4-OH-17β-oestradiol

6α-OH-17β-oestradiol

7α-OH-17β-oestradiol

2-OH-17α-oestradiol 2-alkoxy-17α-oestradiol (such as $C_{1-6}$ alkoxy-17α-oestradiol, such as 2-methoxy-17α-oestradiol)

4-OH-17α-oestradiol

6α-OH-17α-oestradiol

7α-OH-17α-oestradiol

16α-OH-17α-oestradiol

16α-OH-17β-oestradiol

16β-OH-17α-oestradiol

16β-OH-17β-oestradiol

17α-oestradiol

17β-oestradiol

17α-ethinyl-17β-oestradiol

17β-ethinyl-17α-oestradiol

Oestriols and Substituted Oestriols, Viz:

oestriol

2-OH-oestriol 2-alkoxy-oestriol (such as $C_{1-6}$ alkoxy-oestriol, such as 2-methoxy-oestriol)

4-OH-oestriol

6α-OH-oestriol

7α-OH-oestriol

Dehydroepiandrosterones and Substituted Dehydroepiandrosterones, Viz:

dehydroepiandrosterones

6α-OH-dehydroepiandrosterone

7α-OH-dehydroepiandrosterone

16α-OH-dehydroepiandrosterone

16β-OH-dehydroepiandrosterone

In general terms the ring system A'B'C'D' may contain a variety of non-interfering substituents. In particular, the ring system A'B'C'D' may contain one or more hydroxy, alkyl especially lower ($C_1$-$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$-$C_6$) alkoxy, e.g. methoxy, ethoxy, propoxy etc., alkinyl, e.g. ethinyl, or halogen, e.g. fluoro substituents.

In an alternative embodiment, the polycyclic compound may not contain or be based on a steroid nucleus. In this regard, the polycyclic compound may contain or be based on a non-steroidal ring system—such as diethylstilboestrol, stilboestrol, coumarins, and other ring systems. Other suitable non-steroidal compounds for use in or as the composition of the present invention may be found in U.S. Pat. No. 5,567,831.

$R^1$ and $R^2$

In one preferred aspect the compound is of Formula I

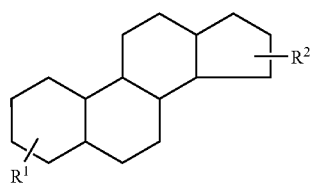

Formula I wherein $R^1$ is an optional group selected from any one of —OH, a sulphamate group, a phosphonate group, a thiophosphonate group, a sulphonate group or a sulphonamide group.

In one preferred aspect the compound is of Formula II

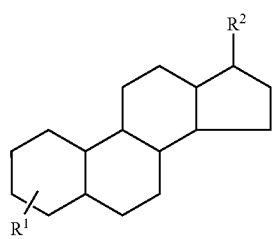

Formula II wherein $R^1$ is an optional group selected from any one of —OH, a sulphamate group, a phosphonate group, a thiophosphonate group, a sulphonate group or a sulphonamide group.

In one preferred aspect the compound is of Formula III

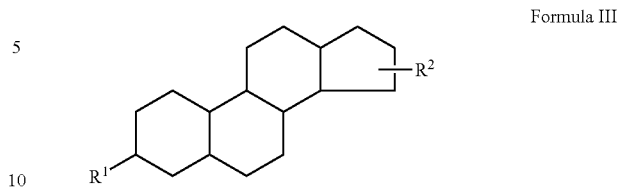

Formula III wherein $R^1$ is an optional group selected from any one of —OH, a sulphamate group, a phosphonate group, a thiophosphonate group, a sulphonate group or a sulphonamide group.

In one preferred aspect the compound is of Formula IV

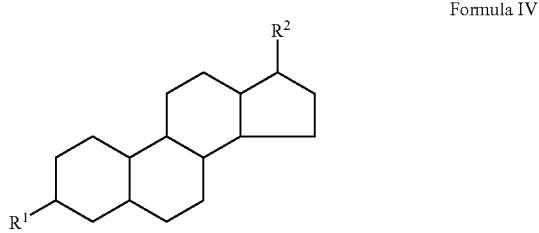

Formula IV wherein $R^1$ is an optional group selected from any one of —OH, a sulphamate group, a phosphonate group, a thiophosphonate group, a sulphonate group or a sulphonamide group.

It will be readily understood that the A ring of the steroidal ring system in Formulae I to IV is additionally substituted at position 2 or 4 with a group $R^4$.

$R^1$

It will be appreciated by one skilled in the art that $R^1$ is an optional group which may or may not be present. In one preferred aspect $R^1$ is present. In this aspect $R^1$ is a group selected from any one of —OH, a sulphamate group, a phosphonate group, a thiophosphonate group, a sulphonate group or a sulphonamide group.

Sulphamate Group

In one aspect $R^1$ is an optional sulphamate group.

The term "sulphamate" includes an ester of sulphamic acid, or an ester of an N-substituted derivative of sulphamic acid, or a salt thereof.

In one aspect $R^1$ is a sulphamate group. In this aspect the compound of the present invention may be referred to as a sulphamate compound.

Preferably the sulphamate group of $R^1$, is a sulphamate group of the formula

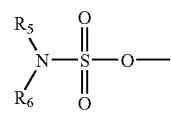

wherein $R^5$ and $R^6$ are independently selected from H or a hydrocarbyl group.

Preferably $R^5$ and $R^6$ are independently selected from H, alkyl, cycloalkyl, alkenyl, acyl and aryl, or combinations thereof, or together represent alkylene, wherein the or each alkyl or cycloalkyl or alkenyl or aryl optionally contains one or more hetero atoms or groups.

When substituted, the N-substituted compounds of this invention may contain one or two N-alkyl, N-alkenyl, N-cycloalkyl, N-acyl, or N-aryl substituents, preferably containing or each containing a maximum of 10 carbon atoms. When $R^5$ and/or $R^6$ is alkyl, the preferred values are those where $R^5$ and $R^6$ are each independently selected from lower alkyl groups containing from 1 to 5 carbon atoms, that is to say methyl, ethyl, propyl etc. Preferably $R^5$ and $R^6$ are both methyl. When $R^5$ and/or $R^6$ is aryl, typical values are phenyl and tolyl (—PhCH$_3$; o-, m- or p-). Where $R^5$ and $R^6$ represent cycloalkyl, typical values are cyclopropyl, cyclopentyl, cyclohexyl etc. When joined together $R^5$ and $R^6$ typically represent an alkylene group providing a chain of 4 to 6 carbon atoms, optionally interrupted by one or more hetero atoms or groups, e.g. —O— or —NH— to provide a 5-, 6- or 7-membered heterocycle, e.g. morpholino, pyrrolidino or piperidino.

Within the values alkyl, cycloalkyl, alkenyl, acyl and aryl we include substituted groups containing as substituents therein one or more groups which do not interfere with the sulphatase inhibitory activity of the compound in question. Exemplary non-interfering substituents include hydroxy, amino, halo, alkoxy, alkyl and aryl. A non-limiting example of a hydrocarbyl group is an acyl group.

In some embodiments, the sulphamate group may form a ring structure by being fused to (or associated with) one or more atoms in or on the steroidal ring system.

In some embodiments, there may be more than one sulphamate group. By way of example, there may be two sulphamates (i.e. bis-sulphamate compounds).

In some preferred embodiments, at least one of $R^5$ and $R^6$ is H.

In some preferred embodiments, each of $R^5$ and $R^6$ is H.

In some preferred embodiments $R^1$ is a sulphamate group and the compound is suitable for use as an inhibitor of oestrone sulphatase (E.C. 3.1.6.2).

In some preferred embodiments if the sulphamate group on the sulphamate compound were to be replaced with a sulphate group to form a sulphate compound then the sulphate compound would be hydrolysable by a steroid sulphatase enzyme (E.C. 3.1.6.2).

In some preferred embodiments if the sulphamate group on the sulphamate compound were to be replaced with a sulphate group to form a sulphate compound and incubated with a steroid sulphatase enzyme (E.C.3.1.6.2) at a pH 7.4 and 37° C. it would provide a $K_m$ value of less than 50 mM.

In some preferred embodiments if the sulphamate group on the sulphamate compound were to be replaced with a sulphate group to form a sulphate compound and incubated with a steroid sulphatase enzyme (E.C.3.1.6.2) at a pH 7.4 and 37° C. it would provide a $K_m$ value of less than 50 µM.

Phosphonate Group

If the compound of the present invention comprises a phosphonate group then the compound of the present invention is referred to as a phosphonate compound.

Typically, the phosphonate group has the formula:

$(R^{18})$—P(O)(OH)—O— wherein preferably $R^{18}$ is H, alkyl, cycloalkyl, alkenyl, acyl or aryl, or combinations thereof, wherein the or each alkyl or cycloalkyl or alkenyl or aryl optionally contains one or more hetero atoms or groups.

When $R^{18}$ is alkyl, $R^{18}$ may be a lower alkyl groups containing from 1 to 6 carbon atoms, that is to say methyl, ethyl, propyl etc. By way of example, $R^{18}$ may be methyl. When $R^{18}$ is aryl, typical values are phenyl and tolyl (PhCH$_3$;o-, m-, p-). Where $R^{18}$ represents cycloalkyl, typical values are cyclopropyl, cyclopentyl, cyclohexyl etc. $R^{18}$ may even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl, acyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the phosphonate group may form a ring structure by being fused to (or associated with) one or more atoms in or on the steroidal ring system.

In some embodiments, there may be more than one phosphonate group. By way of example, there may be two phosphonates (i.e. bis-phosphonate compounds). If these compounds are based on a steroidal nucleus, preferably the second (or at least one of the additional) phosphonate group is located at position 17 of the steroidal nucleus. These groups need not be the same.

Thiophosphonate Group

If the compound of the present invention comprises a thiophosphonate group then the compound of the present invention is referred to as a thiophosphonate compound.

Typically, the thiophosphonate group has the formula:

$(R^{19})$—P(S)(OH)—O— wherein preferably $R^{19}$ is H, alkyl, cycloalkyl, alkenyl, acyl or aryl, or combinations thereof, wherein the or each alkyl or cycloalkyl or alkenyl or aryl optionally contains one or more hetero atoms or groups.

When $R^{19}$ is alkyl, $R^{19}$ may be a lower alkyl groups containing from 1 to 6 carbon atoms, that is to say methyl, ethyl, propyl etc. By way of example, $R^{19}$ may be methyl. When $R^{19}$ is aryl, typical values are phenyl and tolyl (PhCH$_3$;o-, m-, p-). Where $R^{19}$ represents cycloalkyl, typical values are cyclopropyl, cyclopentyl, cyclohexyl etc. $R^{19}$ may even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl, acyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the thiophosphonate group may form a ring structure by being fused to (or associated with) one or more atoms in or on the steroidal ring system.

In some embodiments, there may be more than one thiophosphonate group. By way of example, there may be two thiophosphonates (i.e. bis-thiophosphonate compounds). If these compounds are based on a steroidal nucleus, preferably the second (or at least one of the additional) thiophosphonate group is located at position 17 of the steroidal nucleus. These groups need not be the same.

Sulphonate Group

If the compound of the present invention comprises a sulphonate group then the compound of the present invention is referred to as a sulphonate compound.

Typically, the sulphonate group has the formula:

$(R^{20})$—S(O)(O)—O— wherein preferably $R^{20}$ is H, alkyl, cycloalkyl, alkenyl, acyl or aryl, or combinations thereof, wherein the or each alkyl or cycloalkyl or alkenyl or aryl optionally contains one or more hetero atoms or groups.

When $R^{20}$ is alkyl, $R^{20}$ may be a lower alkyl groups containing from 1 to 6 carbon atoms, that is to say methyl, ethyl, propyl etc. By way of example, $R^{20}$ may be methyl. When $R^{20}$ is aryl, typical values are phenyl and tolyl ($PhCH_3$;o-, m-, p-). Where $R^{20}$ represents cycloalkyl, typical values are cyclopropyl, cyclopentyl, cyclohexyl etc. $R^{20}$ may even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl, acyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the sulphonate group may form a ring structure by being fused to (or associated with) one or more atoms in or on the steroidal ring system.

In some embodiments, there may be more than one sulphonate group. By way of example, there may be two sulphonates (i.e. bis-sulphonate compounds). If these compounds are based on a steroidal nucleus, preferably the second (or at least one of the additional) sulphonate group is located at position 17 of the steroidal nucleus. These groups need not be the same.

Other Substituents

The compound of the present invention may have substituents other than those of formula I. By way of example, these other substituents may be one or more of: one or more sulphamate group(s), one or more phosphonate group(s), one or more thiophosphonate group(s), one or more sulphonate group(s), one or more sulphonamide group(s), one or more halo groups, one or more O groups, one or more hydroxy groups, one or more amino groups, one or more sulphur containing group(s), one or more hydrocarbyl group(s)—such as an oxyhydrocarbyl group.

$R^2$

The D ring of the steroidal ring system of the present compound is substituted by a group $R^2$ of the formula -L-$R^3$, wherein L is an optional linker group and $R^3$ selected from groups which are or which comprise one of a nitrile group, an alcohol, an ester, an ether, an amine and an alkene.

In some preferred embodiments $R^2$ is of the formula —$R^3$, In other words no group L is present.

In some preferred aspects group $R^2$ is in an α conformation. Preferably group $R^2$ is in an α conformation on the 17 position of the D ring.

In some embodiments L is a hydrocarbyl group. In some embodiments L is a hydrocarbon group, such as an alkylene group.

L may typically be a $C_{1-10}$ alkylene, a $C_{1-5}$ alkylene, a $C_1$ or $C_2$ alkylene.

$R^3$

As discussed above $R^3$ is selected from groups which are or which comprise one of a nitrile group, an alcohol, an ester, an ether, an amine and an alkene in some preferred aspects $R^3$ is selected the groups nitrile, alcohol, ester, ether, amine and alkene. Preferably $R^3$ is or comprises a nitrile group. Preferably $R^3$ is a nitrile group.

$R^3$ may be a cyclic group or an acyclic group.

When $R^3$ is a cyclic group is may form a ring which is fused with the D ring of the steroid or which is not fused with the D ring of the steroid. When $R^3$ forms a cyclic group which is fused with the D ring of the steroid, preferably $R^3$ forms a ring joining adjacent members of the D ring, more preferably $R^3$ forms a ring joining positions 16 and 17 of the D ring.

In some preferred aspects $R^3$ is selected from groups of the formula $=CH_2$, $=CH-CH_3$, $=C(CN)_2$, $=C(CH_3)(CN)$, and —$(R^7)_n(CR^{14}R^{15})_pR^8$, wherein n is 0 or 1, p is an integer, $R^7$ is selected from $=CH$—, —O— and $NR^{13}$; $R^8$ is selected from —$SO_2$—$R^9$, —C(O)O$R^{17}$, —O$R^{10}$, $(CH_2)_q$—X—$R^{16}$, —C≡N, —$NR^{11}R^{12}$—C≡CH and —CH=$CH_2$; $R^9$ is selected from H and hydrocarbyl, $R^{10}$ is selected from H and hydrocarbyl; $R^{11}$ and $R^{12}$ are each independently selected from H and hydrocarbyl; $R^{13}$ is selected from H and hydrocarbyl, $R^{14}$ and $R^{15}$ are each independently selected from H and hydrocarbyl, q is an integer, X is O or S, $R^{16}$ is selected from H and hydrocarbyl and $R^{17}$ is selected from H and hydrocarbyl.

In some preferred aspects $R^3$ is a group of the formula —$(R^7)_n(CR^{14}R^{15})_pR^8$, wherein n is 0 or 1, p is an integer, $R^7$ is selected from $=CH$—, —O— and $NR^{13}$; $R^8$ is selected from —$SO_2$—$R^9$, —C(O)O$R^{17}$, —O$R^{10}$, $(CH_2)_q$—X—$R^{16}$, —C≡N, —$NR^{11}R^{12}$—C≡CH and CH=$CH_2$; $R^9$ is selected from H and hydrocarbyl, $R^{10}$ is selected from H and hydrocarbyl; $R^{11}$ and $R^{12}$ are each independently selected from H and hydrocarbyl; $R^{13}$ is selected from H and hydrocarbyl, $R^{14}$ and $R^{15}$ are each independently selected from H and hydrocarbyl, q is an integer, X is O or S, $R^{16}$ is selected from H and hydrocarbyl and $R^{17}$ is selected from H and hydrocarbyl.

In some preferred aspects $R^3$ is a group of the formula —$(CR^{14}R^{15})_pR^8$, p is an integer; $R^8$ is selected from —$SO_2$—$R^9$, —C(O)O$R^{17}$, —O$R^{10}$, $(CH_2)_q$—X—$R^{16}$, —C≡N, —$NR^{11}R^{12}$—C≡CH and —CH=$CH_2$; $R^9$ is selected from H and hydrocarbyl, $R^{10}$ is selected from H and hydrocarbyl; $R^{11}$ and $R^{12}$ are each independently selected from H and hydrocarbyl, $R^{14}$ and $R^{15}$ are each independently selected from H and hydrocarbyl, q is an integer, X is O or S, $R^{16}$ is selected from H and hydrocarbyl and $R^{17}$ is selected from H and hydrocarbyl.

In some preferred aspects $R^3$ is a group of the formula —$(CH_2)_pR^8$, p is an integer; $R^8$ is selected from —$SO_2$—$R^9$, —C(O)O$R^{17}$, —O$R^{10}$, $(CH_2)_q$—X—$R^{16}$, —C≡N, —$NR^{11}R^{12}$—C≡CH and —CH=$CH_2$; $R^9$ is selected from H and hydrocarbyl, $R^{10}$ is selected from H and hydrocarbyl; $R^{11}$ and $R^{12}$ are each independently selected from H and hydrocarbyl, q is an integer, X is O or S, $R^{16}$ is selected from H and hydrocarbyl and $R^{17}$ is selected from H and hydrocarbyl.

In some preferred aspects $R^3$ is a group of the formula —$(R^7)_nR^8$, wherein n is 0 or 1, $R^7$ is selected from $=CH$—, —O— and $NR^{13}$; $R^8$ is selected from —$SO_2$—$R^9$, —C(O)O$R^{17}$, —O$R^{10}$, $(CH_2)_q$—X—$R^{16}$, —C≡N, —$NR^{11}R^{12}$—C≡CH and —CH=$CH_2$; $R^9$ is selected from H and hydrocarbyl, $R^{10}$ is selected from H and hydrocarbyl; $R^{11}$ and $R^{12}$ are each independently selected from H and hydrocarbyl; $R^{13}$ is selected from H and hydrocarbyl, q is an integer, X is O or S, $R^{16}$ is selected from H and hydrocarbyl and $R^{17}$ is selected from H and hydrocarbyl.

p may be any integer. p may be from 0 to 20. p may be from 0 to 10. Typically p is from 0 to 5. In one aspect p is 0, 1 or 2.

q may be any integer. q may be from 0 to 20. q may be from 0 to 10. Typically q is from 0 to 5. In one aspect q is 0, 1 or 2.

$R^8$ is selected from —$SO_2$—$R^9$, —C(O)O$R^{17}$, —O$R^{10}$, $(CH_2)_q$—X—$R^{16}$, —N$R^{11}R^{12}$, —C≡N, —NR$^{11}$R$^{12}$—C≡CH and —CH═CH$_2$. In one preferred aspect $R^8$ is —$SO_2$—$R^9$. In one preferred aspect $R^8$ is —$SO_2$—$R^9$ wherein $R^9$ is hydrocarbyl. Preferably in this aspect, $R^7$ is —O—, n is 1 and p is 0 such that $R^3$ is —O—$SO_2R^9$.

$R^9$ is selected from H and hydrocarbyl. In one aspect $R^9$ is hydrocarbyl. In one preferred embodiment of the present invention $R^9$ is selected from one of H, $C_1$-$C_{20}$ hydrocarbyl, $C_1$-$C_{10}$ hydrocarbyl, $C_1$-$C_5$ hydrocarbyl, $C_1$-$C_3$ hydrocarbyl, hydrocarbon groups, $C_1$-$C_{20}$ hydrocarbon, $C_1$-$C_{10}$ hydrocarbon, $C_1$-$C_5$ hydrocarbon, $C_1$-$C_3$ hydrocarbon, alkyl groups, $C_1$-$C_{20}$ alkyl, $C_1$-$C_{10}$ alkyl, $C_1$-$C_5$ alkyl, and $C_1$-$C_3$ alkyl.

In one aspect $R^9$ is selected from H and $C_{1-10}$ alkyl. In one aspect $R^9$ is $C_{1-10}$ alkyl. In one aspect $R^9$ is selected from H and $C_{1-5}$ alkyl. In one aspect $R^9$ is $C_{1-5}$ alkyl. In one aspect $R^9$ is selected from H and $C_{1-3}$ alkyl. In one aspect $R^9$ is $C_{1-3}$ alkyl. Preferably $R^9$ is —$CH_2CH_3$.

In one aspect $R^9$ is a substituted or unsubstituted amine. When substituted, the N-substituted compounds of this invention may contain one or two N-alkyl, N-alkenyl, N-cycloalkyl, N-acyl, or N-aryl substituents, preferably containing or each containing a maximum of 10 carbon atoms. In a preferred aspect, $R^9$ is an unsubstituted amine, i.e. $R^9$ is $NH_2$.

$R^{10}$ is selected from H and hydrocarbyl. In one preferred embodiment of the present invention $R^{10}$ is selected from one of H, $C_1$-$C_{20}$ hydrocarbyl, $C_1$-$C_{10}$ hydrocarbyl, $C_1$-$C_5$ hydrocarbyl, $C_1$-$C_3$ hydrocarbyl, hydrocarbon groups, $C_1$-$C_{20}$ hydrocarbon, $C_1$-$C_{10}$ hydrocarbon, $C_1$-$C_5$ hydrocarbon, $C_1$-$C_3$ hydrocarbon, alkyl groups, $C_1$-$C_{20}$ alkyl, $C_1$-$C_{10}$ alkyl, $C_1$-$C_5$ alkyl, and $C_1$-$C_3$ alkyl.

In one aspect $R^{10}$ is selected from H and $C_{1-10}$ alkyl. In one aspect $R^{10}$ is selected from H and $C_{1-5}$ alkyl. In one aspect $R^{10}$ is selected from H and $C_{1-3}$ alkyl. In one aspect $R^{10}$ is $C_{1-3}$ alkyl. Preferably $R^{10}$ is —H or —$CH_3$.

As previously mentioned, $R^{11}$ and $R^{12}$ of N$R^{11}R^{12}$ are each independently selected from H and hydrocarbyl. When substituted, the N-substituted compounds of this invention may contain one or two N-alkyl, N-alkenyl, N-cycloalkyl, N-acyl, or N-aryl substituents, preferably containing or each containing a maximum of 10 carbon atoms. When $R^{11}$ and/or $R^{12}$ is alkyl, the preferred values are those where $R^{11}$ and $R^{12}$ are each independently selected from lower alkyl groups containing from 1 to 5 carbon atoms, that is to say methyl, ethyl, propyl etc. Preferably $R^{11}$ and $R^{12}$ are both methyl. When $R^{11}$ and/or $R^{12}$ is aryl, typical values are phenyl and tolyl (—Ph$CH_3$; o-, m- or p-). Where $R^{11}$ and $R^{12}$ represent cycloalkyl, typical values are cyclopropyl, cyclopentyl, cyclohexyl etc. When joined together $R^{11}$ and $R^{12}$ typically represent an alkylene group providing a chain of 4 to 6 carbon atoms, optionally interrupted by one or more hetero atoms or groups, e.g. —O— or —NH— to provide a 5-, 6- or 7-membered heterocycle, e.g. morpholino, pyrrolidino or piperidino.

In one aspect $R^{11}$ and $R^{12}$ are each independently hydrocarbyl. In one preferred embodiment of the present invention $R^{11}$ and $R^{12}$ are each independently selected from one of H, $C_1$-$C_{20}$ hydrocarbyl, $C_1$-$C_{10}$ hydrocarbyl, $C_1$-$C_5$ hydrocarbyl, $C_{1-3}$ hydrocarbyl, hydrocarbon groups, $C_1$-$C_{20}$ hydrocarbon, $C_1$-$C_{10}$ hydrocarbon, $C_1$-$C_5$ hydrocarbon, $C_1$-$C_3$ hydrocarbon, alkyl groups, $C_1$-$C_{20}$ alkyl, $C_1$-$C_{10}$ alkyl, $C_1$-$C_5$ alkyl, and $C_1$-$C_3$ alkyl In one aspect $R^{11}$ and $R^{12}$ are each independently selected from H and $C_{1-10}$ alkyl. In one aspect $R^{11}$ and $R^{12}$ are each independently $C_{1-10}$ alkyl. In one aspect $R^{11}$ and $R^{12}$ are each independently selected from H and $C_{1-5}$ alkyl. In one aspect $R^{11}$ and $R^{12}$ are each independently $C_{1-5}$ alkyl. In one aspect $R^{11}$ and $R^{12}$ are each independently selected from H and $C_{1-3}$ alkyl. In one aspect $R^{11}$ and $R^{12}$ are each independently $C_{1-3}$ alkyl. Preferably $R^{11}$ and $R^{12}$ are independently selected from —H and —$CH_3$.

$R^{13}$ is selected from H and hydrocarbyl. In one preferred embodiment of the present invention $R^{13}$ is selected from one of H, $C_1$-$C_{20}$ hydrocarbyl, $C_1$-$C_{10}$ hydrocarbyl, $C_1$-$C_5$ hydrocarbyl, $C_1$-$C_3$ hydrocarbyl, hydrocarbon groups, $C_1$-$C_{20}$ hydrocarbon, $C_1$-$C_{10}$ hydrocarbon, $C_1$-$C_5$ hydrocarbon, $C_1$-$C_3$ hydrocarbon, alkyl groups, $C_1$-$C_{20}$ alkyl, $C_1$-$C_{10}$ alkyl, $C_1$-$C_5$ alkyl, and $C_1$-$C_3$ alkyl.

In one aspect $R^{13}$ is selected from H and $C_{1-10}$ alkyl. In one aspect $R^{13}$ is selected from H and $C_{1-5}$ alkyl. In one aspect $R^{13}$ is selected from H and $C_{1-3}$ alkyl. In one aspect $R^{13}$ is $C_{1-3}$ alkyl. Preferably $R^{13}$ is —H.

$R^{14}$ and $R^{15}$ are each independently selected from H and hydrocarbyl. In one aspect $R^{14}$ and $R^{15}$ are each independently hydrocarbyl. In one preferred embodiment of the present invention $R^{14}$ and $R^{15}$ are each independently selected from one of H, $C_1$-$C_{20}$ hydrocarbyl, $C_1$-$C_{10}$ hydrocarbyl, $C_1$-$C_5$ hydrocarbyl, $C_1$-$C_3$ hydrocarbyl, hydrocarbon groups, $C_1$-$C_{20}$ hydrocarbon, $C_1$-$C_{10}$ hydrocarbon, $C_1$-$C_5$ hydrocarbon, $C_1$-$C_3$ hydrocarbon, alkyl groups, $C_1$-$C_{20}$ alkyl, $C_1$-$C_{10}$ alkyl, $C_1$-$C_5$ alkyl, and $C_1$-$C_3$ alkyl.

In one aspect $R^{14}$ and $R^{15}$ are each independently selected from H and $C_{1-10}$ alkyl. In one aspect $R^{14}$ and $R^{15}$ are each independently $C_{1-10}$ alkyl. In one aspect $R^{14}$ and $R^{15}$ are each independently selected from H and $C_{1-5}$ alkyl. In one aspect $R^{14}$ and $R^{15}$ are each independently $C_{1-5}$ alkyl. In one aspect $R^{14}$ and $R^{15}$ are each independently selected from H and $C_{1-3}$ alkyl. In one aspect $R^{14}$ and $R^{15}$ are each independently $C_{1-3}$ alkyl. Preferably $R^{14}$ and $R^{15}$ are independently selected from —H and —$CH_3$.

X is selected from O or S. In one aspect X is S. In one aspect X is O.

$R^{16}$ is selected from H and hydrocarbyl. In one preferred embodiment of the present invention $R^{16}$ is selected from one of H, $C_1$-$C_{20}$ hydrocarbyl, $C_1$-$C_{10}$ hydrocarbyl, $C_1$-$C_5$ hydrocarbyl, $C_1$-$C_3$ hydrocarbyl, hydrocarbon groups, $C_1$-$C_{20}$ hydrocarbon, $C_1$-$C_{10}$ hydrocarbon, $C_1$-$C_5$ hydrocarbon, $C_1$-$C_3$ hydrocarbon, alkyl groups, $C_1$-$C_{20}$ alkyl, $C_1$-$C_{10}$ alkyl, $C_1$-$C_5$ alkyl, and $C_1$-$C_3$ alkyl.

In one aspect $R^{16}$ is selected from H and $C_{1-10}$ alkyl. In one aspect $R^{16}$ is selected from H and $C_{1-5}$ alkyl. In one aspect $R^{16}$ is selected from H and $C_{1-3}$ alkyl. In one aspect $R^{16}$ is $C_{1-3}$ alkyl. Preferably $R^{16}$ is —H.

In one-highly preferred aspect $R^3$ is a group selected from ═CHC(O)OEt, —$CH_2$C(O)OEt, ═CHCH$_2$OH, —$CH_2CH_2$OH, —$CH_2$C≡N, ═CHC≡N, —NH$CH_2CH_2$N(Me)$_2$, —O$CH_2CH_2$—OMe.

Particularly preferred $R^3$ groups are selected from the D ring substitutions given below

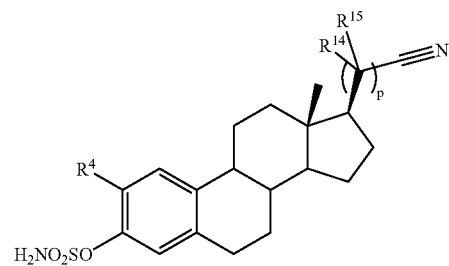

-continued

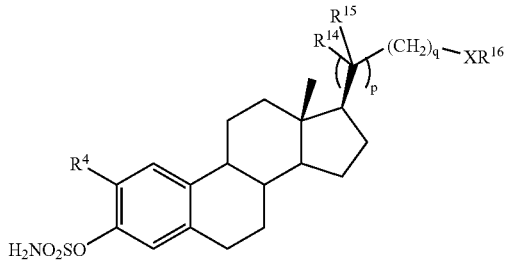

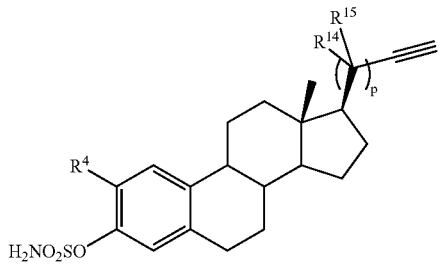

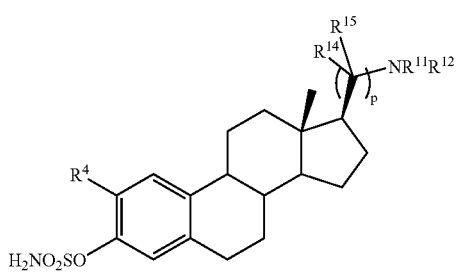

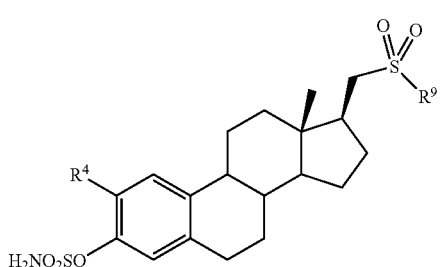

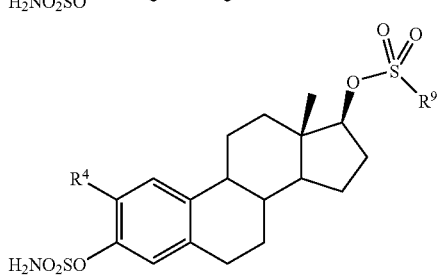

In one aspect $R^3$ may be selected from the D substitutions shown below wherein each Q is independently selected from O, S, NH and $CH_2$ and y is an integer from 3 to 8, preferably 5, 6, 7 or 8.

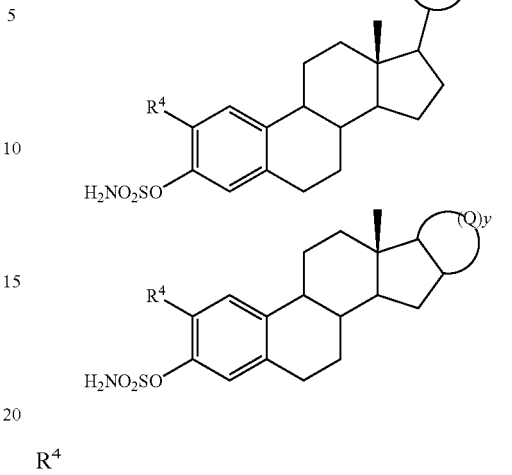

$R^4$

As previously mentioned, the A ring of the steroidal ring system is substituted with a group $R^4$, wherein $R^4$ is a hydrocarbyl group.

In one preferred aspect $R^4$ is an oxyhydrocarbyl group.

As discussed above the term "oxyhydrocarbyl group" as used herein with respect to $R^4$ means a group comprising at least C, H and O and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the oxyhydrocarbyl group comprises more than one C then those carbons need not necessarily be linked to each other. For example, at least two of the carbons may be linked via a suitable element or group. Thus, the oxyhydrocarbyl group may contain hetero atoms. Suitable hetero atoms will be apparent to those skilled in the art and include, for instance, sulphur and nitrogen.

In one preferred embodiment of the present invention, the $R^4$ is a oxyhydrocarbon group.

Here the term "oxyhydrocarbon" means, or $R^4$ is, any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch.

Preferably the oxyhydrocarbyl group $R^4$ is an alkoxy group. Preferably the oxyhydrocarbyl group $R^4$ is of the formula $C_{1-6}O$ (such as a $C_{1-3}O$). Preferably the oxyhydrocarbyl group $R^4$ is of the formula $-O(CH_2)_{1-10}CH_3$, $-O(CH_2)_{1-5}CH_3$, $-O(CH_2)_{1-2}CH_3$. In a highly preferred aspect $R^4$ is methoxy.

Preferably the oxyhydrocarbyl group $R^4$ is an ether group. Preferably the oxyhydrocarbyl group $R^4$ is of the formula $C_{1-6}OC_{1-6}$ (such as a $C_{1-3}OC_{1-3}$). Preferably the oxyhydrocarbyl group $R^4$ is of the formula $-(CH_2)_{1-10}O(CH_2)_{1-10}CH_3$, $-(CH_2)_{1-5}O(CH_2)_{1-5}CH_3$, $-(CH_2)_{1-2}O(CH_2)_{1-2}CH_3$. In a highly preferred aspect $R^4$ is $-CH_2OCH_3$.

In one preferred embodiment of the present invention, $R^4$ is a hydrocarbon group. Preferably $R^4$ is an alkyl group. Preferably the alkyl group is a $C_{1-6}$ alkyl group (such as a $C_{1-3}$ alkyl group). Preferably the hydrocarbyl group $R^4$ is of the formula —$(CH_2)_{1-10}CH_3$, —$(CH_2)_{1-5}CH_3$, —$(CH_2)_{1-2}CH_3$. In a highly preferred aspect $R^4$ is ethyl.

In one preferred embodiment of the present invention $R^4$ is selected from one of $C_1$-$C_{10}$ hydrocarbyl, $C_1$-$C_5$ hydrocarbyl, $C_1$-$C_3$ hydrocarbyl, hydrocarbon groups, $C_1$-$C_{10}$ hydrocarbon, $C_1$-$C_5$ hydrocarbon, $C_1$-$C_3$ hydrocarbon, alkyl groups, $C_1$-$C_{10}$ alkyl, $C_1$-$C_5$ alkyl, and $C_1$-$C_3$ alkyl.

In one preferred embodiment of the present invention, the $R^4$ is a hydrocarbylsulphanyl group.

The term "hydrocarbylsulphanyl" means a group that comprises at least hydrocarbyl group (as herein defined) and sulphur. That sulphur group may be optionally oxidised. Preferably the hydrocarbylsulphanyl is of the formula —S-hydrocarbyl wherein the hydrocarbyl is as described herein.

The term "hydrocarbylsulphanyl group" as used herein with respect to $R^4$ means a group comprising at least C, H and S and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the hydrocarbylsulphanyl group comprises more than one C then those carbons need not necessarily be linked to each other. For example, at least two of the carbons may be linked via a suitable element or group. Thus, the hydrocarbylsulphanyl group may contain further hetero atoms. Suitable hetero atoms will be apparent to those skilled in the art and include, for instance, nitrogen.

In one preferred embodiment of the present invention, the $R^4$ is a hydrocarbonsulphanyl group. The term "hydrocarbonsulphanyl group" as used herein with respect to $R^4$ means a group consisting of C, H and S. Preferably the hydrocarbonsulphanyl is of the formula —S-hydrocarbon wherein the hydrocarbon is as described herein.

Preferably the hydrocarbonsulphanyl group $R^4$ is of the formula $C_{1-6}S$ (such as a $C_{1-3}S$). Preferably the oxyhydrocarbyl group $R^4$ is of the formula —$S(CH_2)_{1-10}CH_3$, —$S(CH_2)_{1-5}CH_3$, —$S(CH_2)_{1-2}CH_3$. In a highly preferred aspect $R^4$ is —S-Me.

As previously mentioned, $R^4$ is at position 2 or 4 of the A ring. Thus the compound may have the formula

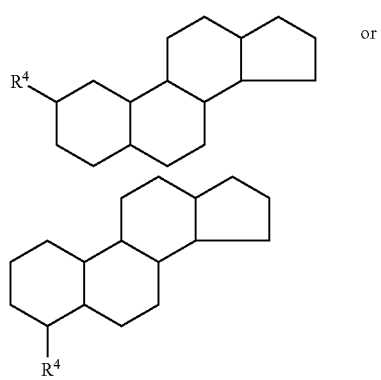

or

Preferably $R^4$ is at position 2 of the A ring.

In a further preferred aspect when the A ring is substituted with $R^1$ and $R^4$, $R^4$ is ortho with respect to $R^1$.

In a preferred embodiment, the compound of the present invention has the formula:

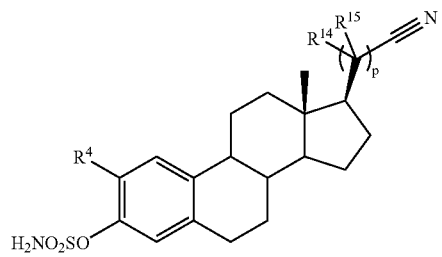

wherein $R^4$ is a hydrocarbyl group and $R^{14}$ and $R^{15}$ are each independently selected from H and hydrocarbyl and p is an integer.

In a preferred embodiment, the compound of the present invention has the formula:

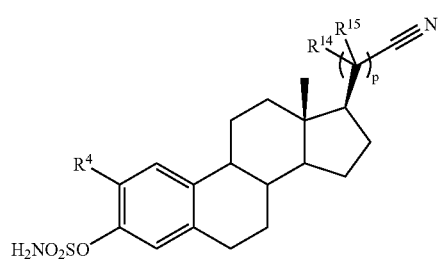

wherein $R^4$ is an oxyhydrocarbon group or a hydrocarbon group and $R^{14}$ and $R^{15}$ are each independently selected from H and $C_{1-10}$ alkyl and p is an integer from 0 to 5.

In this aspect preferably $R^4$ is an alkoxy group, such as a $C_{1-6}O$ group or an alkyl group, such as a $C_{1-6}$ alkyl group. Preferably $R^4$ is methoxy or ethyl.

In this aspect preferably $R^{14}$ and $R^{15}$ are each independently selected from H and $CH_3$, more preferably $R^{14}$ and $R^{15}$ are both H.

In this aspect, preferably p is 0, 1, or 2. More preferably p is 1.

In a highly preferred embodiment, the compound of the present invention has the formula:

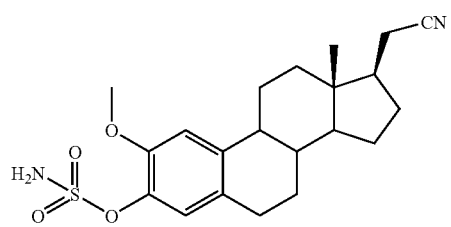

In a preferred embodiment, the compound of the present invention has the formula:

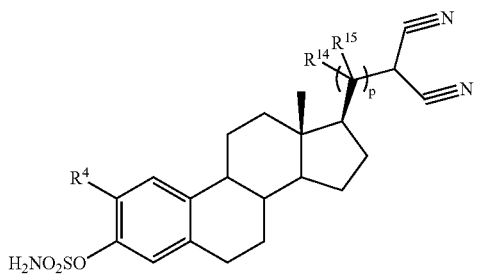

wherein $R^4$ is a hydrocarbyl group and $R^{14}$ and $R^{15}$ are each independently selected from H and hydrocarbyl and p is an integer.

In a preferred embodiment, the compound of the present invention has the formula:

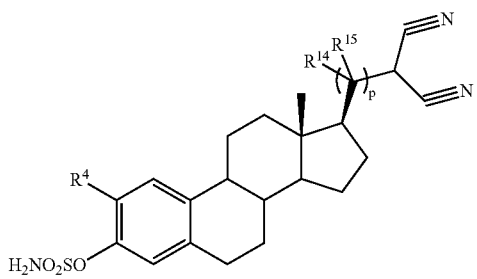

wherein $R^4$ is an oxyhydrocarbon group or a hydrocarbon group and $R^{14}$ and $R^{15}$ are each independently selected from H and $C_{1-10}$ alkyl and p is an integer from 0 to 5.

In this aspect preferably $R^4$ is an alkoxy group, such as a $C_{1-8}O$ group or an alkyl group, such as a $C_{1-5}$ alkyl group. Preferably $R^4$ is methoxy or ethyl.

In this aspect preferably $R^{14}$ and $R^{15}$ are each independently selected from H and $CH_3$, more preferably $R^{14}$ and $R^{15}$ are both H.

In this aspect, preferably p is 0, 1, or 2. More preferably p is 1.

In a highly preferred embodiment, the compound of the present invention has the formula:

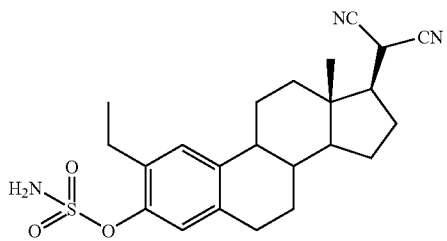

Highly preferred compounds of the present invention are shown below and may be selected from:

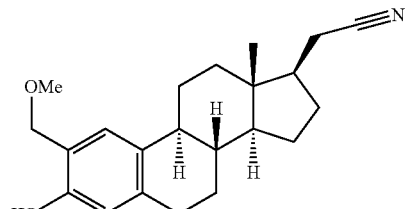

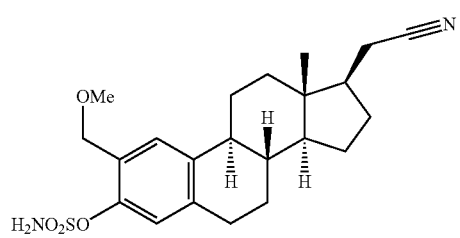

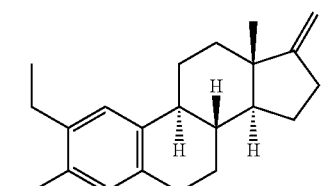

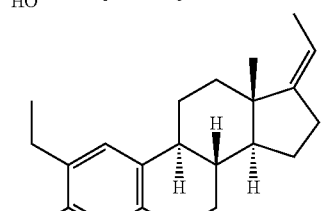

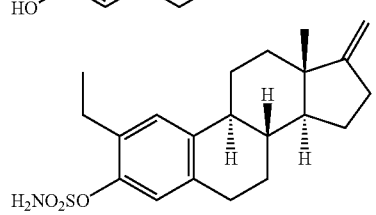

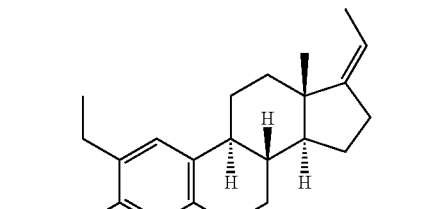

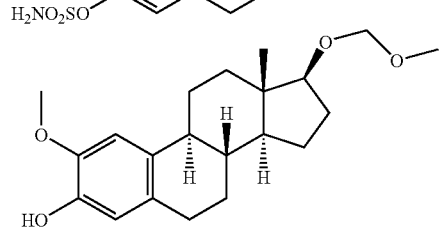

-continued
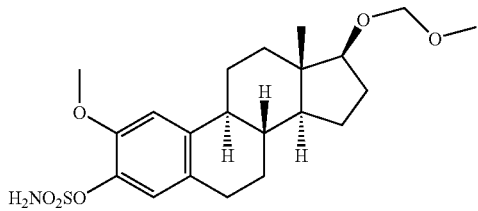
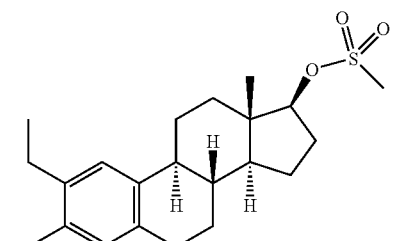
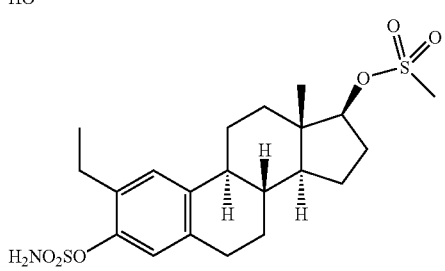
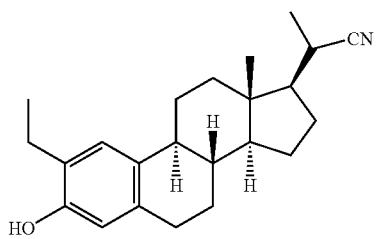
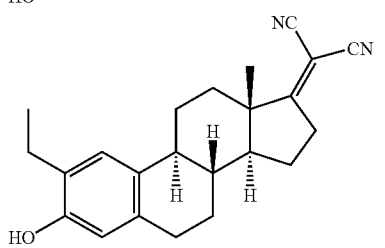
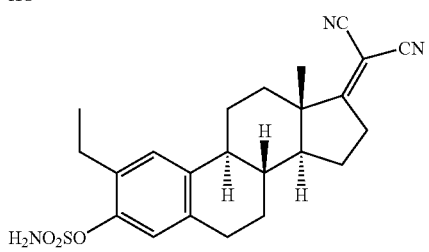
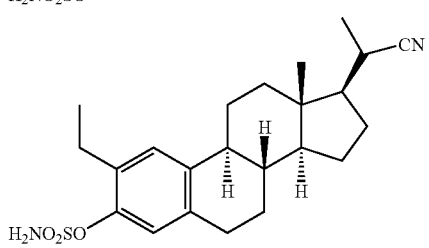
-continued
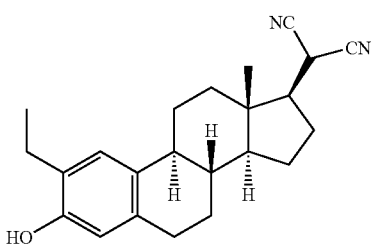
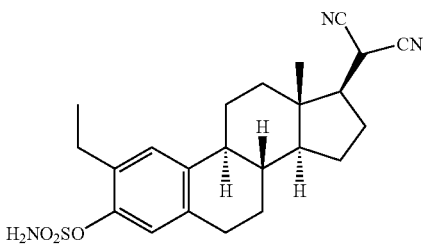
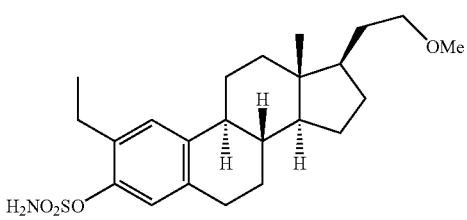
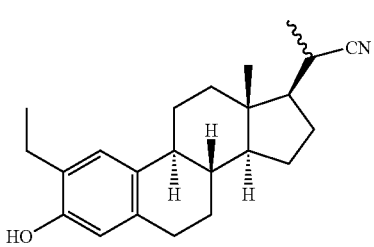
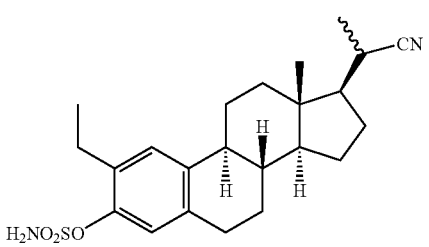
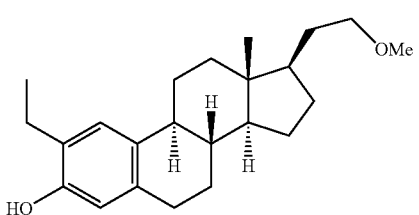
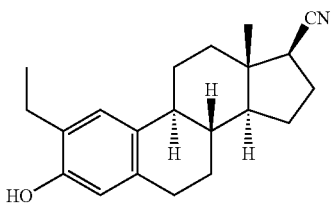

-continued

Composition

As described above according to one aspect of the present invention, there is provided a pharmaceutical composition comprising (a) (i) a compound as defined herein, or (ii) a composition as defined herein, and (b) a pharmaceutically acceptable carrier, diluent, excipient or adjuvant.

In accordance with the present invention the composition of the present invention may comprise more than one biological response modifier.

The term biological response modifier ("BRM") includes cytokines, immune modulators, growth factors, haematopoiesis regulating factors, colony stimulating factors, chemotactic, haemolytic and thrombolytic factors, cell surface receptors, ligands, leukocyte adhesion molecules, monoclonal antibodies, preventative and therapeutic vaccines, hormones, extracellular matrix components, fibronectin, etc.

BRMs may play a role in modulating the immune and inflammatory response in disorders. Examples of BRMs include: Tumour Necrosis Factor (TNF), granulocyte colony stimulating factor, erythropoietin, insulin-like growth factor (IGF), epidermal growth factor (EGF), transforming growth factor (TGF), platelet-derived growth factor (PDGF), interferons (IFNs), interleukins, tissue plasminogen activators, P-, E- or L-Selectins, ICAM-1, VCAM, Selectins, addressins etc.

Preferably, the biological response modifier is a cytokine.

A cytokine is a molecule—often a soluble protein—that allows immune cells to communicate with each other. These molecules exert their biological functions through specific receptors expressed on the surface of target cells. Binding of the receptors triggers the release of a cascade of biochemical signals which profoundly affect the behaviour of the cell bearing the receptor (Poole, S 1995 TibTech 13: 81-82). Many cytokines and their receptors have been identified at the molecular level (Paul and Sedar 1994, Cell 76: 241-251) and make suitable molecules of therapeutic value as well as therapeutic targets in their own right.

More details on cytokines can be found in Molecular Biology and Biotechnology (Pub. VCH, Ed. Meyers, 1995, pages 202, 203, 394, 390, 475, 790).

Examples of cytokines include: interleukins (IL)—such as IL-1, IL-2, IL-3, IL-4, IL-5, IL-6, IL-7, IL-8, IL-9, IL-10, IL-11, IL-12, IL-19; Tumour Necrosis Factor (TNF)— such as TNF-α; Interferon alpha, beta and gamma; TGF-β.

For the present invention, preferably the cytokine is tumour necrosis factor (TNF).

More preferably the cytokine is TNF-α.

TNF is a cytokine produced by macrophages and lymphocytes which mediates inflammatory and immunopathological responses. TNF has been implicated in the progression of diseases which include but are not limited to immunomodulation disorder, infection, cell proliferation, angiogenesis (neovascularisation), tumour metastasis, apoptosis, sepsis, and endotoxaemia.

The necrotising action of TNF in vivo mainly relates to capillary injury. TNF causes necrosis not only in tumour tissue but also in granulation tissue. It causes morphological changes in growth inhibition of and cytoxicity against cultured vascular endothelial cells (Haranka et al 1987 Ciba Found Symp 131: 140-153).

For the preferred aspect of the present invention, the TNF may be any type of TNF—such as TNF-α, TNF-β, including derivatives or mixtures thereof.

Teachings on TNF may be found in the art—such as WO-A-98108870 and WO-A-98/13348.

The TNF can be prepared chemically or it can be extracted from sources. Preferably, the TNF is prepared by use of recombinant DNA techniques.

With this aspect of the present invention the compositions of the present invention are more potent in vivo than the compounds alone or TNF alone. Moreover, in some aspects the combination of compounds and TNF is more potent than one would expect from the potency of the compound alone i.e. this is a synergistic relationship between them.

In addition, the present invention contemplates the composition of the present invention further comprising an inducer of the biological response modifier—such as in vivo inducer of the biological response modifier.

In accordance with the present invention, the components of the composition can be added in admixture, simultaneously or sequentially. Furthermore, in accordance with the present invention it may be possible to form at least a part of the composition in situ (such as in vivo) by inducing the expression of—or increasing the expression of—one of the components. For example, it may be possible to induce the expression of—or increase the expression of—the biological response modifier, such as TNF. By way of example, it may be possible to induce the expression of—or increase the expression of—TNF by adding bacterial lipopolysaccharide (LPS) and muramyl dipeptide (MDP). In this regard, bacterial LPS and MDP in combination can stimulate TNF production from murine spleen cells in vitro and tumour regression in vivo (Fuks et al Biull Eksp Biol Med 1987 104: 497-499).

In the method of treatment, the subject is preferably a mammal, more preferably a human. For some applications, preferably the human is a woman.

The present invention also covers novel intermediates that are useful to prepare the compounds of the present invention. For example, the present invention covers novel alcohol precursors for the compounds. By way of further example, the present invention covers bis protected precursors for the compounds. Examples of each of these precursors are presented herein. The present invention also encompasses a process comprising each or both of those precursors for the synthesis of the compounds of the present invention.

Steroid Sulphatase

Steroid sulphatase—which is sometimes referred to as steroid sulphatase or steryl sulphatase or "STS" for short—hydrolyses several sulphated steroids, such as oestrone sulphate, dehydroepiandrosterone sulphate and cholesterol sulphate. STS has been allocated the enzyme number EC 3.1.6.2.

STS has been cloned and expressed. For example see Stein et al (J. Biol. Chem. 264:13865-13872 (1989)) and Yen et al (Cell 49:443-454(1987)).

STS is an enzyme that has been implicated in a number of disease conditions.

By way of example, workers have found that a total deficiency in STS produces ichthyosis. According to some workers, STS deficiency is fairly prevalent in Japan. The same workers (Sakura et al, J Inherit Metab Dis 1997 November; 20(6):807-10) have also reported that allergic diseases—such as bronchial asthma, allergic rhinitis, or atopic dermatitis—may be associated with a steroid sulphatase deficiency.

In addition to disease states being brought on through a total lack of STS activity, an increased level of STS activity may also bring about disease conditions. By way of example, and as indicated above, there is strong evidence to support a role of STS in breast cancer growth and metastasis.

STS has also been implicated in other disease conditions. By way of example, Le Roy et al (Behav Genet 1999 March; 29(2):131-6) have determined that there may be a genetic correlation between steroid sulphatase concentration and initiation of attack behaviour in mice. The authors conclude that sulphatation of steroids may be the prime mover of a complex network, including genes shown to be implicated in aggression by mutagenesis.

STS Inhibition

It is believed that some disease conditions associated with STS activity are due to conversion of a nonactive, sulphated oestrone to an active, nonsulphated oestrone. In disease conditions associated with STS activity, it would be desirable to inhibit STS activity.

Here, the term "inhibit" includes reduce and/or eliminate and/or mask and/or prevent the detrimental action of STS.

STS Inhibitor

In accordance with the present invention, the compound of the present invention is capable of acting as an STS inhibitor.

Here, the term "inhibitor" as used herein with respect to the compound of the present invention means a compound that can inhibit STS activity—such as reduce and/or eliminate and/or mask and/or prevent the detrimental action of STS. The STS inhibitor may act as an antagonist.

The ability of compounds to inhibit oestrone sulphatase activity can be assessed using either intact JEG3 choriocarcinoma cells or placental microsomes. In addition, an animal model may be used. Details on suitable Assay Protocols are presented in following sections. It is to be noted that other assays could be used to determine STS activity and thus STS inhibition. For example, reference may also be made to the teachings of WO-A-99/50453.

In one aspect, for some applications, the compound is further characterised by the feature that if the sulphamate group were to be substituted by a sulphate group to form a sulphate derivative, then the sulphate derivative would be hydrolysable by an enzyme having steroid sulphatase (E.C. 3.1.6.2) activity—i.e. when incubated with steroid sulphatase EC 3.1.6.2 at pH 7.4 and 37° C.

In one preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a Km value of less than 200 mmolar, preferably less than 150 mmolar, preferably less than 100 mmolar, preferably less than 75 mmolar, preferably less than 50 mmolar, when incubated with steroid sulphatase EC 3.1.6.2 at pH 7.4 and 37° C.

In a preferred embodiment, the compound of the present invention is not hydrolysable by an enzyme having steroid sulphatase (E.C. 3.1.6.2) activity.

For some applications, preferably the compound of the present invention has at least about a 100 fold selectivity to a desired target (e.g. STS and/or aromatase), preferably at least about a 150 fold selectivity to the desired target, preferably at least about a 200 fold selectivity to the desired target, preferably at least about a 250 fold selectivity to the desired target, preferably at least about a 300 fold selectivity to the desired target, preferably at least about a 350 fold selectivity to the desired target.

It is to be noted that the compound of the present invention may have other beneficial properties in addition to or in the alternative to its ability to inhibit STS and/or aromatase activity.

Assay for Determining STS Activity Using Cancer Cells (Protocol 1)

Inhibition of Steroid Sulphatase Activity in JEG3 Cells

Steroid sulphatase activity is measured in vitro using intact JEG3 choriocarcinoma cells. This cell line may be used to study the control of human breast cancer cell growth. It possesses significant steroid sulphatase activity (Boivin et al., J. Med. Chem., 2000, 43: 4465-4478) and is available in from the American Type Culture Collection (ATCC).

Cells are maintained in Minimal Essential Medium (MEM) (Flow Laboratories, Irvine, Scotland) containing 20 mM HEPES, 5% foetal bovine serum, 2 mM glutamine, non-essential amino acids and 0.075% sodium bicarbonate. Up to 30 replicate 25 cm2 tissue culture flasks are seeded with approximately $1\times10^5$ cells/flask using the above medium. Cells are grown to 80% confluency and the medium is changed every third day.

Intact monolayers of JEG3 cells in triplicate 25 cm² tissue culture flasks are washed with Earle's Balanced Salt Solution (EBSS from ICN Flow, High Wycombe, U.K.) and incubated for 3-4 hours at 37° C. with 5 pmol ($7\times10^5$ dpm) [6,7-3H] oestrone-3-sulphate (specific activity 60 Ci/mmol from New England Nuclear, Boston, Mass., U.S.A.) in serum-free MEM (2.5 ml) together with oestrone-3-sulphamate (5 concentrations: 1 nM, 10 nM, 100 nM, 1000 nM and 10 uM.). After incubation each flask is cooled and the medium (1 ml) is pipetted into separate tubes containing [14C]oestrone ($7\times10^3$ dpm) (specific activity 97 Ci/mmol from Amersham International Radiochemical Centre, Amersham, U.K.). The mixture is shaken thoroughly for 30 seconds with toluene (5 ml). Experiments have shown that >90% [14C] oestrone and <0.1% [3H]oestrone-3-sulphate is removed from the aqueous phase by this treatment. A portion (2 ml) of the organic phase is removed, evaporated and the 3H and 14C content of the residue determined by scintillation spectrometry. The mass of oestrone-3-sulphate hydrolysed was calculated from the 3H counts obtained (corrected for the volumes of the medium and organic phase used, and for recovery of [14C] oestrone added) and the specific activity of the substrate. Each batch of experiments includes incubations of microsomes prepared from a sulphatase-positive human placenta (positive control) and flasks without cells (to assess apparent non-enzymatic hydrolysis of the substrate). The number of cell nuclei per flask is determined using a Coulter Counter after treating the cell monolayers with Zaponin. One flask in each batch is used to assess cell membrane status and viability using the Trypan Blue exclusion method (Phillips, H. J. (1973) In: Tissue culture and applications, [eds: Kruse, D. F. & Patterson, M. K.]; pp. 406-408; Academic Press, New York).

Results for steroid sulphatase activity are expressed as the mean±1 S.D. of the total product (oestrone+oestradiol) formed during the incubation period (3-4 hours) calculated for 106 cells and, for values showing statistical significance, as a percentage reduction (inhibition) over incubations containing no oestrone-3-sulphamate. Unpaired Student's t-test was used to test the statistical significance of results.

Assay for Determining STS Activity Using Placental Microsomes (Protocol 2)

Inhibition of Steroid Sulphatase Activity in Placental Microsomes

Sulphatase-positive human placenta from normal term pregnancies are thoroughly minced with scissors and washed once with cold phosphate buffer (pH 7.4, 50 mM) then re-suspended in cold phosphate buffer (5 ml/g tissue). Homogenisation is accomplished with an Ultra-Turrax homogeniser, using three 10 second bursts separated by 2 minute cooling periods in ice. Nuclei and cell debris are removed by centrifuging (4° C.) at 2000 g for 30 minutes and portions (2 ml) of the supernatant are stored at 20° C. The protein concentration of the supernatants is determined by the method of Bradford (Anal. Biochem., 72, 248-254 (1976)).

Incubations (1 ml) are carried out using a protein concentration of 100 mg/ml, substrate concentration of 20 mM [6,7-3H]oestrone-3-sulphate (specific activity 60 Ci/mmol from New England Nuclear, Boston, Mass., U.S.A.) and an incubation time of 20 minutes at 37° C. If necessary six concentrations of compounds are employed: 0.1 nM, 1.0 nM, 10 nM, 100 nM, 1000 nM and 10 uM. After incubation each sample is cooled and the medium (1 ml) was pipetted into separate tubes containing [14C]oestrone ($7\times10^3$ dpm) (specific activity 97 Ci/mmol from Amersham International Radiochemical Centre, Amersham, U.K.). The mixture is shaken thoroughly for 30 seconds with toluene (5 ml). Experiments have shown that >90% [14C]oestrone and <0.1% [3H]oestrone-3-sulphate is removed from the aqueous phase by this treatment. A portion (2 ml) of the organic phase was removed, evaporated and the 3H and 14C content of the residue determined by scintillation spectrometry. The mass of oestrone-3-sulphate hydrolysed is calculated from the 3H counts obtained (corrected for the volumes of the medium and organic phase used, and for recovery of [14C]oestrone added) and the specific activity of the substrate.

Animal Assay Model for Determining STS Activity (Protocol 3)

Inhibition of Oestrone Sulphatase Activity In Vivo

The compounds of the present invention may be studied using an animal model, in particular in ovariectomised rats. In this model compounds which are oestrogenic stimulate uterine growth.

The compound (0.1 mg/Kg/day for five days) is administered orally to rats with another group of animals receiving vehicle only (propylene glycol). At the end of the study samples of liver tissue were obtained and oestrone sulphatase activity assayed using 3H oestrone sulphate as the substrate as previously described (see PCT/GB95/02638).

Animal Assay Model for Determining Oestrogenic Activity (Protocol 4)

The compounds of the present invention may be studied using an animal model, in particular in ovariectomised rats. In this model, compounds which are oestrogenic stimulate uterine growth.

The compound (0.1 mg/Kg/day for five days) was administered orally to rats with another group of animals receiving vehicle only (propylene glycol). At the end of the study uteri were obtained and weighed with the results being expressed as uterine weight/whole body weight×100.

Compounds having no significant effect on uterine growth are not oestrogenic.

Biotechnological Assays for Determining STS Activity (Protocol 5)

The ability of compounds to inhibit oestrone sulphatase activity can also be assessed using amino acid sequences or nucleotide sequences encoding STS, or active fragments, derivatives, homologues or variants thereof in, for example, high-through put screens.

Any one or more of appropriate targets—such as an amino acid sequence and/or nucleotide sequence—may be used for identifying an agent capable of modulating STS in any of a variety of drug screening techniques. The target employed in such a test may be free in solution, affixed to a solid support, borne on a cell surface, or located intracellularly. The abolition of target activity or the formation of binding complexes between the target and the agent being tested may be measured.

The assay of the present invention may be a screen, whereby a number of agents are tested. In one aspect, the assay method of the present invention is a high through put screen.

Techniques for drug screening may be based on the method described in Geysen, European Patent Application 84/03564, published on Sep. 13, 1984. In summary, large numbers of different small peptide test compounds are synthesised on a solid substrate, such as plastic pins or some other surface. The peptide test compounds are reacted with a suitable target or fragment thereof and washed. Bound entities are then detected—such as by appropriately adapting methods well known in the art. A purified target can also be coated directly onto plates for use in a drug screening techniques. Alternatively, non-neutralising antibodies can be used to capture the peptide and immobilise it on a solid support.

This invention also contemplates the use of competitive drug screening assays in which neutralising antibodies capable of binding a target specifically compete with a test compound for binding to a target.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

In one preferred aspect, the present invention relates to a method of identifying agents that selectively modulate STS, which compounds have the formula (I).

Reporters

A wide variety of reporters may be used in the assay methods (as well as screens) of the present invention with preferred reporters providing conveniently detectable signals (e.g. by spectroscopy). By way of example, a reporter gene may encode an enzyme which catalyses a reaction which alters light absorption properties.

Other protocols include enzyme-linked immunosorbent assay (ELISA), radioimmunoassay (RIA) and fluorescent activated cell sorting (FACS). A two-site, monoclonal-based immunoassay utilising monoclonal antibodies reactive to two non-interfering epitopes may even be used. These and other assays are described, among other places, in Hampton R et al (1990, Serological Methods, A Laboratory Manual, APS Press, St Paul Minn.) and Maddox D E et al (1983, J Exp Med 15 8:1211).

Examples of reporter molecules include but are not limited to (β-galactosidase, invertase, green fluorescent protein, luciferase, chloramphenicol, acetyltransferase, (-glucuronidase, exo-glucanase and glucoamylase. Alternatively, radiolabelled or fluorescent tag-labelled nucleotides can be incorporated into nascent transcripts which are then identified when bound to oligonucleotide probes.

By way of further examples, a number of companies such as Pharmacia Biotech (Piscataway, N.J.), Promega (Madison, Wis.), and US Biochemical Corp (Cleveland, Ohio) supply commercial kits and protocols for assay procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241.

Host Cells

The term "host cell"—in relation to the present invention includes any cell that could comprise the target for the agent of the present invention.

Thus, a further embodiment of the present invention provides host cells transformed or transfected with a polynucleotide that is or expresses the target of the present invention. Preferably said polynucleotide is carried in a vector for the replication and expression of polynucleotides that are to be the target or are to express the target. The cells will be chosen to be compatible with the said vector and may for example be prokaryotic (for example bacterial), fungal, yeast or plant cells.

The gram negative bacterium *E. coli* is widely used as a host for heterologous gene expression. However, large amounts of heterologous protein tend to accumulate inside the cell. Subsequent purification of the desired protein from the bulk of *E. coli* intracellular proteins can sometimes be difficult.

In contrast to *E. coli*, bacteria from the genus *Bacillus* are very suitable as heterologous hosts because of their capability to secrete proteins into the culture medium. Other bacteria suitable as hosts are those from the genera *Streptomyces* and *Pseudomonas*.

Depending on the nature of the polynucleotide encoding the polypeptide of the present invention, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

Examples of suitable expression hosts within the scope of the present invention are fungi such as *Aspergillus* species (such as those described in EP-A-0184438 and EP-A-0284603) and *Trichoderma* species; bacteria such as *Bacillus* species (such as those described in EP-A-0134048 and EP-A-0253455), *Streptomyces* species and *Pseudomonas* species; and yeasts such as *Kluyveromyces* species (such as those described in EP-A-0096430 and EP-A-0301670) and *Saccharomyces* species. By way of example, typical expression hosts may be selected from *Aspergillus niger, Aspergillus niger* var. *tubigenis, Aspergillus niger* var. *awamori, Aspergillus aculeatis, Aspergillus nidulans, Aspergillus oryzae, Trichoderma reesei, Bacillus subtilis, Bacillus licheniformis, Bacillus amyloliquefaciens, Kluyveromyces lactis* and *Saccharomyces cerevisiae*.

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

Organism

The term "organism" in relation to the present invention includes any organism that could comprise the target according to the present invention and/or products obtained therefrom. Examples of organisms may include a fungus, yeast or a plant.

The term "transgenic organism" in relation to the present invention includes any organism that comprises the target according to the present invention and/or products obtained.

Transformation of Host Cells/Host Organisms

As indicated earlier, the host organism can be a prokaryotic or a eukaryotic organism. Examples of suitable prokaryotic hosts include *E. coli* and *Bacillus subtilis*. Teachings on the transformation of prokaryotic hosts is well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc.

If a prokaryotic host is used then the nucleotide sequence may need to be suitably modified before transformation—such as by removal of introns.

In another embodiment the transgenic organism can be a yeast: In this regard, yeast have also been widely used as a vehicle for heterologous gene expression. The species *Saccharomyces cerevisiae* has a long history of industrial use, including its use for heterologous gene expression. Expression of heterologous genes in *Saccharomyces cerevisiae* has been reviewed by Goodey et al (1987, Yeast Biotechnology, D R Berry et al, eds, pp 401-429, Allen and Unwin, London) and by King et al (1989, Molecular and Cell Biology of Yeasts, E F Walton and G T Yarronton, eds, pp 107-133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae.*

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic *Saccharomyces*, expression constructs are prepared by inserting the nucleotide sequence into a construct designed for expression in yeast. Several types of constructs used for heterologous expression have been developed. The constructs contain a promoter active in yeast fused to the nucleotide sequence, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic *Saccharomyces* according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163-168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, e.g. G418.

Another host organism is a plant. The basic principle in the construction of genetically modified plants is to insert genetic information in the plant genome so as to obtain a stable maintenance of the inserted genetic material. Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205-225) and Christou (Agro-Food-Industry Hi-Tech March/April 1994 17-27). Further teachings on plant transformation may be found in EP-A-0449375.

Thus, the present invention also provides a method of transforming a host cell with a nucleotide sequence that is to be the target or is to express the target. Host cells transformed with the nucleotide sequence may be cultured under conditions suitable for the expression of the encoded protein. The protein produced by a recombinant cell may be displayed on the surface of the cell. If desired, and as will be understood by those of skill in the art, expression vectors containing coding sequences can be designed with signal sequences which direct secretion of the coding sequences through a particular prokaryotic or eukaryotic cell membrane. Other recombinant constructions may join the coding sequence to nucleotide sequence encoding a polypeptide domain which will facilitate purification of soluble proteins (I<roll D J et al (1993) DNA Cell Biol 12:441-53).

Variants/Homologues/Derivatives

In addition to the specific amino acid sequences and nucleotide sequences mentioned herein, the present invention also encompasses the use of variants, homologue and derivatives thereof. Here, the term "homology" can be equated with "identity".

In the present context, an homologous sequence is taken to include an amino acid sequence which may be at least 75, 85 or 90% identical, preferably at least 95 or 98% identical. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Besffit program.

A further useful reference is that found in FEMS Microbiol Lett 1999 May 15; 174(2):247-50 (and a published erratum appears in FEMS Microbiol Lett 1999 Aug. 1; 177(1):187-8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Expression Vectors

The nucleotide sequence for use as the target or for expressing the target can be incorporated into a recombinant replicable vector. The vector may be used to replicate and express the nucleotide sequence in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The protein produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Fusion Proteins

The target amino acid sequence may be produced as a fusion protein, for example to aid in extraction and purification. Examples of fusion protein partners include glutathione-S-transferase (GST), 6×His, GAL4 (DNA binding and/or transcriptional activation domains) and □-galactosidase. It may also be convenient to include a proteolytic cleavage site between the fusion protein partner and the protein sequence of interest to allow removal of fusion protein sequences. Preferably the fusion protein will not hinder the activity of the target.

The fusion protein may comprise an antigen or an antigenic determinant fused to the substance of the present invention. In this embodiment, the fusion protein may be a non-naturally occurring fusion protein comprising a substance which may act as an adjuvant in the sense of providing a generalised stimulation of the immune system. The antigen or antigenic determinant may be attached to either the amino or carboxy terminus of the substance.

In another embodiment of the invention, the amino acid sequence may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

Therapy

The compounds of the present invention may be used as therapeutic agents—i.e. in therapy applications.

The term "therapy" includes curative effects, alleviation effects, and prophylactic effects.

The therapy may be on humans or animals, preferably female animals.

Pharmaceutical Compositions

In one aspect, the present invention provides a pharmaceutical composition, which comprises a compound according to the present invention and optionally a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Combination Pharmaceutical

The compound of the present invention may be used in combination with one or more other active agents, such as one or more other pharmaceutically active agents.

By way of example, the compounds of the present invention may be used in combination with other STS inhibitors aid/or other inhibitors such as an aromatase inhibitor (such as for example, 4-hydroxyandrostenedione (4-OHA)) and/or steroids—such as the naturally occurring neurosteroids dehydroepiandrosterone sulfate (DHEAS) and pregnenolone sulfate (PS) and/or other structurally similar organic compounds. Examples of other STS inhibitors may be found in the above references. By way of example, STS inhibitors for use in the present invention include either or both of the 2-ethyl and 2-methoxy 17-deoxy compounds that are analogous to compound 5 presented herein.

In addition, or in the alternative, the compound of the present invention may be used in combination with a biological response modifier.

The term biological response modifier ("BRM") includes cytokines, immune modulators, growth factors, haematopoiesis regulating factors, colony stimulating factors, chemotactic, haemolytic and thrombolytic factors, cell surface receptors, ligands, leukocyte adhesion molecules, monoclonal antibodies, preventative and therapeutic vaccines, hormones, extracellular matrix components, fibronectin, etc. For some applications, preferably, the biological response modifier is a cytokine. Examples of cytokines include: interleukins (IL)—such as IL-1, IL-2, IL-3, IL-4, IL-5, IL-6, IL-7, IL-8, IL-9, IL-10, IL-11, IL-12, IL-19; Tumour Necrosis Factor (TNF)— such as TNF-α; Interferon alpha, beta and gamma; TGF-β. For some applications, preferably the cytokine is tumour necrosis factor (TNF). For some applications, the TNF may be any type of TNF—such as TNF-α, TNF-β, including derivatives or mixtures thereof. More preferably the cytokine is TNF-α. Teachings on TNF may be found in the art—such as WO-A-98108870 and WO-A-98/13348.

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The compositions of the present invention may be administered by direct injection. The composition may be formulated for parenteral, mucosal, intramuscular, intravenous, subcutaneous, intraocular or transdermal administration. Depending upon the need, the agent may be administered at a dose of from 0.01 to 30 mg/kg body weight, such as from 0.1 to 10 mg/kg, more preferably from 0.1 to 1 mg/kg body weight.

By way of further example, the agents of the present invention may be administered in accordance with a regimen of 1 to 4 times per day, preferably once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Aside from the typical modes of delivery—indicated above—the term "administered" also includes delivery by techniques such as lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

Thus, for pharmaceutical administration, the STS inhibitors of the present invention can be formulated in any suitable manner utilising conventional pharmaceutical formulating techniques and pharmaceutical carriers, adjuvants, excipients, diluents etc. and usually for parenteral administration. Approximate effective dose rates may be in the range from 1 to 1000 mg/day, such as from 10 to 900 mg/day or even from 100 to 800 mg/day depending on the individual activities of the compounds in question and for a patient of average (70 Kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

Cell Cycling

The compounds of the present invention may be useful in the method of treatment of a cell cycling disorder.

As discussed in "Molecular Cell Biology" 3rd Ed. Lodish et al. pages 177-181 different eukaryotic cells can grow and divide at quite different rates. Yeast cells, for example, can divide every 120 min., and the first divisions of fertilised eggs in the embryonic cells of sea urchins and insects take only 1530 min. because one large pre-existing cell is subdivided. However, most growing plant and animal cells take 10-20 hours to double in number, and some duplicate at a much slower rate. Many cells in adults, such as nerve cells and striated muscle cells, do not divide at all; others, like the fibroblasts that assist in healing wounds, grow on demand but are otherwise quiescent.

Still, every eukaryotic cell that divides must be ready to donate equal genetic material to two daughter cells. DNA synthesis in eukaryotes does not occur throughout the cell division cycle but is restricted to a part of it before cell division.

The relationship between eukaryotic DNA synthesis and cell division has been thoroughly analysed in cultures of mammalian cells that were all capable of growth and division. In contrast to bacteria, it was found, eukaryotic cells spend only a part of their time in DNA synthesis, and it is completed hours before cell division (mitosis). Thus a gap of time occurs after DNA synthesis and before cell division; another gap was found to occur after division and before the next round of DNA synthesis. This analysis led to the conclusion that the eukaryotic cell cycle consists of an M (mitotic) phase, a $G_1$ phase (the first gap), the S (DNA synthesis) phase, a $G_2$ phase (the second gap), and back to M. The phases between mitoses ($G_1$, S, and $G_2$) are known collectively as the interphase.

Many nondividing cells in tissues (for example, all quiescent fibroblasts) suspend the cycle after mitosis and just prior to DNA synthesis; such "resting" cells are said to have exited from the cell cycle and to be in the $G_0$ state.

It is possible to identify cells when they are in one of the three interphase stages of the cell cycle, by using a fluorescence-activated cell sorter (FACS) to measure their relative DNA content: a cell that is in $G_1$ (before DNA synthesis) has a defined amount x of DNA; during S (DNA replication), it has between x and 2x; and when in $G_2$ (or M), it has 2x of DNA.

The stages of mitosis and cytokinesis in an animal cell are as follows (a) Interphase. The $G_2$ stage of interphase immediately precedes the beginning of mitosis. Chromosomal DNA has been replicated and bound to protein during the S phase, but chromosomes are not yet seen as distinct structures. The nucleolus is the only nuclear substructure that is visible under light microscope. In a diploid cell before DNA replication there are two morphologic chromosomes of each type, and the cell is said to be 2n. In $G_2$, after DNA replication, the cell is 4n. There are four copies of each chromosomal DNA. Since the sister chromosomes have not yet separated from each other, they are called sister chromatids.

b) Early prophase. Centrioles, each with a newly formed daughter centriole, begin moving toward opposite poles of the cell; the chromosomes can be seen as long threads. The nuclear membrane begins to disaggregate into small vesicles.

(c) Middle and late prophase. Chromosome condensation is completed; each visible chromosome structure is composed of two chromatids held together at their centromeres. Each chromatid contains one of the two newly replicated daughter DNA molecules. The microtubular spindle begins to radiate from the regions just adjacent to the centrioles, which are moving closer to their poles. Some spindle fibres reach from pole to pole; most go to chromatids and attach at kinetochores.

(d) Metaphase. The chromosomes move toward the equator of the cell, where they become aligned in the equatorial plane. The sister chromatids have not yet separated.

(e) Anaphase. The two sister chromatids separate into independent chromosomes. Each contains a centromere that is linked by a spindle fibre to one pole, to which it moves. Thus one copy of each chromosome is donated to each daughter cell. Simultaneously, the cell elongates, as do the pole-to-pole spindles. Cytokinesis begins as the cleavage furrow starts to form.

(f) Telophase. New membranes form around the daughter nuclei; the chromosomes uncoil and become less distinct, the nucleolus becomes visible again, and the nuclear membrane forms around each daughter nucleus. Cytokinesis is nearly complete, and the spindle disappears as the microtubules and other fibres depolymerise. Throughout mitosis the "daughter" centriole at each pole grows until it is full-length. At telophase the duplication of each of the original centrioles is completed, and new daughter centrioles will be generated during the next interphase.

(g) Interphase. Upon the completion of cytokinesis, the cell enters the $G_1$ phase of the cell cycle and proceeds again around the cycle.

It will be appreciated that cell cycling is an extremely important cell process. Deviations from normal cell cycling can result in a number of medical disorders. Increased and/or unrestricted cell cycling may result in cancer. Reduced cell cycling may result in degenerative conditions. Use of the compound of the present invention may provide a means to treat such disorders and conditions.

Thus, the compound of the present invention may be suitable for use in the treatment of cell cycling disorders such as cancers, including hormone dependent and hormone independent cancers.

In addition, the compound of the present invention may be suitable for the treatment of cancers such as breast cancer, ovarian cancer, endometrial cancer, sarcomas, melanomas, prostate cancer, pancreatic cancer etc. and other solid tumours.

For some applications, cell cycling is inhibited and/or prevented and/or arrested, preferably wherein cell cycling is prevented and/or arrested. In one aspect cell cycling may be inhibited and/or prevented and/or arrested in the $G_2$/M phase. In one aspect cell cycling may be irreversibly prevented and/or inhibited and/or arrested, preferably wherein cell cycling is irreversibly prevented and/or arrested.

By the term "irreversibly prevented and/or inhibited and/or arrested" it is meant after application of a compound of the present invention, on removal of the compound the effects of the compound, namely prevention and/or inhibition and/or arrest of cell cycling, are still observable. More particularly by the term "irreversibly prevented and/or inhibited and/or arrested" it is meant that when assayed in accordance with the cell cycling assay protocol presented herein, cells treated with a compound of interest show less growth after Stage 2 of the protocol I than control cells. Details on this protocol are presented below.

Thus, the present invention provides compounds which: cause inhibition of growth of oestrogen receptor positive (ER+) and ER negative (ER−) breast cancer cells in vitro by preventing and/or inhibiting and/or arresting cell cycling; and/or cause regression of nitroso-methyl urea (NMU) induced mammary tumours in intact animals (i.e. not ovariectomised), and/or prevent and/or inhibit and/or arrest cell cycling in cancer cells; and/or act in vivo by preventing and/or inhibiting and/or arresting cell cycling and/or act as a cell cycling agonist.

Cell Cycling Assay (Protocol 7)

Procedure

Stage 1

MCF-7 breast cancer cells are seeded into multi-well culture plates at a density of 105 cells/well. Cells were allowed to attach and grown until about 30% confluent when they are treated as follows:

Control—no treatment

Compound of Interest (COI) 20 μM

Cells are grown for 6 days in growth medium containing the COI with changes of medium/COI every 3 days. At the end of this period cell numbers were counted using a Coulter cell counter.

Stage 2

After treatment of cells for a 6-day period with the COI cells are re-seeded at a density of $10^4$ cells/well. No further treatments are added. Cells are allowed to continue to grow for a further 6 days in the presence of growth medium. At the end of this period cell numbers are again counted.

Cancer

As indicated, the compounds of the present invention may be useful in the treatment of a cell cycling disorder. A particular cell cycling disorder is cancer.

Cancer remains a major cause of mortality in most Western countries. Cancer therapies developed so far have included blocking the action or synthesis of hormones to inhibit the growth of hormone-dependent tumours. However, more aggressive chemotherapy is currently employed for the treatment of hormone-independent tumours.

Hence, the development of a pharmaceutical for anti-cancer treatment of hormone dependent and/or hormone independent tumours, yet lacking some or all of the side-effects associated with chemotherapy, would represent a major therapeutic advance.

It is known that oestrogens undergo a number of hydroxylation and conjugation reactions after their synthesis. Until recently it was thought that such reactions were part of a metabolic process that ultimately rendered oestrogens water soluble and enhanced their elimination from the body. It is now evident that some hydroxy metabolites (e.g. 2-hydroxy and 16alpha-hydroxy) and conjugates (e.g. oestrone sulphate, E1S) are important in determining some of the complex actions that oestrogens have in the body.

Workers have investigated the formation of 2- and 16-hydroxylated oestrogens in relation to conditions that alter the risk of breast cancer. There is now evidence that factors which increase 2-hydroxylase activity are associated with a reduced cancer risk, while those increasing 16alpha-hydroxylation may enhance the risk of breast cancer. Further interest in the biological role of estrogen metabolites has been stimulated by the growing body of evidence that 2-methoxyoestradiol is an endogenous metabolite with anti-mitotic properties. 2-MeOE2 is formed from 2-hydroxy estradiol (2-OHE2) by catechol estrogen methyl transferase, an enzyme that is widely distributed throughout the body.

Workers have shown that in vivo 2-MeOE2 inhibits the growth of tumours arising from the subcutaneous injection of Meth A sarcoma, B16 melanoma or MDA-MB-435 estrogen receptor negative (ER−) breast cancer cells. It also inhibits endothelial cell proliferation and migration, and in vitro angiogenesis. It was suggested that the ability of 2-MeOE2 to inhibit tumour growth in vivo may be due to its ability to inhibit tumour-induced angiogenesis rather than direct inhibition of the proliferation of tumour cells.

The mechanism by which 2-MeOE2 exerts its potent antimitogenic and anti-angiogenic effects is still being elucidated. There is evidence that at high concentrations it can inhibit microtubule polymerisation and act as a weak inhibitor of colchicine binding to tubulin. Recently, however, at concentrations that block mitosis, tubulin filaments in cells were not found to be depolymerised but to have an identical morphology to that seen after taxol treatment. It is possible, therefore, that like taxol, a drug that is used for breast and ovarian breast cancer therapy, 2-MeOE2 acts by stabilising microtubule dynamics.

While the identification of 2-MeOE2 as a new therapy for cancer represents an important advance, the bioavailability of orally administered oestrogens is poor. Furthermore, they can undergo extensive metabolism during their first pass through the liver. As part of a research programme to develop a steroid sulphatase inhibitor for breast cancer therapy, oestrone-3-O-sulphamate (EMATE) was identified as a potent active site-directed inhibitor. Unexpectedly, EMATE proved to possess potent oestrogenic properties with its oral uterotrophic activity in rats being a 100-times higher than that of estradiol. Its enhanced oestrogenicity is thought to result from its absorption by red blood cells (rbcs) which protects it from inactivation during its passage through the liver and which act as a reservoir for its slow release for a prolonged period of time. A number of A-ring modified analogues were synthesised and tested, including 2-methoxyoestrone-3-O-sulphamate. While this compound was equipotent with EMATE as a steroid sulphatase inhibitor, it was devoid of oestrogenicity.

We believe that the compound of the present invention provides a means for the treatment of cancers and, especially, breast cancer.

In addition or in the alternative the compound of the present invention may be useful in the blocking the growth of cancers including leukaemias and solid tumours such as breast, endometrium, prostate, ovary and pancreatic tumours.

Therapy Concerning Oestrogen

We believe that some of the compounds of the present invention may be useful in the control of oestrogen levels in the body—in particular in females. Thus, some of the compounds may be useful as providing a means of fertility control—such as an oral contraceptive tablet, pill, solution or lozenge. Alternatively, the compound could be in the form of an implant or as a patch.

Thus, the compounds of the present invention may be useful in treating hormonal conditions associated with oestrogen.

In addition or in the alternative the compound of the present invention may be useful in treating hormonal conditions in addition to those associated with oestrogen. Hence, the compound of the present invention may also be capable of affecting hormonal activity and may also be capable of affecting an immune response.

Neurodegenerative Diseases

We believe that some of the compounds of the present invention may be useful in the treatment of neurodegenerative diseases, and similar conditions.

By way of example, it is believed that STS inhibitors may be useful in the enhancing the memory function of patients suffering from illnesses such as amnesia, head injuries, Alzheimer's disease, epileptic dementia, presenile dementia, post traumatic dementia, senile dementia, vascular dementia and post-stroke dementia or individuals otherwise seeking memory enhancement

TH1

We believe that some of the compounds of the present invention may be useful in TH1 implications.

By way of example, it is believed that the presence of STS inhibitors within the macrophage or other antigen presenting cells may lead to a decreased ability of sensitised T cells to mount a TH1 (high IL-2, IFNγ low IL-4) response. The normal regulatory influence of other steroids such as glucocorticoids would therefore predominate.

Inflammatory Conditions

We believe that some of the compounds of the present invention may be useful in treating inflammatory conditions—such as conditions associated with any one or more of: autoimmunity, including for example, rheumatoid arthritis, type I and II diabetes, systemic lupus erythematosus, multiple sclerosis, myasthenia gravis, thyroiditis, vasculitis, ulcerative colitis and Crohn's disease, skin disorders e.g. psoriasis and contact dermatitis; graft versus host disease; eczema; asthma and organ rejection following transplantation.

By way of example, it is believed that STS inhibitors may prevent the normal physiological effect of DHEA or related steroids on immune and/or inflammatory responses.

The compounds of the present invention may be useful in the manufacture of a medicament for revealing an endogenous glucocorticoid-like effect Other Therapies It is also to be understood that the compound/composition of the present invention may have other important medical implications.

For example, the compound or composition of the present invention may be useful in the treatment of the disorders listed in WO-A-99/52890—viz:

In addition, or in the alternative, the compound or composition of the present invention may be useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the compound or composition of the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the composition of the present invention may be useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Compound Preparation

The compounds of the present invention may be prepared by reacting an appropriate alcohol with a suitable chloride. By way of example, the sulphamate compounds of the present invention may be prepared by reacting an appropriate alcohol with a suitable sulfamoyl chloride, of the formula $R^5R^6NSO_2Cl$.

Typical conditions for carrying out the reaction are as follows.

Sodium hydride and a sulfamoyl chloride are added to a stirred solution of the alcohol in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous $MgSO_4$. Filtration followed by solvent evaporation in vacuo and co-evaporated with toluene affords a crude residue which is further purified by flash chromatography.

Preferably, the alcohol is derivatised, as appropriate, prior to reaction with the sulfamoyl chloride. Where necessary, functional groups in the alcohol may be protected in known manner and the protecting group or groups removed at the end of the reaction.

Preferably, the sulphamate compounds are prepared according to the teachings of Page et al (1990 Tetrahedron 46; 2059-2068).

The phosphonate compounds may be prepared by suitably combining the teachings of Page et al (1990 Tetrahedron 46; 2059-2068) and PCT/GB92/01586.

The sulphonate compounds may be prepared by suitably adapting the teachings of Page et al (1990 Tetrahedron 46; 2059-2068) and PCT/GB92/01586.

The thiophosphonate compounds may be prepared by suitably adapting the teachings of Page et al (1990 Tetrahedron 46; 2059-2068) and PCT/GB91/00270.

Preferred preparations are also presented in the following text.

EXAMPLES

The present invention will now be described in further detail by way of example only with reference to the accompanying figures in which:—

Figure 1:
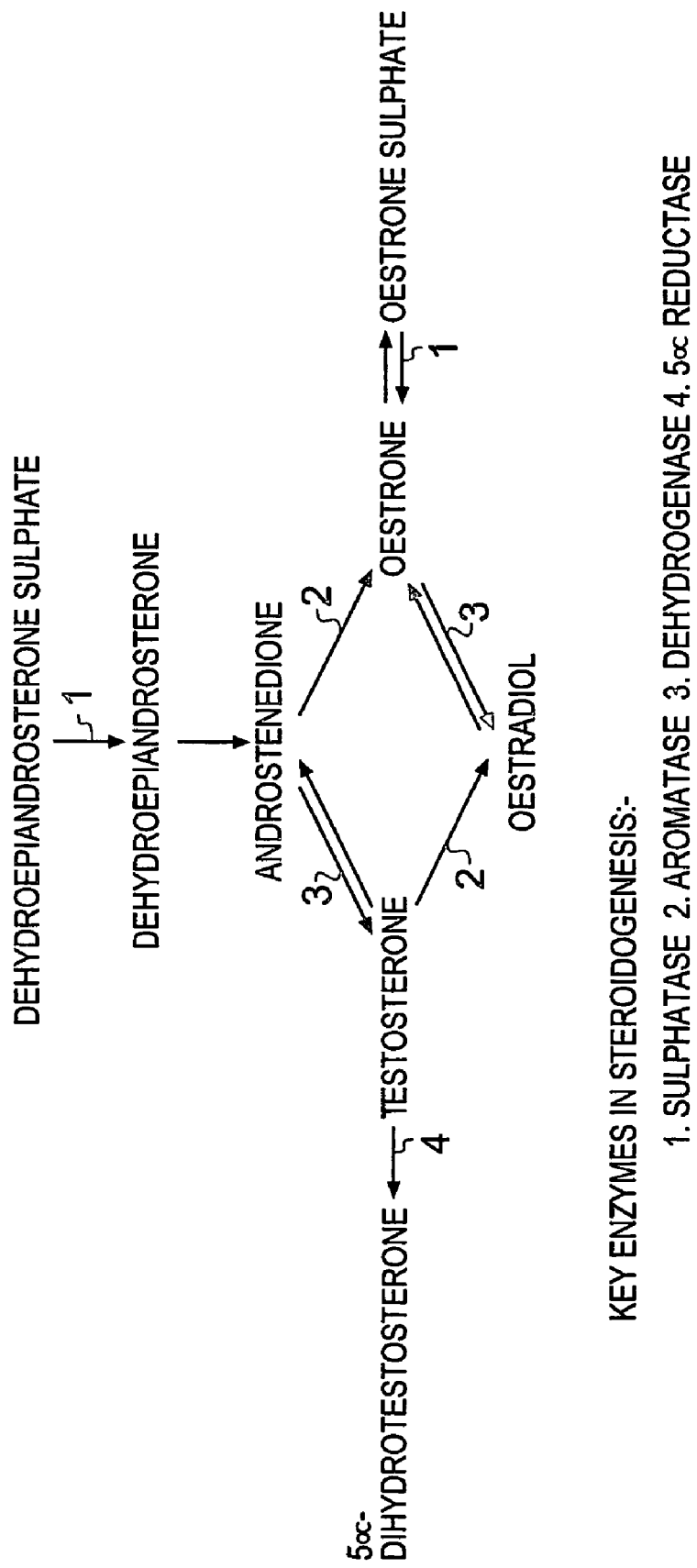
FIG. 1 shows a summary scheme.
Figure 2:
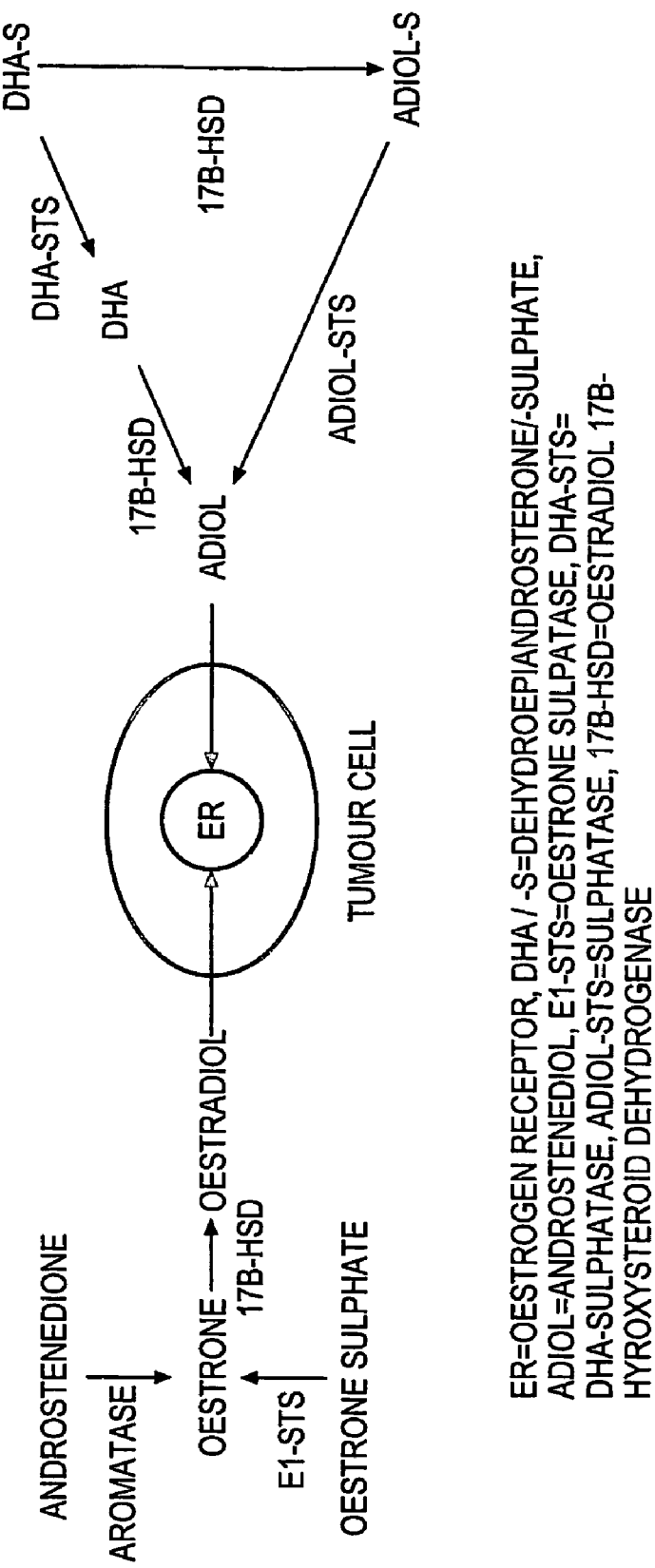
FIG. 2 shows a summary scheme.

The present invention will now be described only by way of example. However, it is to be understood that the examples also present preferred compounds of the present invention, as well as preferred routes for making same and useful intermediates in the preparation of same.

Syntheses
The following schemes were followed
The synthesis of 2-substituted-17-alkenyl sulfamates
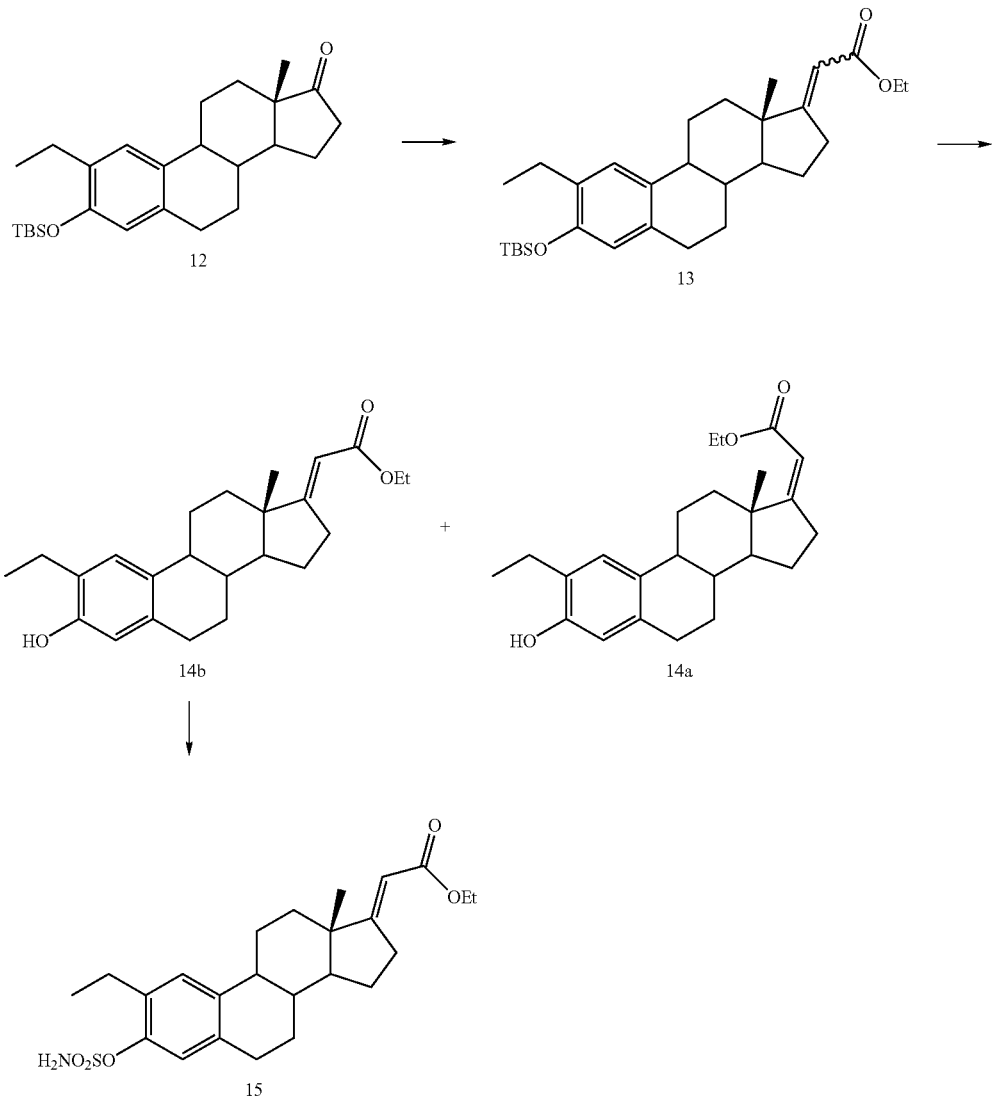
Transformations of the 17-alkenyl Ester Function
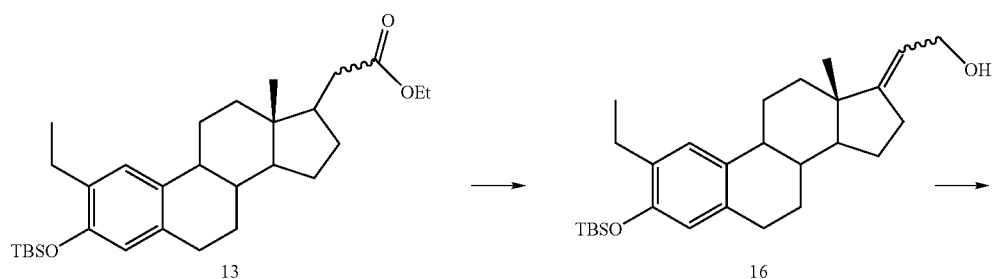

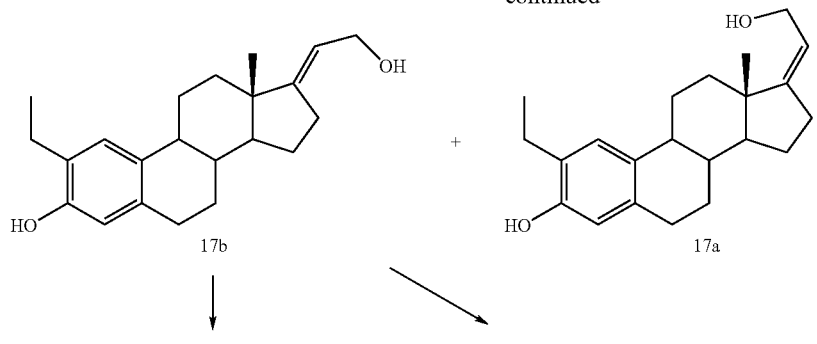
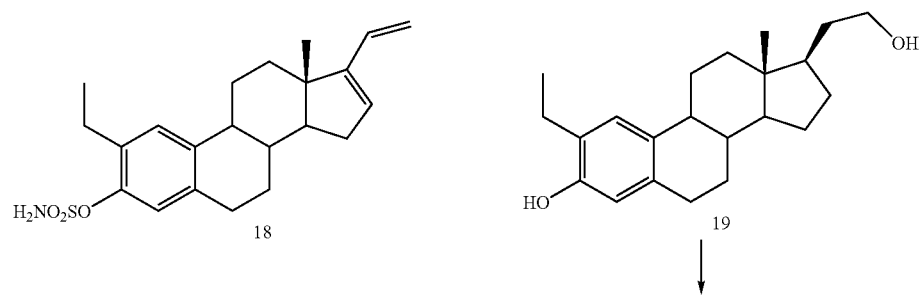
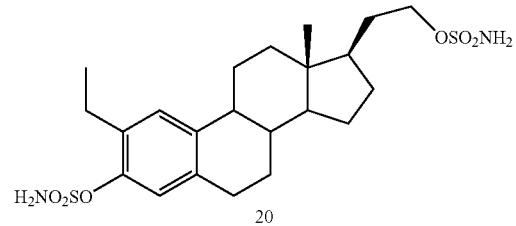
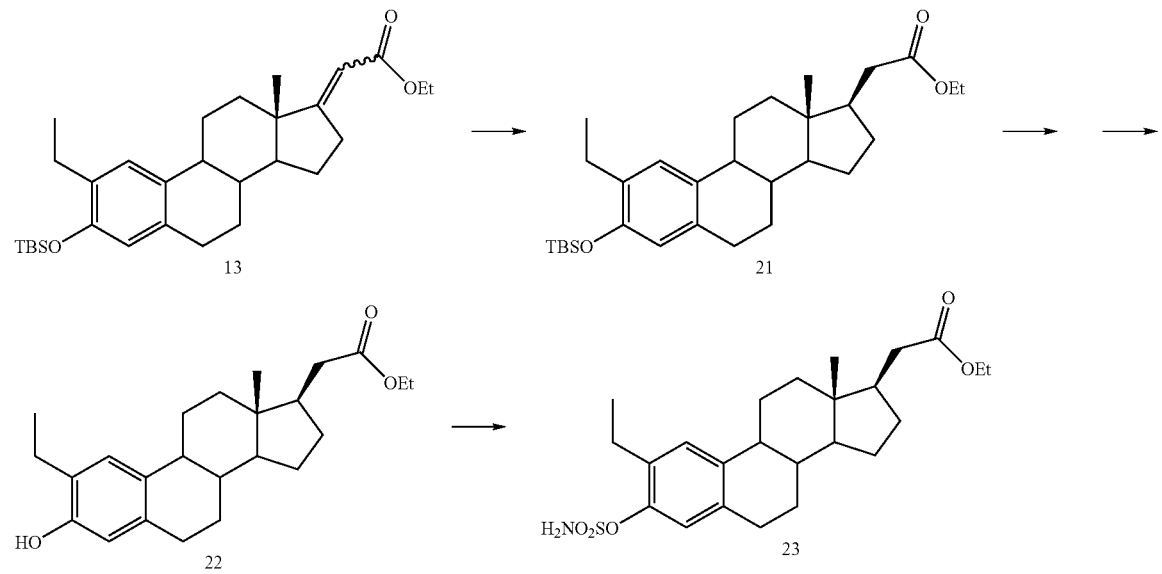

Synthesis of Nitrile Functionalised EMATES
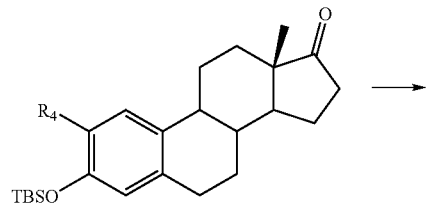
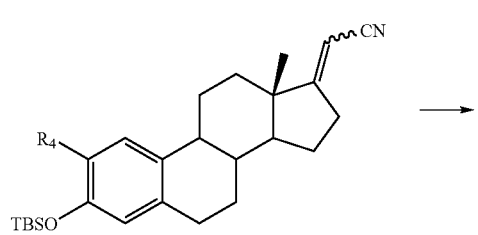
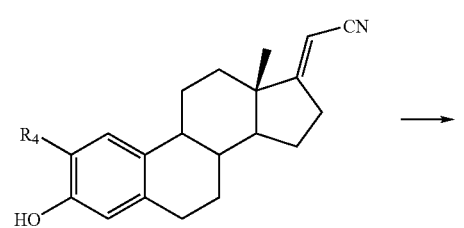
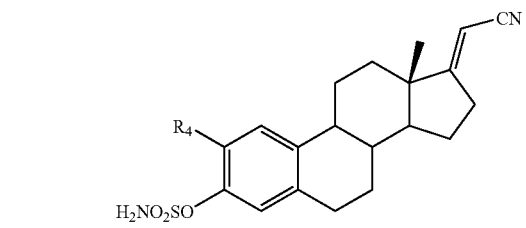
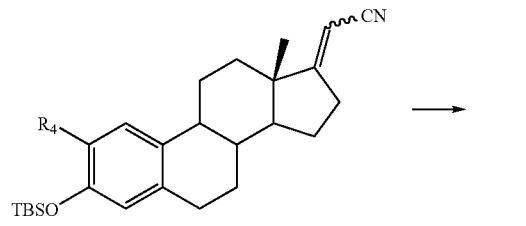
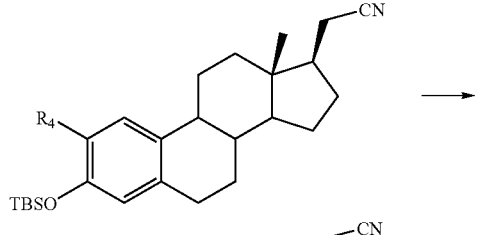
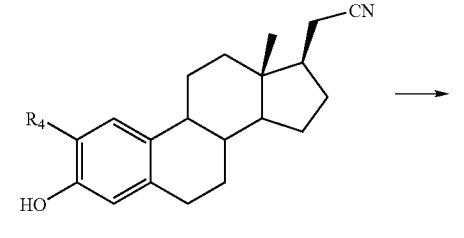
-continued
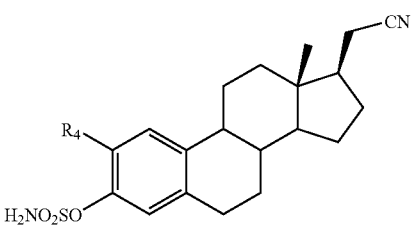
17-Alkyl-EMATEs
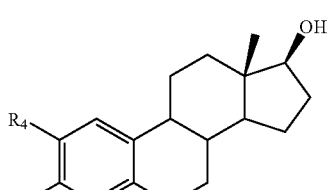
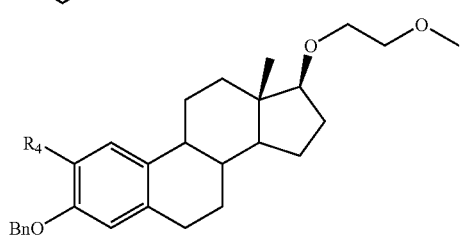
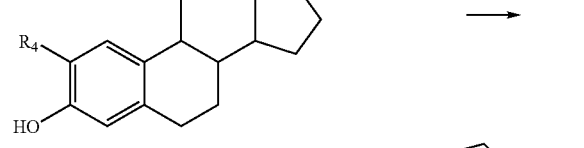
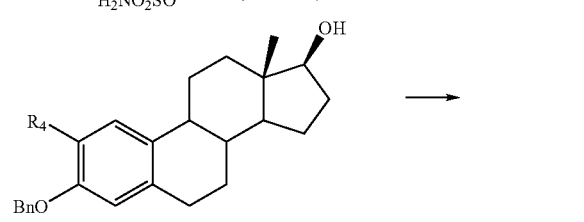
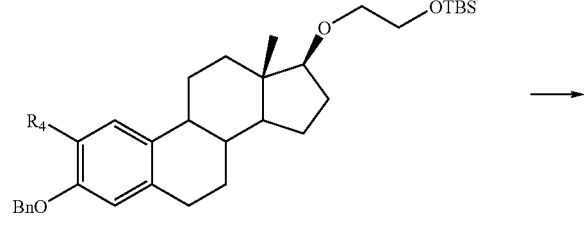

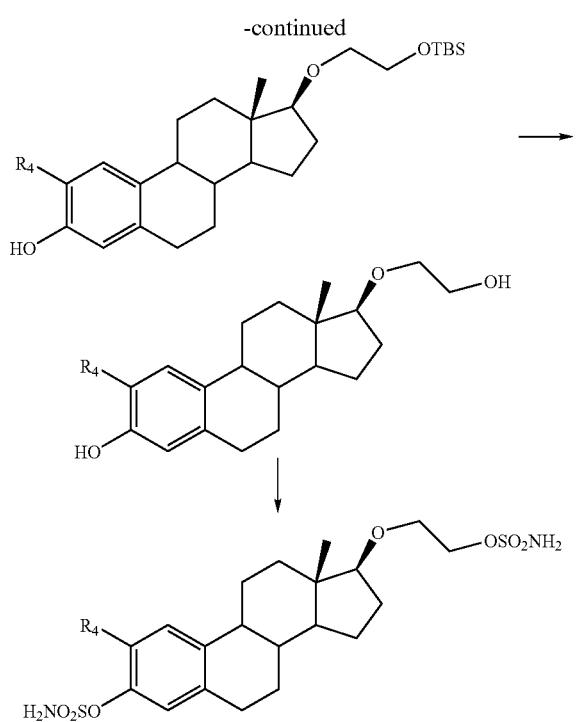

17-Amino Estrogens

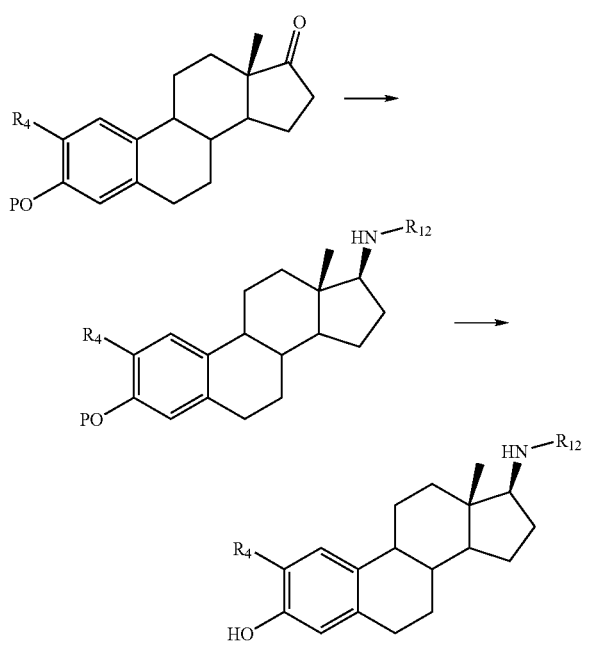

Wherein P is a protecting group.

Procedure A

A 0.745 M toluene solution of sulfamoyl chloride (680 μl, 0.507 mmol) was concentrated in vacuo (water bath temperature below 30° C.) and cooled in an ice bath before addition of DMA (1.5 ml). The appropriate phenol (0.253 mmol) was then added and the reaction allowed to come to room temperature overnight. Water was added and the mixture extracted with ethyl acetate (3×10 ml). The combined organic fractions were combined, washed with water (5×10 ml) and brine (10 ml), dried ($Na_2SO_4$) and concentrated in vacuo.

Estrone 3-O-tert-butyldimethylsilyl Ether 1

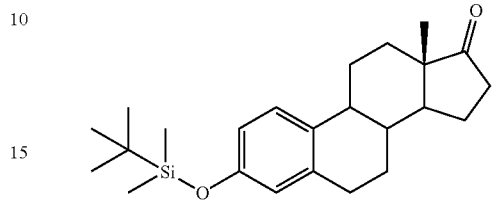

Procedure B

Estrone (10 g, 37 mmol), imidazole (6.4 g, 94 mmol) and tert-butyldimethylsilylchloride (6.7 g, 44.4 mmol) were dissolved in dimethylformamide (130 ml) and stirred under nitrogen overnight at room temperature. Water was added and the mixture extracted with dichloromethane (3×100 ml). The combined organic fractions were washed with water (2×100 ml) and brine (10 ml), dried ($Na_2SO_4$) and concentrated in vacuo.

Recrystallisation from ethanol afforded protected estrone as white crystalline needles (11.34 g, 29.6 mmol, 80%). m.p. 172-173° C. (lit. m.p. 170-172° C.). $\delta_H$ (CDCl$_3$) 0.19 [6H, s, Si(CH$_3$)$_2$)], 0.91 (3H, s CH$_3$), 0.98 [9H, s, C(CH$_3$)$_3$], 1.36-1.68 (5H, m, alkyl H), 1.90-2.55 (7H, m, alkyl H), 2.82-2.88 (2H, m, alkyl H), 6.57 (1H, d, J=2.3, ArH-4), 6.62 (1H, dd, J=8.6, 2.3, ArH-2), 7.12 (1H, d, J=8.6, ArH-1).

m.p.: Fevig et al. J. Org. Chem. 52: 1987, 247-251.

[3-(tert-Butyl-dimethyl-silanyloxy)-13-methyl-6,7,8, 9,11,12,13,14,15,16-decahydro-cyclopenta[a] phenanthren-17-ylidene]-acetic acid ethyl ester 2

Procedure C

Sodium hydride (520 mg, 17.4 mmol) was stirred in dry THF (15 ml) under nitrogen at room temperature until all of the solid had dissolved. Triethylphosphonoacetate (3.20 g, 2.84 ml, 7.14 mmol) was added and stirred for 10 min prior to addition of TBS estrone 1 (2 g, 5.2 mmol). The resultant mixture was heated at reflux overnight. Water was added and the mixture extracted with ethyl acetate (3×50 ml). The combined organic fractions were washed with water (2×50 ml) and brine (10 ml), dried ($Na_2SO_4$) and concentrated in vacuo.

Flash column chromatography (SiO$_2$ hexane:ethyl acetate 9:1) afforded a mixture of two isomers as a white crystalline solid (1.73 g, 3.77 mmol, 73%). The ratio of isomers was determined to be 5:1 from NMR. m/z (EI⁺) 454 (M⁺, 50%), 397 (90%), 82.9 (100%). HRMS (FAB⁺) calcd for $C_{28}H_{42}O_3Si$ 454.2903, found 454.2910.

Method: Ewers et al. Tetrahedron, 54: 1998, 4277-4282.

(3-Hydroxy-13-methyl-6,7,8,9,11,12,13,14,15,16-decahydro-cyclopenta[a]phenanthren-17-ylidene)-acetic acid ethyl ester 3

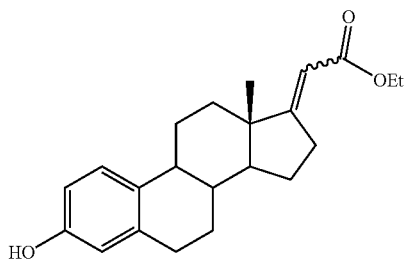

Procedure D

TBS ether 2 (100 mg, 0.220 mmol), 1 M tert-butyl ammonium fluoride in THF (300 μl, 0.300 mmol) and THF (5 ml) were stirred at room temperature for 2 h under nitrogen. Water was added and the mixture extracted with ethyl acetate (3×5 ml). The combined organic fractions were combined, washed with water (2×5 ml) and brine (5 ml), dried (Na₂SO₄) and concentrated in vacuo.

Flash column chromatography (SiO₂ hexane:ethyl acetate 9:1) afforded a mixture of two isomers as a white crystalline solid (74 mg, 0.218 mmol, 99%). m.p. 118-120° C. The ratio of isomers was determined to be 5:1 from NMR. $\delta_H$ (CDCl₃) 0.86 (3H, s, CH₃), 1.30 (3H, t, J=7.0, CH₃), 1.41-2.91 (15H, m, alkyl H), 4.17 (2H, q, J=7.0), 5.20 (1H, s, OH), 5.59 (1H, t, J=2.3, olefinic H), 6.58 (1H, d, J=2.7, ArH-4), 6.64 (1H, dd, J=8.2, 2.7, ArH-2), 7.15 (1H, d, J=8.2, ArH-1); m/z (FAB⁺) 341.1 [(MH)⁺, 100%]; HRMS (FAB⁺) calcd for $C_{22}H_{28}O_3$+H 341.2116, found 341.2111.

2-[3-(tert-Butyl-dimethyl-silanyloxy)-13-methyl-6,7,8,9,11,12,13,14,15,16-decahydro-cyclopenta[a]phenanthren-17-ylidene]-ethanol 4

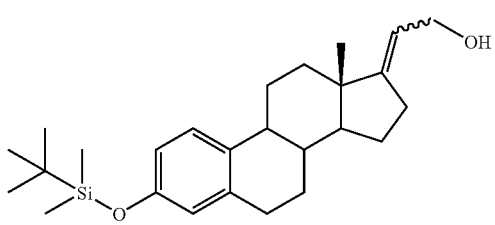

Procedure E

To a solution of TBS ether 2 (300 mg, 0.66 mmol) in THF (5 ml) was added a 1.5 M solution of diisobutylammonium hydride in toluene (1 ml, 1.5 mmol) at −78° C. under nitrogen. The solution was warmed to 0° C. and stirred for 1.5 h. Methanol and water were added at 0° C. and the solution allowed to warm to room temperature and stirred for 30 min. The cloudy solution was extracted with ethyl acetate (3×10 ml) and the combined organic fractions washed with water (2×10 ml) and brine (10 ml), dried (Na₂SO₄) and concentrated in vacuo.

The resultant white solid (179 mg, 0.434 mmol, 66%) was used without further purification. m.p. 128-130° C. (lit, m.p. 128-130° C.). $\delta_H$ (CDCl₃) 0.18 [6H, s, Si(CH₃)₂)], 0.81 (3H, s CH₃), 0.98 [9H, s, C(CH₃)₃], 1.03-1.61 (7H, m, alkyl H), 1.74-1.97 (3H, m, alkyl H), 2.16-2.42 (3H, m, alkyl H), 2.75-2.86 (2H, m, alkyl H), 4.07-4.23 (2H, m, CH₂OH), 5.26-5.31 (1H, m, olefinic H), 6.55 (1H, d, J=2.3, ArH-4), 6.61 (1H, dd, J=8.6, 2.3, ArH-2), 7.13 (1H, d, J=8.6, ArH-1). The ratio of isomers was determined to be 8:1 from NMR.

m/z (FAB⁺) 412.1 (M⁺, 7%), 73.0 (100%), 147 (35%); HRMS (FAB⁺) calcd for $C_{26}H_{40}O_2Si$ 412.2798, found 412.2778.

Method: Tanabe et al. U.S. Pat. No. 6,281,205 B1. 2001. Anti-estrogenic steroids and associated pharmaceutical compositions and methods of use.

m.p.: Ewers et al. Tetrahedron, 54: 1998, 4277-4282.

17-(2-Hydroxyethylidene)-13-methyl-7,8,9,11,12,13,14,15,16,17-decahydro-6H-cyclopenta[a]phenanthren-3-ol, 5

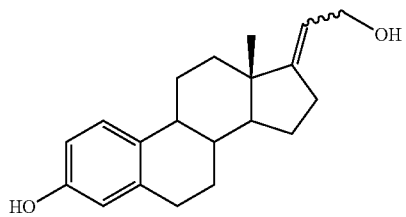

The reaction was carried out as described in procedure D on allylic alcohol 4 (179 mg, 434 mmol). Flash column chromatography (SiO₂ hexane:ethyl acetate 4:1) afforded a mixture of two isomers as a white powder (74 mg, 0.218 mmol, 99%). m.p. 200-202° C. $\delta_H$ (CDCl₃) 0.81 (3H, s, CH₃), 1.13-1.56 (7H, m, alkyl H), 1.82-1.98 (3H, m, alkyl H), 2.16-2.43 (3H, m, alkyl H), 2.82-2.87 (2H, m, alkyl H), 5.27-5.32 (2H, m, CH₂OH), 4.53 (1H, s, OH), 5.27-5.32 (1H, m, olefinic H), 6.56 (1H, d, J=2.3, ArH-4), 6.63 (1H, dd, J=8.6, 2.3, ArH-2), 7.17 (1H, d, J=8.6, ArH-1); m/z (FAB⁺) 298.1 (M⁺, 75%), 281.1 (100%); HRMS (FAB⁺) calcd for $C_{20}H_{26}O_2$ 298.1933, found 298.1935.

[3-(tert-Butyl-dimethyl-silanyloxy)-13-methyl-7,8,9,11,12,13,14,15,16,17-decahydro-6H-cyclopenta[a]phenanthren-17-yl]-acetic acid ethyl ester 6

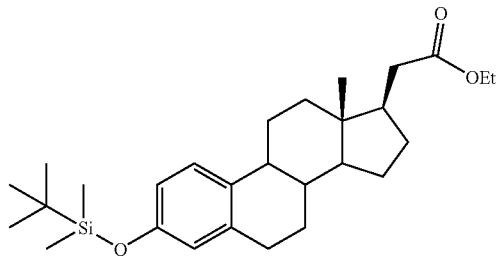

Procedure F

A solution of ester 2 (300 mg, 0.66 mmol) and 5% palladium on calcium carbonate (17 mg) in ethanol (5 ml) was stirred under an atmosphere of hydrogen overnight. The reaction mixture was filtered through a bed of Celite washed with ethanol. The filtrate was concentrated in vacuo.

Flash column chromatography (SiO$_2$ hexane:ethyl acetate 4:1) afforded the reduced product 6 as a white crystalline solid (233 mg, 0.51 mmol, 77%). m.p. 64-66° C. $\delta_H$ (CDCl$_3$) 0.18 [6H, s, Si(CH$_3$)$_2$)], 0.64 (3H, s CH$_3$), 0.97 [9H, s, C(CH$_3$)$_3$], 1.27 (3H, t, J=7.4, CH$_3$), 1.30-1.56 (5H, m, alkyl H), 1.73-2.42 (9H, m, alkyl H), 2.79-2.82 (2H, m, alkyl H), 4.13 (2H, q, J=7.4, CH$_2$), 6.54 (1H, d, J=2.7, ArH-4), 6.60 (1H, dd, J=8.6, 2.7, ArH-2), 7.11 (1H, d, J=8.6, ArH-1); m/z (FAB$^+$) 456.1 (M$^+$, 100%); HRMS (FAB$^+$) calcd for C$_{28}$H$_{44}$O$_3$Si 456.3060, found 456.3041.

Method: Tanabe et al. U.S. Pat. No. 6,281,205 B1. 2001. Anti-estrogenic steroids and associated pharmaceutical compositions and methods of use.

(3-Hydroxy-13-methyl-7,8,9,11,12,13,14,15,16,17-decahydro-6H-cyclopenta[a]phenanthren-17-yl)-acetic acid ethyl ester 7

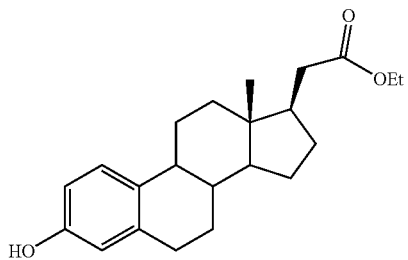

The reaction was carried out as described in procedure D using ester 6 (100 mg, 0.211 mmol). Flash column chromatography (SiO$_2$ hexane:ethyl acetate 4:1) afforded the phenol 7 as off white needles (56 mg, 0.164 mmol, 78%). m.p. 126-128° C. $\delta_H$ (CDCl$_3$) 0.63 (3H, s CH$_3$), 1.27 (3H, t, J=7.0, CH$_3$), 1.30-2.43 (14H, m, alkyl H), 2.78-2.84 (2H, m, alkyl H), 4.13 (2H, q, J=7.0, CH$_2$), 4.60 (1H, s, OH), 6.56 (1H, d, J=2.7, ArH-4), 6.62 (1H, dd, J=8.2, 2.7, ArH-2), 7.14 (1H, d, J=8.2, ArH-1). m/z (FAB$^+$) 342.1 (M$^+$, 100%); HRMS (FAB$^+$) calcd for C$_{22}$H$_{30}$O$_3$ 342.2195, found 342.2201.

2-(3-Hydroxy-13-methyl-6,7,8,9,11,12,13,14,15,16-decahydro-cyclopenta[a]phenanthren-17-ylidene)-propionic acid ethyl ester 8

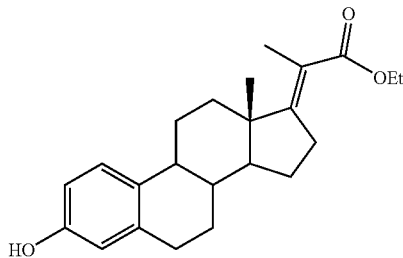

The reaction was carried out as described in procedure C using TBS estrone 1 (1 g, 2.6 mmol) and triethyl 2-phosphonopropionate (1.7 g, 1.53 ml, 7.14 mmol). Flash column chromatography (SiO$_2$ hexane:ethyl acetate 9:1) afforded a single isomer of the deprotected product 8 as a white powder (170 mg, 0.48 mmol, 18%). m.p. 113-115° C. $\delta_H$ (CDCl$_3$) 0.91 (3H, s CH$_3$), 1.40 (3H, t, J=6.6, CH$_3$), 1.43-1.68 (7H, m, alkyl H), 1.91-2.28 (6H, m, alkyl H), 2.37-2.42 (2H, m, alkyl H), 2.87-2.91 (2H, m, CH$_2$), 4.00 (2H, q, J=7.0, CH$_2$), 6.64 (1H, d, J=2.7, ArH-4), 6.71 (1H, dd, J=8.6, 2.7, ArH-2), 7.19 (1H, d, J=8.6, ArH-1).

[3-(tert-Butyl-dimethyl-silanyloxy)-13-methyl-6,7,8,9,11,12,13,14,15,16-decahydro-cyclopenta[a]phenanthren-17-ylidene]-acetonitrile 9

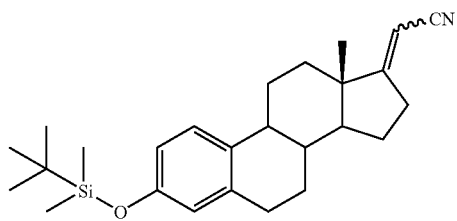

The reaction was carried out as described in procedure C using TBS estrone 1 (5 g, 13.0 mmol) and diethyl(cyanomethyl)phosphonate (4.02 g, 4.4 ml, 22.7 mmol). TLC and $^1$H NMR of the crude reaction mixture following work up indicated that the starting material was no longer present and that the product was a mixture of two isomers 9 in a ratio of 6:1. This mixture was used without further purification.

(3-Hydroxy-13-methyl-6,7,8,9,11,12,13,14,15,16-decahydro-cyclopenta[a]phenanthren-17-ylidene) acetonitrile 10

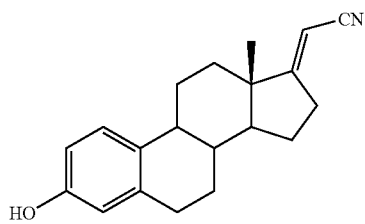

The reaction was carried out as described in procedure D on silyl ether 9 (100 g, 0.246 mmol). Flash column chromatography (SiO$_2$ hexane:ethyl acetate 4:1) afforded a single isomer of the phenol 10 as a white powder (53 mg, 0:18 mmol, 73%). m.p. 264-266° C. $\delta_H$ (DMSO) 0.84 (3H, s CH$_3$), 1.24-1.50 (8H, m, alkyl H), 1.82-1.87 (2H, m, alkyl H), 1.93-1.97 (1H, m, alkyl H), 2.09-2.16 (1H, m, alkyl H), 2.18-2.34 (1H, m, alkyl H), 2.66-2.77 (2H, m, alkyl H), 5.37 (1H, m, olefinic H), 6.44 (1H, d, J=2.64, ArH-4), 6.51 (1H, dd, J=8.2, 2.6, ArH-2), 7.06 (1H, d, J=8.2, ArH-1), 9.02 (1H, s, OH); m/z (FAB$^+$) 293.1 (M$^+$, 100%); HRMS (FAB$^+$) calcd for C$_{20}$H$_{23}$ON 293.1780, found 293.1783.

13-Methyl-17-methylene-7,8,9,11,12,13,14,15,16, 17-decahydro-6H-cyclopenta[a]phenanthren-3-ol 11

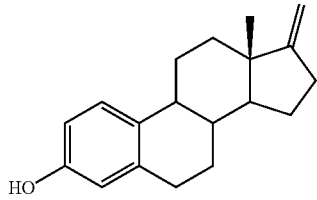

Potassium tert-butoxide (220 mg, 1.96 mmol) was added to dry THF (5 ml) and stirred for 10 minutes to complete dissolution of the salt. Methyl triphenylphosphonium bromide (700 mg, 1.96 mmol) was added portionwise to the salt solution. Estrone (500 mg, 1.85 mmol) was dissolved in THF (5 ml) and added dropwise via a syringe to the bright yellow solution. After stirring at room temperature for 2 h, the reaction was heated at reflux overnight. The reaction was cooled, water added (10 ml) and the mixture extracted using ethyl acetate (3×10 ml). The combined organic fractions were combined, washed with water (2×10 ml) and brine (10 ml), dried ($Na_2SO_4$) and concentrated in vacuo. Flash column chromatography ($SiO_2$ hexane:ethyl acetate 9:1) and recrystallisation from toluene/hexane afforded alkene 11 as a white crystalline solid (53 mg, 0.198 mmol, 11%). m.p. 130-132° C. (lit. m.p. 134-137° C.). $\delta_H$ (CDCl$_3$) 0.82 (3H, s CH$_3$), 1.20-1.62 (6H, m, alkyl H), 1.78-1.85 (1H, m, alkyl H), 1.90-1.99 (2H, m, alkyl H), 2.16-2.38 (3H, m, alkyl H), 2.50-2.59 (1H, m, alkyl H), 2.78-2.92 (2H, m, alkyl H), 4.50 (1H, s, OH), 4.67 (2H, t, J=2.0, olefinic H), 6.57 (1H, d, J=2.7, ArH-4), 6.63 (1H, dd, J=8.6, 2.7, ArH-2), 7.17 (1H, d, J=8.6, ArH-1).

Method: Williams, Preparation of Alkenes, Oxford University Press, 1996, p 32. m.p.: Forcellese et al. J. Org. Chem. 46: 1981, 3326-3328.

3-(tert-Butyl-dimethyl-silanyloxy)-2-ethyl-13-methyl-6,7,8,9,11,12,13,14,15,16-decahydro-cyclopenta[a]phenanthren-17-one 12

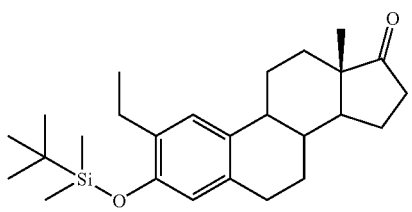

The reaction was carried out as described in procedure B using 2-ethyl estrone (4 g, 13.4 mmol). Flash column chromatography ($SiO_2$ hexane:ethyl acetate 9:1) afforded the silyl ether 12 as a white crystalline solid (5.02 g, 12.2 mmol, 91%). $\delta_H$ (CDCl$_3$) 0.24 [6H, s, Si(CH$_3$)$_2$], 0.98 (3H, s, CH$_3$), 1.01 [9H, s, C(CH$_3$)$_3$], 1.17 (3H, t, J=7.8, CH$_3$), 1.40-1.66 (6H, m, alkyl H), 1.94-2.52 (7H, m, alkyl H), 2.57 (2H, q, J=7.8, CH$_2$), 2.82-2.86 (2H, m, alkyl H), 6.50 (1H, s, ArH), 7.06 (1H, s, ArH).

[3-(tert-Butyl-dimethyl-silanyloxy)-2-ethyl-13-methyl-6,7,8,9,11,12,13,14,15,16-decahydro-cyclopenta[a]phenanthren-17-ylidene]-acetic acid ethyl ester 13

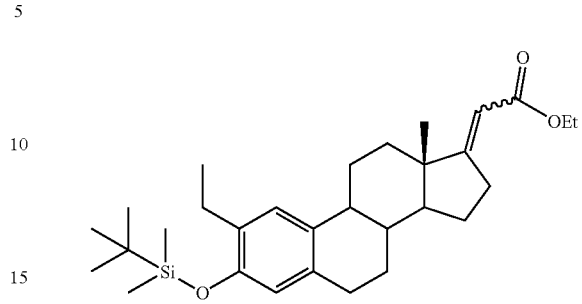

The reaction was carried out as described in procedure C using silyl ether 12 (412 mg, 1 mmol) and triethylphosphonoacetate (271 mg, 240 µl, 1.2 mmol). Flash column chromatography ($SiO_2$ hexane:ethyl acetate 19:1) afforded the two isomers 13 as a colourless oil (290 mg, 0.602 mmol, 60%). The ratio of isomers was determined to be 6:1 from $^1$H NMR. $\delta_H$ (CDCl$_3$) 0.22 [6H, s, Si(CH$_3$)$_2$], 0.97 (3H, s CH$_3$), 1.00 [9H, s, C(CH$_3$)$_3$], 1.17 (3H, t, J=7.8, CH$_3$), 1.29 (3H, t, J=7.0, CH$_3$), 1.59-2.44 (11H, m, alkyl H), 2.56 (2H, q, J=7.8, CH$_2$), 2.76-2.92 (4H, m, alkyl H), 4.15 (2H, q, J=7.0, CH$_2$), 5.62 (1H, t, J=2.0, olefinic H), 6.48 (1H, s, ArH), 7.06 (1H, s, ArH); m/z (FAB$^+$) 482.1 (M$^+$, 90%), 73.0 (100%); HRMS (FAB$^+$) calcd for C$_{30}$H$_{46}$O$_3$Si 482.3216, found ??.

Z- and E-(2-Ethyl-3-hydroxy-13-methyl-6,7,8,9,11, 12,13,14,15,16-decahydro-cyclopenta[a]phenanthren-17-ylidene)acetic acid ethyl ester 14a and 14b

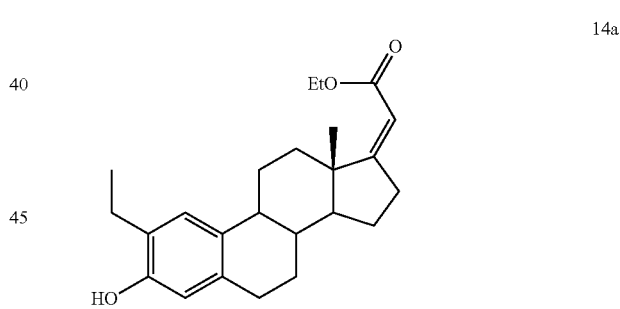

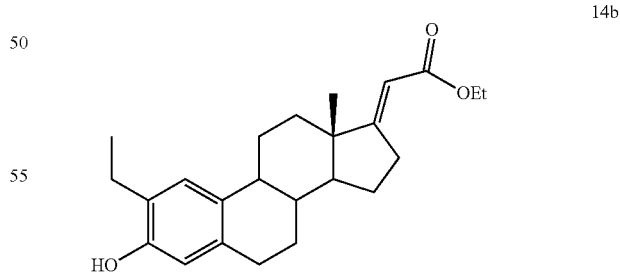

The reaction was carried out as described in procedure D using ester 13 (290 mg, 0.639 mmol). Flash column chromatography ($SiO_2$ hexane:ethyl acetate 19:1) afforded the Z-isomer 14a as a white powder (28 mg, 0.0757 mmol, 12%). m.p. 157-159° C. $\delta_H$ (CDCl$_3$) 1.04 (3H, s CH$_3$), 1.22 (3H, t, J=7.4, CH$_3$), 1.29 (3H, t, J=7.0, CH$_3$), 1.35-2.48 (13H, m, alkyl H), 2.60 (2H, q, J=7.4, CH$_2$), 2.78-2.84 (2H, m, alkyl H), 4.09-

4.12 (2H, m, CH$_2$), 4.46 (1H, s, OH), 5.68 (1H, t, J=2.0, olefinic H), 6.50 (1H, s, ArH), 1.04 (1H, s, ArH); m/z (FAB$^+$) 368.1 (M$^+$, 100%); HRMS (FAB$^+$) calcd for C$_{24}$H$_{32}$O$_3$ 368.2351, found 368.2364.

Further elution afforded the E isomer 14b as a pale yellow oil (184 mg, 0.497 mmol, 78%). $\delta_H$ (CDCl$_3$) 0.86 (3H, s CH$_3$), 1.23 (3H, t, J=7.4, CH$_3$), 1.29 (3H, t, J=7.0, CH$_3$), 1.33-2.45 (11H, m, alkyl H), 2.60 (2H, q, J=7.4, CH$_2$), 2.74-2.91 (4H, m, alkyl H), 4.15 (2H, q, J=7.0, CH$_2$), 4.52 (1H, s, OH), 5.59 (1H, t, J=2.3, olefinic H), 6.51 (1H, s, ArH), 7.06 (1H, s, ArH).

(2-Ethyl-13-methyl-3-sulfamoyloxy-6,7,8,9,11,12,13,14,15,16-decahydro-cyclopenta[a]phenanthren-17-ylidene)-acetic acid ethyl ester 15

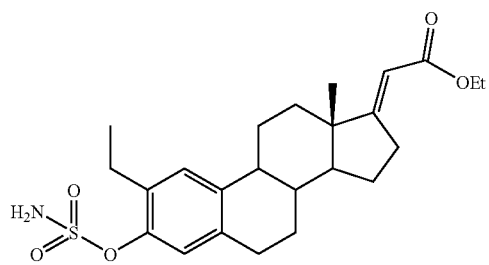

The reaction was carried out as described in procedure A using ester 14b (132 mg, 0.357 mmol). Preparative HPLC was used to purify the sulfamate 15 as a white solid (28 mg, 0.0757 mmol, 21%). $\delta_H$ (d$_6$-acetone) 0.91 (3H, s CH$_3$), 1.18 (3H, t, J=7.7, CH$_3$), 1.23 (3H, t, J=7.2, CH$_3$), 1.28-1.65 (6H, m, alkyl H), 1.86-2.08 (5H, m, alkyl H), 2.24-2.34 (1H, m, alkyl H), 2.47-2.54 (1H, m, alkyl H), (2H, q, J=7.7, CH$_2$), 2.81-2.89 (2H, m, alkyl H), 4.10 (2H, q, J=7.2, CH$_2$), 5.56 (1H, t, J=2.5, olefinic H), 7.09 (1H, s, ArH), 7.26 (1H, s, ArH).

2-[3-(tert-Butyl-dimethyl-silanyloxy)-2-ethyl-13-methyl-6,7,8,9,11,12,13,14,15,16-decahydro-cyclopenta[a]phenanthren-17-ylidene]-ethanol 16

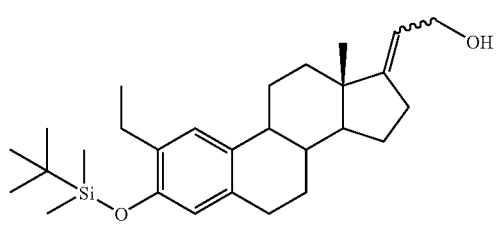

The reaction was carried out as described in procedure E using ester 14b (412 mg, 1 mmol). Both TLC and $^1$H NMR indicated that starting material was not present and the product vinylic alcohol 16 was used without further purification.

Z- and E-2-Ethyl-17-(2-hydroxy-ethylidene)-13-methyl-7,8,9,11,12,13,14,15,16,17-decahydro-6H-cyclopenta[a]phenanthren-3-ol 17a and 17b

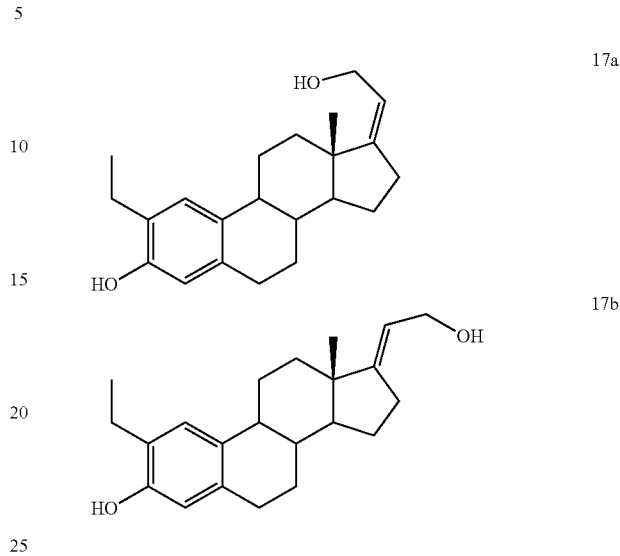

The reaction was carried out as described in procedure D using vinylic alcohol 16 (520 mg, 1.18 mmol). Flash column chromatography (SiO$_2$ hexane:ethyl acetate 19:1) afforded the Z-phenol 17a as a white powder (27 mg, 0.0831 mmol, 7%). m.p. 205-207° C. $\delta_H$ (CDCl$_3$) 0.93 (3H, s CH$_3$), 1.23 (3H, t, J=7.4, CH$_3$), 1.26-1.61 (5H, m, alkyl H), 1.72-1.79 (2H, m, alkyl H), 1.89-1.92 (1H, m, alkyl H), 2.18-2.39 (4H, m, alkyl H), 2.47-2.53 (1H, m, alkyl H), 2.60 (2H, q, J=7.4, CH$_2$), 2.74-2.87 (2H, m, alkyl H), 4.21 (1H, dd, J=7.0, 12.1, CHOH), 4.35 (1H, dd, J=12.1, 7.0, CHOH), 4.62 (1H, s, OH), 5.33-5.37 (1H, m, olefinic H), 6.50 (1H, s, ArH), 7.04 (1H, s, ArH); m/z (FAB$^+$) 326.1 (M$^+$, 100%); HRMS (FAB$^+$) calcd for C$_{22}$H$_{30}$O$_2$ 326.2246, found 326.2259.

Further elution afforded the E-phenol 17b as a white powder (245 mg, 0.754 mmol, 64%). m.p. 169-171° C. $\delta_H$ (CDCl$_3$) 0.79 (3H, s CH$_3$), 1.21 (3H, t, J=7.4, CH$_3$), 1.27-1.61 (5H, m, alkyl H), 1.74-1.97 (3H, m, alkyl H), 2.20-2.48 (5H, m, alkyl H), 2.59 (2H, q, J=7.4, CH$_2$), 2.77-2.83 (2H, m, alkyl H), 4.11-4.60 (2H, m, CH$_2$OH), 4.50 (1H, s, OH), 5.26-5.37 (1H, m, olefinic H), 6.48 (1H, s, ArH), 7.06 (1H, s, ArH); m/z (FAB$^+$) 326.1 (M$^+$, 50%), 73.0 (100%); HRMS (FAB$^+$) calcd for C$_{22}$H$_{30}$O$_2$ 326.2246, found 326.2256.

Sulfamic acid 2-ethyl-13-methyl-17-vinyl-7,8,9,11,12,13,14,15-octahydro-6H-cyclopenta[a]phenanthren-3-yl ester 18

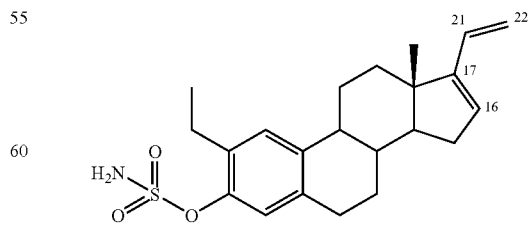

The reaction was carried out as described in procedure A using 17b (65 mg, 0.200 mmol). Flash column chromatography (SiO$_2$ CHCl$_3$) afforded sulfamate 18 as a colourless oil (36 mg, 0.093 mmol, 47%). $\delta_H$ (CDCl$_3$) 0.91 (3H, s CH$_3$), 1.21 (3H, t, J=7.4, CH$_3$), 1.27-1.55 (2H, m, alkyl H), 1.61-1.73 (4H, m, alkyl H), 1.85-2.07 (2H, m, alkyl H), 2.18-2.39 (4H, m, alkyl H), 2.69 (2H, q, J=7.4, CH$_2$), 2.83-2.92 (2H, m, alkyl H), 4.88-4.97 (1H, m, olefinic H-16), 4.99 (2H, s NH$_2$), 5.35 (1H, d, J=18.0, olefinic H-22), 5.73 (1H, br s, olefinic H-22), 6.32 (1H, dd, J=18.0, 11.4, olefinic H-21), 7.10 (1H, s, ArH), 7.18 (1H, s, ArH).

2-Ethyl-17-(2-hydroxy-ethyl)-13-methyl-7,8,9,11,12,13,14,15,16,17-decahydro-6H-cyclopenta[a]phenanthren-3-ol 19

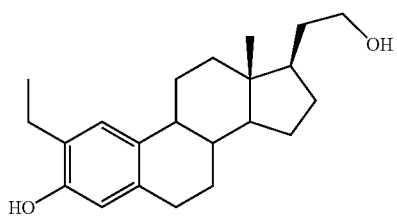

The reaction was carried out as described in procedure F using vinylic alcohol 16 (76 mg, 0.233 mmol). Flash column chromatography (SiO$_2$ hexane:ethyl acetate 5:1) afforded the diol 19 as a white powder (51 mg, 0.155 mmol, 67%). m.p. 162-164° C. $\delta_H$ (CDCl$_3$) 0.63 (3H, s CH$_3$), 1.22 (3H, t, J=7.4, CH$_3$), 1.24-1.50 (10H, m, alkyl H), 1.72-1.88 (4H, m, alkyl H), 2.15-2.32 (2H, m, alkyl H), 2.59 (2H, q, J=7.4, CH$_2$), 2.76-2.81 (2H, m, alkyl H), 3.61-3.75 (2H, m, CH$_2$OH), 5.0 (1H, s, OH), 6.49 (1H, s, ArH), 7.05 (1H, s, ArH); $\delta_C$ (CDCl$_3$) 12.6 (CH$_3$), 14.4 (CH$_3$), 23.0 (CH$_2$), 24.4 (CH$_2$), 26.5 (CH$_2$), 27.9 (CH$_2$), 28.4 (CH$_2$), 29.3 (CH$_2$), 33.7 (CH$_2$), 37.8 (CH$_2$), 38.9 (OH), 42.5 (C), 44.2 (CH), 47.2 (CH), 54.7 (CH), 62.7 (CH$_2$), 115.2 (CH), 126.3 (CH), 127.1 (C), 132.8 (C), 135.5 (C), 151.1 (C). m/z (FAB$^+$) 328.1 (M$^+$, 100%); HRMS (FAB$^+$) calcd for C$_{22}$H$_{32}$O$_2$ 328.2402, found 328.2407.

Sulfamic acid 2-ethyl-13-methyl-17-(2-sulfamoyloxy-ethyl)-7,8,9,11,12,13,14,15,16,17-decahydro-6H-cyclopenta[a]phenanthren-3-yl ester 20

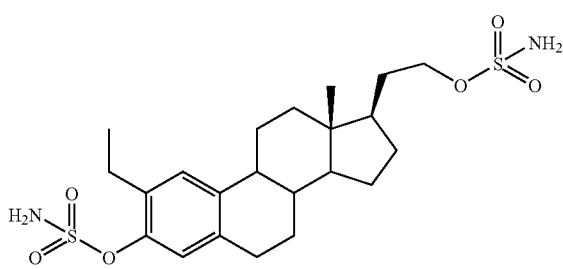

The reaction was carried out as described in procedure A using diol 19 (35 mg, 0.107 mmol); Preparative HPLC was used to purify the sulfamate 20 as a white solid (28 mg, 0.0576 mmol, 54%). $\delta_H$ (d$_6$-acetone) 0.69 (3H, s CH$_3$), 1.18 (3H, t, J=7.4, CH$_3$), 1.29-1.62 (10H, m, alkyl H), 1.76-1.42 (6H, m, alkyl H), 1.70 (2H, q, J=7.4, CH$_2$), 2.80-2.84 (2H, m, alkyl H), 4.16-4.18 (2H, m, CH$_2$), 6.63 (2H, s, NH$_2$), 7.09 (1H, s, ArH), 7.13 (2H, s, NH$_2$), 7.24 (1H, s, ArH); m/z (FAB−) 485.1 [(M−H)$^+$, 100%]; HRMS (FAB$^+$) calcd for C$_{22}$H$_{34}$O$_6$N$_2$S$_2$ 486.1858, found 486.1854.

[3-(tert-Butyl-dimethyl-silanyloxy)-2-ethyl-13-methyl-7,8,9,11,12,13,14,15,16,17-decahydro-6H-cyclopenta[a]phenanthren-17-yl]-acetic acid ethyl ester 21

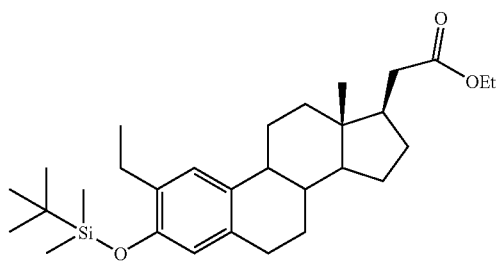

The reaction was carried out as described in procedure F using ester 13 (100 mg, 0.220 mmol). $^1$H NMR indicated that starting material was not present and the product ester 21 was used without further purfication.

(2-Ethyl-3-hydroxy-13-methyl-7,8,9,11,12,13,14,15,16,17-decahydro-6H-cyclopenta[a]phenanthren-17-yl)-acetic acid ethyl ester 22

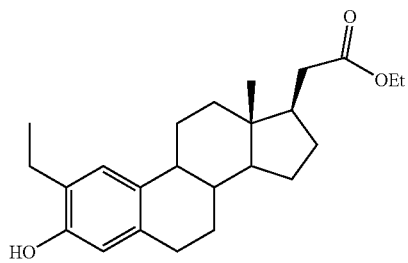

The reaction was carried out as described in procedure D using ester 21 (66 mg, 0.145 mmol). Flash column chromatography (SiO$_2$ hexane:ethyl acetate 19:1) afforded the saturated ester 22 as a colourless oil (38 mg, 0.103 mmol, 71%). $\delta_H$ (CDCl$_3$) 0.63 (3H, s CH$_3$), 1.22 (3H, t, J=7.4, CH$_3$), 1.27 (3H, t, J=7.4, CH$_3$), 1.24-2.00 (11H, m, alkyl H), 2.12-2.22 (3H, m, alkyl H), 2.27-2.33 (1H, m, alkyl H), 2.41 (1H, dd, J=14.5, 5.1, alkyl H), 2.59 (2H, q, J=7.4, CH$_2$), 2.73-2.81 (2H, m, alkyl H), 4.13 (2H, q, J=7.4, CH$_2$), 4.62 (1H, s, OH), 6.49 (1H, s, ArH), 7.06 (1H, s, ArH); m/z (FAB) 370.2 (M$^+$, 100%); HRMS (FAB$^+$) calcd for C$_{24}$H$_{34}$O$_3$ 370.2508, found 370.2537.

(2-Ethyl-13-methyl-3-sulfamoyloxy-7,8,9,11,12,13,14,15,16,17-decahydro-6H-cyclopenta[a]phenanthren-17-yl)-acetic acid ethyl ester 23

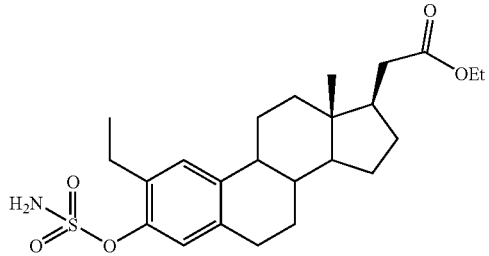

The reaction was carried out as described in procedure A using ester 22 (100 mg, 0.270 mmol). Flash column chromatography (SiO₂ hexane:ethyl acetate 9:1) afforded the sulfamate 23 as a white powder (83 mg, 0.185 mmol, 68%). m.p. 120-122° C. $\delta_H$ (CDCl₃) 0.63 (3H, s CH₃), 1.21 (3H, t, J=7.4, CH₃), 1.27 (3H, t, J=7.0, CH₃), 1.24-1.50 (7H, m, alkyl H), 1.74-1.98 (5H, m, alkyl H), 2.11-2.42 (4H, m, alkyl H), 2.68 (2H, q, J=7.4, CH₂), 2.82-2.84 (2H, m, alkyl H), 4.12 (2H, q, J=7.0, CH₂), 5.08 (2H, s, NH₂), 7.05 (1H, s, ArH), 7.16 (1H, s, ArH). $\delta_C$ (CDCl₃) 12.5, 14.2, 14.6, 23.0, 24.2, 26.2, 27.5, 28.2, 29.2, 35.4, 37.3, 38.4, 42.3, 44.2, 46.9, 54.3, 60.2, 121.4, 126.9, 133.6, 136.0, 139.6, 146.1, 174.0; m/z (FAB) 449.1 (M⁺, 10%), 135.0 (100%); HRMS (FAB⁺) calcd for C₂₄H₃₅O₅NS 449.2236, found 449.2237.

[3-(tert-Butyl-dimethyl-silanyloxy)-2-ethyl-13-methyl-6,7,8,9,11,12,13,14,15,16-decahydro-cyclopenta[a]phenanthren-17-ylidene]-acetonitrile 24

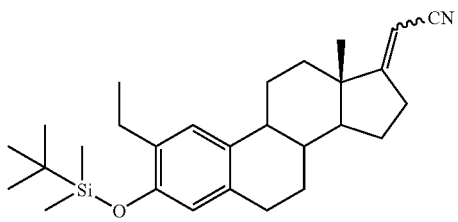

The reaction was carried out as described in procedure C using silyl ether 12 (1 g, 2.6 mmol) and diethyl(cyanomethyl)phosphonate (691 mg, 631 μl, 3.9 mmol). Flash column chromatography (SiO₂ hexane:ethyl acetate 20:1) afforded the two isomers 24 as a colourless oil (641 mg, 1.47 mmol, 57%). m/z (FAB) 435.3 (M⁺, 100%); HRMS (FAB⁺) calcd for C₂₈H₄₁ONSi 435.2957, found 435.2961.

(2-Ethyl-3-hydroxy-13-methyl-6,7,8,9,11,12,13,14,15,16-decahydro-cyclopenta[a]phenanthren-17-ylidene)-acetonitrile 25

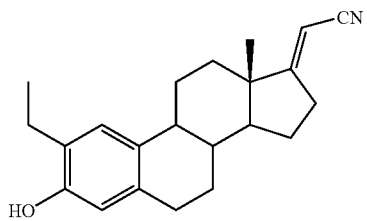

The reaction was carried out as described in procedure D using silyl ether 24 (540 mg, 1.24 mmol). Flash column chromatography (SiO₂ hexane:ethyl acetate 4:1) afforded the phenol 25 as a pale yellow oil (284 mg, 0.88 mmol, 71%). $\delta_H$ (CDCl₃) 0.88 (3H, s CH₃), 1.22 (3H, t, J=7.4, CH₃), 1.25-1.62 (6H, m, alkyl H), 1.90-1.97 (3H, m, alkyl H), 2.18-2.24 (1H, m, alkyl H), 2.40-2.45 (1H, m, alkyl H), 2.59 (2H, q, J=7.4, CH₂), 2.63-2.84 (4H, m, alkyl H), 4.53 (1H, s, OH), 5.04 (1H, t, J=2.3, olefinic H), 6.49 (1H, s, ArH), 7.02 (1H, s, ArH); $\delta_H$ (CDCl₃) 14.4 (CH₃), 18.0 (CH₃), 23.0 (CH₃), 23.5 (CH₂), 26.3 (CH₂), 27.4 (CH₂), 29.1 (CH₂), 30.3 (CH₂), 34.7 (CH₂), 38.5 (CH), 43.7 (CH), 46.4 (C), 52.8 (CH), 87.7 (CH), 115.2 (CH), 117.5 (C), 126.2 (CH), 127.4 (C), 131.7 (C), 135.2 (C), 151.4 (C), 181.1 (C); m/z (FAB) 321.3 (M⁺, 100%); HRMS (FAB⁺) calcd for C₂₂H₂₇ON 321.2093, found 321.2088.

[3-(tert-Butyl-dimethyl-silanyloxy)-2-ethyl-13-methyl-7,8,9,11,12,13,14,15,16,17-decahydro-6H-cyclopenta[a]phenanthren-17-yl]-acetonitrile 26

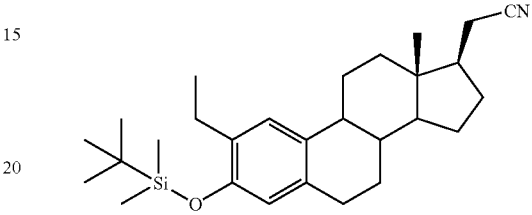

The reaction was carried out as described in procedure F using silyl ether 24 (100 mg, 0.230 mmol). Flash column chromatography (SiO₂ hexane:ethyl acetate 19:1) afforded the saturated nitrile 26 as a colourless oil (81 mg, 0.185 mmol, 81%). $\delta_H$ (CDCl₃) 0.22 [6H, s, Si(CH₃)₂], 0.67 (3H, s CH₃), 1.00 [9H, s, C(CH₃)₃], 1.16 (3H, t, J=7.4, CH₃), 1.26-1.53 (7H, m, alkyl H), 1.78-2.17 (5H, m, alkyl H), 2.20-2.29 (2H, m, alkyl H), 2.31-2.40 (2H, m, CH₂CN), 2.56 (2H, q, J=7.4, CH₂), 2.74-2.81 (2H, m, alkyl H), 6.47 (1H, s, ArH), 7.04 (1H, s, ArH); m/z (FAB) 437.4 (M⁺, 100%); HRMS (FAB⁺) calcd for C₂₈H₄₃OSiN 437.3114, found 437.3121.

(2-Ethyl-3-hydroxy-13-methyl-7,8,9,11,12,13,14,15,16,17-decahydro-6H-cyclopenta[a]phenanthren-17-yl)-acetonitrile 27

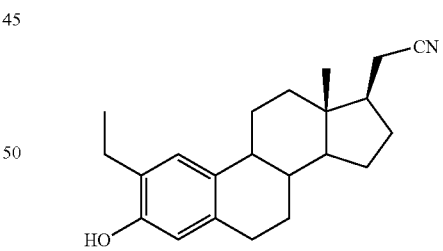

The reaction was carried out as described in procedure D using nitrile 26 (73 mg, 0.167 mmol). Flash column chromatography (SiO₂ hexane:ethyl acetate 9:1) afforded the phenol 27 as a white solid (38 mg, 0.118 mmol, 70%). m.p. 195-197° C. $\delta_H$ (CDCl₃) 0.67 (3H, s CH₃), 1.22 (3H, t, J=7.4, CH₃), 1.27-1.53 (7H, m, alkyl H), 1.74-1.89 (3H, m, alkyl H), 1.99 (1H, dt, J=12.1, 3.1, alkyl H), 2.03-2.12 (1H, m, alkyl H), 2.14-2.42 (4H, m, alkyl H), 2.59 (2H, q, J=7.4, CH₂), 2.75-2.86 (2H, m, alkyl H), 4.67 (1H, s OH), 6.49 (1H, S, ArH), 7.04 (1H, s, ArH); m/z (FAB) 323.2 (M⁺, 100%); HRMS (FAB⁺) calcd for C₂₂H₂₉ON 323.2249, found 323.2252.

Sulfamic acid 17-cyanomethyl-2-ethyl-13-methyl-7,8,9,11,12,13,14,15,16,17-decahydro-6H-cyclopenta[a]phenanthren-3-yl ester 28 (STX 564)

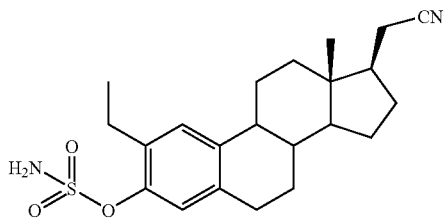

The reaction was carried out as described in procedure A using phenol 27 (182 mg, 0.591 mmol). Flash column chromatography (CHCl$_3$) afforded the sulfamate 28 as white needles (120 mg, 0.299 mmol, 51%). m.p. 175-177° C. $\delta_H$ (d$_6$-acetone) 0.73 (3H, s CH$_3$), 1.17 (3H, t, J=7.4, CH$_3$), 1.26-1.56 (7H, m, alkyl H), 1.77-2.13 (5H, m, alkyl H), 2.26-2.58 (3H, m, alkyl H), 2.69 (2H, q, J=7.4, CH$_2$), 2.80-2.83 (2H, m, alkyl H), 7.08 (1H, s, ArH), 7.12 (2H, s, NH$_2$), 7.23 (1H, s, ArH); m/z (FAB) 402.0 (M$^+$, 100%); HRMS (FAB$^+$) calcd for C$_{22}$H$_{30}$O$_3$N$_2$S 402.1977, found 402.1975.

[3-(tert-Butyl-dimethyl-silanyloxy)-2-methoxy-13-methyl-6,7,8,9,11,12,13,14,15,16-decahydro-cyclopenta[a]phenanthren-17-ylidenemethyl]-methylene-amine 29

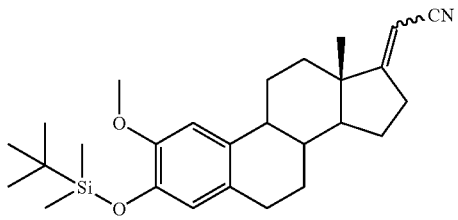

The reaction was carried out as described in procedure C using 2-methoxy-3-tert-butyldimethylsilyloxyestrone (1 g, 2.42 mmol) and diethyl(cyanomethyl)phosphonate (712 g, 650 µl, 4.02 mmol). Flash column chromatography (SiO$_2$ hexane:ethyl acetate 19:1) afforded the two isomeric alkenes 29 as a colourless oil (481 mg, 1.14 mmol, 27%). The ratio of the two isomers was determined from NMR to be 1:1. m/z (FAB$^+$) 438.1 [(MH)$^+$, 50%], 380.1 (100%), 73.0 (80%); HRMS (FAB$^+$) calcd for C$_{27}$H$_{39}$O$_2$NSi 437.2750, found 437.2731.

Z- and E-(3-Hydroxy-2-methoxy-13-methyl-6,7,8,9,11,12,13,14,15,16-decahydro-cyclopenta[a]phenanthren-17-ylidene)-acetonitrile 30

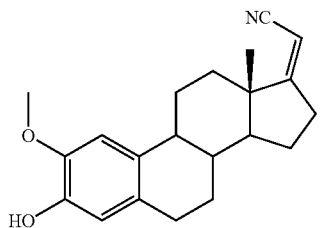

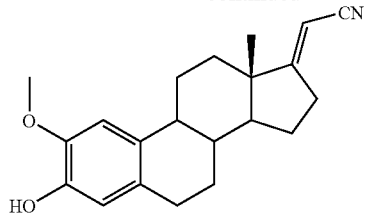

The reaction was carried out as described in procedure D using silyl ether 29 (400 mg, 0.95 mmol). Flash column chromatography (SiO$_2$ hexane:ethyl acetate 9:1) afforded a mixture of the two isomers as a white powder (91 mg, 0.281 mmol, 30%).

Further elution afforded the E isomer 30 as a white solid (115 mg, 0.356 mmol, 37%). $\delta_H$ (CDCl$_3$) 0.89 (3H, s CH$_3$), 1.25-1.64 (6H, m, alkyl H), 1.90-1.99 (3H, m, alkyl H), 2.22-2.27 (1H, m, alkyl H), 2.35-2.40 (1H, m, alkyl H), 2.60-2.69 (1H, m, alkyl H), 2.74-2.82 (3H, m alkyl H), 3.86 (3H, s OCH$_3$), 5.05 (1H, t, J=2.7, olefinic H), 5.43 (1H, s, OH), 6.65 (1H, s, ArH), 6.77 (1H, s, ArH); m/z (FAB$^+$) 323.1 (M$^+$, 100%); HRMS (FAB$^+$) calcd for C$_{21}$H$_{25}$O$_2$N 323.1885, found 323.1885.

Sulfamic acid 2-methoxy-13-methyl-17-methylene-aminomethylene-7,8,9,11,12,13,14,15,16,17-decahydro-6H-cyclopenta[a]phenanthren-3-yl ester 31 (STX 639)

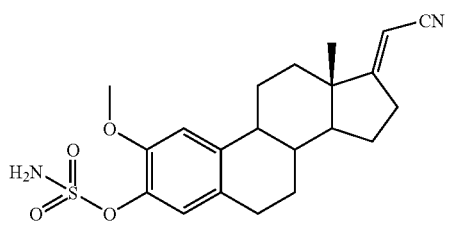

The reaction was carried out as described in procedure A using phenol 30 (40 mg, 0.124 mmol). Flash column chromatography (SiO$_2$ hexane:ethyl acetate 4:1) afforded the sulfamate 31 as white needles (36 mg, 0.0896 mmol, 72%). m.p. 202-204° C. $\delta_H$ (d$_6$-acetone) 0.95 (3H, s CH$_3$), 1.25-1.65 (7H, m, alkyl H), 1.94-2.08 (2H, m, alkyl H), 2.26-2.35 (1H, m, alkyl H), 2.46-2.66 (2H, m, alkyl H), 2.74-2.84 (3H, m, alkyl H), 3.84 (3H, s OCH$_3$), 5.27 (1H, t, J=2.3, olefinic H), 6.90 (2H, s, NH$_2$), 7.02 (1H, s, ArH), 7.04 (1H, s, ArH); m/z (FAB$^+$) 402.0 (M$^+$, 100%); HRMS (FAB$^+$) calcd for C$_{21}$H$_{26}$O$_4$N$_2$S 402.1613, found 402.1611.

(3-Hydroxy-2-methoxy-13-methyl-7,8,9,11,12,13,14,15,16,17-decahydro-6H-cyclopenta[a]phenanthren-17-yl)-acetonitrile 32

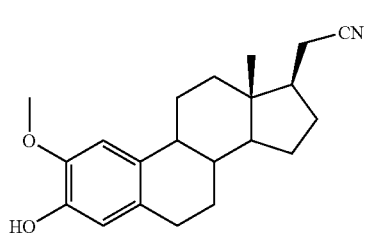

The reaction was carried out as described in procedure F using alkene 30 (100 mg, 0.310 mmol). Flash column chromatography (SiO$_2$ hexane:ethyl acetate 4:1) afforded the saturated nitrile 32 as a white solid (81 mg, 0.249 mmol, 80%). m.p. 172-174° C. $\delta_H$(d$_6$-acetone) 0.71 (3H, s CH$_3$), 1.22-1.52 (7H, m, alkyl H), 1.73-1.90 (3H, m, alkyl H), 1.98-2.08 (2H, m, alkyl H), 2.14-2.22 (1H, m, alkyl H), 2.30-2.39 (2H, m, alkyl H), 2.45-2.54 (1H, m, alkyl H), 2.65-2.80 (2H, m, alkyl H), 3.80 (3H, s OCH$_3$), 6.52 (1H, s, ArH), 6.84 (1H, s, ArH), 8.00 (1H, s, OH). m/z [FAB+] 325 (100%, M$^+$); HRMS [FAB+] found 325.20418, C$_{21}$H$_{27}$NO$_2$ requires 325.20418; Calculated C, 77.5%; H, 8.36%; N, 4.30%. Found C, 77.2%; H, 8.41%; N, 4.01%.

Sulfamic acid 17-cyanomethyl-2-methoxy-13-methyl-7,8,9,11,12,13,14,15,16,17-decahydro-6H-cyclopenta[a]phenanthren-3-yl ester 33 (STX 641)

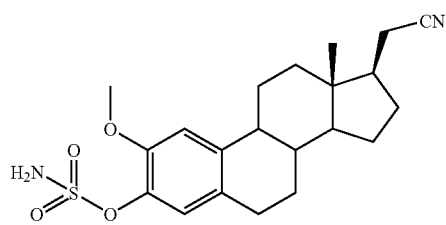

The reaction was carried out as described in procedure A using nitrile 32 (60 mg, 0.185 mmol). Flash column chromatography (SiO$_2$ hexane:ethyl acetate 4:1) and recrystallisation from acetone/hexane afforded the sulfamate 33 as a white crystalline solid (20.3 mg, 0.0547 mmol, 30%). m.p. 183-185° C. $\delta_H$(CDCl$_3$) 0.69 (3H, s CH$_3$), 1.20-1.55 (7H, m, alkyl H), 1.70-1.94 (3H, m, alkyl H), 1.98-2.50 (6H, m, alkyl H), 2.74-2.84 (2H, m, alkyl H), 3.87 (3H, s OCH$_3$), 5.06 (2H, s, NH$_2$), 6.92 (1H, s, ArH), 7.04 (1H, s, ArH); $\delta_C$ (CDCl$_3$) 12.2 (CH$_3$), 17.6 (CH$_2$), 23.9 (CH$_2$), 26.3 (CH$_2$), 27.4 (CH$_2$), 28.3 (CH$_2$), 28.6 (CH$_2$), 37.3 (CH$_2$), 38.3 (CH), 42.5 (C), 44.3 (CH), 46.7 (CH), 54.4 (CH), 56.4 (CH$_3$), 110.4 (CH), 119.5 (C), 124.2 (CH), 130.2 (C), 138.2 (C), 140.4 (C), 149.0 (C); m/z (FAB$^+$) 404.1 (M$^+$, 100%); HRMS (FAB$^+$) calcd for C$_{21}$H$_{28}$O$_4$N$_2$S 404.1770, found 404.1767; C$_{21}$H$_{28}$O$_4$N$_2$S requires C, 62.35%; H, 6.98%; N, 6.93%. found C, 62.50%; H, 6.96%; N, 6.85%.

3-O-(tert-Butyl-dimethyl-silyl)-17-(2-Dimethylamino-ethylamino)-estrone 34

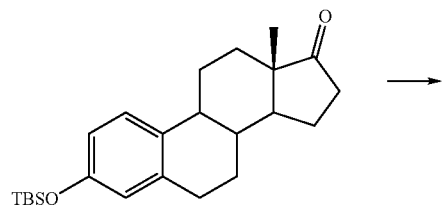

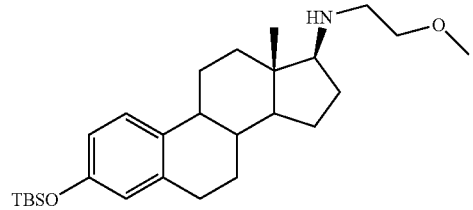

To a solution of 3-OTBS estrone (200 mg, 0.52 mmol) in THF (20 mL) was added 2-methoxyethylamine (226 μL, 4 eq), and then, after 10 minutes, sodium triacetoxyborohydride (449 mg, 4.5 eq) and acetic acid (150 μL). After stirring for four days at room temperature the reaction was quenched with sodium hydroxide (4 mL, 1M aq.) and diluted with ethyl acetate (50 mL). Standard aqueous workup gave the desired amine 34 as a white solid which showed $\delta_H$ (400 MHz, CDCl$_3$, ref. TMS=0) 7.09 (1H, d, J 8.4, ArH), 6.58 (1H, dd, J 8.4 and 2.5, ArH), 6.52 (1H, d, J 2.5, ArH), 3.34-3.51 (2H, m, OCH$_2$), 3.34 (3H, s, OMe), 2.57-2.92 (5H, m, 6-CH$_2$, CH$_2$N and CHN), 1.20-2.30 (14H, m), 0.96 (9H, s, $^t$Bu), 0.74 (3H, s, 18-CH$_3$) and 0.17 (6H, s, SiMe$_2$); $\delta_C$ 153.6, 137.8, 133.2, 126.1, 119.9, 117.1, 72.4, 69.3, 58.7, 52.4, 48.5, 44.0, 43.2, 38.7, 38.3, 29.7, 29.6, 27.5, 26.4, 25.7, 23.5, 1801, 11.8 and −4.4. FAB+ 444.3.

17-(2-Dimethylamino-ethylamino)-estrone 35

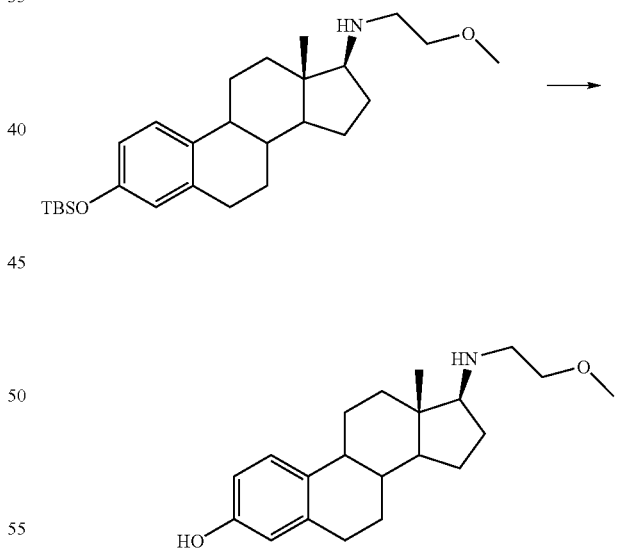

A solution of TBS protected estratriene 34 (160 mg) in THF (10 mL) was treated with TBAF (0.4 mL, 1M solution in THF). After stirring overnight a standard aqueous work-up was carried out to give the desired product 35 which showed $\delta_H$ (400 MHz, CDCl$_3$, ref. TMS=0) 7.10 (1H, d, J 8.6, ArH), 6.58 (1H, dd, J 8.6 and 2.7, ArH), 6.52 (1H, d, J 2.7, ArH), 3.48-3.52 (2H, m, OCH$_2$), 3.34 (3H, s, OMe), 2.62-2.94 (5H, m, 6-CH$_2$, CH$_2$N and CHN), 1.24-2.52 (15H, m) and 0.75 (3H, s, 18-CH$_3$)

17-(2-Dimethylamino-ethylamino)-2-methoxy-13-methyl-7,8,9,11,12,13,14,15,16,17-decahydro-6H-cyclopenta[a]phenanthren-3-ol 36

2-Methoxy-17-(2-morpholin-4-yl-ethylamino)-13-methyl-7,8,9,11,12,13,14,15,16,17-decahydro-6H-cyclopenta[a]phenanthren-3-ol 37

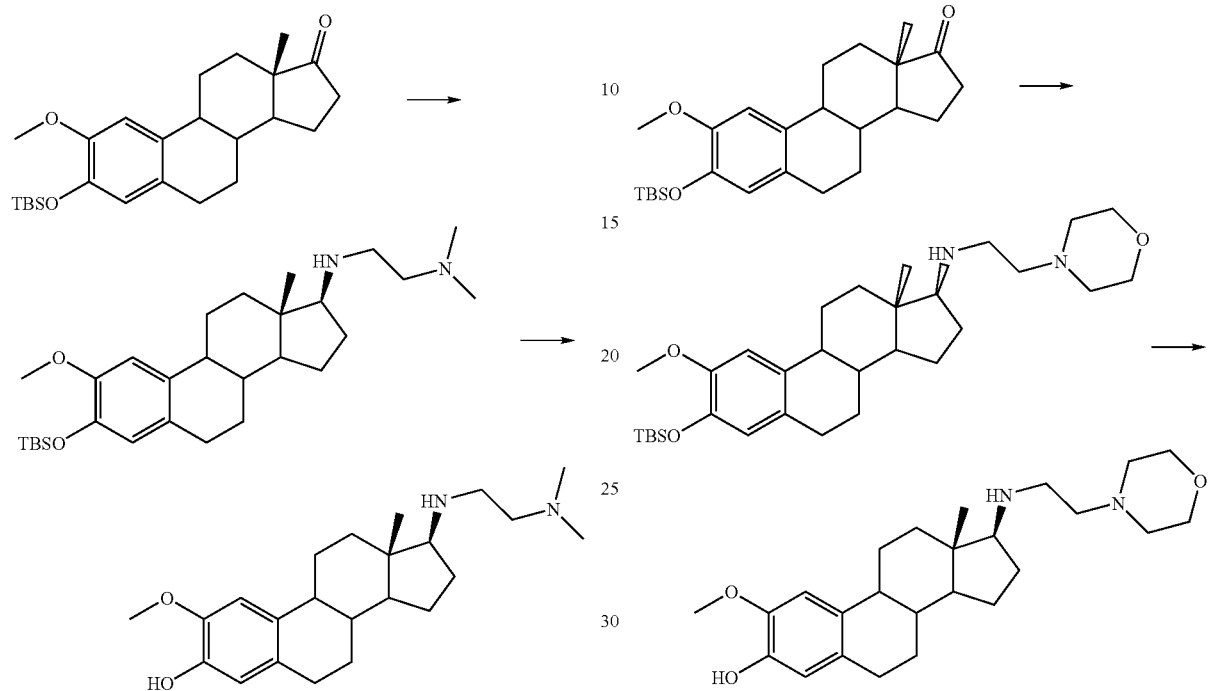

To a solution of 2-MeO-3-OTBS estrone (415 mg) in THF (10 mL) was added N,N-dimethylethylene diamine (439 μL, 4 mmol), and then, after 10 minutes, sodium triacetoxy borohydride (954 mg, 4.5 mmol) and acetic acid (300 μL). After stirring for three day at room temperature the reaction was quenched with sodium hydroxide (4 mL, 1M aq.) and diluted with ethyl acetate (50 mL). Standard aqueous workup gave the desired amine as a pale yellow oil which showed $\delta_H$ (400 MHz, CDCl$_3$, ref. TMS=0) 6.76 (1H, s, ArH), 6.53 (1H, s, ArH), 3.76 (3H, s, OMe), 2.65-2.82 (4H, m, 6-CH$_2$ and CH$_2$N), 2.62 (1H, dd, J 8.6 and 8.6, CHN), 2.36-2.48 (2H, m, CH$_2$N), 1.20-2.30 (20H, m including 2.23 (6H, s, NMe$_2$)), 0.99 (9H, s, $^t$Bu), 0.76 (3H, s, 18-CH$_3$) and 0.15 (6H, s, SiMe$_2$). The TBS protected amino steroid was then dissolved in THF (20 mL) and treated with TBAF (1.5 mL, 1M in THF) and KF (10 mg) before stirring for 8 h. Ethyl acetate (50 mL) was then added and the resultant solution was washed with sodium bicarbonate solution (50 mL, saturated), water (50 mL) and brine (2×50 mL), dried (Na$_2$SO$_4$) and evaporated. The resultant pale yellow oil was purified by column chromatography (CHCl$_3$/MeOH 99:1 to 1:1) to give the desired amine 36 as a clear colourless oil which was then triturated from ether/hexane to give a white powder m.p. 108° C. which showed $\delta_H$ (400 MHz, CDCl$_3$, ref. TMS=0) 6.77 (1H, s, ArH), 6.61 (1H, s, ArH), 3.85 (3H, s, OMe), 2.68-2.84 (4H, m, 6-CH$_2$ and CH$_2$N), 2.63 (1H, dd, J 8.6 and 8.6, CHN), 2.38-2.46 (2H, m, CH$_2$N), 1.20-2.30 (21H, m including 2.24 (6H, s, NMe$_2$)) and 0.76 (3H, s, 18-CH$_3$). $\delta_C$ 144.6, 143.4, 131.5, 129.3, 114.7, 108.1, 69.4, 59.3, 56.0, 52.4, 46.3, 45.5, 44.3, 43.2, 38.8, 38.3, 29.7, 29.1, 27.6, 26.9, 23.5 and 11.9.

To a solution of 2-MeO-3-OTBS estrone (315 mg, 0.76 mmol) in THF (10 mL) was added 4-(2-aminoethyl) morpholine (395 mg, 4 eq), and then, after 10 minutes, sodium triacetoxy borohydride (723 mg, 4.5 eq) and acetic acid (240 μL). After stirring for four days at room temperature the reaction was quenched with sodium hydroxide (4 mL, 1M aq.) and diluted with ethyl acetate (50 mL). Standard aqueous workup gave the desired amine as a white powder which showed $\delta_H$ (400 MHz, CDCl$_3$, ref. TMS=0) 6.78 (1H, s, ArH), 6.54 (1H, s, ArH), 3.78 (3H, s, OMe), 3.66-3.76 (4H, m, 2×OCH$_2$), 1.20-2.88 (25H, m) 0.99 (9H, s, $^t$Bu), 0.76 (3H, s, 18-CH$_3$) and 0.16 (6H, s, SiMe$_2$). The TBS protected amino steroid was then dissolved in THF (20 mL) and treated with TBAF (1.5 mL, 1M in THF) and KF (10 mg) before stirring for 8 h. Ethyl acetate (50 mL) was then added and the resultant solution was washed with sodium bicarbonate solution (50 mL, saturated), water (50 mL) and brine (2×50 mL), dried (Na$_2$SO$_4$) and evaporated. The resultant pale yellow oil was purified by column chromatography (CHCl$_3$MeOH 99:1 to 1:1) to give the desired amine 37 as a clear colourless oil which was then triturated from ether/hexane to give a white powder m.p. 144-146° C. which showed $\delta_H$ (400 MHz, CDCl$_3$, ref. TMS=0) 6.75 (1H, s, ArH), 6.61 (1H, s, ArH), 3.84 (3H, s, OMe), 3.67-3.71 (4H, m, 2×OCH$_2$) 2.72-2.86 (4H, m, 6-CH$_2$ and CH$_2$N), 2.65 (1H, dd, J 9.0 and 8.2, CHN), 2.52 (2H, dd, J 6.3 and 6.3, CH$_2$N) 2.46-2.50 (4H, m, 2×CH$_2$N), 1.20-2.26 (15H, m) and 0.76 (3H, s, 18-CH$_3$). $\delta_C$ 144.5, 143.4, 131.3, 129.3 (all C), 114.6, 108.0 (both CH), 69.2 (CH), 67.0, 57.9 (both CH$_2$), 56.0 (CH$_3$), 53.7 (CH$_2$), 52.3 (CH), 45.0 (CH$_2$), 44.3 (CH), 43.2 (C), 38.8 (CH), 38.2, 29.4, 29.1, 27.6, 26.9, 23.5 (all CH$_2$) and 12.0 CH$_3$).

2-Ethyl-17-[(furan-2-ylmethyl)-amino]-13-methyl-7,8,9,11,12,13,14,15,1,6,17-decahydro-6H-cyclopenta[a]phenanthren-3-ol 38

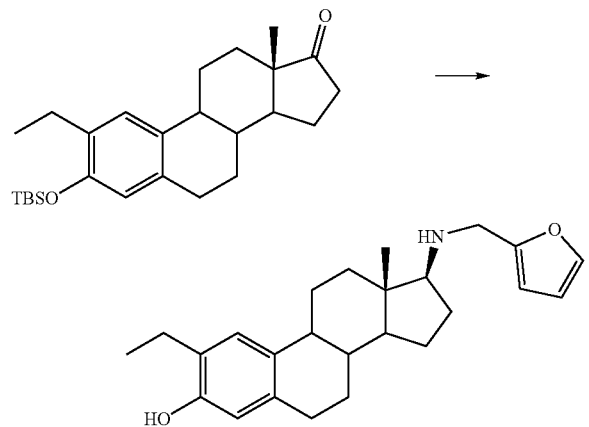

To a solution of 2-Et-3-O-TBS estrone (414 mg, 1 mmol) in THF (10 mL) was added furfurylamine (354 µL, 4 mmol), and then, after 10 minutes, sodium triacetoxy borohydride (954 mg, 4.5 mmol) and acetic acid (300 µL). After stirring for three days at room temperature the reaction was quenched with sodium hydroxide (4 mL, 1M aq.) and diluted with ethyl acetate (50 mL). Standard aqueous workup gave the desired amine as a pale yellow oil. To a solution of protected steroid in THF was added TBAF (1.5 mL) and potassium fluoride (10 mg). After stirring at room temperature for 14 h ether (50 mL) and water (50 mL) were added. The organic layer was then separated, washed with sodium hydrogen carbonate solution (25 mL), water (25 mL) and brine (25 mL) then dried and evaporated to give a pale yellow oil (270 mg). The desired product 38 was then isolated by column chromatography (0-3% methanol in chloroform) as a clear colourless oil which showed $\delta_H$ (CDCl$_3$, TMS=0) 7.37 (1H, dd, J 1.8 & 0.8), 7.03 (1H, s, ArH), 6.49 (1H, s, ArH), 6.32 (1H, dd, J 3.2 & 1.8), 6.24 (1H, dd, J 3.2 & 0.8), 3.85-3.95 (2H, m, CH2N), 2.76-2.84 (2H, m, 6-CH$_2$), 2.67 (1H, dd, 8.8 & 8.5, CHN), 2.60 (2H, q, J 7.6, CH$_2$Me), 2.27-2.35 (1H, m), 2.14-2.22 (1H, m), 1.26-2.07 (13H, m), 1.23 (3H, t, J 7.6, CH$_2$Me) and 0.81 (3H, s, 18-CH$_3$).

(2-Ethyl-3-methoxymethoxy-13-methyl-7,8,9,11,12,13,14,15,16,17-decahydro-6H-cyclopenta[a]phenanthren-17-yl)-pyridin-2-ylmethyl-amine dihydrochloride 39

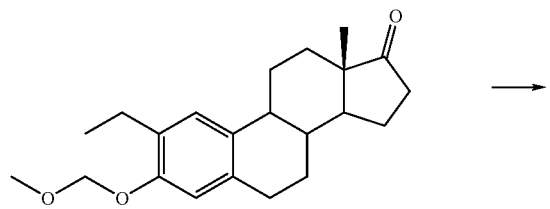

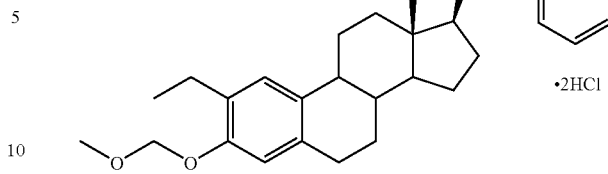

A solution of 2-Et-3-O-MOM estrone (342 mg, 1 mmol) and 2-(aminomethyl) pyridine (515 µl, 5 mmol) in THF (10 ml) was stirred for 1 h and then treated with acetic acid. (300 mg) and sodium triacetoxy borohydride (848 mg, 4 mmol). After 3d stirring sodium hydroxide (5 mL of 2M aq.) was added followed by ethyl acetate (30 ml). The organic layer was then separated, washed with water and brine, dried and evaporated. The resultant yellow oil was taken up in THF and then treated with ethereal HCl (1 mL of 2M), then solvent was removed under vacuum and then resultant gum was triturated with ether to give the product 39 as the bis-HCl salt, an off white powder which shows $\delta_H$ (CD$_3$OD, TMS=0) 8.86 (1H, app d, J 5.1), 8.38 (1H, app t, J 7.8), 8.06 (1H, app d, J 7.8), 7.87 (1H, dd, J 7.8 & 5.1), 7.02 (1H, s, ArCH), 6.73 (1H, s ArH), 5.14 (2H, s, OCH$_2$), 4.59 (2H, br, CH$_2$N), 3.43 (3H, s, OMe), 2.78-2.86 (2H, m, 6-CH$_2$), 2.59 (2H, q, J 7.4, CH$_2$Me), 1.30-2.41 (12H, m), 1.17 (3H, t, J 7.4, CH$_2$Me) and 1.01 (3H, s, 18-CH$_3$).

2-Ethyl-13-methyl-17-[(pyridin-2-ylmethyl)-amino]-7,8,9,11,12,13,14,15,16,17-decahydro-6H-cyclopenta[a]phenanthren-3-ol 40

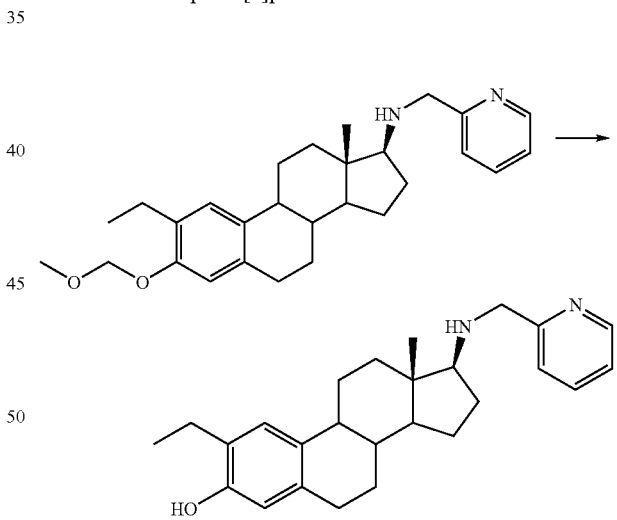

Methanolic HCl was prepared by the reaction of acetyl chloride (957 µL) with methanol (2.5 mL) at 0° C. and then added to MOM protected estrone MPL03139, after sonication for 2 minutes the reaction was evaporated to dryness. The HCl salt was precipitated from methanol ether but proved too hygroscopic to collect, instead the compound was dissolved in ethanol, basified with NaHCO$_3$ (saturated) and then extracted with ethyl acetate. The organic layer was washed with water, then brine, dried and evaporated to give the product 40 as a colourless oil which showed $\delta_H$ (CDCl3, TMS=0) 8.54-8.57 (1H, m), 7.65 (1H, ddd, J 7.8 7.8 & 1.9), 7.39 (1H, app d, J 7.8), 7.16 (1H, m), 7.03 (1H, s, ArH), 6.45 (1H, s, ArH), 3.97 (2H, s, NCH2), 2.73-2.78 (2H, m, 6-CH$_2$), 2.67 (1H, dd, 9.0 & 8.6, CHN), 2.60 (2H, q, J 7.4 CH$_2$Me), 1.25-2.32 (13H, m), 1.22 (3H, t, J 7.4, CH$_2$Me) and 0.77 (3H, s, 18-CH$_3$).

(3-Benzyloxy-2-methoxy-13-methyl-7,8,9,11,12,13, 14,15,16,17-decahydro-6H-cyclopenta[a]phenanthren-17-yl)-(2-morpholin-4-yl-ethyl)-amine 41

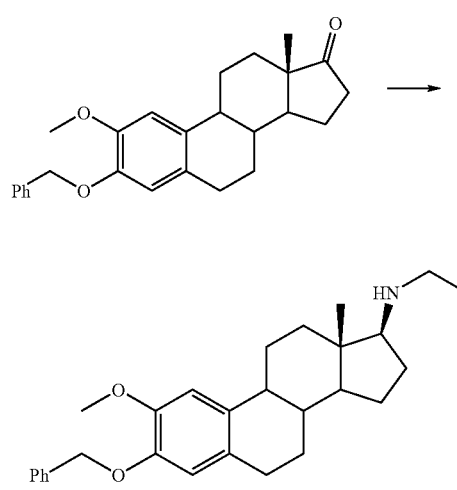

A solution of 2-MeO-3-O-benzyl estrone (390 mg, 1 mmol) and 4-(2-ethylamino)morpholine (651 mg, 5 mmol) in THF (15 ml) was stirred for 1 h and then treated with acetic acid (300 mg) and sodium triacetoxy borohydride (954 mg, 4.5 mmol). After 5d stirring sodium hydroxide (5 mL of 2M aq.) was added followed by ethyl acetate (30 ml). The organic layer was then separated, washed with water and brine, dried and evaporated. The desired product 41, a yellow oil showed $\delta_H$ (CDCl$_3$, TMS=0) 7.25-7.46 (5H, m), 6.84 (1H, s, ArH), 6.62 (1H, s, ArH), 5.10 (2H, s, PhCH$_2$O), 3.86 (3H, s, OMe), 3.68-3.74 (4H, m, 2×CH$_2$O), 1.20-2.80 (25H, m) and 0.75 (3H, s, 18-CH$_3$).

(3-Benzyloxy-2-methoxy-13-methyl-7,8,9,11,12,13, 14,15,16,17-decahydro-6H-cyclopenta[a]phenanthren-17-yl)-pyridin-2-ylmethyl-amine 42

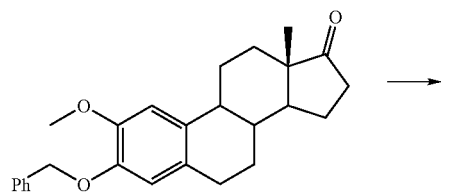

A solution of 2-MeO-3-O-benzyl estrone (390 mg, 1 mmol) and 2-(aminomethyl)pyridine (515 µL, 5 mmol) in THF (20 ml) was stirred for 1 h and then treated with acetic acid (300 mg) and sodium triacetoxyborohydride (954 mg, 4.5 mmol). After 6d stirring sodium hydroxide (5 mL of 2M aq.) was added followed by ethyl acetate (30 ml). The organic layer was then separated, washed with water and brine, dried and evaporated. The desired amine 42, a yellow showed $\delta_H$ (CDCl$_3$, TMS=0) 8.52 (1H, m), 7.62 (1H, ddd, J 7.8, 7.8 & 1.9) 7.24-7.46 (7H, m), 7.12-7.17 (1H, m), 6.84 (1H, s, ArH), 6.61 (1H, s, ArH), 5.10 (2H, s, PhCH$_2$O), 3.96 (2H, s, CH$_2$Ar) 3.86 (3H, s, OMe), 2.63-2.82 (3H, m, 6-CH$_2$ and CHN) 1.20-2.32 (13H, m) and 0.75 (3H, s, 18-CH$_3$).

(3-Benzyloxy-2-ethyl-13-methyl-7,8,9,11,12,13,14, 15,16,17-decahydro-6H-cyclopenta[a]phenanthren-17-yl)-(2-methoxyethyl)-amine 43

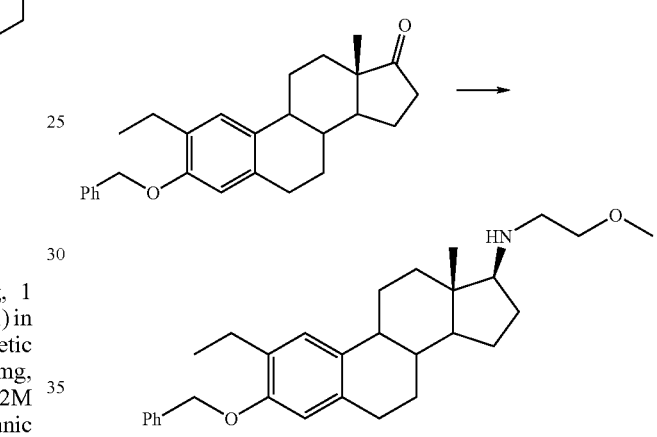

A solution of 2-Et-3-O-benzyl estrone (220 mg, 0.57 mmol) and 2-methoxyethylamine (197 µl, 2.26 mmol) in THF (10 ml) was stirred for 1 h and then treated with acetic acid (150 mg) and sodium triacetoxy borohydride (540 mg, 2.55 mmol). After 3d stirring sodium hydroxide (5 mL of 2M aq.) was added followed by ethyl acetate (30 ml). The organic layer was then separated, washed with water and brine, dried and evaporated. The desired amine 43, a yellow showed $\delta_H$ (CDCl$_3$, TMS=0) 7.27-7.44 (5H, m), 7.08 (1H, s, ArH), 6.61 (1H, s, ArH), 5.02 (2H, s, PhCH$_2$O), 3.47-3.51 (2H, m, OCH$_2$), 2.74-2.92 (4H, m, 6-CH$_2$ & CH$_2$N), 2.58-2.70 (3H, m, CHN & ArCH$_2$Me), 1.24-2.34 (14H, m), 1.21 (3H, t, J 7.6, CH$_2$Me) and 0.75 (3H, s, 18-CH$_3$).

N'-(2-Ethyl-3-methoxymethoxy-13-methyl-7,8,9,11, 12,13,14,15,16,17-decahydro-6H-cyclopenta[a] phenanthren-17-yl)-N,N-dimethyl-ethane-1,2-diamine 44

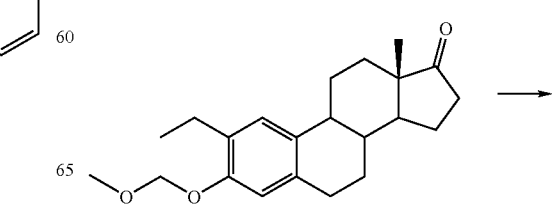

-continued

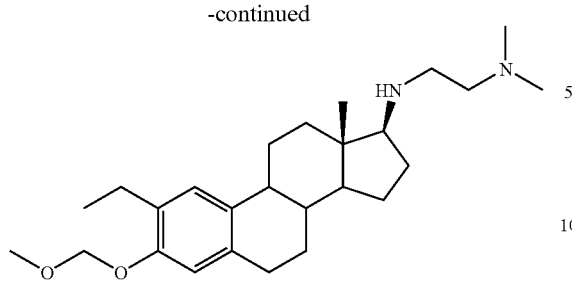

A solution of 2-Et-3-O-MOM estrone (342 mg, 1 mmol) and N,N-dimethylethylene diamine (549 µl, 5 mmol) in THF (10 ml) was stirred for 1 h and then treated with acetic acid (300 mg) and sodium triacetoxy borohydride (848 mg, 4 mmol). After 3d stirring sodium hydroxide (5 mL of 2M aq.) was added followed by ethyl acetate (30 ml). The organic layer was then separated, washed with water and brine, dried and evaporated. The resultant yellow oil was purified by column chromatography (10% MeOH in CHCl$_3$) to give the desired product 44 which showed $\delta_H$ (CDCl$_3$, TMS=0) 7.08 (1H, s, ArCH), 6.78 (1H, s ArH), 5.17 (2H, s, OCH$_2$), 3.48 (3H, s, OMe), 2.24-2.86 (9H, m, 6-CH$_2$, ArCH$_2$ and 2×NCH$_2$ and NCH), 2.23 (6H, s, NMe$_2$), 1.20 (3H, t, J 7.6, —CH$_2$Me) and 0.75 (3H, s, 18-CH$_3$).

N'-3-Benzyloxy-2-methoxy-13-methyl-7,8,9,11,12,13,14,15,16,17-decahydro-6H-cyclopenta[a]phenanthren-17-yl)-N,N-dimethyl-ethane-1,2-diamine 45

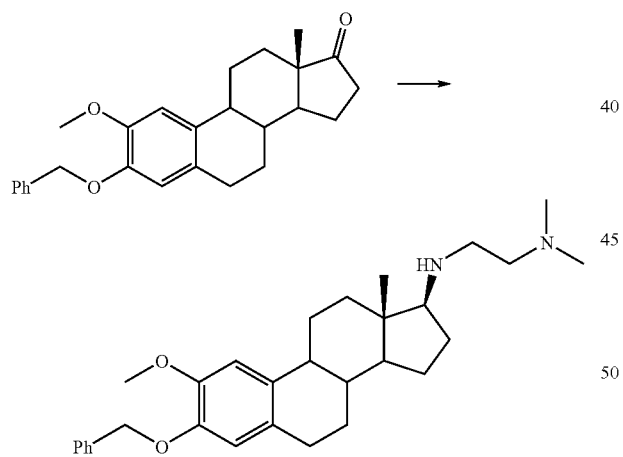

A solution of 2-MeO-3-O-benzyl estrone (390 mg, 1 mmol) and N,N-dimethylethylene diamine (439 µl, 4 mmol) in THF (10 ml) was stirred for 1 h and then treated with acetic acid (300 mg) and sodium triacetoxy borohydride (954 mg, 4.5 mmol). After 3d stirring sodium hydroxide (5 mL of 2M aq.) was added followed by ethyl acetate (30 ml). The organic layer was then separated, washed with water and brine, dried and evaporated. The product 45, a yellow oil showed $\delta_H$ (CDCl$_3$, TMS=0) 7.28-7.46 (5H, m), 6.84 (1H, s, ArH), 6.61 (1H, s, ArH), 5.10 (2H, s, PhCH$_2$O), 3.86 (3H, s, OMe), 2.37-2.83 (7H, m, 6-CH$_2$, 2×NCH$_2$ and NCH), 2.22 (6H, s, NMe$_2$), 1.24-2.14 (14H, m) and 0.75 (3H, s, 18-CH$_3$).

[2-(3-Benzyloxy-2-methoxy-13-methyl-7,8,9,11,12,13,14,15,16,17-decahydro-6H-cyclopenta[a]phenanthren-17-yloxy)-ethoxy]-tert-butyl-dimethyl-silane 46

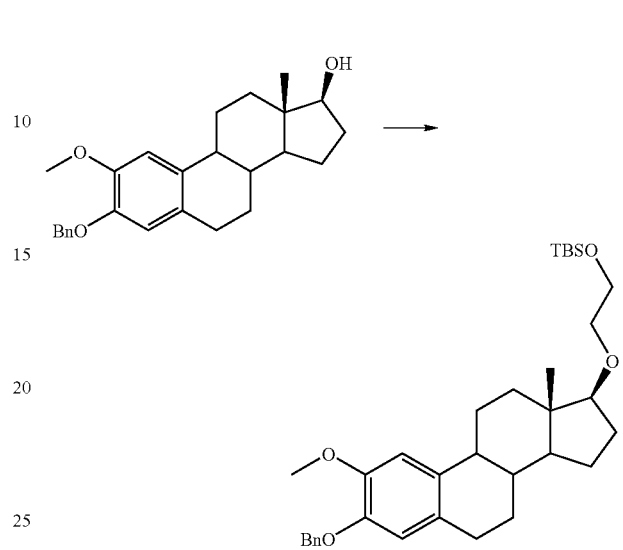

A solution of 3-O-Bn-2-MeO-estradiol (340 mg, 0.86 mmol) in toluene (8 mL) was treated with sodium hydride (2 eq.) and then heated in a sealed tube to 130° C. for 0.25 h, cooled to rt then treated with 2-(tert-butyldimethylsilyloxy) ethyl bromide (429 µL, 2 mmol) before heating in the sealed tube at 130° C. for 16 h. After standard aqueous work up the crude material was purified by column chromatography to give the desired ether 46 as a white solid (208 mg) which showed $\delta_H$ (400 MHz, CDCl$_3$, ref. TMS=0) 7.26-7.46 (5H, m, ArH), 6.85 (1H, s, ArH), 6.62 (1H, s, ArH), 5.11 (2H, s, OCH$_2$Ph), 3.87 (3H, s, OMe), 3.71-3.77 (2H, m, OCH2), 3.39-3.69 (3H, m, OCH$_2$ and HCO), 2.72-2.82 (2H, m, 6-CH2), 1.10-2.40 (13H, m), 0.91 (9H, s, tBu), 0.80 (3H, s, 18-CH$_3$) and 0.10 (6H, s, SiMe$_2$).

17-[2-(tert-Butyl-dimethyl-silanyloxy)-ethoxy]-2-methoxy-13-methyl7,8,9,11,12,13,14,15,16,17-decahydro-6H-cyclopenta[a]phenanthren-3-ol 47

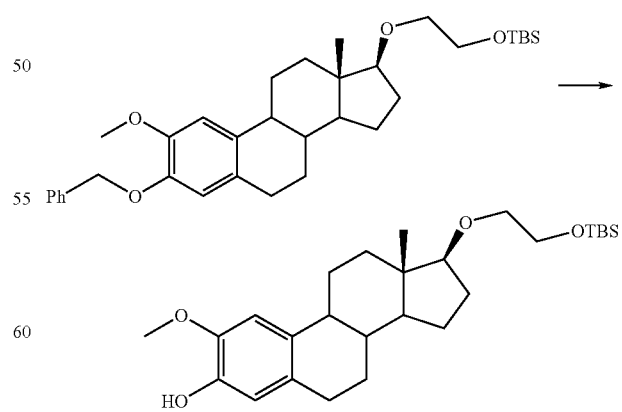

A stirred, degassed, solution of ether 46 (200 mg, 0.36 mmol) in THF (10 mL) was treated with 10% Pd/C (20 mg) and placed under an atmosphere of hydrogen overnight. The reaction was then filtered through celite and evaporated to give the desired phenol 47 as a clear colourless oil $\delta_H$ 6.80 (1H, s, ArH), 6.65 (1H, s, ArH), 5.55 (1H, s, OH), 3.87 (3H, s, OMe), 3.52-3.82 (4H, m, 2×OCH$_2$), 3.42-3.48 (1H, m, 17-CH), 2.72-2.84 (2H, m, 6-CH$_2$), 1.20-2.36 (13H, m), 0.94 (9H, s, $^t$Bu), 0.89 (3H, s, 18-Me) and 0.12 (6H, s, SiMe$_2$).

17-[2-(Hydroxy)-ethoxy]-2-methoxy-13-methyl-7,8,9,11,12,13,14,15,16,17-decahydro-6H-cyclopenta[a]phenanthren-3-ol 48

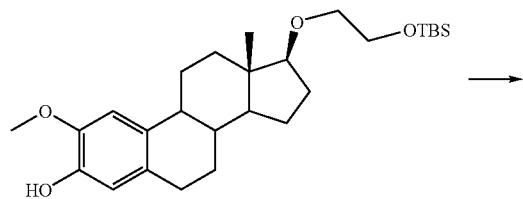

A solution of TBS protected alcohol 47 (110 mg, 0.24 mmol) in THF (5 mL) was treated with TBAF (250 mL, 0.25 mmol). After stirring overnight the reaction was extracted with ethyl acetate (25 mL), the organics washed with water and brine, dried and evaporated. The resultant pale yellow oil was purified by column chromatography (2% methanol in chloroform) to give the desired diol 48 as a clear colourless oil (65 mg) which showed $\delta_H$ 6.78 (1H, s, ArH), 6.64 (1H, s, ArH), 5.51 (1H, s, OH), 3.86 (3H, s, OMe), 3.40-3.68 (5H, m, 2×OCH$_2$ and CHOR), 2.72-2.82 (2H, m, 6-CH$_2$), 1.20-2.30 (14H, m) and 0.81 (3H, s, 18-Me); $\delta_C$ 144.6, 143.5, 131.7, 129.5, 114.6, 109.1, 89.4, 70.9, 62.1, 56.1, 50.2, 44.2, 38.6, 38.0, 28.9, 28.1, 27.2, 26.6, 23.0 and 11.7.

Sulfamic acid 2-methoxy-13-methyl-17-(2-sulfamoyloxy-ethoxy)-7,8,9,11,12,13,14,15,16,17-decahydro-6H-cyclopenta[a]phenanthren-3-yl ester 49

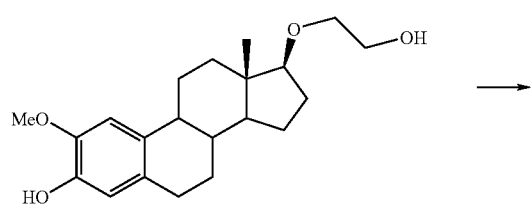

-continued

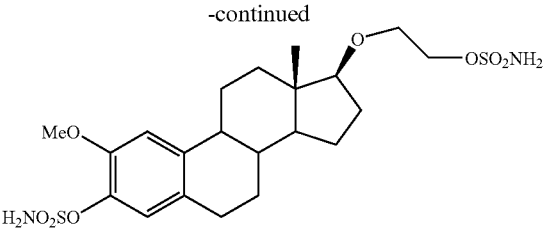

A toluene solution of sulfamoyl chloride (1 ml, 0.69 mmol) was evaporated to dryness, cooled to 0° C. and then treated with dimethylacetamide (1.5 mL) then diol 48 (45 mg). After 3 h stirring at rt the reaction was diluted in ethyl acetate (20 mL), then treated with water (10 ml), the organic layer was separated and extracted with brine (5×10 mL), dried and evaporated to give a yellow oil. Column chromatography (gradient 5-10% methanol in chloroform) was used to purify the desired bis-sulfamate 49 as a clear colourless oil (21 mg) which showed $\delta_H$ (CDCl$_3$, TMS=0) 7.03 (1H, s, ArH), 6.90 (1H, s, ArH), 5.02 (4H, br, 2×NH$_2$), 4.37-4.42 (2H, m, CH$_2$OS), 3.87 (3H, s, OMe), 3.75-3.82 (2H, m, OCH$_2$), 3.48 (1H, dd, J 8.6 & 7.9, OCH), 2.74-2.85 (2H, m, 6-CH$_2$), 1.25-2.50 (H, m) and 0.79 (3H, s, 18-CH$_3$); m/z 504.6.

tert-Butyl-[2-methoxy-17-(2-methoxy-ethoxy)-13-methyl-7,8,9,11,12,13,14,15,16,17-decahydro-6H-cyclopenta[a]phenanthren-3-yloxy]-dimethyl-silane 50

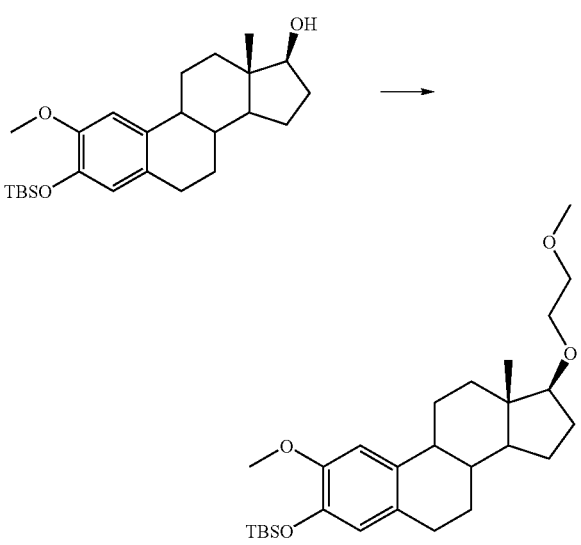

A toluene (20 mL) solution of 2-MeO-3-O-TBS estradiol (340 mg, 0.81 mmol) was treated with sodium hydride (98 mg, 2.45 mmol) and then brought to reflux for 1 h prior to addition of 2-(methoxy)ethyl bromide (153 μL, 1.62 mmol). The reaction was refluxed for 14 h then treated with further aliquots of sodium hydride (80 mg, 2 mmol) and 2-(methoxy)ethyl bromide (141 μL, 1.5 mmol) before refluxing for a further 8 hours after which time another aliquot of base and alkyl bromide were added. After a further 14 h reflux the reaction was cooled to room temperature, diluted in ethyl acetate (30 mL) and then treated with saturated ammonium chloride (20 mL). The organic layer were separated, washed with water (2×20 mL), brine, dried and evaporated. The desired ether 50 was then isolated by column chromatography (eluant hexane/ethyl acetate 11:1), as white needles mp 98-100° C. (276 mg, %) which showed $\delta_H$ (400 MHz, CDCl$_3$, ref. TMS=0) 6.76 (1H, s, ArH), 6.54 (1H, s, Ar, H), 3.77 (3H, s, OMe), 3.41-3.73 (7H, m), 3.40 (3H, s, OMe), 2.68-2.80 (2H, m, 6-CH$_2$), 1.16-2.27 (11H, m), 0.99 (9H, s, $^t$Bu), 0.82 (3H, s, 18-CH$_3$) and 0.15 (6H, s, SiMe$_2$) $\delta_C$ 148.6, 142.9, 133.2, 129.0, 121.0, 110.0, 89.6, 72.3, 69.5, 59.2, 50.4, 43.4, 38.5, 38.2, 29.7, 28.8, 28.2, 27.4, 26.6, 25.8, 23.0, 18.5, 11.7 and −4.6. m/z FAB+ 473.2.

2-Methoxy-17-(2-methoxy-ethoxy)-13-methyl-7,8,9,11,12,13,14,15,16,17-decahydro-6H-cyclopenta[a]phenanthren-3-ol 51

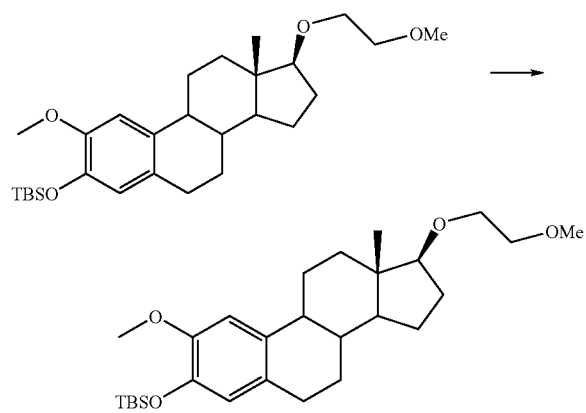

A solution of TBS protected ether 50 (232 mg) in THF (10 mL) was treated with TBAF (0.5 mL, 1M solution in THF). After stirring overnight a standard aqueous work-up was carried out and the desired phenol 51 was purified by column chromatography (4:1 Hex/EA) to give a white solid which showed $\delta_H$ (400 MHz, CDCl$_3$, ref. TMS=0) 6.77 (1H, s, ArH), 6.63 (1H, s, ArH), 5.50 (1H, s, OH), 3.85 (3H, s, ArOMe), 3.41-3.72 (5H, m, 2×OCH$_2$ and CHOR), 3.40 (3H, s, OMe), 2.69-2.83 (6-CH$_2$), 1.16-2.26 (13H, m) and 0.81 (3H, s, 18-Me); $\delta_C$ 144.5, 143.4, 131.7, 129.5 (all C), 114.6, 108.1, 89.6 (all CH), 72.3, 69.5 (both CH$_2$), 59.1 (CH), 56.0 (CH$_3$), 50.3, 44.2 (both CH), 43.3 (C), 38.6 (CH), 38.1, 28.9, 28.1, 27.2, 26.7, 23.0 (all CH$_2$) and 11.6 (CH$_3$).

2-Ethyl-3-methoxymethoxy-13-methyl-6,7,8,9,11,12,13,14,15,16-decahydro-cyclopenta[a]phenanthren-17-one 52

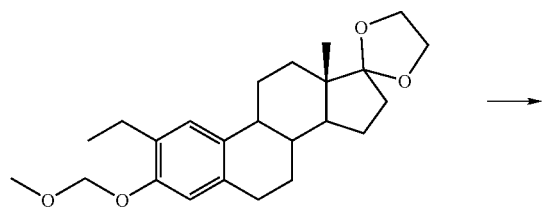

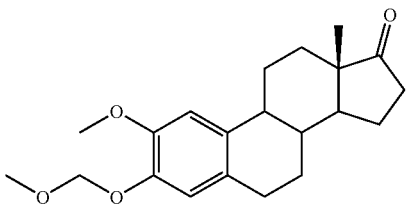

A solution of 2-Et-3O-MOM-17-(ethylenedioxyketal) estrone (15 g) in acetone (200 mL) and water (10 mL) was treated with para-pyridinium toluene sulphonate (333 mg) and then bought to reflux for 14 h. The solvent was then removed by rotary evaporation to give a white solid which was then recrystallised from ethanol water to give the desired product 52 as a white solid (5.6 g) which showed $\delta_H$ (400 MHz, CDCl$_3$, ref. TMS=0) 7.09 (1H, s, ArH), 6.81 (1H, s, ArH), 5.18 (2H, s, OCH$_2$), 3.49 (3H, s, OMe), 2.84-2.92 (2H, m, 6-CH$_2$), 2.61 (2H, q, J 7.4, CH$_2$Me), 1.38-2.56 (13H, m), 1.19 (3H, t, J 7.4, CH$_2$Me) and 0.91 (3H, s, 18-CH$_3$); $\delta_C$ 220.1, 152.8, 134.8, 132.6, 130.6, 126.2, 114.0, 94.3, 56.0, 50.4, 48.1, 44.1, 38.4, 36.0, 31.7, 29.6, 26.7, 26.0, 23.6, 21.7, 14.9 and 14.0.

2-Ethyl-3-methoxymethoxy-13-methyl-7,8,9,11,12,13,14,15,16,17-decahydro-6H-cyclopenta[a]phenanthren-17-ol 53

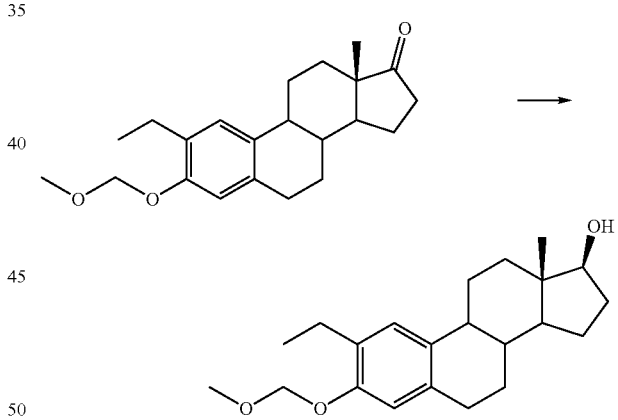

To a stirred, rt, solution of 2-Et-3-O-MOM estrone 52 (743 mg, 2.18 mmol) in THF (10 mL)/methanol (40 mL) solution was added sodium borohydride (76 mg, 2 mmol). After one hour the reaction was quenched by addition of ammonium chloride (2 mL of saturated solution), diluted with ethyl acetate (50 mL) and water (25 mL), the organic layer separated and washed with water, brine, dried and evaporated. Column chromatography (hexane/ethyl acetate gradient) gave the desired alcohol 53 as a clear colourless oil (650 mg) which showed $\delta_H$ (400 MHz, CDCl$_3$, ref. TMS=0) 7.09 (1H, s, ArH), 6.78 (1H, s, ArH), 5.17 (2H, s, OCH$_2$), 3.69-3.78 (1H, m, CHOH) 3.48 (3H, s, OMe), 2.78-2.86 (2H, m, 6-CH$_2$), 2.61 (2H, q, J 7.4, CH$_2$Me), 1.24-2.38 (13H, m), 1.19 (3H, t, J 7.4, CH$_2$Me) and 0.77 (3H, s, 18-CH$_3$).

2-Ethyl-17-(2-methoxy-ethoxy)-3-methoxymethoxy-13-methyl-7,8,9,11,12,13,14,15,16,17-decahydro-6H-cyclopenta[a]phenanthrene 54

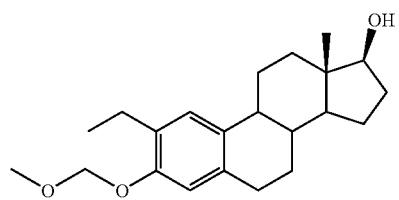

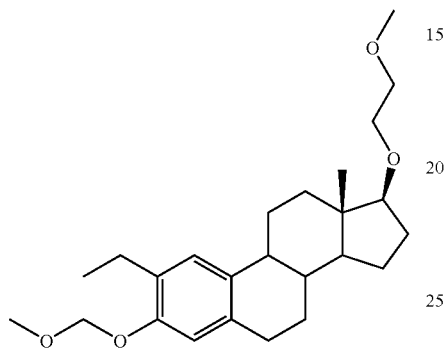

A toluene (10 mL) solution of 2-Et-3-O-MOM estradiol 53 (170 mg, 0.5 mmol) was treated with sodium hydride (80 mg, 2 mmol) and then brought to reflux for 0.5 h prior to addition of 2-(methoxy)ethyl bromide (141 µL, 1.5 mmol). The reaction was refluxed for 14 h then treated with further aliquots of sodium hydride (80 mg, 2 mmol) and 2-(methoxy)ethyl bromide (141 µL, 1.5 mmol) before refluxing for a further 8 hours after which time no residual starting material remained. The reaction was then cooled to room temperature, diluted in ethyl acetate (30 mL) and then treated with saturated ammonium chloride (20 mL). The organic layer were separated, washed with water (2×20 mL), brine, dried and evaporated. The desired ether 54, a clear colourless oil (128 mg, %) was isolated by column chromatography (gradient 0 to 20% ethyl acetate in hexane) and showed $\delta_H$ (400 MHz, CDCl$_3$, ref. TMS=0) 7.08 (1H, s, ArH), 6.78 (1H, s, Ar, H), 5.17 (2H, s, OCH$_2$), 3.67-3.74 (1H, m), 3.52-3.56 (2H, m), 3.48 (3H, s, OMe), 3.43 (1H, dd, J 8.6 and 8.2, CHO), 3.40 (3H, s, OMe), 2.78-2.86 (2H, m, 6-CH$_2$), 2.63 (2H, q, J 7.4, CH$_2$Me), 2.37-2.44 (1H, m), 2.14-2.22 (1H, m), 2.01-2.11 (2H, m), 1.83-1.90 (1H, m), 1.23-1.72 (8H, m), 1.19 (3H, t, J 7.4, CH$_2$Me) and 0.81 (3H, s, 18-CH$_3$) $\delta_C$ 152.6, 135.0, 133.2, 130.3, 126.1, 114.0, 94.3, 89.6, 72.3, 69.6, 59.2, 56.0, 50.4, 44.1, 43.5, 38.7, 38.3, 29.7, 28.3, 27.4, 26.6, 23.6, 23.2, 15.0 and 11.7.

The following schemes were followed.

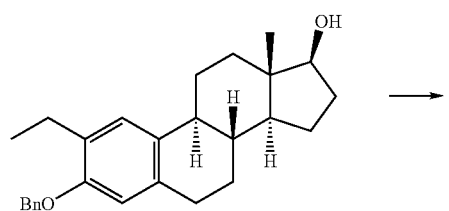

-continued

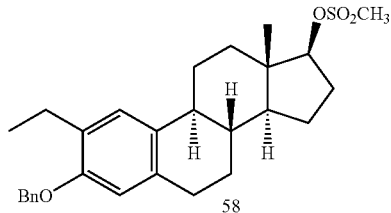

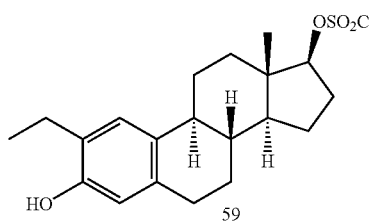

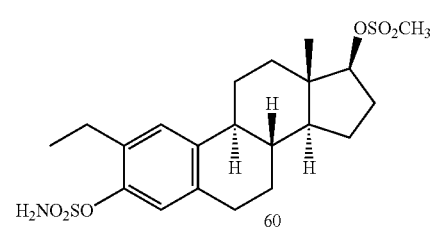

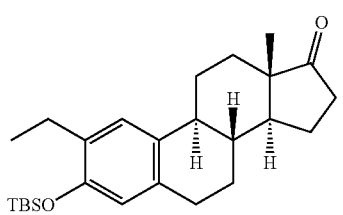

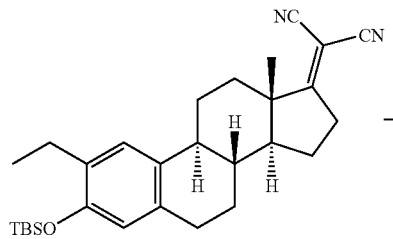

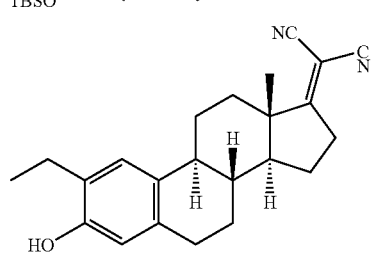

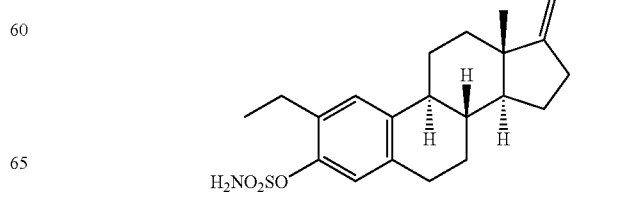

-continued

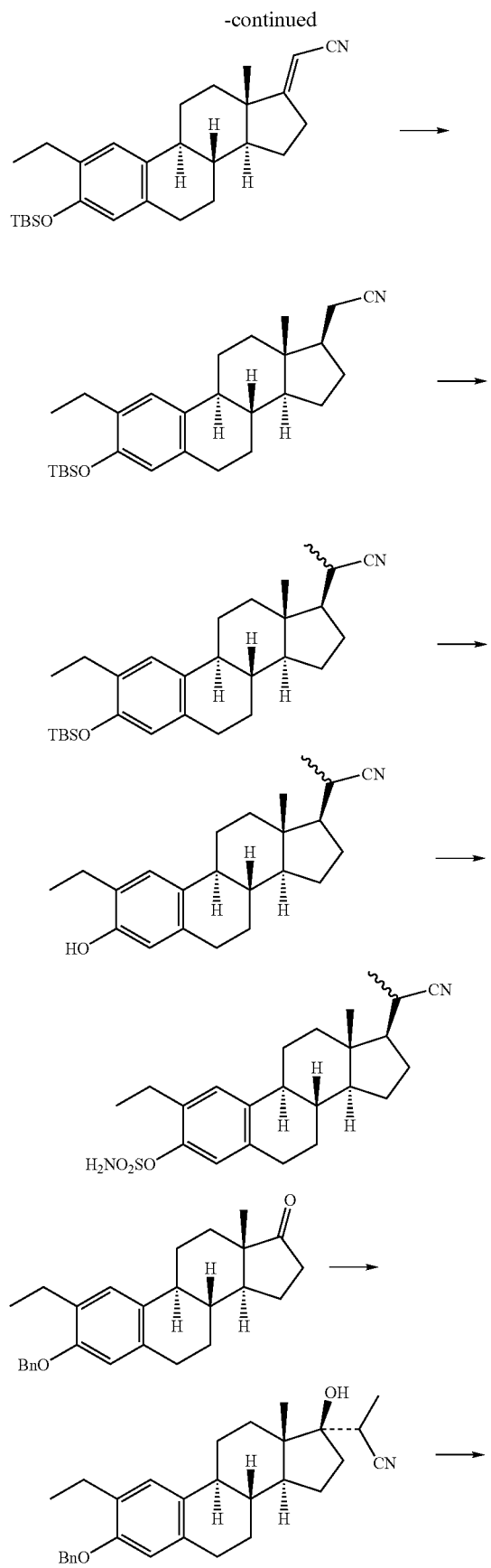

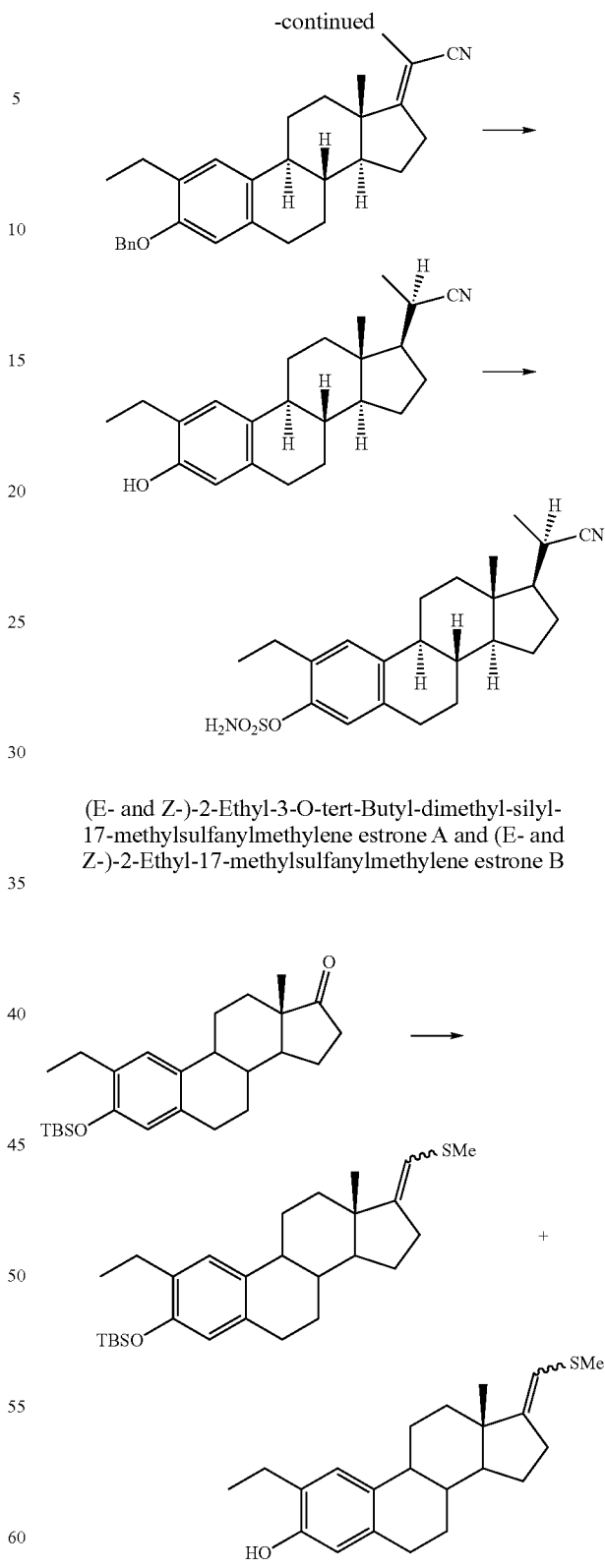

(E- and Z-)-2-Ethyl-3-O-tert-Butyl-dimethyl-silyl-17-methylsulfanylmethylene estrone A and (E- and Z-)-2-Ethyl-17-methylsulfanylmethylene estrone B Sodium hydride (120 mg, 3 mmol) was washed with three aliquots of hexane (1 mL each), dried under nitrogen and then treated with THF (5 mL). Diethyl (methylthiomethyl)phosphonate (526 μL, 3 mmol) was then introduced to the suspension causing vigorous gas evolution prior to formation of a clear colourless solution. The reaction mixture was then treated with a solution of 2-Et-3-OTBS estrone (412 mg, 1 mmol) in THF (5 mL) and then refluxed for 48 h. The cooled reaction was then diluted with ethyl acetate (30 mL), poured onto water (20 mL) and the aqueous layer separated. The organic layer was then washed with water (3×35 mL), brine (50 mL), then dried and evaporated. The resultant oil was purified by column chromatography (5% ethyl acetate/hexane) to give as the first fraction, the desired TBS-protected alkene A product as a mixture of isomers, a colourless oil (196 mg, 43%) and as the second fraction a colourless oil which proved to be a the desilylated alkenes B (150 mg, 44%).

F1 $\delta_H$ (CDCl$_3$) 7.05 (1H, s, ArH), 6.54, 6.47 (1H, s, ArH, both isomers), 5.48-5.55 (1H, m, :CHSMe, both isomers), 2.75 (2H, m, 6-CH$_2$), 2.56 (2H, q, J 7.4, CH$_2$Me), 2.26, 2.21 (3H, s, SMe of both isomers), 1.19 (3H, t, J 7.4, CH$_2$Me), 1.00 (9H, s, tBu), 0.92, 0.81 (3H, s, 18-CH$_3$), and 0.21 (6H, s, SiMe$_2$). m/z [FAB+] Found 456.28822, C$_{28}$H$_{44}$SOSi requires 456.28821.

F2 $\delta_H$ (CDCl$_3$) 7.04 (1H, s, ArH), 6.48 (1H, s, ArH), 5.51 (t, 1.9, :CHSMe), 5.49 (t, 2.3, :CHSMe), 4.43-4.46 (1H, m, OH), 2.72-2.88 (2H, m, 6-CH$_2$), 2.59 (2H, q, J 7.4, CH$_2$Me), 2.27 and 2.22 (3H, 2×s, SMe of both isomers), 1.22 (3H, t, J 7.4, CH$_2$Me), 0.93 and 0.81 (3H, s, 18-CH$_3$ of both isomers); m/z [FAB+] Found 342.20174, C$_{22}$H$_{30}$SO requires 342.20173.

2-Ethyl-17-methylsulfanylmethyl estrone C

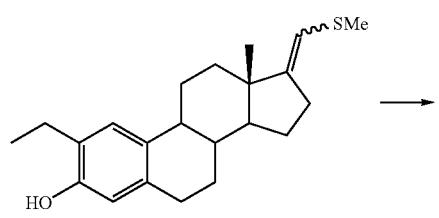

(E- and Z->2-Ethyl-17-methylsulfanylmethylene estrone B (150 mg) was dissolved in THF (1 mL) and ethanol (10 mL) then treated with Pd/C (25 mg, 5%), degassed and then stirred under a hydrogen atmosphere for 16 h. The reaction was then filtered through a pad of celite and evaporated. The desired reduced product C was isolated by column chromatography as a colourless oil (85 mg) which showed $\delta_H$ (CDCl$_3$) 7.04 (1H, s, ArH), 6.48 (1H, s, ArH), 4.48 (1H, s, OH), 2.74-2.84 (2H, m, 6-CH$_2$), 2.58 (2H, q, J 7.4, CH$_2$Me), 2.11 (3H, s, SMe), 1.21 (3H, t, J 7.4, CH$_2$Me) and 0.65 (3H, s, 18-CH$_3$).

2-Ethyl-3-O-sulfamoyl-17-methylsulfanylmethyl estrone E

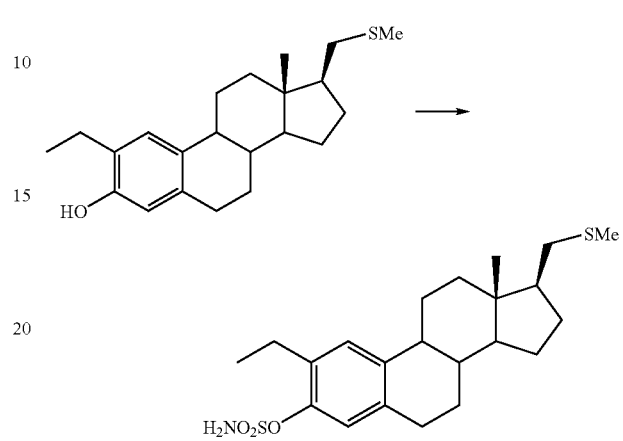

Sulfamoyl chloride (1.5 mL of 0.56M solution) was evaporated to dryness and then dissolved in DMA (1.5 mL) at 0° C. before adding to 2-Ethyl-13-methyl-17-methylsulfanylmethyl estrone C (80 mg). The stirred reaction was allowed to come to room temperature over 14 h. Ethyl acetate (10 mL) was then added and the solution was washed with water (3×10 mL) and brine (10 mL), dried (Na$_2$SO$_4$) and then evaporated to dryness. The crude product was purified by column chromatography (0-7.5% ethyl acetate in chloroform) to give the desired sulfamate as E a white foam (65 mg) which showed $\delta_H$ (CDCl$_3$) 7.18 (1H, s, ArH), 7.06 (1H, s, ArH), 4.90 (2H, br, NH$_2$), 2.78-2.88 (2H, m, 6-CH$_2$), 2.68 (2H, q, J 7.4, CH$_2$Me), 2.11 (3H, s, SMe), 1.21 (3H, t, J 7.4, CH$_2$Me) and 0.66 (3H, s, 18-CH$_3$).

2-Hydroxymethyl-3-O-methoxymethyl-17-ethylenedioxy estrone

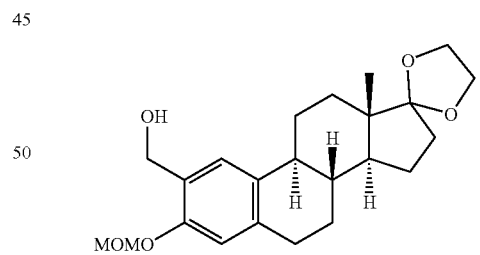

A solution of 2-formyl-3-O-methoxymethyl-17-ethylenedioxy estrone (2.00 g, 5.18 mmol) in THF (10 mL) and methanol (20 mL) was treated with sodium borohydride (189 mg, 5 mmol). After 10 minutes no starting material remained and the excess borohydride was destroyed by addition of ammonium chloride. The reaction was extracted into ethyl acetate (50 mL), washed with water (2×25 mL), brine (25 mL), dried and evaporated to give 2-hydroxymethyl-3-O-methoxymethyl-17-ethylenedioxy estrone (1.98 g) as a white foam $\delta_H$ (CDCl$_3$) 7.23 (1H, s, ArH), 6.82 (1H, s, ArH), 5.20 (2H, s, OCH$_2$), 4.64-4.70 (2H, m, ArCH$_2$O), 3.88-4.00 (4H, m, OCH$_2$CH$_2$O), 3.49 (3H, s, OCH$_3$), 2.82-2.88 (2H, m, 6-CH$_2$), 1.30-2.40 (14H, m) and 0.88 (3H, s, 18-CH$_3$); δ$_C$ 152.9, 137.7, 133.9, 127.2, 126.2, 119.3, 114.5, 94.6, 65.2, 64.5, 61.9, 56.1, 49.3, 46.1, 43.6, 38.9, 34.2, 30.6, 29.7, 26.9, 26.0, 22.3 and 14.3; m/z [ES+] 411.2 (100%, M$^+$+Na).

2-Methoxymethyl-3-O-methoxymethyl-17-ethylenedioxy estrone

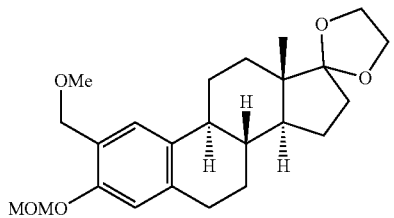

To a rt stirred solution of 2-hydroxymethyl-3-O-methoxymethyl-17-ethylenedioxy estrone (1.989, 5.10 mmol) in THF (25 ml) was added sodium hydride (306 mg) and then, after 0.5 h, methyl iodide. The reaction was stirred overnight prior to standard aqueous work up. Chromatography (hexane/ethyl acetate) gave the desired product as a colourless oil (1 g) together with recovered starting material (600 mg). The product 2-Methoxymethyl-3-O-methoxymethyl-17-ethylenedioxy estrone showed δ$_H$ (CDCl$_3$) 7.26 (1H, s, ArH), 6.80 (1H, s, ArH), 5.16 (2H, s, OCH$_2$), 4.43-4.50 (2H, m, ArCH$_2$O), 3.86-3.98 (4H, m, OCH$_2$CH$_2$O), 3.46 (3H, s, OCH$_3$), 3.39 (3H, s, OMe), 2.80-2.86 (2H, m, 6-CH$_2$), 1.26-2.40 (13H, m) and 0.86 (3H, s, 18-CH$_3$); δ$_C$ 152.6, 137.4, 133.6, 126.4, 124.4, 119.3, 114.3, 94.4, 69.5, 65.2, 64.5, 58.1, 55.9, 49.3, 46.1, 43.6, 38.9, 34.2, 30.6, 29.6, 26.9, 26.1, 22.3 and 14.3; m/z [ES+] 425.3 (100%, M$^+$+Na). HRMS [FAB+] 402.24063.

2-Methoxymethyl 3-O-TBS estrone

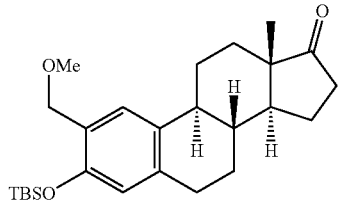

2-Methoxymethyl-3-O-methoxymethyl-17-ethylenedioxy estrone (1 g) in THF (10 mL) was treated with methanolic HCl (10 mL, 4M) for 0.25 h, after standard aqueous work up the product was dissolved in DMF (10 mL) and treated with imidazole (425 mg) and TBSCl (453 mg). After 14 h the reaction was extracted into ethyl acetate (25 mL) and then washed with water (5×20 mL) and brine (20 mL), dried and evaporated. Column chromatography (0-15% ethyl acetate in hexane) gave the desired product as a white solid (360 mg) which showed δ$_H$ (CDCl$_3$) 7.25 (1H, s, ArH), 6.51 (1H, s, ArH), 4.43 (1H, d, J 11.7, ArCH$_a$), 4.40 (1H, d, J 11.7, ArCH$_b$), 3.39 (3H, s, OCH$_3$), 2.82-2.88 (2H, m, 6-CH$_2$), 2.42-2.54 (2H, m), 1.92-2.29 (5H, m), 1.36-1.68 (6H, m), 1.01 (9H, s, t-Bu), 0.91 (3H, s, 18-CH$_3$) and 0.22 (6H, s, SiMe$_2$); δ$_C$ 221.1, 151.3, 136.7, 132.3, 126.4, 126.1, 118.6, 69.8, 58.2, 50.4, 48.0, 44.0, 38.3, 35.9, 31.5, 29.4, 26.6, 25.9, 25.7, 21.6, 18.2, 13.8 and −4.3.

2-Methoxymethyl-3-O-TBS-17-cyanomethylene estrone

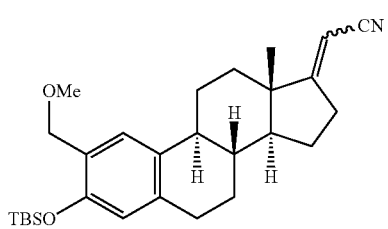

Diethyl(cyanomethyl)phosphonate (506 μL, 3 mmol) in THF (10 mL) was treated with sodium hydride (124 mg) and then, upon cessation of gas evolution, 2-methoxymethyl 3-O-TBS estrone (320 mg) in THF (5 mL). The reaction was heated to 70° C. for 1.5 h then worked up. The product was purified by chromatography (7:1 hexane/ethyl acetate) as a 1:1 mixture of isomers (240 mg), The clear colourless oil showed δ$_H$ (CDCl$_3$) 7.24 & 7.25 (1H, 2×s, ArH), 6.51 & 6.50 (1H, 2×s, ArH), 5.13 (dd, J 2.3 and 2.0:CHCN) & 5.05 (dd, J 2.5 and 2.3) (1H, 2×dd, :CHCN both isomers), 4.43 (1H, d, J 12.8, OCH$_a$), 4.40 (1H, d, J 12.8, OCH$_b$), 3.39 & 3.39 (3H, 2×s, OCH$_3$), 0.99 and 0.88 (3H, 2×s, 18-CH$_3$, both isomers).

2-Methoxymethyl-3-O-TBS-17-β-cyanomethyl estrone

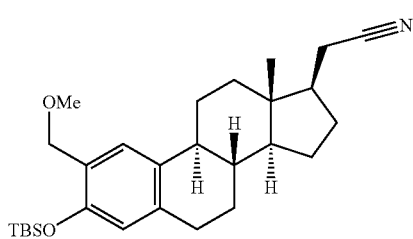

2-Methoxymethyl-3-O-TBS-17-cyanomethylene estrone (220 mg) in THF (1 mL) and ethanol (5 mL) was hydrogenated in the presence of Pd/C (200 mg, 5%) over 14 h. The reaction was then filtered through celite and evaporated to give the desired product, 2-Methoxymethyl-3-O-TBS-17-β-cyanomethyl estrone, as a clear colourless oil (200 mg) which showed δ$_H$(CDCl$_3$) 7.23 (1H, s, ArH), 6.50 (1H, s, ArH), 4.42 (1H, d, J 11.8, ArCH$_a$), 4.41 (1H, d, J=11.8, ArCH$_b$), 3.39 (3H, s, OCH$_3$), 2.72-2.86 (2H, m, 6-CH$_2$), 1.15-2.46 (16H, m), 1.01 (9H, s, t-Bu), 0.67 (3H, s, 18-CH$_3$) and 0.21 (6H, s, SiMe$_2$); δ$_C$ 151.20, 136.9, 132.7, 126.4, 125.9, 119.8, 118.6, 69.8, 58.2, 54.4, 46.8, 44.0, 42.7, 38.8, 37.3, 28.6, 28.4, 27.8, 26.3, 25.7, 24.0, 18.2, 17.6, 12.3 and −4.1.

2-Methoxymethyl-17-β-cyanomethyl estrone

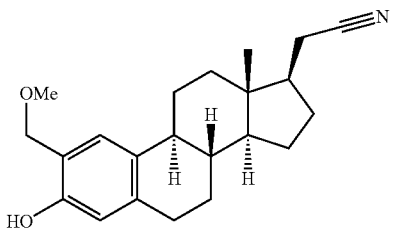

2-Methoxymethyl-3-O-TBS-17-β-cyanomethyl estrone (200 mg) in THF (5 mL) was treated with TBAF (1 mL, 1M in THF). After 0.5 h the reaction was worked up. Chromatography (hexane/ether) gave the desired product, 2-methoxymethyl-17-βcyanomethyl estrone, as a crystalline solid (120 mg) which showed $\delta_H$ (CDCl$_3$) 7.22 (1H, s, ArH), 6.91 (1H, s, ArH), 6.62 (1H, s, OH), 4.64 (1H, d, J 12.5, ArCH$_a$), 4.59 (1H, d, J 12.5, ArCH$_b$), 3.43 (3H, s, OCH$_3$), 2.78-2.86 (2H, m, 6-CH$_2$), 1.24-2.42 (15H, m) and 0.67 (3H, s, 18-CH$_3$); $\delta_C$ 153.8, 138.0, 131.5, 125.0, 119.8, 119.4, 116.3, 74.1, 58.1, 54.3, 46.7, 43.6, 42.5, 38.7, 37.3, 29.3, 28.2, 27.6, 26.2, 25.6, 23.9, 17.6 and 12.2. m/z [APCI-] 338.3 (100%, M$^+$–H).

2-Methoxymethyl-3-O-sulfamoyl-17-β-cyanomethyl estrone

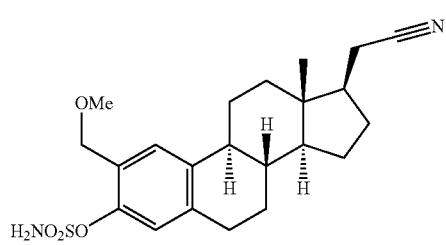

Sulfamoyl chloride (1.7 mmol) was cooled to 0° C., dissolved in dimethyl acetamide (1.5 mL) and then after 5 minutes treated with 2-methoxymethyl-17-β-cyanomethyl estrone (60 mg). External cooling was removed after 15 minutes and the reaction was left to stir at ambient temperature for 3 h. The reaction was then diluted in ethyl acetate (15 mL), poured onto brine (15 mL) and the organic layer was separated. The organic extract was washed with water (3×15 mL) and brine (15 mL) dried and evaporated. Chromatography (0-5% MeOH in DCM) gave the product, 2-methoxymethyl-3-O-sulfamoyl-17-β-cyanomethyl estrone, as colourless oil (65 mg). Crystallisation from chloroform/hexane gave a white crystalline solid which showed $\delta_H$ (CDCl$_3$) 7.29 (1H, s, ArH), 7.17 (1H, s, ArH), 5.55 (2H, s, NH$_2$), 4.48 (2H, s, OCH$_2$), 3.44 (3H, s, OCH$_3$), 2.86-2.92 (2H, m, 6-CH$_2$), 1.26-2.42 (15H, m) and 0.69 (3H, s, 18-CH$_3$); $\delta_C$ 147.3, 139.4, 139.3, 128.5, 126.8, 122.7, 119.6, 70.6, 58.3, 54.3, 46.6, 43.9, 42.6, 38.2, 37.3, 29.2, 28.2, 27.2, 26.1, 23.9, 17.6 and 12.2. m/z [APCI-] 417.3 (100%, M$^+$–H).

2-Ethyl-17-methylene estrone

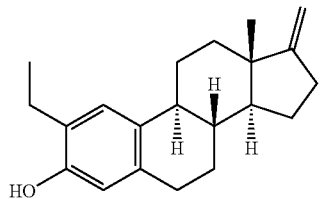

Methyl triphenylphosphonium iodide (10 mmol) in DMSO (15 mL) was treated with sodium hydride (400 mg). After 0.5 h 2-ethyl estrone (600 mg) in DMSO (15 mL) was added to the resultant yellow ylid and the reaction was brought to 60° C. for 16 h. The reaction was cooled to room temperature, poured onto ice water (50 mL), extracted with ether (3×50 mL), the combined organic extracts was with water (3×50 mL), dried and evaporated. Chromatography (10% ether in hexane) gave the desired product, 2-ethyl-17-methylene estrone, as a white foam (390 mg) which showed $\delta_H$ (CDCl$_3$) 7.05 (1H, s, ArH), 6.47 (1H, s, ArH), 4.65-4.68 (2H, m, :CH$_2$), 4.53 (1H, s, OH), 2.72-2.87 (2H, m, 6-CH$_2$), 2.59 (2H, q, J 7.4, CH$_2$Me), 1.25-2.56 (13H, m), 1.22 (3H, t, J 7.4, CH$_2$Me) and 0.81 (3H, s, 18-CH$_3$); $\delta_C$ 161.6, 150.9, 135.4, 132.6, 127.0, 126.2, 115.1, 100.7, 53.5, 44.4, 44.1, 38.9, 35.8, 29.5, 29.4, 27.7, 26.8, 24.0, 23.1, 18.7 and 14.6; HRMS [FAB+] 296.21402.

2-Ethyl-17-ethylidene estrone

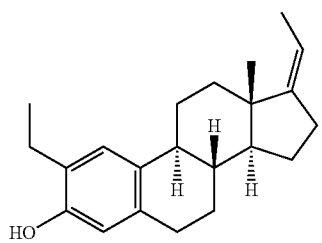

Ethyl triphenylphosphonium iodide (10 mmol) in DMSO (15 mL) was treated with sodium hydride (400 mg). After 0.5 h 2-ethyl estrone (600 mg) in DMSO (15 mL) was added to the resultant yellow ylid and the reaction was brought to 60° C. for 16 h. The reaction was cooled to room temperature, poured onto ice water (50 mL), extracted with ether (3×50 mL), the combined organic extracts was with water (3×50 mL), dried and evaporated. Chromatography (10% ether in hexane) gave the desired product, cis-2-ethyl-17-ethylidene estrone, as a white foam (460 mg) which showed $\delta_H$ (CDCl$_3$) 7.03 (1H, s, ArH), 6.47 (1H, s, ArH), 5.14 (1H, qdd, J 7.0, 2.0, 2.0, :CHMe), 4.45 (1H, s, OH), 2.72-2.88 (2H, m, 6-CH$_2$), 2.59 (2H, q, J 7.4, CH$_2$Me), 2.14-2.46 (5H, m), 1.87-1.95 (1H, m), 1.70-1.78 (1H, m), 1.69 (3H, ddd, J 7.0, 2.0, 2.0, MeHC:), 1.25-1.62 (6H, m), 1.22 (3H, t, J 7.4, CH$_2$Me) and 0.91 (3H, s, 18-CH$_3$); $\delta_C$ 150.8, 150.1, 135.4, 132.7, 126.9, 126.1, 115.1, 113.3, 55.2, 44.6, 43.9, 38.5, 37.3, 31.5, 29.4, 27.7, 27.1, 24.3, 23.1, 17.1, 14.7 and 13.3; HRMS [FAB+] 310.22967.

2-Ethyl-3-O-sulfamoyl 17-methylene estrone

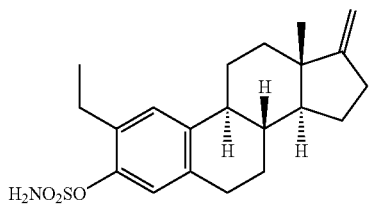

To a solution of 2-ethyl-17-methylene estrone (231 mg) in dichloromethane (5 mL) was added 2,6-di-t-butyl-4-methylpyridine (320 mg) and sulfamoyl chloride (1.56 mmol). After 14 stirring at rt the reaction was diluted in ethyl acetate (20 mL) then washed with water (3×20 mL) and brine (20 mL), dried and evaporated. Column chromatography gave the desired product, 2-ethyl-3-O-sulfamoyl 17-methylene estrone, as a clear colourless oil (200 mg) which solidified on standing and showed $\delta_H$ (CDCl$_3$) 7.19 (1H, s, ArH), 7.09 (1H, s, ArH), 5.06-5.14 (2H, br, NH$_2$), 4.56-4.60 (2H, m, :CH$_2$), 2.82-2.87 (2H, m, 6-CH$_2$), 2.69 (2H, q, J 7.4, CH$_2$Me), 1.32-2.60 (13H, m), 1.22 (3H, t, J 7.4, CH$_2$Me) and 0.82 (3H, s, 18-CH$_3$); $\delta_C$ 161.3, 145.9, 139.5, 135.8, 126.8 (all C), 126.8, 121.3 (both CH), 100.9 (:CH$_2$), 53.5 (CH), 44.3 (C), 44.3, 38.4 (both. CH), 35.7, 29.5, 29.3, 27.5, 26.5, 24.0, 23.1 (all CH$_2$), 18.6 and 14.7 (both CH$_3$); HRMS [FAB+] 375.18681.

2-Ethyl-3-O-sulfamoyl-17-ethylidene estrone

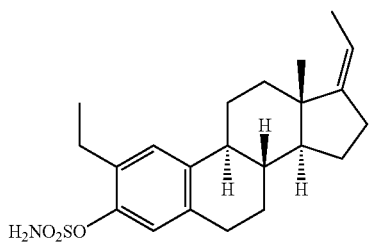

To a solution of 2-ethyl-17-ethylidene estrone (329 mg) in dichloromethane (5 mL) was added 2,6-di-t-butyl-4-methylpyridine (435 mg) and sulfamoyl chloride (2.12 mmol). After 14 stirring at rt the reaction was diluted in ethyl acetate (20 mL) then washed with water (3×20 mL) and brine (20 mL), dried and evaporated. Column chromatography gave the desired product, cis-2-ethyl-3-O-sulfamoyl 17-ethylidene estrone, as a clear colourless oil which solidified on standing and showed $\delta_H$ (CDCl$_3$) 7.17 (1H, s, ArH), 7.04 (1H, s, ArH), 5.15 (1H, qdd, J 7.0, 2.0, 2.0, :CHMe), 5.09 (2H, s, NH$_2$), 2.80-2.86 (2H, m, 6-CH$_2$), 2.69 (2H, q, J 7.4, CH$_2$Me), 2.18-2.46 (5H, m), 1.89-1.96 (1H, m), 1.70-1.78 (1H, m), 1.69 (3H, ddd, J 7.0, 2.0, 2.0, MeHC:), 1.23-1.63 (6H, m), 1.21 (3H, t, J 7.4, CH$_2$Me) and 0.90 (3H, s, 18-CH$_3$); $\delta_C$ 149.8, 145.9, 139.5, 135.8, 133.4 (all C), 126.8, 121.2, 113.4, 55.4 (all CH), 44.5 (C), 44.1, 38.0 (both CH), 37.2, 31.5, 29.3, 27.4, 26.9, 24.2, 23.1 (all CH$_2$), 17.0, 14.7 and 13.3; HRMS [FAB+] 389.20246.

2-Methoxy-3-Benzyloxy-17-O-methoxymethyl estradiol

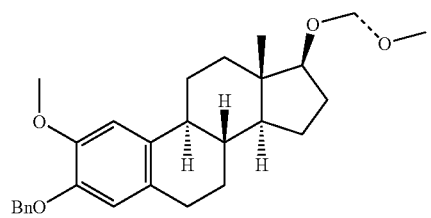

A solution of 2-methoxy-3-benzyloxy estradiol (800 mg) in DMF (10 mL) was treated with sodium hydride (120 mg) and then after 0.25 h chloromethyl methyl ether (266 µL). The reaction was stirred for 14 h at room temperature prior to standard aqueous work-up. Chromatography (6:1 hexane/ethylacetate) afforded the desired product as a clear coloourless oil (590 mg) which solidified on standing m.p. 87-88° C. which showed $\delta_H$ (CDCl$_3$) 7.24-7.45 (5H, m), 6.85 (1H, s, ArH), 6.62 (1H, s, ArH), 5.10 (2H, s, OCH$_2$), 4.66 (2H, s, OCH$_2$), 3.86 (3H, s, OMe), 3.62 (1H, dd, J 8.4, 8.2, 17-αH), 3.37 (3H, s, OCH$_3$) 2.70-2.80 (2H, m, 6-CH$_2$), 1.20-2.32 (13H, m), and 0.82 (3H, s, 18-CH$_3$). m/z [FAB+] 436.1 (100%, M$^+$+H). HRMS [FAB+] 436.26136.

2-Methoxy-17-O-methoxymethyl estradiol

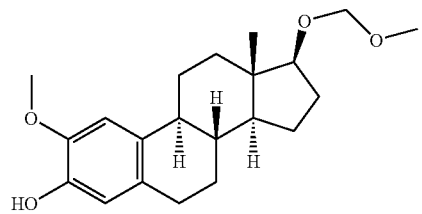

A solution of 2-methoxy-3-benzyloxy-17-O-methoxymethyl estradiol (500 mg) in THF (2 mL) and ethanol (10 mL) was hydrogenated (1 atm) for 16 h in the presence of Pd/C (50 mg, 5%). The reaction was worked-up by filtering through celite and evaporating to give the desired product as a white solid (500 mg). White crystals were obtained by recystallisation from ether/hexane $\delta_H$ (CDCl$_3$) 6.78 (1H, s, ArH), 6.63 (1H, s, ArH), 4.65 (2H, s, OCH$_2$), 3.86 (3H, s, OMe), 3.56-64

(1H, m, 17αH), 3.37 (3H, s, OCH₃) 2.72-2.80 (2H, m, 6-CH₂), 1.15-2.30 (13H, m), and 0.82 (3H, s, 18-CH₃).

2-Methoxy-3-O-sulfamoyl-17-O-methoxymethyl estradiol

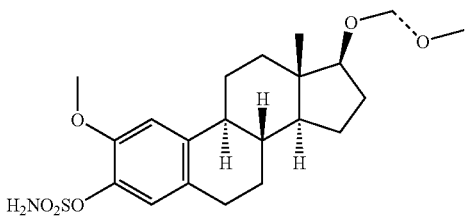

A 0° C. solution of sulfamoyl chloride (1.7 mmol) in DMA (2 mL) was treated with 2-methoxy-17-O-methoxymethyl estradiol (170 mg). After 3 h the reaction was worked up by diluting in ethyl acetate (15 mL) and then washing with water (4×15 mL) and brine (15 mL), dried and evaporated. Chromatography (acetone/chloroform gradient) gave the desired product, 2-Methoxy-3-O-sulfamoyl-17-O-methoxymethyl estradiol, as a white solid (160 mg) which was then crystallised from ether/hexane. $\delta_H$ (CDCl₃) 7.02 (1H, s, ArH), 6.91 (1H, s, ArH), 4.99 (2H, s, NH₂), 4.65 (1H, d, 9.0, CH$_a$H$_b$O), 4.64 (1H, d, 9.0, CH$_a$H$_b$O), 3.86 (3H, s, OMe), 3.60 (1H, dd, J 8.6, 8.2, 17-αH), 3.37 (3H, s, OCH₃) 2.76-2.82 (2H, m, 6-CH₂), 1.15-2.30 (13H, m), and 0.82 (3H, s, 18-CH₃); $\delta_C$ 148.7, 140.4, 136.6, 130.1, 124.0, 110.4, 96.0, 86.5, 56.4, 55.2, 50.0, 44.5, 43.0, 38.2, 37.3, 28.7, 27.1, 26.5, 23.2 and 11.9.

2-Ethyl-3-benzyloxy-17-O-mesyl estradiol 58

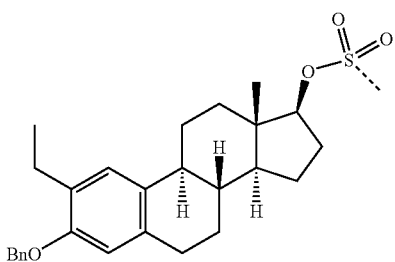

To a solution of 2-ethyl-3-O-benzyl estradiol (1 mmol) in 5 ml of dry pyridine stirred under nitrogen and cooled to 0° C. was added methylsulphonyl chloride (0.09 ml, 1.2 mmol). The solution was stirred at 0° C. for 2 h before addition of water (20 ml). The organics were extracted with ethyl acetate (2×60 ml) and the organic layer was washed successively with water and brine then dried over MgSO₄. After elimination of the solvents under vacuum and column chromatography (hexane/ethyl acetate 5:1) 2-ethyl-3-benzyloxy-17-O-mesyl estradiol was obtained as a white solid. 0.36 g (77%), mp=133° C. ¹H NMR (CDCl₃, 270 MHz): 0.87 (s, 3H, CH₃), 1.22 (t, J$_{H-H}$=7.4 Hz, 3H, CH₃), 1.25-1.60 (m, 6H), 1.70-1.95 (m, 3H), 2.05 (m, 1H), 2.15-2.45 (m, 3H), 2.68 (q, J$_{H-H}$=7.4 Hz, 2H, CH₂), 2.85 (m, 2H, H6), 3.02 (s, 3H, CH₃SO₂), 4.57 (m, 1H, H17), 5.05 (s, 2H, CH₂Ph), 6.64 (s, 1H, ArH, 7.10 (s, 1H, ArH), 7.36-7.44 (m, 5H, Ph). ¹³C NMR (CDCl3): 11.7 (CH₃), 14.6 (CH₃), 23.0, 23.4, 26.0, 27.1, 27.9, 29.5 36.4, 38.2, 38.6, 43.3, 43.7, 49.0, 69.8 (CH₂Ph), 89.5 (C17), 111.8, 126.2, 127.0, 127.6, 128.4 130.3, 131.7, 134.7, 137.6 and 154.5

2-Ethyl-17-O-mesyl estradiol 59

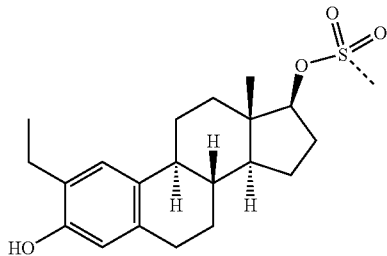

To a solution of 2-ethyl-3-benzyloxy-17-O-mesyl estradiol (0.5 mmol) in 10 ml THF and 40 ml ethanol was added 30 mg of 10% Pd/C. The mixture was stirred at room temperature under hydrogen for 14 hours. The suspension was filtrated over celite, washed with THF and the organic layer was concentrated under vacuum. After column chromatography (hexane/ethyl acetate 1:0 to 2:1) 2-ethyl-17-O-mesyl estradiol was isolated as a white solid. 145 mg (77%), mp=195° C. ¹H NMR (CDCl₃, 270 MHz): 0.86 (s, 3H, CH₃), 1.21 (t, J$_{H-H}$=7.7 Hz, 3H, CH₃), 1.25-1.60 (m, 6H), 1.71-1.91 (m, 3H), 2.03 (m, 1H), 2.13-2.38 (m, 3H), 2.58 (q, J$_{H-H}$=7.7 Hz, 2H, CH₂), 2.79 (m, 2H, H6), 3.01 (s, 3H, CH₃SO₂), 4.53 (s, 1H, OH), 4.56 (dd, 1 J$_{H-H}$=9.1 and 7.9 Hz, 1H, H17), 6.49 (s, 1H, ArH, 7.03 (s, 1H, ArH). ¹³C NMR (CDCl₃): 11.7 (CH₃), 14.6 (CH₃), 23.0, 23.4, 26.0, 27.1, 27.9, 29.5 36.4, 38.2, 38.6, 43.3, 43.7, 49.0, 89.5 (C17), 115.2, 126.3, 127.3, 132.1, 135.2 and 151.2 MS m/z: 350.16 (M⁺) HPLC100%. Microanalysis: C, 66.30 (expected 66.63); H: 7.80 (expected 7.99)

2-Ethyl-3-O-sulfamoyl-17-O-mesyl estradiol 60

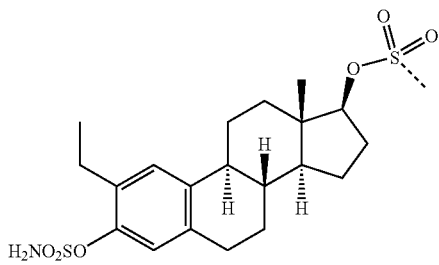

1 ml of a 0.559M solution of sulfamoyl chloride in toluene was concentrated under vacuum and sulfamoyl chloride was dissolved in 1 ml DMA. This solution was cooled to 0° C. and added to 2-ethyl-17-O-mesyl estradiol (0.2 mmol) under nitrogen. The solution was stirred for 15 hours at room temperature. After addition of 5 ml water, the organics was extracted with ethyl acetate (2×50 ml). The organic layer was washed successively with water and brine, dried over MgSO₄ and concentrated under vacuum. After column chromatography (hexane/ethyl acetate 5:2) 2-ethyl-3-O-sulfamoyl-17-O-mesyl estradiol was obtained as a white solid. 60 mg (66%) mp=179° C. ¹H NMR (CDCl₃, 270 MHz): 0.85 (s, 3H, CH₃), 1.20 (t, J$_{H-H}$=7.4 Hz, 3H, CH₃), 1.30-1.55 (m, 6H), 1.73-187 (m, 3H), 2.04 (m, 1H), 2.16-2.36 (m, 3H), 2.68 (q, J$_{H-H}$=7.4

Hz, 2H, CH$_2$), 2.82 (m, 2H, H6), 3.01 (s, 3H, C$\underline{H}$3SO$_2$), 4.57 (dd, 1 J$_{H\text{-}H}$=8.7 and 8.1 Hz, 1H, H17), 5.08 (s, 2H, NH$_2$), 6.49 (s, 1H, ArH), 7.03 (s, 1H, ArH). $^{13}$C NMR (CDCl$_3$): 14.1 (CH$_3$), 17.0 (CH$_3$), 25.4, 23.4, 28.2, 29.2, 30.3, 31.4 38.6, 40.5, 40.6, 45.6, 46.3, 51.4, 91.5 (C17), 123.6, 129.2, 135.9, 137.9, 141.1 and 148.3. LRMS m/z: 457.32 (M$^+$); HPLC 100%; Microanalysis: C, 53.40 (expected 55.12); H, 6.38 (expected 6.34); N, 3.09 (expected 3.06).

2-Ethyl-3-O-TBS-17-dicyanomethylene estrone

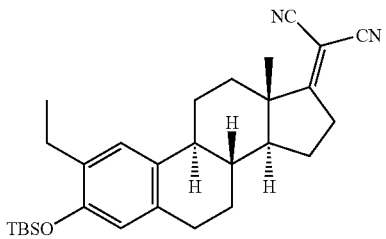

A solution of 2-ethyl-3-O-TBS estrone (2 mmol), malononitrile (6 mmol) and β-alanine was refluxed in 150 ml toluene and 30 ml acetic acid for 3 days. Further, 2 mmol aliquots of malononitrile were added after 24 h and 48 h. After cooling the solution to rt, the solvents were evaporated and the residual solid stirred with 50 ml water and extracted with ethyl acetate (2×100 ml). The organic layer was washed with water, brine, dried over MgSO$_4$ and the solvent removed under vacuum. After column chromatography 2-Ethyl-3-O-TBS-17-dicyanomethylene estrone was obtained as a white powder. 840 mg (91%), mp=168° C. 1H NMR (CDCl$_3$, 270 MHz): 0.21 (s, 6H, CH$_3$Si). 1.00 (s, 9H, (CH$_3$)$_3$Si), 1.06 (s, 3H, CH$_3$), 1.15 (t, J=7.4 Hz, 3H, CH$_3$), 1.40-1.80 (m, 6H), 1.85-2.05 (m, 2H), 2.26 (m, 1H), 2.45-3.05 (m, 7H), 6.4 (s, 1H, ArH), 7.02 (s, 1H, ArH). $^{13}$C NMR (CDCl$_3$): −4.2 and −4.1 (CH$_3$Si), 14.6 (CH$_3$), 16.6, 18.2, 23.2, 23.6, 25.7 ((CH$_3$)$_3$ CSi), 26.3, 27.5, 29.1, 34.0, 34.7, 38.3, 43.4, 49.5, 54.2, 79.6 (C17), 111.1, 112.4, 118.3, 126.1, 131.2, 132.2, 134.3, 151.5 and 196.2.

2-Ethyl-17-dicyanomethylene estrone

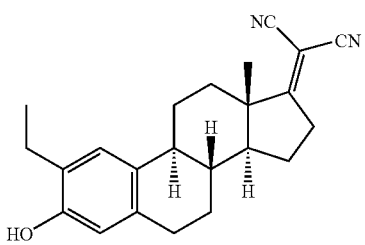

A solution of 2-ethyl-3-O-TBS-17-dicyanomethylene estrone (0.5 mmol) in THF (50 ml) was cooled to 0° C. and TBAF/THF 1M (0.6 mmol, 0.6 ml) was added dropwise. The solution was stirred for 2 hours at 0° C., then warmed to rt. Water (10 ml) and ethyl acetate (80 ml) were then added, the organic layer was successively washed with water and brine, dried over MgSO$_4$ and the solvents were evaporated under vacuum. The residual solid was purified by column chromatography (hexane/ethyl acetate 5:1 to 2:1) to give 2-Ethyl-17-dicyanomethylene estrone as a white solid. 125 mg (72%); mp=270° C.; 1H NMR (CDCl$_3$, 270 MHz): 1.06 (s, 3H, CH$_3$), 1.21 (t, J=7.5 Hz, 3H, CH$_3$), 1.39-1.79 (m, 6H), 1.89-2.05 (m, 2H), 2.25 (m, 1H), 2.45-2.52 (m, 1H), 2.61 (q, J=7.5 Hz, 2H, CH$_2$), 2.63-3.02 (m, 5H), 4.52 (s, 1H, OH), 6.50 (s, 1H, ArH), 7.02 (s, 1H, ArH). $^{13}$C NMR (CDCl$_3$): 14.3, 16.6 (CH$_3$), 23.0, 23.2, 26.4, 27.4, 28.9, 33.9, 34.7, 38.3, 43.3, 49.4, 54.1, 79.6 (C17), 111.2, 112.5, 115.2, 126.2, 127.5, 131.3, 135.0, 151.4 and 196.1. HPLC: 100%

2-Ethyl-3-O-sulfamoyl-17-dicyanomethylene estrone

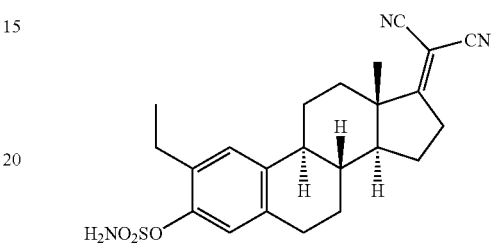

A solution of NH$_2$SO$_2$Cl (0.6 mmol) in DMA (2 ml) cooled to 0° C. was added to 2-ethyl-17-dicyanomethylene estrone (0.2 mmol) and the mixture was stirred for 14 hours at room temperature under nitrogen. Water (10 mL) was then added and the organics were extracted with ethyl acetate (2×50 ml). The organic layer was successively washed with water, brine and dried over MgSO$_4$ before the solvent was removed under vacuum. The residual solids were purified by column chromatography (hexane/ethyl acetate 5/1 to 3/1) to give 2-ethyl-3-O-sulfamoyl-17-dicyanomethylene estrone 62 mg (73%), mp=228° C.; 1H NMR (CDCl$_3$, 270 MHz): 1.06 (s, 3H, CH$_3$), 1.20 (t, J=7.4 Hz, 3H, CH$_3$), 1.44-1.75 (m, 6H), 1.92-2.03 (m, 2H), 2.29 (m, 1H), 2.44-2.55 (m, 1H), 2.69 (q, J=7.4 Hz, 2H, CH$_2$), 2.75-3.04 (m, 5H), 5.03 (s, 2H, NH$_2$), 7.09 (s, 1H, ArH), 7.16 (s, 1H, ArH). $^{13}$C NMR (CDCl$_3$): 14.6, 16.6 (CH$_3$), 23.0, 23.2, 26.2, 27.2, 28.9, 33.8, 34.7, 37.8, 43.4, 49.3, 54.1, 79.7 (C17), 111.0, 112.3, 121.5, 126.9, 134.0, 135.4, 138.0, 146.4 and 195.8. HPLC 100%; Microanalysis: C, 64.90 (expected 64.92); H, 6.45 (expected 6.40); N, 9.68 (expected 9.87).

2-Ethyl-3-O-TBS-17β-dicyanomethyl 17-deoxy estrone

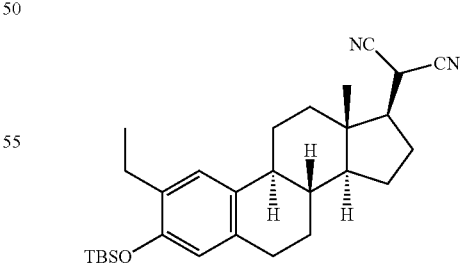

A solution of 2-ethyl-3-O-TBS-17-dicyanomethylene estrone (1 mmol) in methanol (50 ml) and THF (5 ml) was cooled to −10° C. and NaBH$_4$ (76 mg, 2 mmol) was added portion wise. The mixture was stirred at −10° C. for 4 hours. Water (50 ml) was added and the solution was acidified with NH$_4$Cl. The organics were extracted with ethyl acetate (2×60 ml) and the organic layer was successively washed with water and brine, dried over MgSO$_4$ and the solvents evaporated under vacuum. The residual solids were purified by column chromatography to give 2-ethyl-3-O-TBS-17β-dicyanomethyl 17-deoxy estrone 380 mg (83%), mp=162° C. 1H NMR (CDCl$_3$,): 0.22 (s, 6H, CH$_3$Si). 0.80 (s, 3H, CH$_3$), 1.00 (s, 9H, (CH$_3$)$_3$CSi), 1.16 (t, J=7.5 Hz, 3H, CH$_3$), 1.33-1.66 (m, 6H), 1.85 (m, 2H), 2.10-2.40 (m, 6H), 2.55 (q, J=7.5 Hz, 2H, CH$_2$), 2.78 (m, 2H, H6), 3.56 (d, J=9.9 Hz, 1H, CH(CN)$_2$), 6.47 (s, 1H, ArH), 7.03 (s, 1H, ArH). $^{13}$C NMR (CDCl$_3$): −4.2 and −4.1 (CH$_3$Si), 12.4 (CH$_3$), 14.7, 18.2, 23.4, 25.7 ((CH$_3$)$_3$CSi), 26.2, 27.6, 27.7, 29.2, 37.5, 38.8, 43.2, 43.6, 50.3, 54.6, 112.7, 118.2, 126.1, 131.9, 132.1, 134.5, and 151.3.

2-Ethyl-17β-dicyanomethyl 17-deoxy estrone

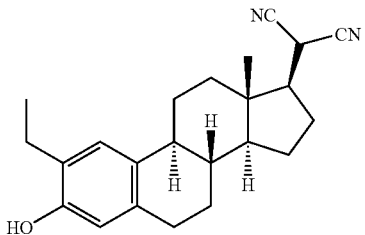

A solution of 2-ethyl-3-O-TBS-17β-dicyanomethyl 17-deoxy estrone (0.5 mmol) in THF (50 ml) was cooled to 0° C. and TBAF/THF 1M (0.6 mmol, 0.6 ml) was added dropwise. The solution was stirred for 2 hours at 0° C., then warmed to rt. Water (10 ml) and ethyl acetate (80 ml) were then added, the organic layer was successively washed with water and brine, dried over MgSO$_4$ and the solvents were evaporated under vacuum. The residual solid was purified by column chromatography (hexane/ethyl acetate 5:1 to 2:1) give 2-ethyl-17β-dicyanomethyl 17-deoxy estrone as a white solid. 124 mg (71%) mp=248° C.; 1H NMR (CDCl$_3$, 270 MHz): 0.80 (s, 3H, CH$_3$), 1.21 (t, J=7.4 Hz, 3H, CH$_3$), 1.30-1.61 (m, 7H), 1.85 (m, 2H), 2.10-2.41 (m, 5H), 2.59 (q, J=7.4 Hz, 2H, CH$_2$), 2.81 (m, 2H, H6), 3.56 (d, J=9.9 Hz, 1H, CH(CN)$_2$), 4.51 (br, 1H, OH), 6.49 (s, 1H, ArH), 7.02 (s, 1H, ArH). $^{13}$C NMR (CDCl$_3$): 12.4 (CH$_3$), 14.4 (CH$_3$), 22.9, 23.4, 26.3, 27.6, 27.7, 29.0, 37.5, 38.8, 43.2, 43.6, 50.3, 54.5, 112.7, 115.2, 126.3, 127.3, 131.9, 135.2, and 151.3. HPLC: 100%; Microanalysis: C, 78.96 (expected 79.27); H, 8.03 (expected 8.10); N, 7.79 (expected 8.04).

2-Ethyl-3-O-sulfamoyl-17β-dicyanomethyl 17-deoxy estrone

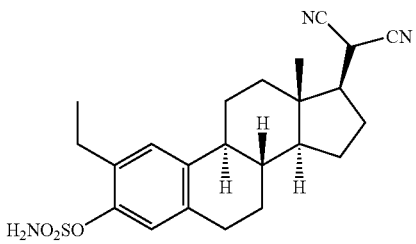

A solution of NH$_2$SO$_2$Cl (0.6 mmol) in DMA (2 ml) cooled to 0° C. was added to 2-ethyl-17β-dicyanomethyl 17-deoxy estrone (0.2 mmol) and the mixture was stirred for 14 hours at room temperature under nitrogen. Water (10 mL) was added and the organics were extracted with ethyl acetate (2×50 ml). The organic layer was successively washed with water, brine and dried over MgSO$_4$ before the solvent was removed under vacuum. The residual solids were purified by column chromatography (hexane/ethyl acetate 5/1 to 3/1) to give 2-ethyl-3-O-sulfamoyl-17β-dicyanomethyl 17-deoxy estrone 170 mg (80%), as a white powder mp=169° C.; 1H NMR (CDCl3, 270 MHz): 0.80 (s, 3H, CH$_3$), 1.21 (t, J=7.4 Hz, 3H, CH$_3$), 1.32-1.55 (m, 7H), 1.87 (m, 2H), 2.10-2.38 (m, 5H), 2.68 (q, J=7.4 Hz, 2H, CH$_2$), 2.83 (m, 2H, H6), 3.57 (d, J=9.9 Hz, 1H, CH(CN)$_2$), 4.91 (br, 2H, NH$_2$), 7.08 (s, 1H, ArH), 7.16 (s, 1H, ArH). $^{13}$C NMR (CDCl3, 270 MHz): 12.4 (CH$_3$), 14.4 (CH$_3$), 22.9, 23.4, 26.3, 27.6, 27.7, 29.0, 37.5, 38.8, 43.2, 43.6, 50.3, 54.5, 112.7, 115.2, 126.3, 127.3, 131.9, 135.2, and 151.3. HPLC: 100%; Microanalysis: C, 64.64 (expected 64.61); H, 7.80 (expected 6.84); N, 9.62 (expected 9.83).

2-Ethyl-3-O-TBS-17β-(1-cyano)ethyl 17-deoxy estrone

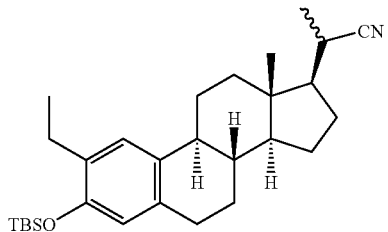

A solution of 2-ethyl-3-O-TBS-17β-cyanomethyl 17-deoxy estrone (0.5 mmol) in THF (50 ml) was stirred under nitrogen at −78° C. and then treated with 1M LDA (1.2 mmol, 1.2 ml) in a dropwise manner. After 30 min CH$_3$I (1.5 mmol, 212 mg) was added and the mixture stirred for 4 hours at −78° C. then 12 hours at rt. Ethylacetate (100 mL) and water (30 mL) were added, the organic layer washed with water, brine, dried over MgSO$_4$ and the solvents evaporated under vacuum. The resulting yellow oil was purified by column chromatography (hexane/ethyl acetate 20:1) to give 2-ethyl-3-O-TBS-17β-(1-cyano)ethyl 17-deoxy estrone, a colourless oil, 176 mg (78%), as a (1:1) mixture of diastereoisomers $^1$H NMR (CDCl3, 270 MHz): 0.23 (s, 6H, CH$_3$Si), 0.76 and 0.78 (s, 3H, CH$_3$), 1.01 (s, 9H, (CH$_3$)$_3$CSi), 1.17 (t, J=7.4 Hz, 2H, CH$_3$), 1.25-1.96 (m, 13H), 2.05-2.50 (m, 3H), 2.57 (q t, J=7.3 Hz, 2H, CH$_2$), 2.66-2.88 (m, 4H, CH$_2$), 6.48 and 6.50 (m, 1H, ArH), 7.03-7.06 (m, 1H, ArH).

2-Ethyl-17-deoxy 17β-(1-cyano)ethyl estrone

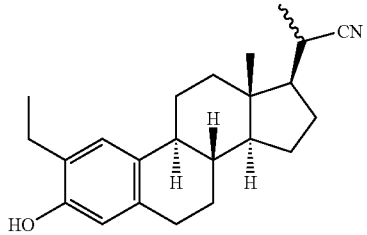

A solution of 2-ethyl-3-O-TBS-17β-(1-cyano)ethyl 17-deoxy estrone (1 mmol) in THF (50 ml) was cooled to 0° C. and TBAF/THF 1M (1.2 mmol, 1.2 ml) was added dropwise. The solution was stirred for 2 hours at 0° C., warmed to RT. Water (10 ml) and ethyl acetate (80 ml) were then added, the organic layer was successively washed with water and brine, dried over MgSO$_4$ and the solvents were evaporated under vacuum. The residual yellow solid (400 mg) was purified by column chromatography (hexane/ethyl acetate 5:1 to 2:1) then recrystallized in hexane/ethylacetate 6:1 to afford 220 mg (71%) of 2-ethyl-17-deoxy 17β-(1-cyano)ethyl estrone as a white powder. mp: 226-228° C. $^1$H NMR (CDCl$_3$, 270 MHz): 0.75 (s, 3H, CH$_3$), 1.20-1.65 (m, 9H), 1.85-1.92 (m, 5H), 2.10-2.58 (m, 4H), 2.5 (m, 2H, H6), 6.55-6.62 (m, 2H, ArH), 7.07 (m, 1H, ArH). HPLC:100% Microanalysis: C, 81.60 (expected 81.51); H, 8.79 (expected 8.79); N, 4.40 (expected 4.53).

2-Ethyl-3-O-sulfamoyl-17-deoxy 17-(1-cyano)ethyl estrone

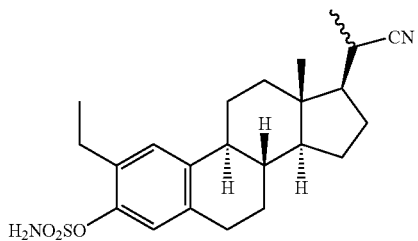

A solution of NH$_2$SO$_2$Cl (0.6 mmol) in DMA (2 ml) cooled to 0° C. was added to 2-ethyl-17-deoxy 17β-(1-cyano)ethyl estrone (0.2 mmol) and the mixture was stirred for 14 hours at room temperature under nitrogen. 10 ml of water were added and the organics were extracted with ethyl acetate (2×50 ml). The organic layer was successively washed with water, brine and dried over MgSO$_4$ before the solvent was removed under vacuum. The residual solid was purified by column chromatography (hexane/ethyl acetate 5/1 to 2/1) then recrystallised (Hexane/ethylacetate 5:1) to give 42 mg (54%) of 2-ethyl-3-O-sulfamoyl-17-deoxy 17β-(1-cyano)ethyl estrone. mp: 157-159° C. $^1$H NMR (CDCl3, 270 MHz): 0.79 (s, 3H, CH$_3$), 1.25-1.64 (m, 11H), 1.73-1.81 (m, 1H), 1.85-2.03 (m, 2H), 2.23-2.37 (m, 2H), 2.40-2.53 (m, 2H), 2.89 (m, 2H, H6), 7.03 (d, J=2.7 Hz, 1H, ArH), 7.07 (dd, J=9.0 and 2.7 Hz, 1H, ArH), 7.31 (d, J=9.0 Hz, 1H, ArH). HPLC:100% Microanalysis: C, 64.90 (expected 64.92); H, 7.52 (expected 7.26); N, 7.23 (expected 7.21).

2-Ethyl-3-O-benzyl-17α-(methyl)cyanomethyl estradiol

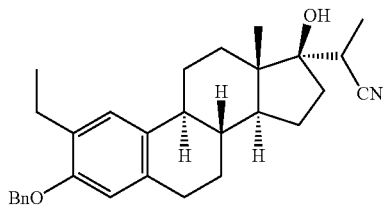

A solution of propionitrile (0.05 mol) in dry THF (50 ml) was stirred under nitrogen at −78° C. and then treated with LDA (0.05 mol) was added dropwise. The mixture was stirred for an 1 h before addition of 2-ethyl-3-O-benzyl estrone (8 mmol) in 20 ml THF (dropwise over a period of 3 h). The mixture was stirred for an additional 3 h then quenched with an aqueous solution of NH$_4$Cl and extracted with ethylacetate. The organic layer was successively washed with water, brine, dried over MgSO4 and the solvents evaporated under vacuum. The crude oil was purified by column chromatography (hexane/ethylacetate 10/1 to 4/1) to give 2-ethyl-3-O-benzyl-17α-(methyl)cyanomethyl estradiol 2.70 g (76%) as a white powder, mp=75-77° C. $^1$H NMR (CDCl$_3$, 270 MHz): 0.97 (s, 3H, CH$_3$), 1.20 (t, J=7.6 Hz, 3H, CH$_3$), 1.25-1.90 (m, 12H), 1.97-2.07 (m, 2H) 2.15-2.23 (m, 1H), 2.41-2.49 (m, 1H), 2.66 (q, J=7.6 Hz, 2H, CH$_2$), 2.77-2.91 (m, 3H), 5.04 (s, 2H, C$\underline{H}_2$Ph),), 6.62 (s, 1H, ArH), 7.09 (s, 1H, ArH), 7.28-7.46 (m, 5H, Ph).

2-Ethyl-3-O-benzyl 17-(1-cyano)ethylidene estrone

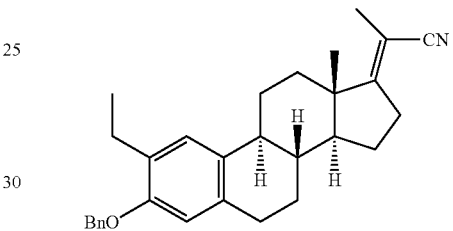

2-Ethyl-3-O-benzyl estradiol-17α-propionitrile (0.05 mol) was added to a solution of TEA (2 ml) and DCM (25 ml) cooled to 0° C. and after addition of CH$_3$SO$_2$Cl (0.055 mol, 0.44 ml) the solution was stirred for 8 hours at 0° C. The solution was quenched with water and the organics were extracted with DCM. The organic layer was successively washed with water and brine, dried over MgSO$_4$ and the solvents were removed under vacuum. The crude oil was purified by column chromatography (hexane/ethyl acetate 10/1) to give 2-ethyl-3-O-benzyl 17-cyanoethylidene estrone. Yield 85%, mp=63-64° C. $^1$H NMR (CDCl$_3$, 270 MHz): 0.95 (s, 3H, CH$_3$), 1.21 (t, J=7.3 Hz, 3H, CH$_3$), 1.30-1.71 (m, 6H), 1.84 (s, 3H, CH$_3$), 1.85-1.96 (m, 2H), 2.21-2.51 (m, 4H), 2.64 (q, J=7.3 Hz, 2H, CH$_2$), 2.75-2.90 (m, 3H), 5.04 (s, 2H, C$\underline{H}_2$Ph), 6.63 (s, 1H, ArH), 7.10 (s, 1H, ArH), 7.28-7.48 (m, 5H, Ph).

2-Ethyl-17-deoxy 17β-(1-cyano)ethyl estrone

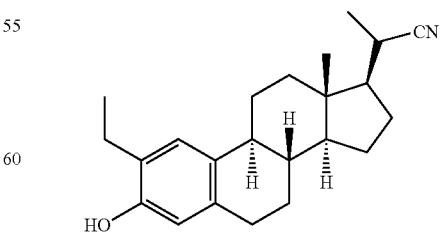

To a solution of 2-Ethyl-3-O-benzyl 17-(1-cyano)ethylidene estrone (1 mmol) in 5 mL THF/45 mL methanol was added 50 mg of 5% Pd/C and the mixture was stirred under hydrogen for 16 hours. The suspension was filtrated over celite/sand, washed with THF and the organic layer was concentrated under vacuum. After column chromatography (hexane/ethyl acetate 10:1 to 1:1) and recrystallization (hexane/ethylacetate 5:1) 2-ethyl-17-deoxy 17β-(1-cyano)ethyl estrone was isolated as a white solid. white powder, 225 mg (67%), mp=235-236° C.; $^1$H NMR (CDCl$_3$, 270 MHz): 0.76 (s, 3H, CH$_3$), 1.20 (t, J=7.4 Hz, 3H, CH$_3$), 1.24-1.69 (m, 13H), 1.71-2.00 (m, 2H), 2.10-2.48 (m, 2H), 2.57 (q, J=7.3 Hz, 2H, CH$_2$), 2.71 (m, 1H, C$\underline{H}$(CH$_3$)CN), 2.78 (m, 2H, H6), 4.47 (br, 1H, OH), 6.49 (s, 1H, ArH), 7.03 (s, 1H, ArH). Microanalysis: C, 81.50 (expected 81.85); H, 9.18 (expected 9.26); N, 3.99 (expected 4.15).

2-Ethyl-3-O-sulfamoyl-17-deoxy 17β-(1-cyano)ethyl estrone

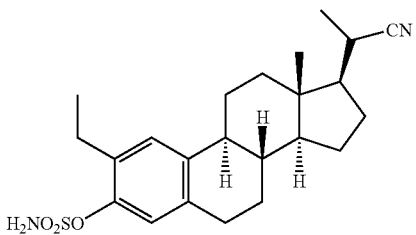

A solution of NH$_2$SO$_2$Cl (1 mmol) in DMA (2 ml) cooled to 0° C. was added to 21a (0.3 mmol) and the mixture was stirred for 14 hours at room temperature under nitrogen. Water (10 mL) was then added and the organics were extracted with ethyl acetate (2×50 ml). The organic layer was successively washed with water, brine and dried over MgSO$_4$ before the solvent was removed under vacuum. The residual solid was purified by column chromatography (hexane/ethyl acetate 5/1 to 2/1) then recrystallized (Hexane/ethyl acetate 5:1) to give 2-ethyl-3-O-sulfamoyl-17-deoxy 17β-(1-cyano) ethyl estrone as a white powder, 86 mg (69%), mp-171-172° C. $^1$H NMR (CDCl3, 270 MHz): 0.76 (s, 3H, CH$_3$), 1.20 (t, J=7.4 Hz, 3H, CH$_3$), 1.22-1.64 (m, 11H), 1.75-2.35 (m, 6H), 2.66 (q, J=7.3 Hz, 2H, CH$_2$), 2.68 (m, 1H, C$\underline{H}$(CH$_3$)CN), 2.84 (m, 2H, H6), 4.92 (br, 2H, NH$_2$), 7.07 (s, 1H, ArH), 7.16 (s, 1H, ArH). $^{13}$C NMR (CDCl3, 270 MHz): 12.4 (CH$_3$), 14.6 (CH$_3$), 18.6 (CH$_3$), 23.0, 23.8, 26.2, 26.8, 27.0, 27.4, 29.1, 38.2, 38.6, 42.9, 44.0, 53.3, 54.8, 121.4, 123.0 (CN), 126.9, 133.6, 135.9, 139.3, 146.2.

Microanalysis: C, 66.40 (expected 66.31); H, 7.73 (expected 7.74); N, 6.52 (expected 6.72).

2-Ethyl-3-O-benzyl-17β-(2-hydroxyethyl) 17-deoxyestrone

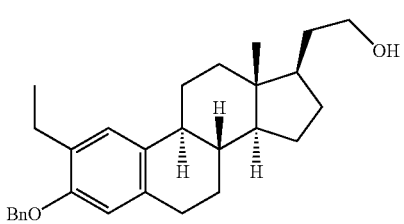

A solution of (3-benzyloxy-2-ethyl-13-methyl-7,8,9,11,12,13,14,15,16,17-decahydro-6H-cyclopenta[a]phenanthren-17-yl)-acetic acid ethyl ester (1.84 g, 4 mmol) in 30 ml dry THF was cooled to 0° C. under nitrogen before LiAlH$_4$ (0.30 g, 8 mmol) was added portion wise. After 3 hours at 0° C., the mixture was quenched with aq. NH$_4$Cl and the organics were extracted with ethyl acetate. The organic layer was washed with water, brine, dried over MgSO$_4$ and the solvents were evaporated under vacuum. The crude oil was purified by chromatography (hexane/ethylacetate 15/1 to 8:1) to give 1.47 g (88%) of 2-ethyl-3-O-benzyl-17β-(2-hydroxyethyl) 17-deoxyestrone as a white powder, mp=98-99° C. $^1$H NMR (CDCl$_3$, 270 MHz): 0.63 (s, 3H, CH$_3$), 1.20 (t, J=7.4 Hz, 3H, CH$_3$), 1.22-1.58 (m, 9H), 1.70-1.92 (m, 5H), 2.16-2.34 (m, 2H), 2.66 (q, J=7.4 Hz, 2H, CH$_2$), 2.82 (m, 2H, H6), 3.68 (m, 2H, C$\underline{H}_2$OH), 5.03 (s, 2H, CH$_2$Ph), 6.62 (s, 1H, ArH), 7.10 (s, 1H, ArH), 7.28-7.45 (m, 5H, Ph).

2-Ethyl-3-O-benzyl-17β-(2-methoxyethyl) 17-deoxyestrone

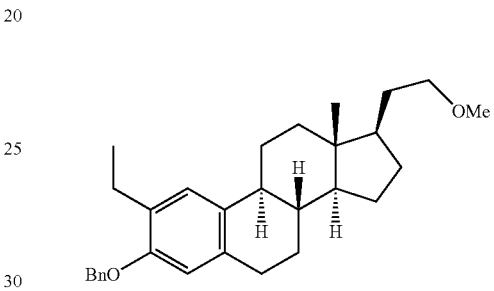

A solution of 2-ethyl-3-benzyl-17β-(2-hydroxyethyl) 17-deoxyestrone (1.26 g, 3 mmol) in 30 ml dry THF was cooled to 0° C. under nitrogen. NaH (0.16 g, 4 mmol of NaH 60% dispersion in mineral oil) was added portion wise and the solution stirred for 30 minutes before CH$_3$I (0.37 ml, 6 mmol) was added dropwise. The solution was then allowed to warm to room temperature and stirred for 18 hours. After addition of water (20 ml) the organics were extracted with ethyl acetate. The organic layer was washed with water, brine, dried over MgSO$_4$ and the solvents were evaporated under vacuum. The crude oil was purified by chromatography (hexane/ethylacetate 20/1) to give 1.25 g (96%) of 2-ethyl-3-O-benzyl-17β-(2-methoxyethyl) 17-deoxyestrone as a white powder, mp=70-71° C. $^1$H NMR (CDCl$_3$, 270 MHz): 0.66 (s, 3H, CH$_3$), 1.25 (t, J=7.4 Hz, 3H, CH$_3$), 1.26-1.60 (m, 9H), 1.76-1.96 (m, 5H), 2.20-2.42 (m, 2H), 2.70 (q, J=7.4 Hz, 2H, CH$_2$), 2.86 (m, 2H, H6), 3.38 (s, 3H, CH$_3$O), 3.44 (m, 2H, CH$_2$O), 5.07 (s, 2H, CH$_2$Ph), 6.66 (s, 1H, ArH), 7.15 (s, 1H, ArH), 7.31-7.50 (m, 5H, Ph).

2-Ethyl-17β-(2-methoxyethyl) 17-deoxyestrone

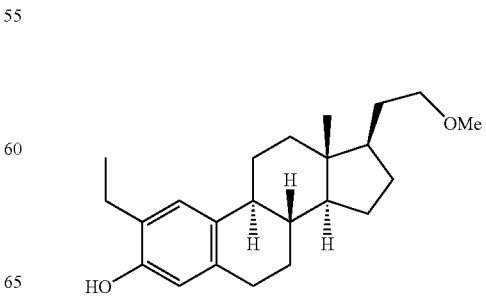

2-Ethyl-3-O-benzyl-17β-(2-methoxyethyl) 17-deoxyestrone 0.87 g (2 mmol) of 35 were dissolved in THF (5 ml) and MeOH (50 ml), 50 mg 5% Pd/C were added and the mixture was stirred under hydrogen for 16 hours. The suspension was filtered over celite/sand, washed with THF and the solvents were evaporated under vacuum. The thick yellowish oil was purified by column chromatography (hexane/ethylacetate 15/1 to 10/1) to give 2-ethyl-17β-(2-methoxyethyl) 17-deoxyestrone 0.66 g (97%), a white powder, mp=58-59° C.; $^1$H NMR (CDCl$_3$, 270 MHz): 0.62 (s, 3H, CH$_3$), 1.19-1.56 (m, 12H), 1.72-1.91 (m, 5H), 2.13-2.34 (m, 2H), 2.60 (q, J=7.4 Hz, 2H, CH$_2$), 2.77 (m, 2H, H6), 3.37 (s, 3H, CH$_3$O), 3.45 (m, 2H, CH$_2$O), 5.26 (s, 1H, OH), 6.48 (s, 1H, ArH), 7.06 (s, 1H, ArH). $^{13}$C NMR (CDCl$_3$): 12.4 (CH$_3$), 12.5 (CH$_3$), 23.0, 24.4, 26.5, 27.9, 28.3, 29.3, 30.2, 37.7, 38.9, 42.4, 44.2, 47.3, 54.6, 58.4, 72.4, 115.1, 126.2, 127.2, 132.6, 135.4, and 151.3. HPLC: 100%; HRMS (FAB+): found 342.255493 calcd. C$_{23}$H$_{34}$O$_2$ 342.255881

2-Ethyl-3-O-sulfamoyl-17β-(2-methoxyethyl) 17-deoxyestrone

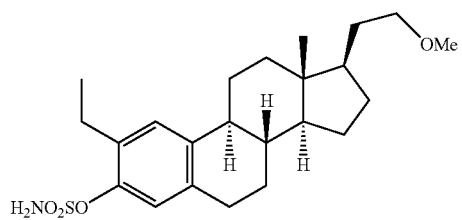

A solution of NH$_2$SO$_2$Cl (3 mmol) in DMA (2 ml) cooled to 0° C. was added to 2-ethyl-17β-(2-methoxyethyl) 17-deoxyestrone (342 mg, 1 mmol) and the mixture was stirred for 24 hours at room temperature under nitrogen. After addition of water (10 ml) the organics were extracted with ethyl acetate (2×50 ml). The organic layer was successively washed with water, brine and dried over MgSO$_4$. The solvent was removed under vacuum and the residual solid was purified by column chromatography (hexane/ethyl acetate 10/1 to 4/1) then recrystallized (Hexane/ethylacetate 5:1) to give 2-ethyl-3-O-sulfamoyl-17β-(2-methoxyethyl) 17-deoxyestrone 0.35 g (84%) as a white powder, mp=168-169° C.; $^1$H NMR (CDCl$_3$, 270 MHz): 0.61 (s, 3H, CH$_3$), 1.20 (t, J=7.4 Hz, 3H, CH$_3$), 1.22-1.54 (m, 9H), 1.70-1.95 (m, 5H), 2.15-2.33 (m, 2H), 2.68 (q, J=7.4 Hz, 2H, CH$_2$), 2.82 (m, 2H, H6), 3.33 (s, 3H, CH$_3$O), 3.35 (m, 2H, CH$_2$O), 4.95 (s, 2H, NH$_2$), 7.06 (s, 1H, ArH), 7.18 (s, 1H, ArH). $^{13}$C NMR (CDCl$_3$, 270 MHz): 12.4 (CH$_3$), 14.6 (CH$_3$), 23.0, 24.4, 26.3, 27.7, 28.3, 29.3, 30.4, 37.6, 38.5, 42.4, 44.4, 47.4, 54.9, 58.7, 72.6, 121.4, 127.0, 133.5, 136.1, 139.9, and 146.1; HPLC: 100%; Microanalysis: C, 65.40 (expected 65.52); H, 8.29 (expected 8.37); N, 3.14 (expected 3.32).

2-Ethyl-3-O-benzyl-17β-(2-(OTBDPS)ethyl) 17-deoxy estrone

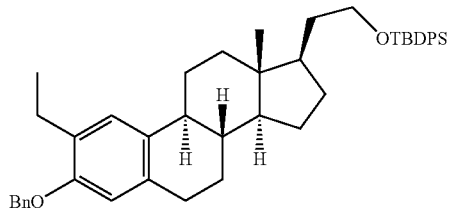

A solution of 2-ethyl-3-O-benzyl-17β-(2-hydroxyethyl) 17-deoxy estrone (0.419 g, 1 mmol), imidazole (0.136 g, 2 mmol) and TPDPSCl (1.1 mmol) in 10 ml dry DMF was stirred at room temperature under nitrogen for 24 hours. After addition of water (10 ml) the organics were extracted with ethyl acetate (2×50 ml). The organic layer was successively washed with water, brine and dried over MgSO$_4$. The solvent was removed under vacuum and the residual oil was purified by column chromatography (hexane/ethyl acetate 25/1) to give [2-(3-Benzyloxy-2-ethyl-13-methyl-7,8,9,11,12,13,14,15,16,17-decahydro-6H-cyclopenta[a]phenan-thren-17-yl)-ethoxy]-tert-butyl-diphenyl-silane as a white powder, 590 mg (90%), mp=48-50° C.; $^1$H NMR (CDCl$_3$, 270 MHz): 0.63 (s, 3H, CH$_3$), 1.12 (s, 9H, (CH$_3$)$_3$C) 1.15-1.60 (m, 11H), 1.71-2.01 (m, 5H) 2.20-2.44 (m, 2H), 2.69 (q, J=7.4 Hz, 2H, CH$_2$), 2.88 (m, 2H, H6), 3.65-3.81 (m, 2H, CH$_2$O), 5.09 (s, 2H, CH$_2$Ph), 6.68 (s, 1H, ArH), 7.20 (s, 1H, ArH), 7.32-7.51 (m, 1H, Ph), 7.72-7.77 (m, 4H, Ph).

2-Ethyl-17β-(2-(OTBDPS)ethyl) 17-deoxy estrone

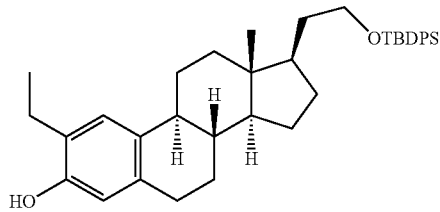

To a solution of 2-ethyl-3-O-benzyl-17β-(2-(OTBDPS) ethyl) 17-deoxy estrone (1 mmol) in THF (2 ml) and ethanol (20 ml) was added 50 mg of 5% Pd/C and the mixture was stirred under hydrogen. The reaction was monitored by TLC. After completion, the suspension was filtered of over celite/sand and the solvents evaporated under vacuum. The residual oil was purified by column chromatography (hexane/ethyl acetate 20/1 to 3:1) to afford 17-[2-(tert-Butyl-diphenyl-silanyloxy)-ethyl]-2-ethyl-13-methyl-7,8,9,11,12,13,14,15,16,17-decahydro-6H-cyclopenta[a]phenanthren-3-ol as a white solid, mp=134-135° C., 0.49 g (87%); $^1$H NMR (CDCl$_3$, 270 MHz): 0.59 (s, 3H, CH$_3$), 1.08 (s, 9H, (CH$_3$)$_3$C), 1.18-1.56 (m, 12H), 1.68-1.89 (m, 5H), 2.10-2.33 (m, 2H), 2.61 (q, J=7.4 Hz, 2H, CH$_2$), 2.78 (m, 2H, H6), 3.61-3.78 (m, 2H, CH$_2$O), 4.71 (s, 1H, OH), 6.49 (s, 1H, ArH), 7.07 (s, 1H, ArH), 7.38 (m, 6H, Ph), 7.70 (m, 4H, Ph).

2-Ethyl-3-O-sulfamoyl-17β-(2-(OTBDPS)ethyl) 17-deoxy estrone

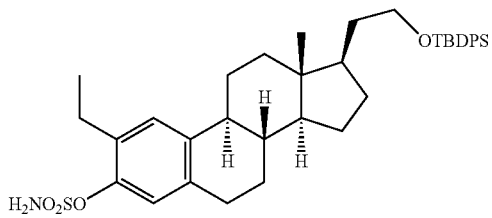

A solution of NH$_2$SO$_2$Cl (3 mmol) in DMA (2 ml) cooled to 0° C. was added to 39c (566 mg, 1 mmol) and the mixture was stirred for 24 hours at room temperature under nitrogen. After addition of water (10 ml) the organics were extracted with ethyl acetate (2×50 ml). The organic layer was successively washed with water, brine and dried over MgSO$_4$. The solvent was removed under vacuum and the residual solid was purified by column chromatography (hexane/ethyl acetate 15/1 to 8/1 to give 2-ethyl-3-O-sulfamoyl-17'-(2-(OTBDPS) ethyl) 17-deoxy estrone as a white solid, 470 mg (72%), mp=185-186° C.; $^1$H NMR (CDCl$_3$, 270 MHz): 0.57 (s, 3H, CH$_3$), 1.05 (s, 9H, (CH$_3$)$_3$C), 1.18-1.55 (m, 13H), 1.68-1.89 (m, 4H), 2.15-2.31 (m, 2H), 2.68 (q, J=7.4 Hz, 2H, CH$_2$), 2.82 (m, 2H, H6), 3.57-3.75 (m, 2H, CH$_2$O), 4.91 (br, 2H, NH$_2$), 7.06 (s, 1H, ArH), 7.19 (s, 1H, ArH), 7.34-7.45 (m, 6H, Ph), 7.67 (m, 4H, Ph). $^{13}$C NMR (CDCl$_3$): 12.9 (CH$_3$), 15.1 (CH$_3$), 20.0, 23.5, 24.9, 26.8, 27.3, 28.1, 28.8, 29.7, 33.9, 38.1, 38.8, 42.7, 44.8, 47.6, 55.0, 63.9, 121.5, 127.2, 127.7, 129.7, 133.7, 134.3, 135.7, 136.3, 140.1, and 146.2. HRMS (FAB+): found 645.326294, calcd. C$_{23}$H$_{34}$O$_2$ 645.330810

2-Ethyl-3-O-sulfamoyl-17β-(2-hydroxyethyl) 17-deoxy estrone

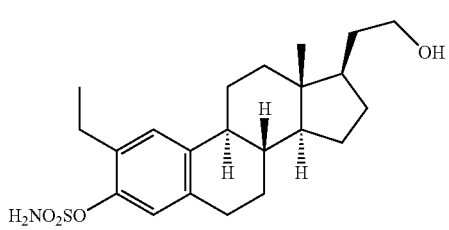

A solution of 2-ethyl-3-O-sulfamoyl-17β-(2-(OTBDPS) ethyl) 17-deoxy estrone (323 mg, 0.5 mmol) in 20 ml THF was cooled to 0° C. before 0.6 ml of 1M TBAF/THF was added dropwise. The solution was stirred at 0° C. for 6 hours then water (10 ml) was added and the organics were extracted with ethyl acetate (2×50 ml). The organic layer was successively washed with water, brine and dried over MgSO$_4$. The solvents were removed under vacuum and the residual solid was purified by column chromatography (hexane/ethyl acetate 10/1 to 2/1) followed by recrystallization in hexane/ethylacetate 4:1 to give 2-ethyl-3-O-sulfamoyl-17β-(2-hydroxyethyl) 17-deoxy estrone as a white powder, 145 mg (72%), mp=157-158° C.; $^1$H NMR ((CD$_3$)$_2$CO) 0.62 (s, 3H, CH$_3$), 1.17-1.55 (m, 12H), 1.70-1.94 (m, 5H), 2.16-2.33 (m, 2H), 2.68 (q, J=7.4 Hz, 2H, CH$_2$), 2.83 (m, 2H, H6), 3.60-3.76 (m, 2H, CH$_2$O), 4.87 (br, 2H, NH$_2$), 7.06 (s, 1H, ArH), 7.19 (s, 1H, ArH); $^{13}$C NMR (CD$_3$COCD$_3$, 400 MHz): 11.8 (CH$_3$), 13.9 (CH$_3$), 22.3, 23.7, 25.7, 27.1, 27.7, 28.5, 33.0, 37.1, 38.0, 41.7, 43.8, 46.7, 54.1, 61.2, 121.1, 126.0, 133.1, 134.9, 138.4 and 145.8; Microanalysis: C, 64.78 (expected 64.83); H, 8.12 (expected 8.16); N, 3.41 (expected 3.44).

2-(3-Benzyloxy-2-ethyl-13-methyl-6,7,8,9,11,12,13,14,15,16-decahydro-cyclopenta[a]phenanthren-17-ylidene)-ethanol

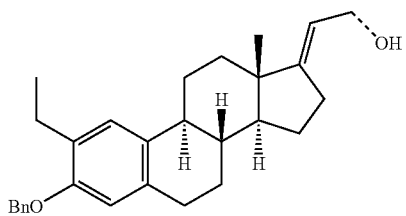

A solution of (3-Benzyloxy-2-ethyl-13-methyl-6,7,8,9,11,12,13,14,15,16-decahydro-cyclopenta[a]phenanthren-17-ylidene)-acetic acid ethyl ester (0.92 g, 2 mmol) in 20 ml dry THF was cooled to 0° C. under nitrogen before LiAlH$_4$ (0.15 g, 4 mmol) was added in a portion wise manner. After 6 hours at 0° C., the mixture was quenched with aq. NH$_4$Cl, the organics were extracted with ethylacetate. The organic layer was washed with water, brine, dried over MgSO$_4$ and the solvents were evaporated under vacuum. The crude oil was purified by chromatography (hexane/ethylacetate 15/1 to 6:1) to give 2-(3-Benzyloxy-2-ethyl-13-methyl-6,7,8,9,11,12,13,14,15,16-decahydro-cyclopenta[a]phenanthren-17-ylidene)-ethanol, 0.75 g (89%), as a white powder, mp=61-62° C.; $^1$H NMR (CDCl$_3$, 270 MHz): 0.84 (s, 3H, CH$_3$), 1.20-1.66 (m, 9H), 1.82-2.02 (m, 3H), 2.21-2.51 (m, 3H), 2.71 (q, J=7.4 Hz, 2H, CH$_2$), 2.87 (m, 2H, H6), 4.16 (m, 2H, CH$_2$OH), 5.07 (s, 2H, CH$_2$Ph), 5.31 (m, 1H, CHCH$_2$OH), 6.66 (s, 1H, ArH), 7.15 (s, 1H, ArH), 7.30-7.48 (m, 5H, Ph).

3-Benzyloxy-2-ethyl-17-(2-methoxy-ethylidene)-13-methyl-7,8,9,11,12,13,14,15,16,17-decahydro-6H-cyclopenta[a]phenanthrene

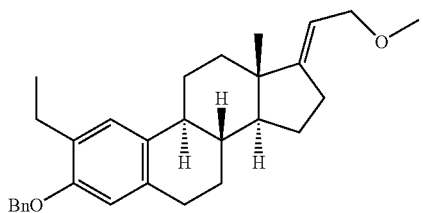

A solution of 2-(3-Benzyloxy-2-ethyl-13-methyl-6,7,8,9,11,12,13,14,15,16-decahydro-cyclopenta[a]phenanthren-17-ylidene)-ethanol (0.62 g, 1.5 mmol) in 10 ml dry THF was cooled to 0° C. under nitrogen. NaH (0.08 g, 2 mmol of NaH 60% dispersion in mineral oil) was added portion wise and the solution stirred for 30 minutes before CH$_3$I (0.19 ml, 3 mmol) was added dropwise. The solution was then allowed to warm to room temperature and stirred for 18 hours. After addition of water (20 ml) the organics were extracted with ethylacetate. The organic layer was washed with water, brine, dried over MgSO$_4$ and the solvents were evaporated under vacuum. The crude oil was purified by chromatography (hexane/ethylacetate 20/1) to give 3-benzyloxy-2-ethyl-17-(2-methoxy-ethylidene)-13-methyl-7,8,9,11,12,13,14,15,16,17-decahydro-6H-cyclopenta[a]phenanthrene, 0.59 g (91%), as a colourless oil; $^1$H NMR (CDCl$_3$, 270 MHz): 0.84 (s, 3H, CH$_3$), 1.24 (t, J=7.4 Hz, 3H, CH$_3$), 1.26-1.66 (m, 6H), 1.82-2.02 (m, 3H), 2.20-2.51 (m, 3H), 2.70 (q, J=7.4 Hz, 2H, CH$_2$), 2.87 (m, 2H, H6), 3.36 (s, 3H, CH$_3$O), 3.94 (m, 2H, CH$_2$OMe), 5.06 (s, 2H, CH$_2$Ph), 5.27 (m, 1H, CHCH$_2$OH), 6.66 (s, 1H, ArH), 7.15 (s, 1H, ArH), 7.31-7.48 (m, 5H, Ph).

2-Ethyl-17-(2-methoxy-ethylidene)-13-methyl-7,8,9,11,12,13,14,15,16,17-decahydro-6H-cyclopenta[a]phenanthren-3-ol

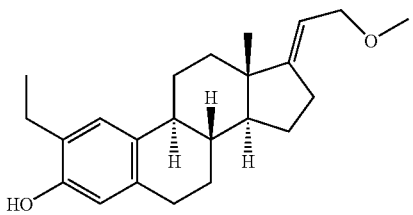

A solution of 3-benzyloxy-2-ethyl-17-(2-methoxy-ethylidene)-13-methyl-7,8,9,11,12,13,14,15,16,17-decahydro-6H-cyclopenta[a]phenanthrene (0.43 g, 1 mmol) in 50 ml tert-butanol was reflux and Na (0.46 g, 20 mmol) was added in small portions over a period of 6 hours. The mixture was refluxed for 18 h, cooled to room temperature and 2-propanol added to destroy excess sodium. The solvents were evaporated and the residual solid poured in water (20 ml). The organics were extracted with ethyl acetate and the organic layer was washed with water, brine, dried over MgSO$_4$. The solvent was evaporated under vacuum. The crude oil was purified by chromatography (hexane/ethylacetate 15/1 to 8:1) to give 2-ethyl-17-(2-methoxy-ethylidene)-13-methyl-7,8,9,11,12,13,14,15,16,17-decahydro-6H-cyclopenta[a]phenanthren-3-ol as a white powder, 230 mg (68%), mp=133-134° C.; $^1$H NMR (CDCl$_3$, 270 MHz): 0.79 (s, 3H, CH$_3$), 1.22 (t, J=7.4 Hz, 3H, CH$_3$), 1.28-1.60 (m, 6H), 1.75-1.96 (m, 3H), 2.18 (m, 1H), 2.39 (m, 3H), 2.59 (q, J=7.4 Hz, 2H, CH$_2$), 2.79 (m, 2H, H6), 3.35 (s, 3H, CH$_3$O), 3.94 (m, 2H, CH$_2$OMe), 5.11 (s, 1H, OH), 5.24 (m, 1H, CHCH$_2$OH), 6.48 (s, 1H, ArH), 7.05 (s, 1H, ArH). $^{13}$C NMR (CDCl$_3$, 400 MHz): 14.9 (CH$_3$), 19.2, 23.5, 24.4, 26.7, 27.1, 28.1, 29.7, 36.4, 39.1, 44.4, 44.8, 53.5, 58.2, 70.2, 112.8, 115.7, 126.4, 127.5, 132.6, 135.5, 151.5, and 157.1. HPLC: 98%; HRMS (FAB$^+$): found 340.24023 calcd. C$_{23}$H$_{32}$O$_2$ 340.24023.

2-Ethyl-3-O-sulfamoyl 17-(2-methoxy-ethylidene)estrone

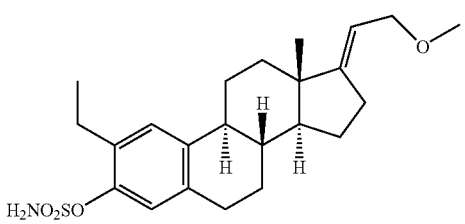

A solution of NH$_2$SO$_2$Cl (2 mmol) in DMA (2 ml) cooled to 0° C. was added to 2-ethyl-17-(2-methoxy-ethylidene)-13-methyl-7,8,9,11,12,13,14,15,16,17-decahydro-6H-cyclopenta[a]phenanthren-3-ol (170 mg, 0.5 mmol) and the mixture was stirred for 24 hours at room temperature under nitrogen. After addition of water (10 ml) the organics were extracted with ethyl acetate (2×50 ml). The organic layer was successively washed with water, brine and dried over MgSO$_4$. The solvent was removed under vacuum and the residual solid was purified by column chromatography (hexane/ethyl acetate 10/1 to 5/1) to give 2-ethyl-3-O-sulfamoyl 17-(2-methoxy-ethylidene) estrone as a white solid, 142 mg (68%), $^1$H NMR (CDCl$_3$, 270 MHz): 0.79 (s, 3H, CH$_3$), 1.20 (t, J=7.4 Hz, 3H, CH$_3$), 1.22-1.67 (m, 6H), 1.78-1.98 (m, 3H), 2.17-2.47 (m, 4H), 2.68 (q, J=7.4 Hz, 2H, CH$_2$), 2.85 (m, 2H, H6), 3.32 (s, 3H, CH$_3$O), 3.90 (m, 2H, CH$_2$OMe), 5.14 (s, 2H, NH$_2$), 5.22 (m, 1H, CHCH$_2$OH), 7.06 (s, 1H, ArH), 7.19 (s, 1H, ArH). $^{13}$C NMR (CDCl$_3$, 400 MHz): 14.6 (CH$_3$), 18.8, 23.1, 24.0, 26.4, 26.5, 27.4, 29.2, 35.8, 38.2, 44.3, 44.4, 53.2, 57.8, 69.8, 112.9, 121.4, 127.0, 133.7, 136.0, 139.6, 146.2 and 156.4. HPLC: 99.7%; HRMS (FAB+): found 419.21303 for calcd. C$_{23}$H$_{33}$O$_4$NS 419.21303

2-Ethyl-3-O-acetyl-17-cyano-17-hydroxy-estrone

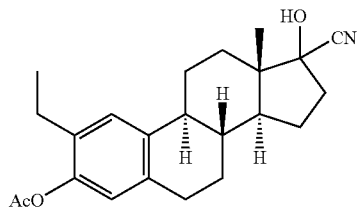

A solution of 2-ethyl estrone acetate (5 mmol) and KCN (3.26 g, 50 mmol) in 20 ml methanol and 5 ml acetic acid was stirred at room temperature for 3-5 days. Ice and water were added to the mixture and the resulting solid was filtered and washed with copious amounts of water. The white solid was dissolved in ethyl acetate (100 ml), the organic layer successively washed with water and brine, dried over MgSO$_4$ and the solvent was evaporated under vacuum to give 2-ethyl-3-O-acetyl-17-cyano-17-hydroxy-estrone as a white solid, 1.6 g (87%), which showed $^1$H NMR (CDCl$_3$, 270 MHz): 0.85 (s, 3H, CH3), 1.16 (t, J=7.4 Hz, 3H, CH$_3$), 1.33-1.70 (m, 6H), 1.80-2.06 (m, 5H), 2.30 (s, 3H, CH$_3$CO), 2.25-2.35 (m, 1H), 2.38-2.58 (m, 3H), 2.70 (q, J=7.4 Hz, 2H, CH$_2$), 2.82 (m, 2H, H6), 6.71 (s, 1H, ArH), 7.15 (s, 1H, ArH).

Acetic acid 17-cyano-13-methyl-7,8,9,11,12,13,14,15-octahydro-6H-cyclopenta[a]phenanthren-3-yl ester

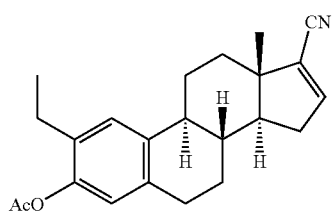

2-Ethyl-3-O-acetyl-17-cyano-17-hydroxy-estrone (4 mmol) was dissolved in 10 ml dry pyridine and $SOCl_2$ (1.46 ml, 20 mmol) was added dropwise. The solution was refluxed for 1 hour under nitrogen, cooled to 0° C. and hydrolysed to pH1 with 5M aqueous HCl. The organics were extracted with ethylacetate and the organic layer washed with water and brine successively, dried over $MgSO_4$. The solvent was evaporated under vacuum and the resulting dark oil was purified by chromatography (hexane/ethylacetate 8:1 to 6:1) to give acetic acid 17-cyano-2-ethyl-13-methyl-7,8,9,11,12,13,14,15-octahydro-6H-cyclopenta[a]phenanthren-3-yl ester as a white powder, 0.50 g (36%), mp 176-177° C.; $^1$H NMR ($CDCl_3$, 270 MHz): 0.94 (s, 3H, $CH_3$), 1.16 (t, J=7.4 Hz, 3H, $CH_3$), 1.36-1.52 (m, 1H), 1.60-1.73 (m, 4H), 1.84-1.94 (m, 1H), 2.05-2.26 (m, 3H), 2.30 (s, 3H, $CH_3CO$), 2.39-2.52 (m, 4H), 2.86 (m, 2H, H6), 6.65 (dd, J=3.5 and 2.0 Hz, 1H, H16), 6.72 (s, 1H, ArH), 7.14 (s, 1H, ArH).

2-Ethyl-3-O-acetyl-17-cyano-17-deoxy estrone

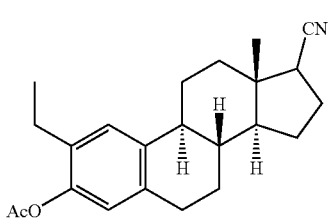

To a solution of acetic acid 17-cyano-13-methyl-7,8,9,11,12,13,14,15-octahydro-6H-cyclopenta[a]phenanthren-3-yl ester (1 mmol) in THF (5 ml) and methanol (30 ml) was added 5% Pd/C (30 mg) and the suspension was stirred at room temperature under hydrogen for 24 hours. The suspension was filtered over celite/sand and the solvents were evaporated under vacuum. The residual solid was purified by chromatography (hexane/ethylacetate 8:1 to 6:1) to give 2-ethyl-3-O-acetyl-17-cyano-17-deoxy estrone as a white powder, 330 mg (94%), mp=195-196° C.; $^1$H NMR ($CDCl_3$, 270 MHz): 0.99 (s, 3H, $CH_3$), 1.21 (t, J=7.4 Hz, 3H, $CH_3$), 1.22-1.32 (m, 1H), 1.37-1.53 (m, 4H), 1.56-1.67 (m, 1H), 1.86-1.95 (m, 2H), 1.99-2.08 (m, 1H), 2.12-2.17 (m, 1H), 2.19-2.32 (m, 2H), 2.35 (s, 3H, $CH_3CO$), 2.38-2.47 (m, 2H), 2.53 (q, J=7.4 Hz, 2H, $CH_2$), 2.88 (m, 2H, H6), 6.76 (s, 1H, ArH), 7.1.9 (s, 1H, ArH).

2-Ethyl-17-cyano-17-deoxy estrone

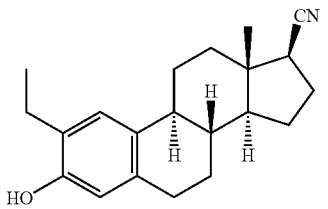

2-Ethyl-3-O-acetyl-17-cyano-17-deoxy estrone (0.8 mmol) was dissolved in acetone (10 ml) and methanol (10 ml) and $K_2CO_3$ (0.55 g, 4 mmol) was added to the solution. The mixture was stirred for 24 hours at room temperature. The salts were filtered off and the solvents evaporated. The resulting solid was treated with aqueous $NH_4Cl$ (to pH1) and the organics were extracted with ethylacetate. The organic layer was washed with water and brine successively, dried over $MgSO_4$. The solvent was evaporated under vacuum and the resulting solid was purified by chromatography (hexanel-ethylacetate 8:1 to 6:1) and recrystallized in hexane/ethyl acetate (4:1) to give 2-ethyl-17-cyano-17-deoxy estrone as a white powder, 210 mg (85%), mp=284-285° C.; $^1$H NMR ($CDCl_3$, 270 MHz): 0.95 (s, 3H, $CH_3$), 1.21 (t, J=7.4 Hz, 3H, $CH_3$), 1.30-1.60 (m, 6H), 1.79-1.91 (m, 2H), 1.94-2.07 (m, 2H), 2.09-2.24 (m, 2H), 2.33-2.42 (m, 2H), 2.58 (q, J=7.4 Hz, 2H, $CH_2$), 2.78 (m, 2H, H6), 4.50 (s, 1H, OH), 6.49 (s, 1H, ArH), 7.03 (s, 1H, ArH); $^{13}$C NMR ($CDCl_3$, 400 MHz): 14.4 ($CH_3$), 14.5, 23.1, 24.3, 26.4, 26.7, 27.8, 29.1, 37.1, 39.2, 40.4, 43.7, 44.7, 53.5, 115.2, 121.3, 126.4, 127.4, 131.9, 135.2, and 151.3; Microanalysis: C, 81.15 (expected 81.51); H, 8.72 (expected 8.79); N, 4.33 (expected 4.53).

2-Ethyl-3-O-sulfamoyl-17-cyano-17-deoxy estrone

A solution of $NH_2SO_2Cl$ (0.8 mmol) in DMA (2 ml) cooled to 0° C. was added to 2-ethyl-17-cyano-17-deoxy estrone (0.3 mmol) and the mixture was stirred for 24 hours at room temperature under nitrogen. After addition of water (10 ml) the organics were extracted with ethyl acetate (2×50 ml). The organic layer was successively washed with water, brine and dried over $MgSO_4$. The solvent was removed under vacuum and the residual solid was purified by column chromatography (hexane/ethyl acetate 5/1) and recrystallized in hexane/ethyl acetate (5/1) to give 2-ethyl-3-O-sulfamoyl-17-cyano-17-deoxy estrone as a white powder, 100 mg (86%), mp=193-194° C.; $^1$H NMR ($CDCl_3$, 270 MHz): 0.95 (s, 3H, $CH_3$), 1.20 (t, J=7.4 Hz, 3H, $CH_3$), 1.28-1.62 (m, 6H), 1.86 (m, 2H), 1.96-2.28 (m, 4H), 2.37 (m, 2H), 2.68 (q, J=7.4 Hz, 2H, $CH_2$), 2.83 (m, 2H, H6), 4.94 (s, 2H, $NH_2$), 7.08 (s, 1H, ArH), 7.18 (s, 1H, ArH); $^{13}$C NMR ($CDCl_3$, 400 MHz): 14.4 ($CH_3$), 14.7, 23.1, 24.3, 26.1, 26.6, 27.5, 29.1, 37.0, 38.8, 40.3, 43.8, 44.6, 53.5, 121.2, 121.5, 127.0, 133.8, 135.7, 138.8 and 146.3. Microanalysis: C, 64.95 (expected 64.92); H, 7.29 (expected 7.26); N, 7.11 (expected 7.21).

Biological Data

The compounds referred to herein may be identified either by the compound numbers used in the synthesis section above or by an STX code. The compound numbers are listed below with their corresponding STX codes.

| Compound No. | STX code |
|---|---|
| 14a | 441 |
| 14b | 442 |
| 15 | 563 |
| 17a | 590 |
| 17b | 504 |
| 19 | 535 |

-continued

| Compound No. | STX code |
|---|---|
| 20 | 537 |
| 22 | 506 |
| 23 | 589 |
| 27 | 505 |
| 28 | 564 |
| 30 | 626 |
| 31 | 639 |
| 32 | 640 |
| 33 | 641 |
| 36 | 621 |
| 51 | 591 |
| 59 | 941 |
| 60 | 940 |

In addition, the following compounds are referred to:

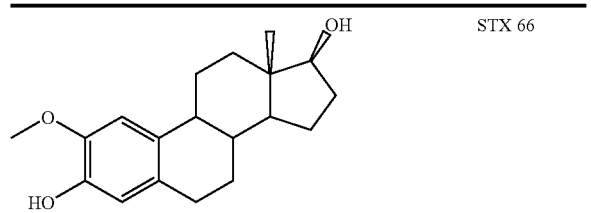
STX 66

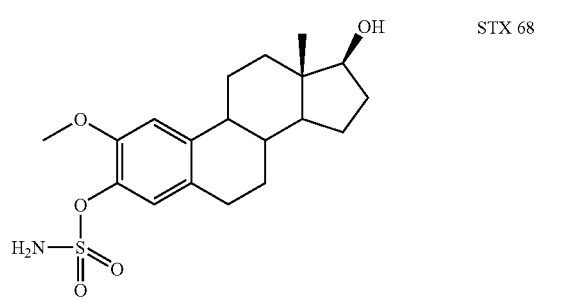
STX 68

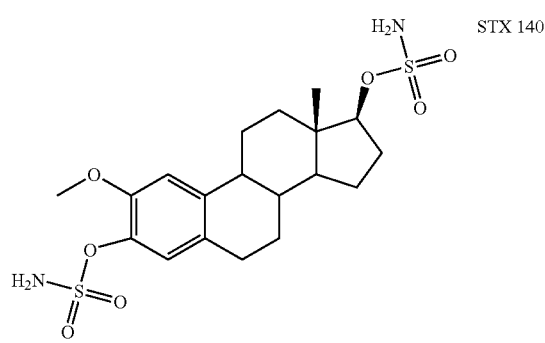
STX 140

Inhibition of Steroid Sulphatase:

| Compound No. | $IC_{50}$ values (nM) for the inhibition of Placental Microsomal Steroid Sulphatase: |
|---|---|
| 28 | 945 |
| 31 | 9000 |
| 33 | 109 |
| 60 | >10,000 |

Cell Proliferation

The effect of drugs on the proliferation of cells was measured using a microtiter plate assay (Cell Titer 96 proliferation assay, Promega, Hampshire, UK).

| Compound No. | $IC_{50}$ in µM for the growth inhibition of MCF-7 cells |
|---|---|
| 14a | 30.6 |
| 14b | 31.1 |
| 15 | 1.85 |
| 17a | 0.67 |
| 17b | 0.77 |
| 19 | 2.52 |
| 20 | 5.64 |
| 22 | 26.4 |
| 23 | 4.19 |
| 27 | 3.24 |
| 28 | 0.06 |
| 30 | 3.22 |
| 31 | 0.03 |
| 32 | 0.30 |
| 33 | 0.15 |
| 36 | 3.25 |
| 51 | 6.02 |
| 59 | 5.58 |
| 60 | 0.09 |

Compound STX 140 was used as a control in the following assays.

| | $IC_{50}$ (µM) | | |
|---|---|---|---|
| Compound | MCF-7 Breast Cancer Cells | A2780 Ovarian Cancer Cells | PC3 Prostate Cancer Cells |
| STX 140 | 0.25 | 0.28 | 0.27 |
| STX 641 | 0.15 | 0.09 | 0.05 |

Human Umbilical Vein Cells; 96 well plate MTS proliferation assay, mean inhibition of three wells +/−Sds.

| Conc. | STX 140 | Compound 33 | Compound 28 |
|---|---|---|---|
| 0.05 µM | 7% +/− 4 | 53% +/− 13 | 0% +/− 6 |
| 0.10 µM | 18% +/− 1* | 60% +/− 8 | 5% +/− 5 |
| 1.00 µM | 59% +/− 3 | 48% +/− 6 | 54% +/− 10 |
| 5.00 µM | 49% +/− 5 | 42% +/− 3 | 49% +/− 7 |

*Duplicate reading only.

Human Dermal Fibroblasts; 96 well plate MTS proliferation assay, mean inhibition of three wells +/−Sds.

| Conc. | STX 140 | Compound 33 | Compound 28 |
|---|---|---|---|
| 0.05 µM | 0% +/− 6 | 2% +/− 2* | 2% +/− 1 |
| 0.10 µM | 2% +/− 6 | 10% +/− 4 | 0% +/− 2 |
| 1.00 µM | 9% +/− 9 | 8% +/− 4 | 1% +/− 4 |
| 5.00 µM | 18% +/− 12 | 0% +/− 7 | 6% +/− 5 |

*Duplicate reading only.

A2780 Ovarian Cancer Cells; Three day study, cell number

|  | Cell Number | | | | | |
|---|---|---|---|---|---|---|
| Treatment | Day 0 | s.d. | Day 3 | s.d. | Day 6 | s.d. |
| untreated | 1326000 | 221873.8 | 7620500 | 149315.9 | 7709500 | 272843.8 |
| STX 641, 0.5 uM | 1326000 | 221873.8 | 345084 | 44136.09 | 78734.83 | 12213.5 |
| STX 641 ®, 0.5 uM | 1326000 | 221873.8 | 345084 | 44136.09 | 88680 | 5448.237 |
| STX 140, 0.5 uM | 1326000 | 221873.8 | 679663.3 | 25472.96 | 204255.5 | 24555.12 |
| STX 140 ®, 0.5 uM | 1326000 | 221873.8 | 679663.3 | 25472.96 | 462869.8 | 21542.44 |

STX 641® and STX 140® signify that the reversibility of the drug-induced effects of STX 641 and STX140 respectively were studied. For these studies the drug was removed on day 3, cells were washed with PBS, and then the culture medium was added. These studies showed that in most cases the effects of the drugs were not reversible.

Figure 8:
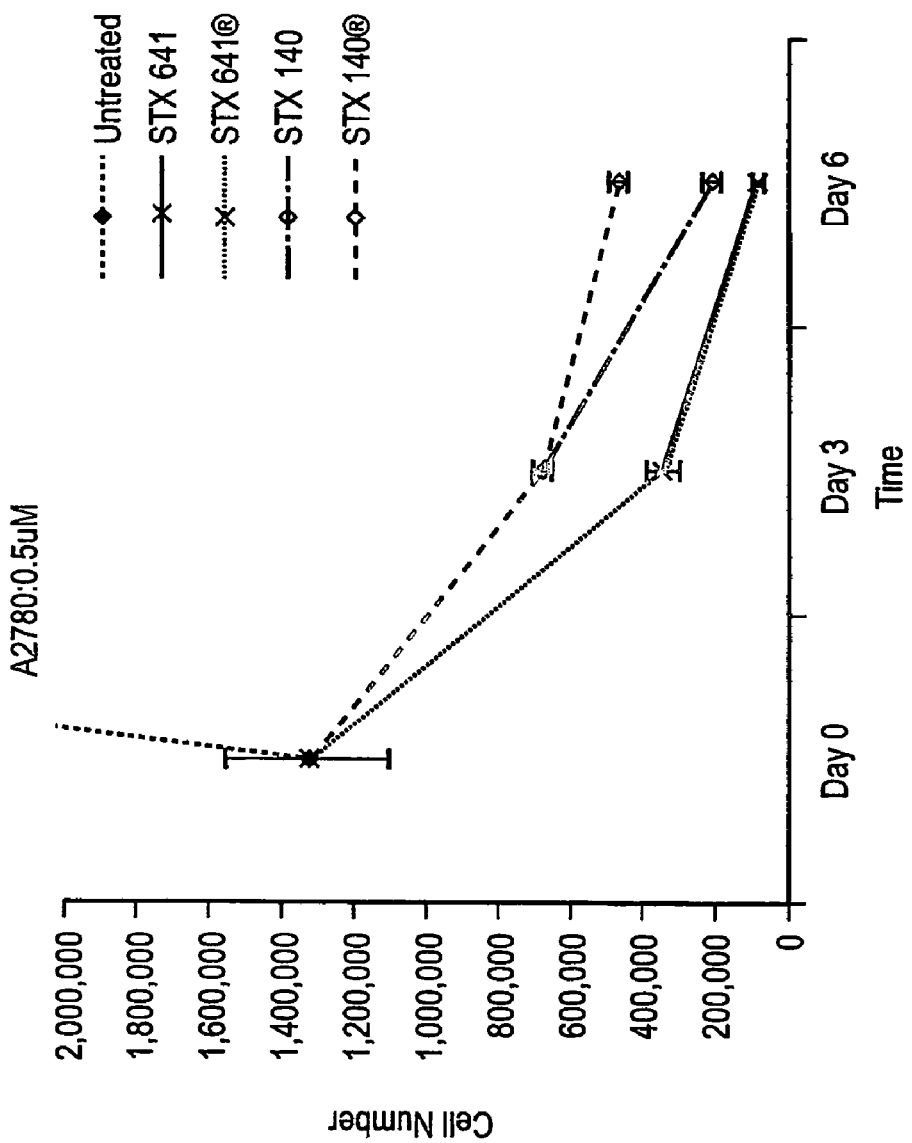
FIG. 8 shows a graph.

These data are displayed in FIG. 8.

PC3 Prostate Cancer Cells; Three day study, cell number

|  | Cell Number | | | | | |
|---|---|---|---|---|---|---|
| Treatment | Day 0 | s.d. | Day 3 | s.d. | Day 6 | s.d. |
| untreated | 168552.3 | 24330.94 | 1402666.7 | 192756.5 | 3142111 | 422890.6 |
| STX 641, 0.5 uM | 168552.3 | 24330.94 | 117351 | 9470.006 | 84191.33 | 15036.01 |
| STX 641 ®, 0.5 uM | 168552.3 | 24330.94 | 117351 | 9470.006 | 95845.33 | 11029.65 |
| STX 140, 0.5 uM | 168552.3 | 24330.94 | 125218.67 | 16505.52 | 100059 | 10827.65 |
| STX 140 ®, 0.5 uM | 168552.3 | 24330.94 | 125218.67 | 16505.52 | 197780 | 3212.232 |

STX 641® and STX 140® signify that the reversibility of the drug-induced effects of STX 641 and STX140 respectively were studied. For these studies the drug was removed on day 3, cells were washed with PBS, and then the culture medium was added. These studies showed that in most cases the effects of the drugs were not reversible.

Figure 9:
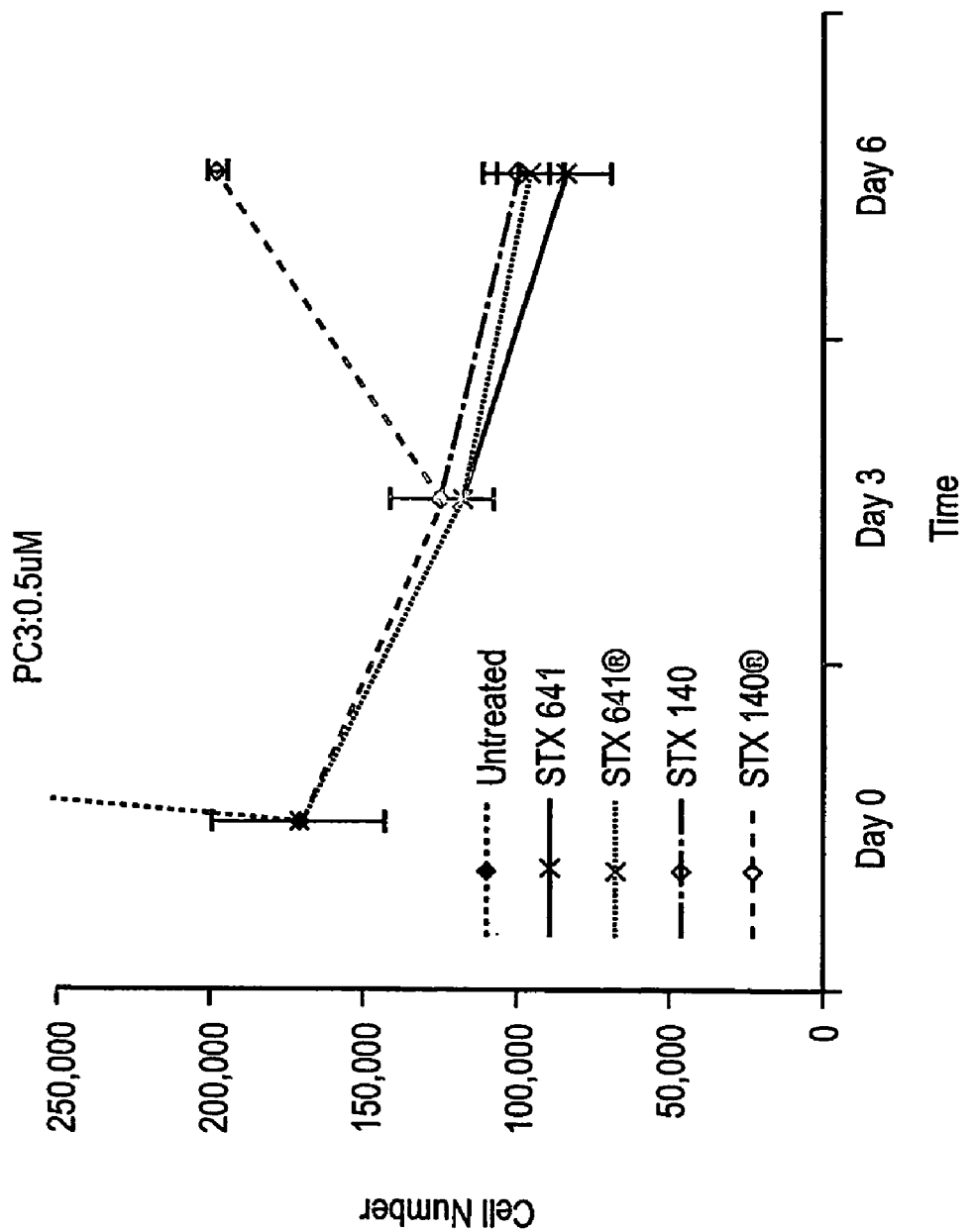
FIG. 9 shows a graph.

These data are displayed in FIG. 9.

Clonogenicity in A2780 Ovarian Cancer Cells

| Treatment | | % clonogenicity (relative to untreated cells) | s.d. |
|---|---|---|---|
| STX 140 | 0.25 µM | 64.42 | 1.71 |
| STX 140 | 1 µM | 0.04 | 0.06 |
| STX 641 | 0.25 µM | 0.24 | 0.33 |
| STX 641 | 1 µM | 0.00 | 0.00 |

Figure 10:
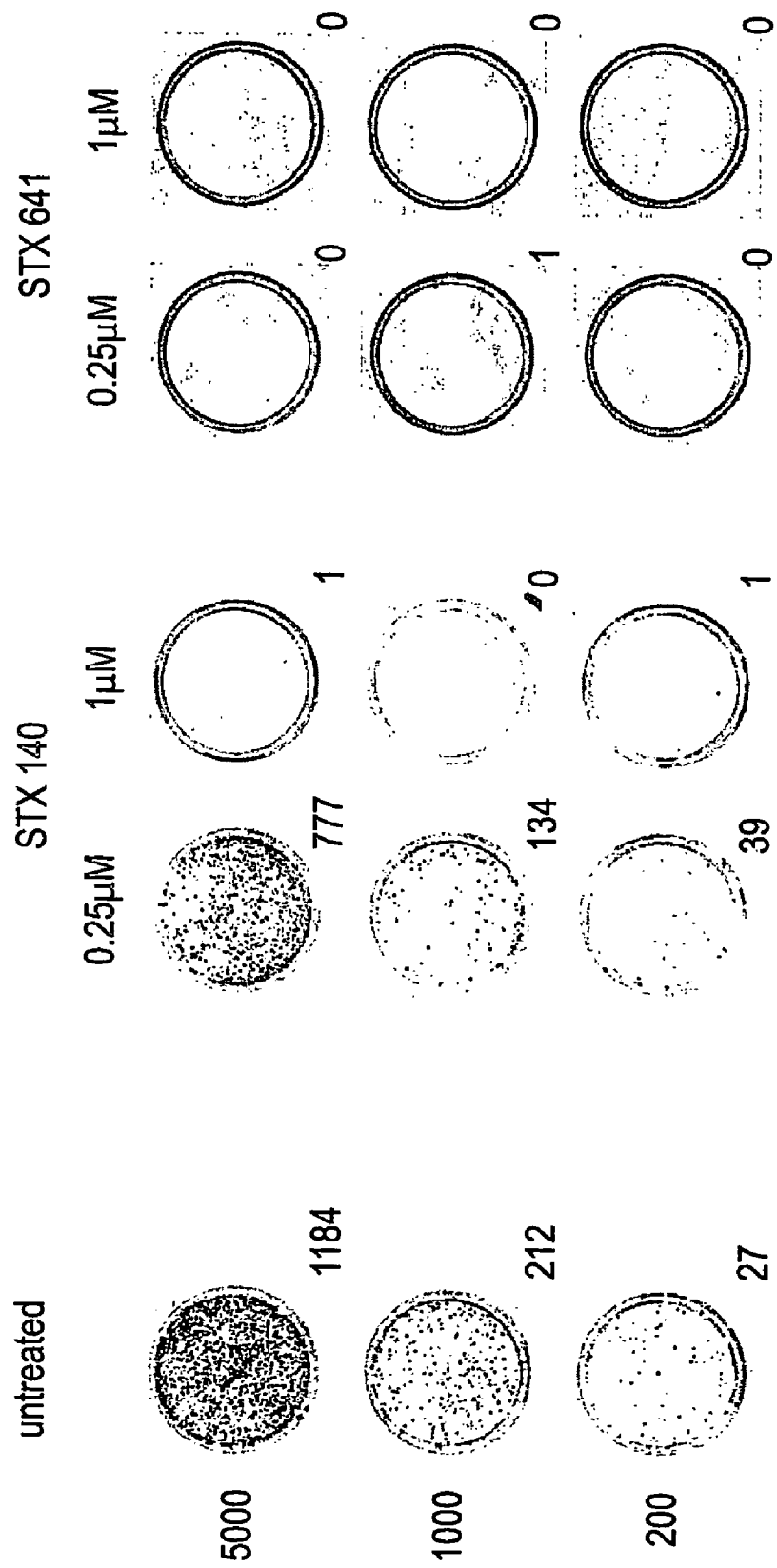
FIG. 10 shows plates.

These data are displayed in FIG. 10.

Inhibition of Taxol-Induced Microtubule Polymerization

The ability of drugs to inhibit taxol-induced polymerisation of tubulin was measured by turbidity at 350 nm. Tubulin (Cryoskeleton Inc., Denver, Colo.), at a final concentration of 1 mg/ml was incubated at 32° C. in G-PEM buffer [80 mM piperazine-N,N'-bis (2-ethane sulfonic acid) sequisodium salt, 1 mM $MgCl_2$, 1 mM EGTA and 1 mM GTP (pH 6.8)] in the presence of taxol with or without estrone derivatives [20 µM].

Figure 3:
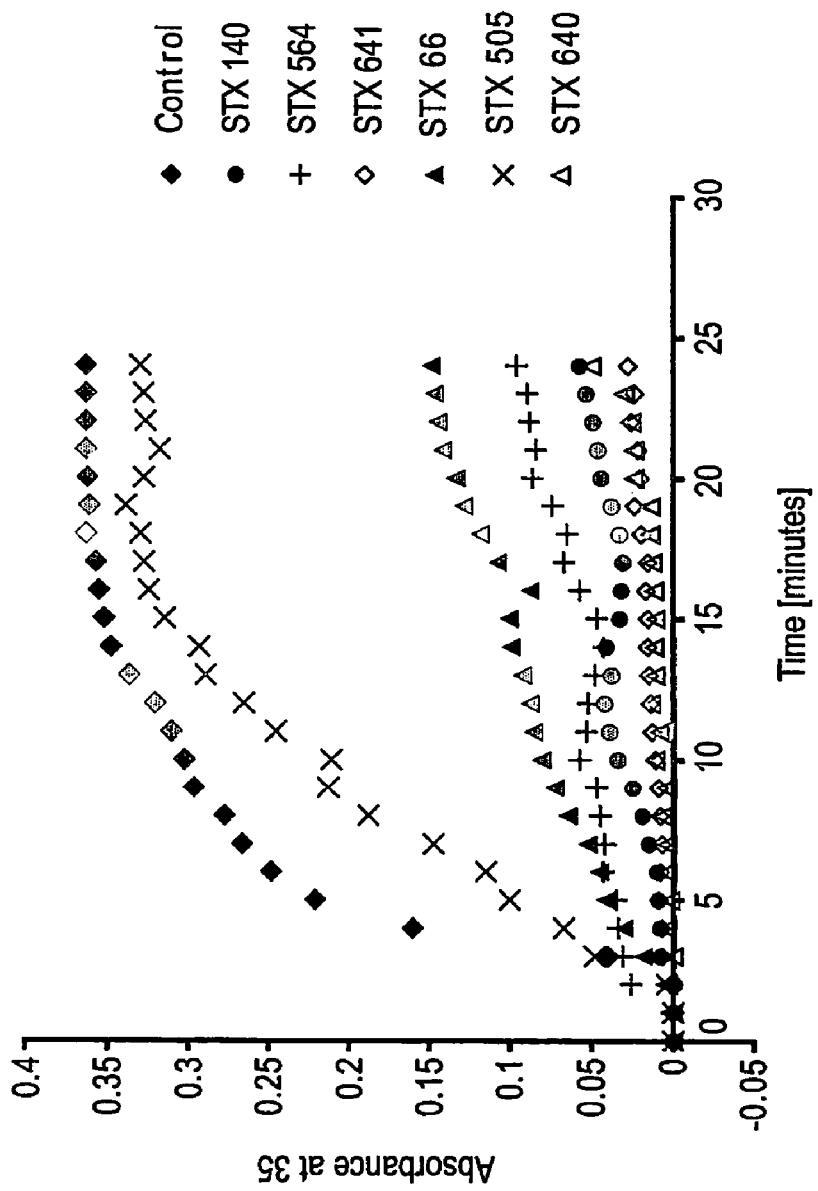
FIG. 3 shows a graph.

FIG. 3 shows the inhibition of taxol-induced polymerisation of tubulin by STX641 and related compounds. STX641 is thought to act as an anti-microtubule agent, i.e. to disrupt microtubule function. To show this, tubulin was incubated in the presence of taxol (a compound known to promote tubulin polymerisation). Taxol induced efficient in vitro microtubule assembly as reflected in the increase in turbidity as measured at 350 nm. Addition of STX641, STX 505, STX564 or STX640 to the tubulin and taxol reaction mixture effectively blocked tubulin assembly with little increase in turbidity being detected. These results show that STX641 and related compounds inhibit tubulin polymerisation in vitro and that such compounds are likely to disrupt microtubule dynamics in vivo (and hence tumour growth).

Inhibition of Glucose Uptake

To measure the inhibition of glucose uptake into cells, cells were plated into 12-well multi-well plates and grown to confluence. Cells were washed with phosphate-buffered saline (PBS) and incubated for 15 min in incubation buffer containing 1 µCi 2-deoxy-D-[1-$^3$H]glucose (NEN-Dupont, UK) per well in the absence or presence of potential inhibitors (0.1-10 µM). Uptake was terminated by washing the cells in cold (4° C.) PBS. The cells were solubilized in. Triton-X in 0.01M sodium hydroxide and processed for liquid scintillation counting (Singh et al., Molecular and Cellular Endocrinology, 160: 61-66, 2000).

|  | % Inhibition of Glucose Uptake | |
|---|---|---|
| Compound | MCF-7 Cells | MDA MB 231 Cells |
| STX 66 | 37% | 32% |
| STX 68 | 66% | 70% |

-continued

| | % Inhibition of Glucose Uptake | |
|---|---|---|
| Compound | MCF-7 Cells | MDA MB 231 Cells |
| STX 140 | 68% | 77% |
| STX 641 | 28% | 60% |

Figure 4:
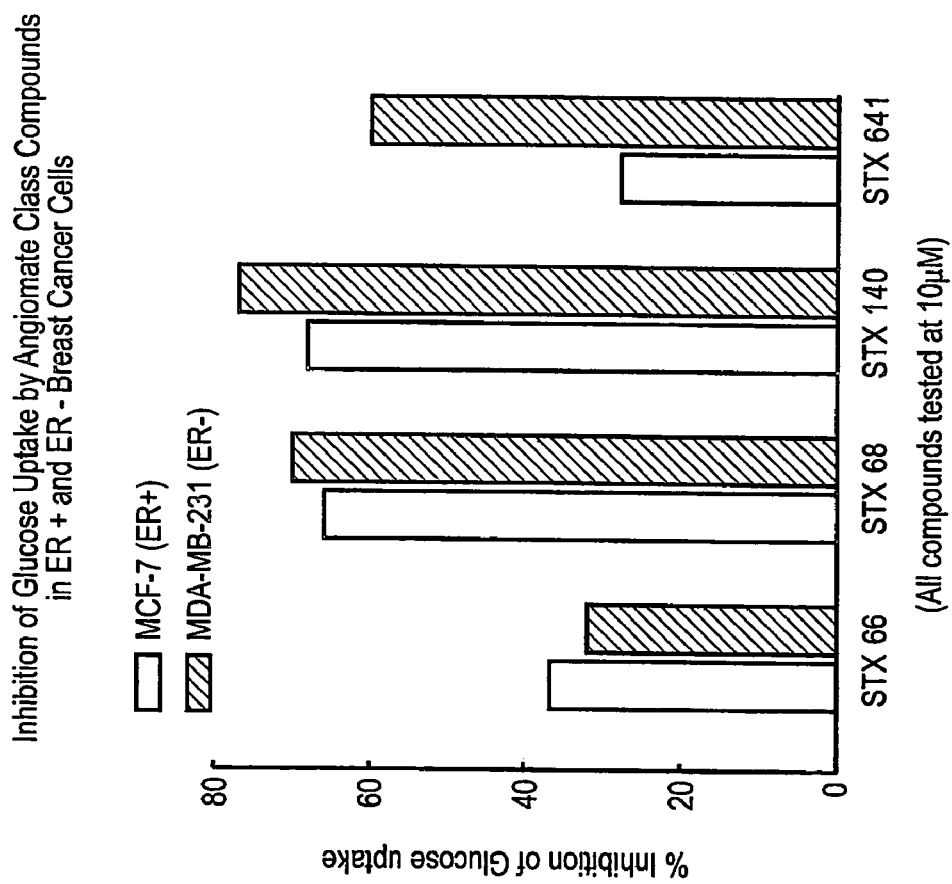
FIG. 4 shows a graph.

FIG. 4 shows the inhibition of glucose uptake. An increased uptake of glucose (as an energy source) is a characteristic feature of most cancer cells. Glucose is taken up into cells by a number of glucose transporters and one such transporter (GLUT 1) is over-expressed in malignant breast tissues. FIG. 4 shows that STX641 (and related compounds) inhibits glucose uptake by MCF-7 (oestrogen receptor positive, ER+) and MDA-MB-231 (ER−) breast cancer cells. Inhibition of glucose uptake in vivo should inhibit tumour growth and this may be an important mechanism by which STX641 and related compounds will act to inhibit tumour growth in patients.

Effects on Tubule Formation

The effects of drugs on tubule formation (measured as a marker of their anti-angiogenic potential) was assessed using an Angiogenesis kit (TCS-Cellworks Ltd (Bucks, UK). For this, human umbilical vein endothelial cells (HUVECs) were cultured in a 24-well plate within a matrix of human diploid fibroblasts of dermal origin. The co-cultured cells were incubated throughout the experiment at 37° C. under 5% $CO_2$ in a humidified incubator. On day 1, the culture medium was removed and replaced with medium containing the drugs under investigation. On days 4, 7 and 9, the medium was replaced with fresh medium containing the drugs under investigation. On day 11, the cells were washed with PBS and 70% ethanol (1 ml) added to each well for 30 min to fix the cells. After fixation, the cells were washed with blocking buffer (1 ml PBS+1% bovine serum albumin, Sigma, UK) and stained with either von Willebrand's factor or CD31. The extent of tubule formation was quantified by manual scoring or by computer analysis. Images were captured using a Kodak DC120 digital camera. In addition, details of changes in tubule formation induced by drugs were also recorded by high definition scanning of plates with some of the scans being presented as Photoshop processed images.

Most solid tumours can only grow beyond 1-2 mm in size if they develop a blood vessel network so that they can obtain essential nutrients to support their growth (a process known as angiogenesis). Drugs that block this angiogenic process should therefore inhibit the growth of a wide range of solid tumours.

Figure 5:
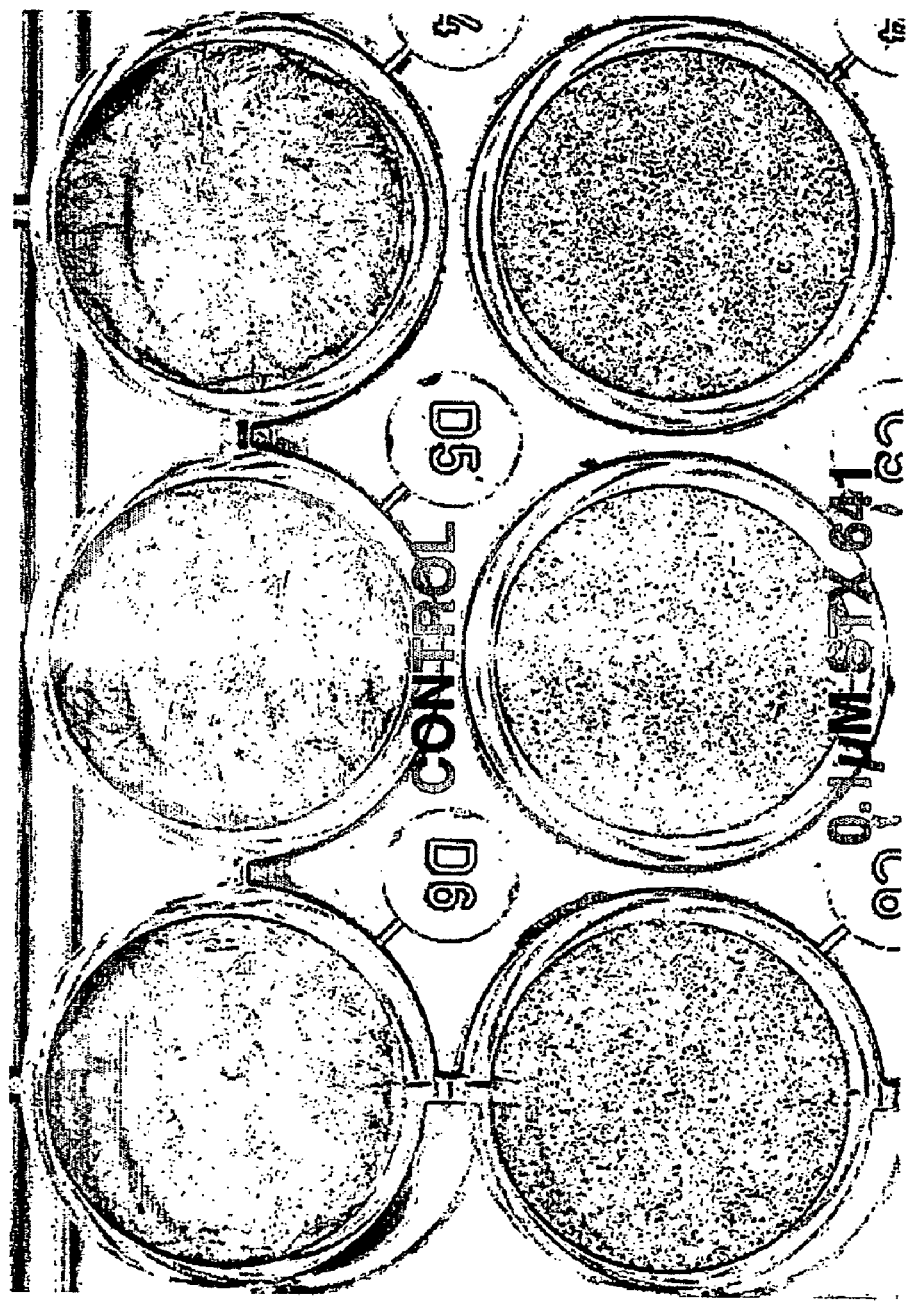
FIG. 5 shows a plate.
Figure 6:
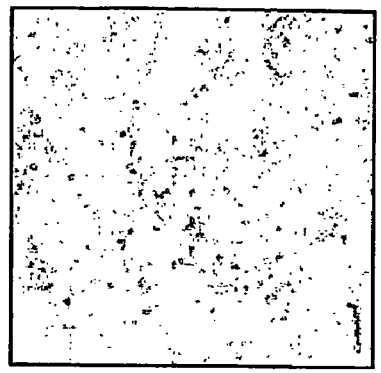
FIG. 6 shows a plate.
Figure 6:
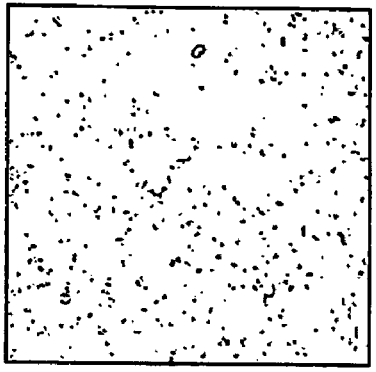
Figure 6:
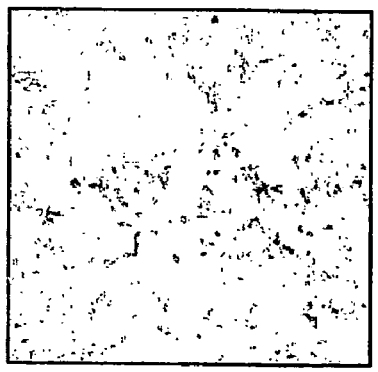
Figure 6:
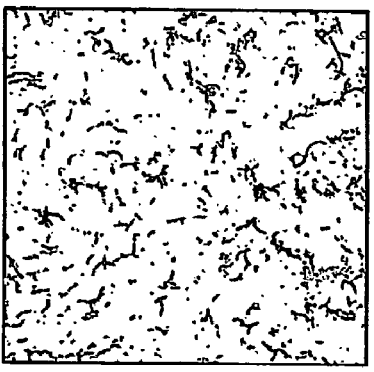
Figure 6:
Figure 6:

In this assay, the ability of STX641 (and related compounds) to act as an inhibitor of angiogenesis was examined using a co-culture of HUVECs and dermal fibroblasts. In this system, the endothelial cells initially form small islands within the fibroblast matrix. They subsequently proliferate and enter a migratory phase during which they move through the matrix to form thread-like tubule structures. These coalesce to form a network of anastomosing tubules. Representative figures showing the effects of STX641 on tubule formation are shown in FIGS. 5 and 6. In FIG. 5, for untreated (control) co-cultures of HUVECs and dermal fibroblasts, the thread-like nature of the extensive tubule network is clearly visible. In contrast, for co-cultured cells treated with STX641 (0.1 µM) the tubules have been completely destroyed showing that this drug has potent anti-angiogenic properties. In FIG. 6, plates have been recorded by high definition scanning and also processed to give pixalated images. Again, the thread-like tubules are clearly visible for the untreated (control) co-cultures whereas STX641 (and STX140) at 0.05 µM completely abolish tubule formation.

Figure 7:
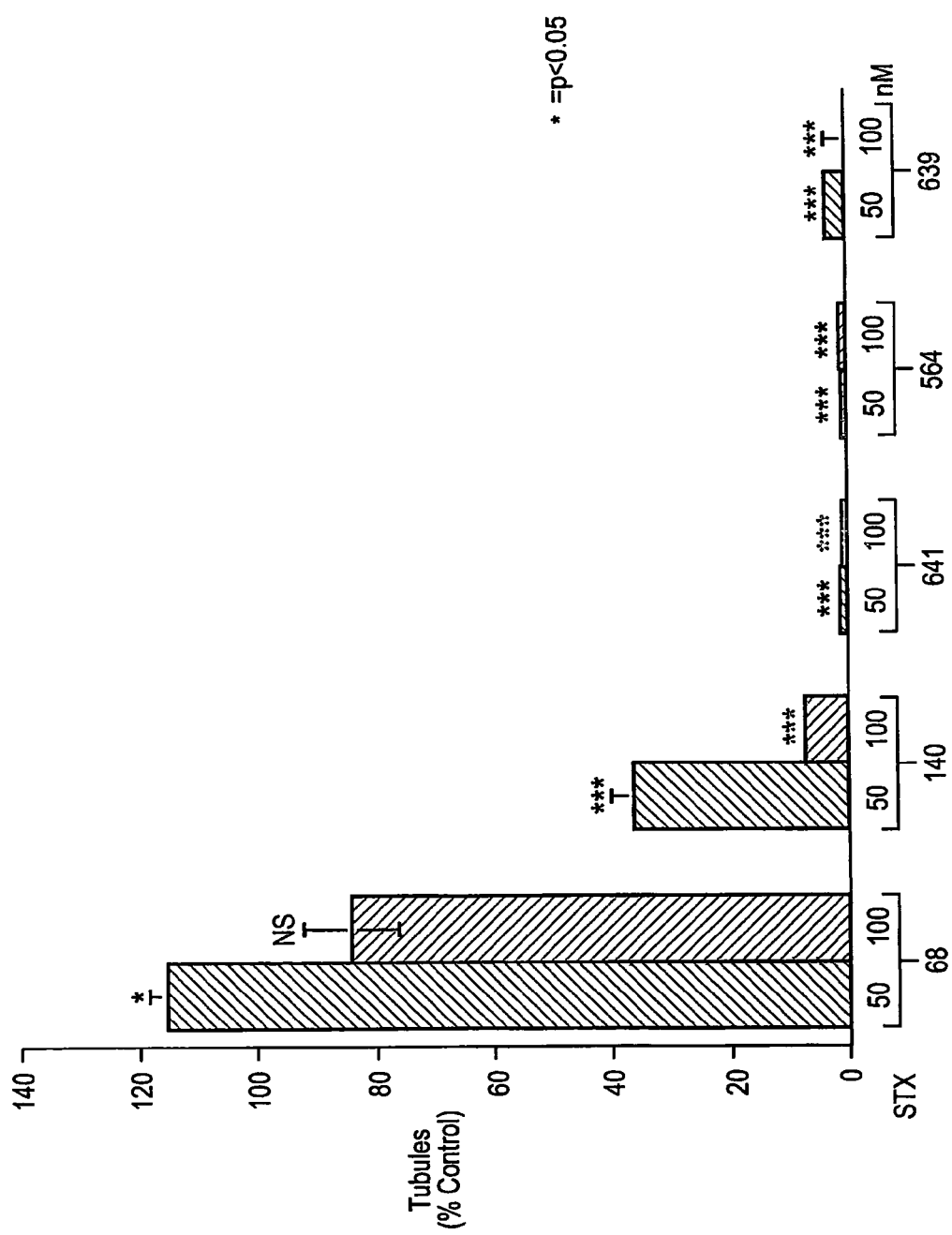
FIG. 7 shows a graph.

The extent of inhibition of tubule formation can be quantified by computer analysis (FIG. 7). As shown STX641, STX564 and STX639 at 0.05 µM and 0.1 µM completely inhibited tubule formation confirming the anti-angiogenic potential of these compounds.

Inhibition of Microvessel Formation

| Test Compound | Conc. | | Field Area | No of Junctions | No of Tubules | Total Tubule Length | Mean Tubule Length |
|---|---|---|---|---|---|---|---|
| Control | | | 701290 | 29 | 150 | 20601.79 | 137.35 |
| | | | 695889 | 28 | 118 | 18467.03 | 156.5 |
| | | | 694610 | 20 | 138 | 21041.03 | 152.47 |
| Control | | 2 ng/ml VEGF | 785729 | 120 | 312 | 37507.58 | 120.22 |
| | | | 762576 | 68 | 230 | 34816.21 | 151.37 |
| | | | 763322 | 93 | 246 | 35338.12 | 143.65 |
| STX 140 | 40 nM | 2 ng/ml VEGF | 627527 | 8 | 37 | 3064.85 | 82.83 |
| | | | 619251 | 5 | 40 | 3851.64 | 96.29 |
| | | | 638786 | 14 | 45 | 3619.74 | 80.44 |
| | 20 nM | 2 ng/ml VEGF | 749415 | 25 | 115 | 13509.76 | 117.48 |
| | | | 687717 | 22 | 94 | 10489.22 | 111.59 |
| | | | 674918 | 26 | 92 | 8191.48 | 89.04 |
| STX 641 | 20 nM | 2 ng/ml VEGF | 593238 | 1 | 5 | 248.31 | 49.66 |
| | | | 605489 | 4 | 14 | 505.5 | 36.11 |
| | | | 582954 | 3 | 13 | 474.05 | 36.47 |
| | 40 nM | 2 ng/ml VEGF | 588528 | 3 | 6 | 99.77 | 16.63 |
| | | | 597370 | 4 | 7 | 244.17 | 34.88 |
| | | | 591356 | 3 | 5 | 83.7 | 16.74 |
| STX 564 | 20 nM | 2 ng/ml VEGF | 661539 | 3 | 24 | 2152.74 | 89.7 |
| | | | 647067 | 2 | 14 | 1047.45 | 74.82 |
| | | | 686243 | 2 | 15 | 1182.8 | 78.85 |
| | 40 nM | 2 ng/ml VEGF | 625377 | 0 | 7 | 497.27 | 71.04 |
| | | | 620605 | 4 | 7 | 431.5 | 61.64 |
| | | | 628052 | 2 | 9 | 565.8 | 62.87 |

In each case the calibration was 1.0 pixels and the image area was 3211216. VEGF is vascular endothelial growth factor.

Figure 11:
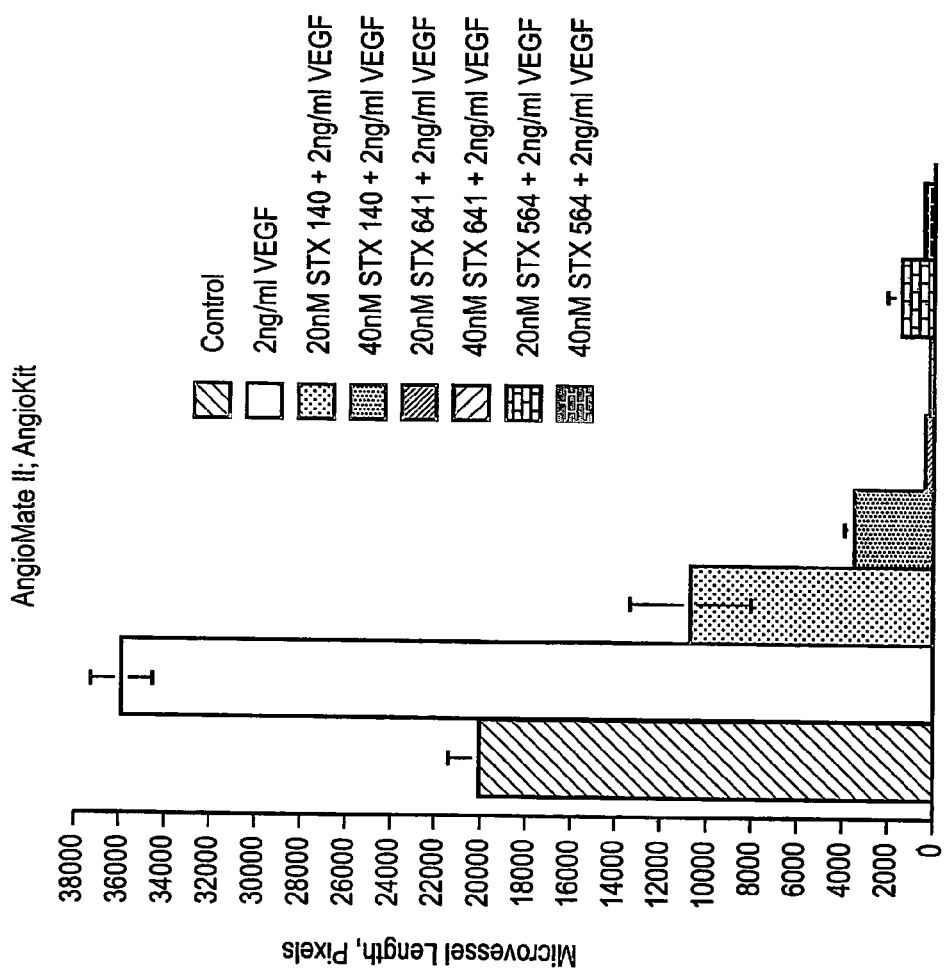
FIG. 11 shows a graph.

These data are displayed in FIG. 11.

Cell Cycle Arrest and Apoptosis

MCF-7 Breast Cancer Cells

Flow cytometric cell cycle analysis was performed on 40% confluent populations of MCF-7s with 500 nM of compound.

At 8 h STX 140, STX 640 and STX 641 induced significant G2/M arrest compared to control (16% to 27%).

After 24 h of STX 641 exposure, 68% of cells were G2/M arrested compared to control (28%), STX 140 (28%) and STX 640 (18%). This increase in the population of G2/M cells was accompanied by a decrease in G1- and S-phase populations (37% to 15%, and 30% to 9% respectively). In STX 140 treated cells, a significant increase in the sub-G1 population was observed, normally indicative of apoptosis (36%, compared to 2% in control cells).

After 48 h, STX 641-treated cells were still G2/M-arrested with no significant increase in the apoptotic sub-G1 population. Cells treated with STX 140 continued to show an increasing population of sub-G1 cells.

A2780 Ovarian Cancer Cells

Figure 12:
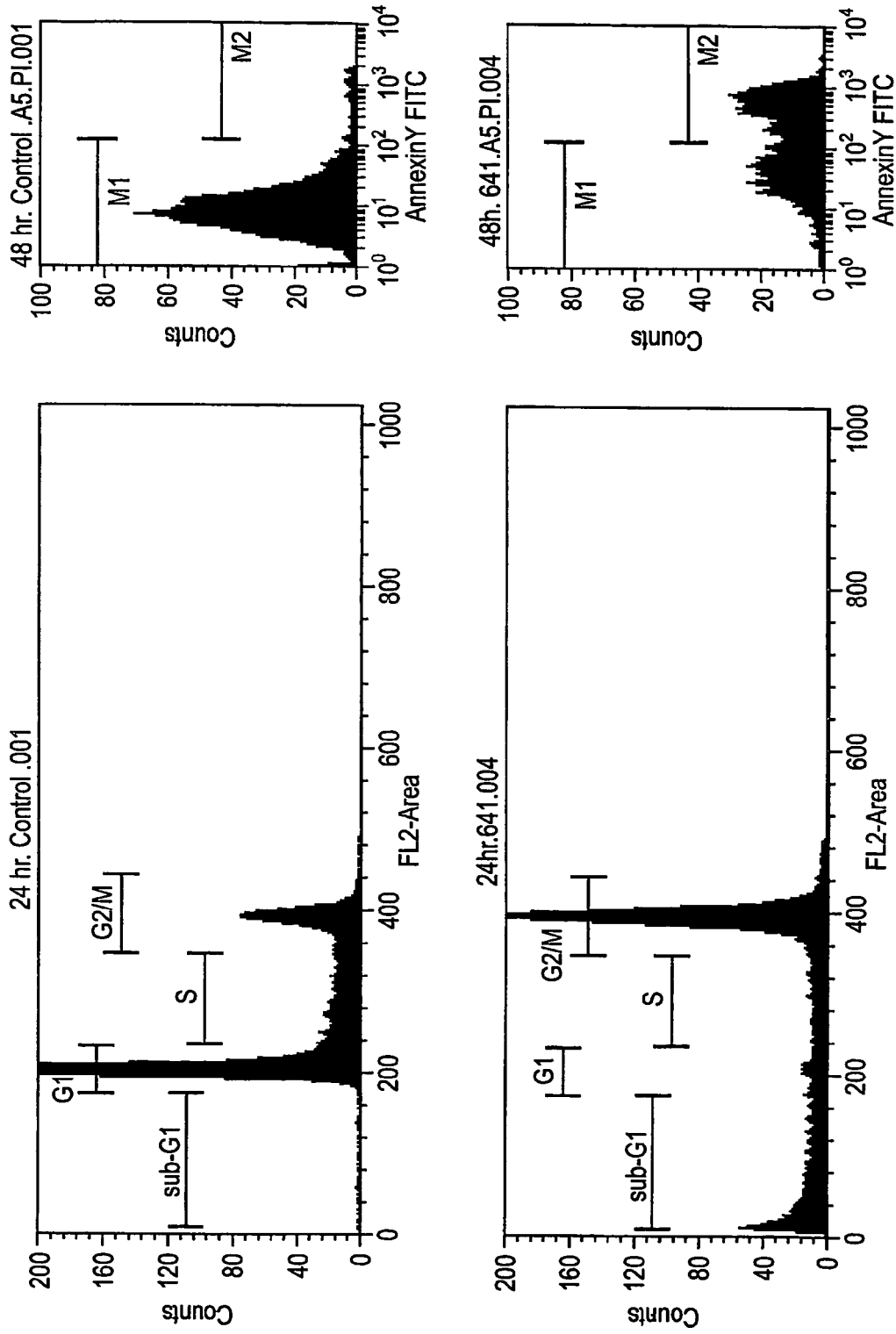
FIG. 12 shows a graph.

FIG. 12 shows the effect of STX 641 at a concentration of 1 μM on A2780 ovarian cancer cells, showing G2/M arrest induced by STX 641 after 24 hours (left hand graphs) The right hand graphs show the results of FACs analysis for cells stained with annexin V antibody. For controls, there is no cell surface expression as indicated by a lack of a peak in the M2 region. In contrast, STX 641 treated cells showed a marked increase in staining for this apoptopic marker, as indicated by the increase in the M2 region, showing that the compound induces apoptosis.

Xenograft Nude Mouse Model

MCF-7 Breast Cancer Nude Mouse Model

Adult female ICRF nude (nu/nu) mice were injected with $10 \times 10^6$ MCF-7 cells/0.1 ml Matrigel s.c and tumour growth was monitored weekly. When tumours reached 100-150 mm$^3$ in volume, the mice were divided into the following groups:

| A: | Control | vehicle 0.1 ml p.o for 5 times a week for a period of 3 weeks |
|---|---|---|
| B: | STX 140 | 20 mg/kg p.o for 5 times a week for a period of 3 weeks |
| C: | STX 641 | 20 mg/kg p.o for 5 times a week for a period of 3 weeks |

The mice were injected intravenously with 0.1 ml of 25 mg/ml FITC-Dextran solution 20 minutes prior to killing to allow the visualisation and quantification of tumour angiogenesis.

The results of this study are shown in the following figures.

Figure 13:
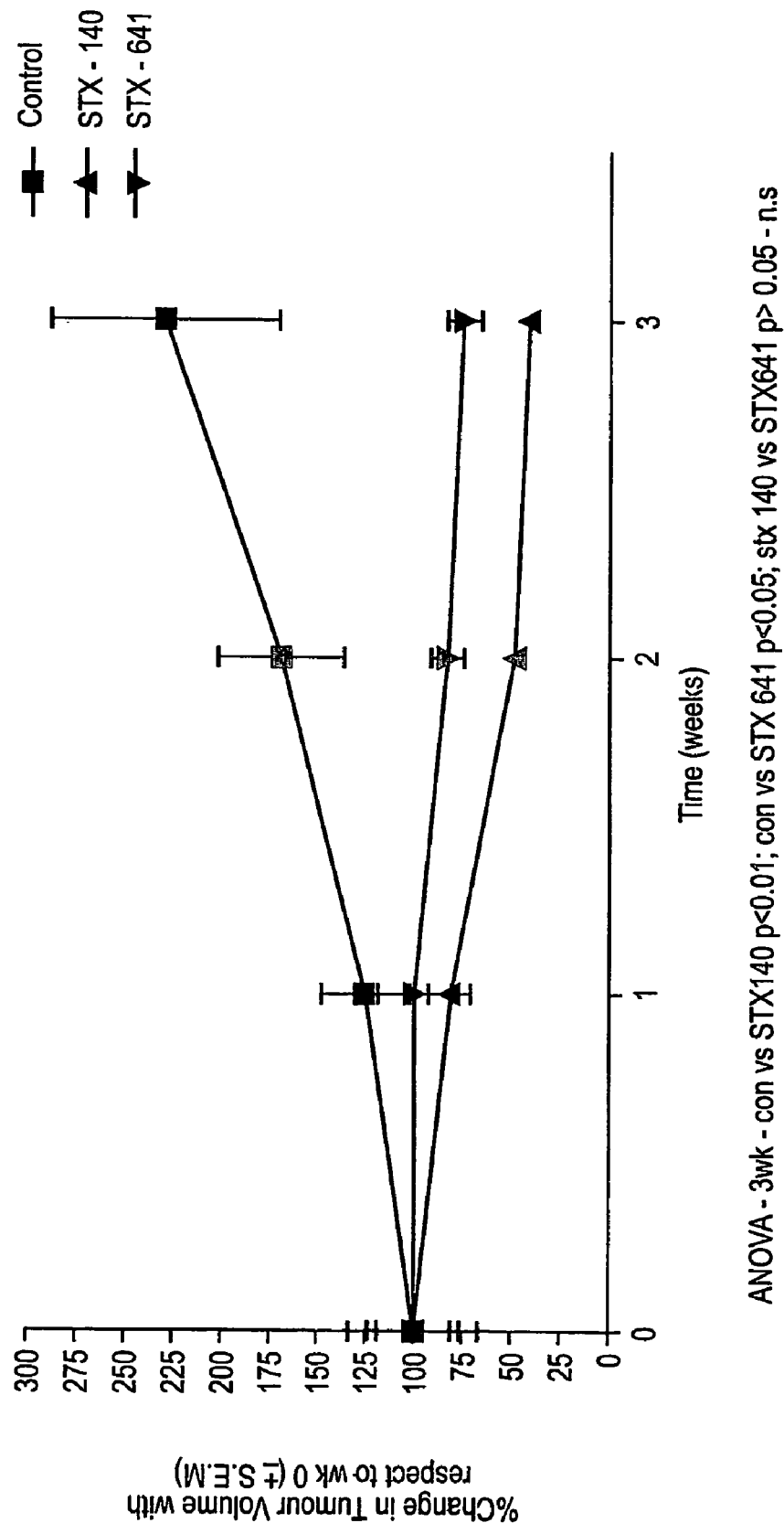
FIG. 13 shows a graph.

FIG. 13 shows the effect of STX 140 and STX 641 (20 mg/kg p.o) on the growth of MCF-7 breast cancer cell tumours in ICRF nude mice.

STX 140 resulted in 59% tumour regression and STX 641 gave 25% tumour regression over the 3 week dosing period.

Figure 14:
FIG. 14 shows fluorescent photographs.
Figure 14:
Figure 14:

FIG. 14 shows fluorescent photographs showing effects of STX 140 and STX 641 (20 mg/kg p.o) treatment on tumour vasculature.

FITC imaging of tumours revealed controls to have well defined structured vasculature, whereas in STX 140 and STX 641 treated animals the tumour vasculature was disrupted and ill defined.

Figure 15:
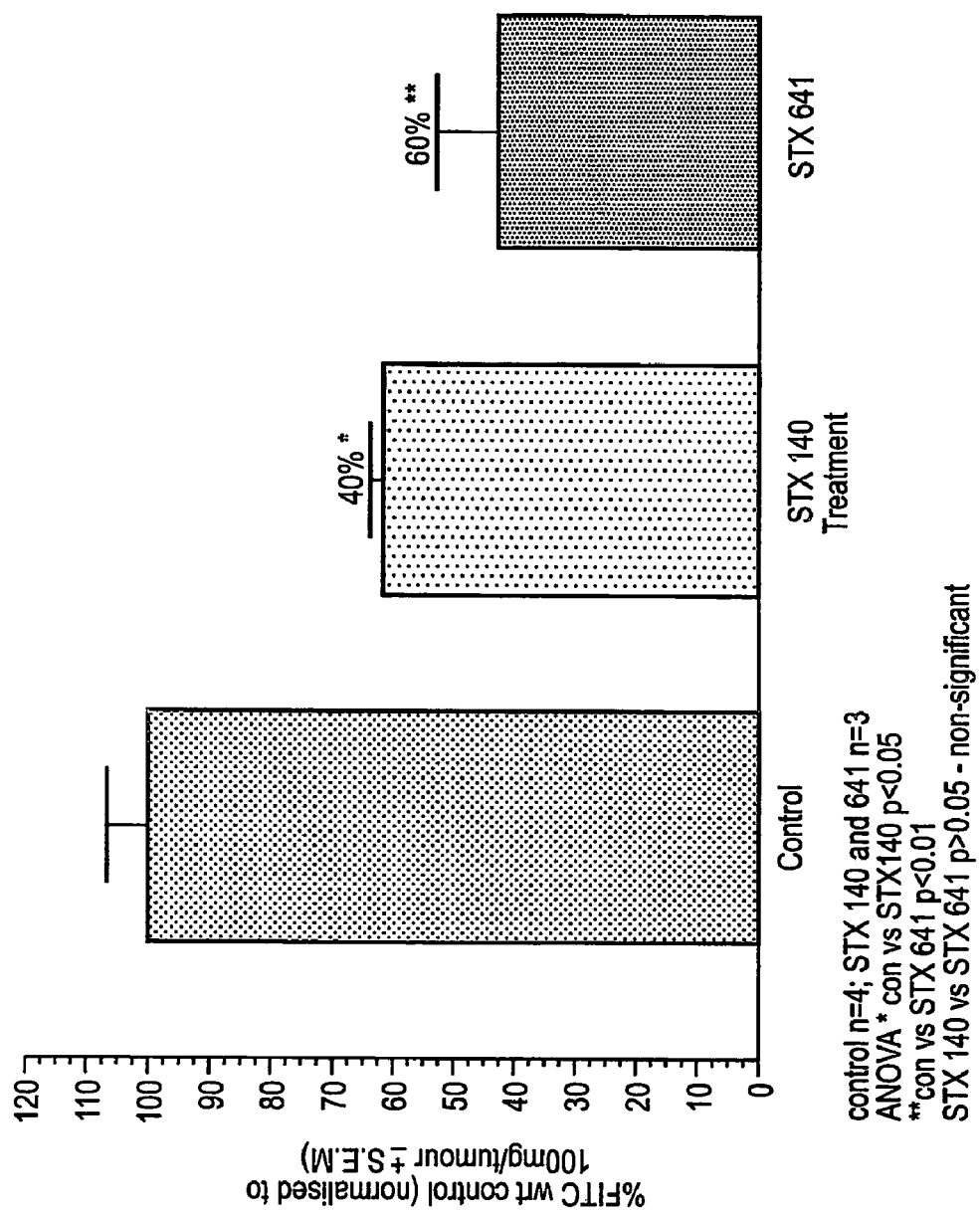
FIG. 15 shows a graph.

FIG. 15 shows the effect of STX-140 and STX641 (20 mg/kg) on tumour angiogenesis in MCF-7 breast tumours.

FITC quantification of tumour angiogenesis showed both STX 140 and STX 641 produced significant inhibition of 40% and 60% of tumour angiogenesis respectively.

Figure 16:
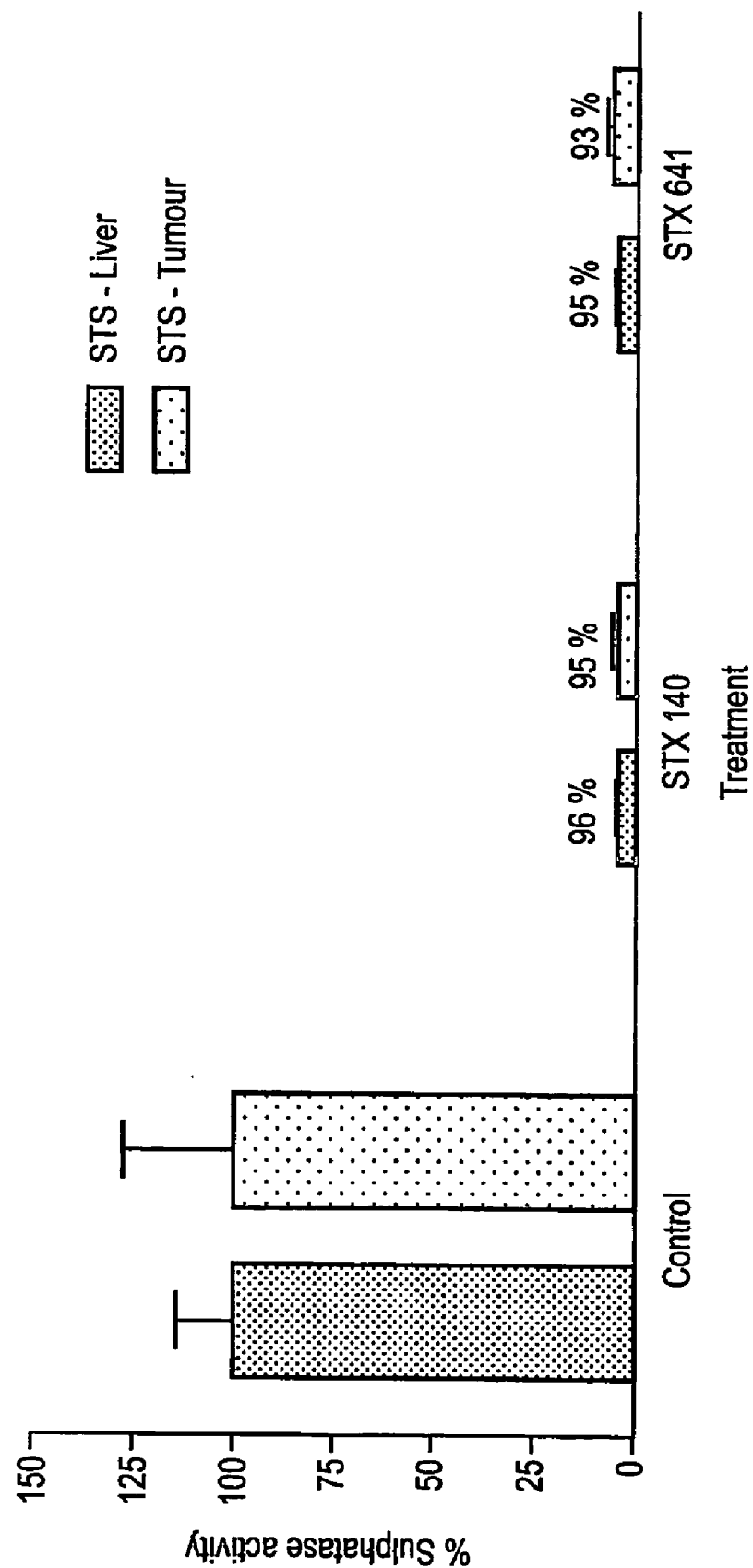
FIG. 16 shows a graph.

FIG. 16 shows the effect of STX 140 and 641 (20 mg/kg op) on liver and tumour sulphatase activity in nude mice.

Liver sulphatase activity was nearly completely inhibited by both STX 140 and STX 641.

Figure 17:
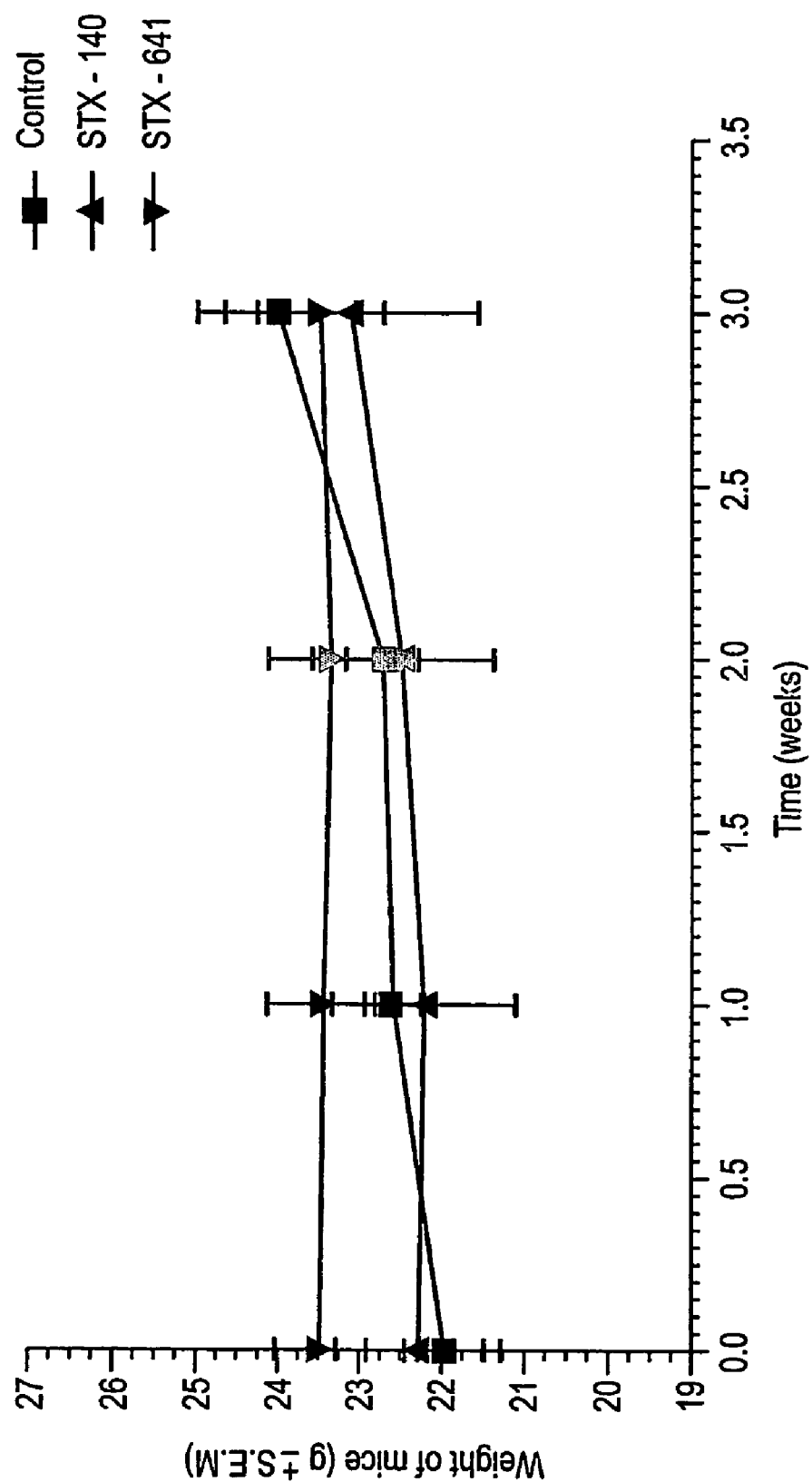
FIG. 17 shows a graph.

FIG. 17 shows the effect of STX 140 and 641 (20 mg/kg op) on the weight of nude mice treated for 3 weeks.

No weight loss was observed over the dosing period in any of the groups.

Carbonic Anhydrase

| Compound | CA2 IC$_{50}$s |
|---|---|
| Acetazolamide | 25 nM |
| STX 140 | 400 nM |
| STX 641 | 1 uM |
| 2-Methoxyoestradiol | no detectable inhibition |

CA2 and CA9 inhibitory activities are linked (Vullo 2003, BioOrg. Med. Chem.).

All publications and patents mentioned in the above specification are herein incorporated by reference.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:
1. A compound of the formula

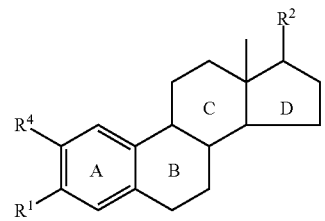

wherein R$^1$ is group selected from any one of —OH, or a sulphamate group of the formula

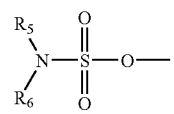

wherein R$^5$ and R$^6$ are independently selected from H, alkyl, cycloalkyl, alkenyl and aryl, or combinations thereof, or together represent alkylene, wherein the or each alkyl or cycloalkyl or alkenyl or aryl optionally contains one or more hetero atoms or groups;

$R^2$ is a group of the formula -L-$R^3$, wherein L is an optional $C_{1-10}$ alkylene group and $R^3$ is a nitrile group, or $R^3$ is:
(a) a group of the formula —$(R^7)_n(CR^{14}R^{15})_pR^8$ wherein n is 0 or 1, p is from 0 to 5;
$R^7$ is selected from =CH—, —O— and $NR^{13}$;
$R^8$ is —C≡N;
$R^{13}$ is selected from H and $C_{1-10}$ alkyl;
$R^{14}$ and $R^{15}$ are each independently selected from H and $C_{1-10}$ alkyl; or
(b) a group of the formula —$(CR^{14}R^{15})_pR^8$,
wherein p is from 0 to 5,
$R^8$ is —C≡N,
$R^{14}$ and $R^{15}$ are each independently selected from H and $C_{1-10}$ alkyl; or
(c) a group of the formula —$(CH2)_pR^8$,
wherein p is from 0 to 5,
$R^8$ is —C≡N; or
(d) a group of the formula —$(R^7)_nR^8$
wherein n is 0 or 1,
$R^7$ is selected from =CH—, —O— and $NR^{13}$,
$R^8$ is —C≡N, and
$R^{13}$ is selected from H and $C_{1-10}$ alkyl;
wherein $R^4$ is an alkyl or alkoxy group.

2. A compound according to claim 1 wherein $R^4$ is methoxy.

3. A compound according to claim 1 wherein $R^4$ is ethyl.

4. A compound according to claim 1 wherein $R^1$ is —OH.

5. A compound according to claim 1 wherein $R^1$ is a sulphamate group.

6. A compound according to claim 5 wherein at least one of $R^5$ and $R^6$ is H.

7. A compound according to claim 6 wherein each of $R^5$ and $R^6$ is H.

8. A compound according to claim 1 wherein p is 0, 1 or 2.

9. A compound according to claim 1 wherein $R^{13}$ is —H.

10. A compound according to claim 1 wherein $R^3$ is a group selected from —$CH_2C$≡N and =CHC≡N.

11. A compound according to claim 1 wherein L is a $C_{1-5}$ alkylene, preferably $C_1$ or $C_2$ alkylene.

12. A compound according to claim 1 wherein $R^2$ is of the formula —$R^3$.

13. A compound according to claim 1 wherein group $R^2$ is in an α conformation.

14. A compound according to claim 1 wherein $R^1$ is a sulphamate group and the compound is suitable for use as an inhibitor of oestrone sulphatase (E.C. 3.1.6.2).

15. A compound according to claim 14 wherein if the sulphamate group on the sulphamate compound were to be replaced with a sulphate group to form a sulphate compound then the sulphate compound would be hydrolysable by a steroid sulphatase enzyme (E.C.3.1.6.2).

16. A compound according to claim 14 wherein if the sulphamate group on the sulphamate compound were to be replaced with a sulphate group to form a sulphate compound and incubated with a steroid sulphatase enzyme (E.C.3.1.6.2) at a pH 7.4 and 37° C. it would provide a $K_m$ value of less than 50 mM.

17. A compound according to claim 14 wherein if the sulphamate group on the sulphamate compound were to be replaced with a sulphate group to form a sulphate compound and incubated with a steroid sulphatase enzyme (E.C.3.1.6.2) at a pH 7.4 and 37° C. it would provide a $K_m$ value of less than 50 μM.

18. A compound according to claim 1 of the following formula:

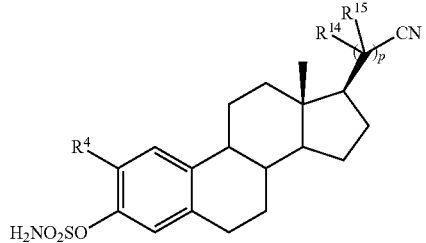

wherein $R^4$, $R^{14}$, $R^{15}$ and p are as defined in claim 1.

19. A compound according to claim 1 wherein the compound is

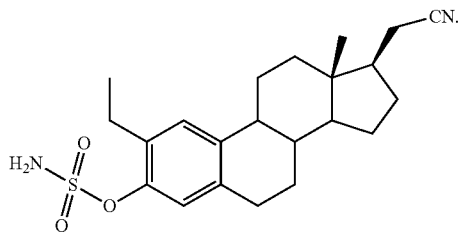

20. A compound according to claim 1 wherein the compound is

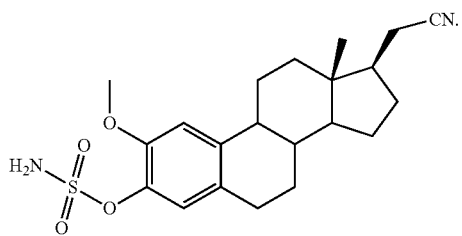

21. A compound according to claim 1 wherein the compound is

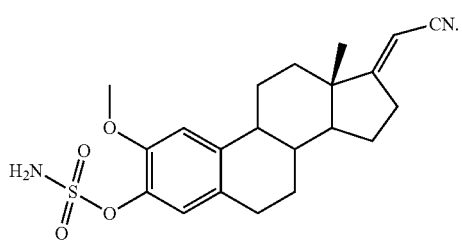

* * * * *